(12) United States Patent
Krames et al.

(10) Patent No.: US 11,511,071 B2
(45) Date of Patent: Nov. 29, 2022

(54) CIRCADIAN-FRIENDLY LED LIGHT SOURCES

(71) Applicant: KORRUS, INC., Los Angeles, CA (US)

(72) Inventors: Michael R. Krames, Los Angeles, CA (US); Aurelien J. F. David, Los Angeles, CA (US); Emil Radkov, Los Angeles, CA (US); Willem Smitt, Los Angeles, CA (US)

(73) Assignee: KORRUS, INC., Los Angeles, CA (US)

( * ) Notice: Subject to any disclaimer, the term of this patent is extended or adjusted under 35 U.S.C. 154(b) by 0 days.

(21) Appl. No.: 17/207,801

(22) Filed: Mar. 22, 2021

(65) Prior Publication Data

US 2021/0402132 A1 Dec. 30, 2021

Related U.S. Application Data

(60) Continuation of application No. 16/397,001, filed on Apr. 29, 2019, now Pat. No. 10,955,608, which is a
(Continued)

(51) Int. Cl.
*A61M 21/00* (2006.01)
*G02F 1/13357* (2006.01)
(Continued)

(52) U.S. Cl.
CPC .............. *A61M 21/00* (2013.01); *F21K 9/23* (2016.08); *F21S 4/20* (2016.01); *G02B 6/0073* (2013.01); *G02F 1/133603* (2013.01); *A61M 2021/0044* (2013.01); *F21K 9/238* (2016.08); *F21V 23/006* (2013.01); *F21V 29/74* (2015.01);
(Continued)

(58) Field of Classification Search
CPC . F21S 4/20; F21K 9/23; G02B 6/0073; G02F 1/133603
See application file for complete search history.

(56) References Cited

U.S. PATENT DOCUMENTS 5,608,554 A 3/1997 Do
6,288,417 B1 9/2001 Nickel
(Continued)

FOREIGN PATENT DOCUMENTS

CN 203139413 8/2013

OTHER PUBLICATIONS

Chen, et al., "Recent Advances on Quantum-Dot-Enhanced Liquid-Crystal Displays", IEEE Journal of Selected Topics in Quantum Electronics, vol. 23, No. 5 p. 1900611, Sep./Oct. 2017, 11 pages.
(Continued)

*Primary Examiner* — Anne M Hines
(74) *Attorney, Agent, or Firm* — FisherBroyles LLP

(57) ABSTRACT

Methods and apparatus for providing circadian-friendly LED light sources are disclosed. A light source is formed to include a first LED emission (e.g., one or more LEDs emitting a first spectrum) and a second LED emission (e.g., one or more LEDs emitting a second spectrum) wherein the first and second LED emissions are combined in a first ratio and in a second ratio such that while changing from the first ratio to the second ratio the relative circadian stimulation is varied while maintaining a color rendering index above 80.

11 Claims, 105 Drawing Sheets

Related U.S. Application Data continuation of application No. 15/878,110, filed on Jan. 23, 2018, now Pat. No. 10,324,250, which is a division of application No. 14/996,143, filed on Jan. 14, 2016, now Pat. No. 9,915,775, which is a continuation-in-part of application No. 14/819,010, filed on Aug. 5, 2015, now Pat. No. 10,041,649, and a continuation-in-part of application No. 14/316,685, filed on Jun. 26, 2014, now Pat. No. 9,410,664.

(60) Provisional application No. 62/103,472, filed on Jan. 14, 2015, provisional application No. 62/033,487, filed on Aug. 5, 2014, provisional application No. 61/871,525, filed on Aug. 29, 2013.

(51) Int. Cl.

| | | |
|---|---|---|
| *F21V 8/00* | (2006.01) | |
| *F21S 4/20* | (2016.01) | |
| *F21K 9/23* | (2016.01) | |
| *F21V 23/00* | (2015.01) | |
| *F21V 29/74* | (2015.01) | |
| *F21Y 105/10* | (2016.01) | |
| *F21Y 115/10* | (2016.01) | |
| *F21Y 113/13* | (2016.01) | |
| *F21Y 105/18* | (2016.01) | |
| *F21K 9/238* | (2016.01) | |
| *F21W 107/10* | (2018.01) | |
| *H05B 45/20* | (2020.01) | |
| *H05B 47/16* | (2020.01) | |
| *F21W 102/00* | (2018.01) | |

(52) U.S. Cl.
CPC ..... *F21W 2102/00* (2018.01); *F21W 2107/10* (2018.01); *F21Y 2105/10* (2016.08); *F21Y 2105/18* (2016.08); *F21Y 2113/13* (2016.08); *F21Y 2115/10* (2016.08); *H05B 45/20* (2020.01); *H05B 47/16* (2020.01)

(56) References Cited

U.S. PATENT DOCUMENTS

| | | |
|---|---|---|
| 8,491,816 B2 | 7/2013 | Hong |
| 9,289,622 B2 | 3/2016 | Feng |
| 2004/0070736 A1 | 4/2004 | Roddy |
| 2007/0058107 A1 | 3/2007 | Im |
| 2007/0188711 A1 | 8/2007 | Sharp |
| 2012/0140466 A1 | 6/2012 | Yang |
| 2013/0027616 A1 | 1/2013 | Takata |
| 2013/0169906 A1 | 7/2013 | Nakanishi |
| 2014/0268152 A1 | 9/2014 | Morrow |
| 2014/0301062 A1 | 10/2014 | David |
| 2015/0116997 A1 | 4/2015 | Tappert |
| 2015/0237688 A1 | 8/2015 | Gambeski |
| 2016/0243379 A1 | 8/2016 | Hommes |
| 2016/0273717 A1 | 9/2016 | Krames |
| 2017/0254933 A1 | 9/2017 | Li |
| 2017/0368210 A1 | 12/2017 | David |

OTHER PUBLICATIONS

Stefani et al., Evaluation of Human Reactions on Displays with LED Backlight and a Technical Concept of a Circadian Effective Display, SID 10 Digest, ISSN 0097-966X/10/4102-1120, 2010, 4 pgs.

Wang, et al., "Highly efficient narrow-band green and red phosphors enabling wider color-gamut LED backlight for more brilliant displays", Optics Express vol. 23, Issue 22, pp. 28707-28717 (2015).

Yang, et al., "Wide Viewing Angle TN LED Enhanced by Printed Quantum-Dots Film", Proc. SID Symp. Dig. Tech. papers vol. 47, pp. 21-24, 2016.

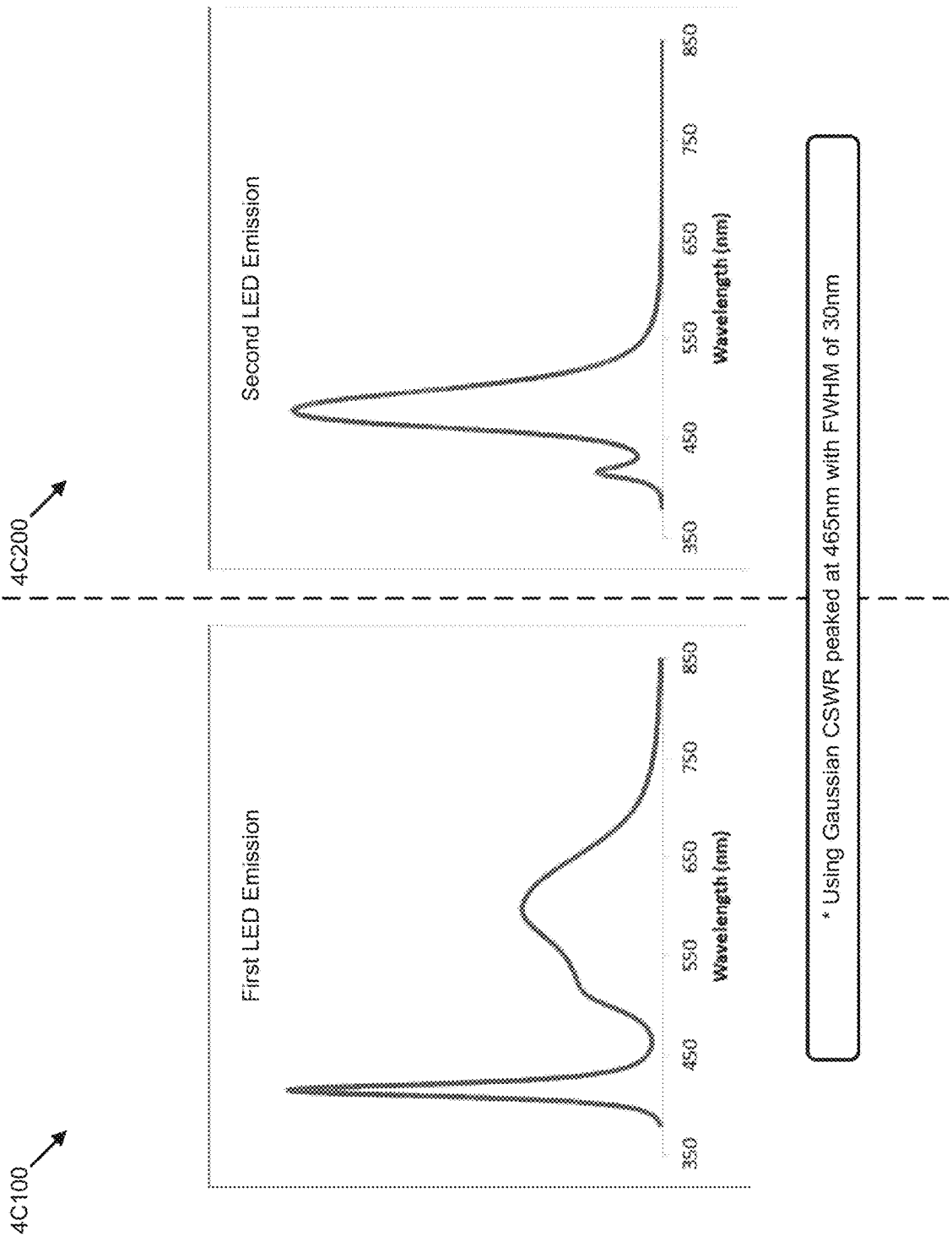

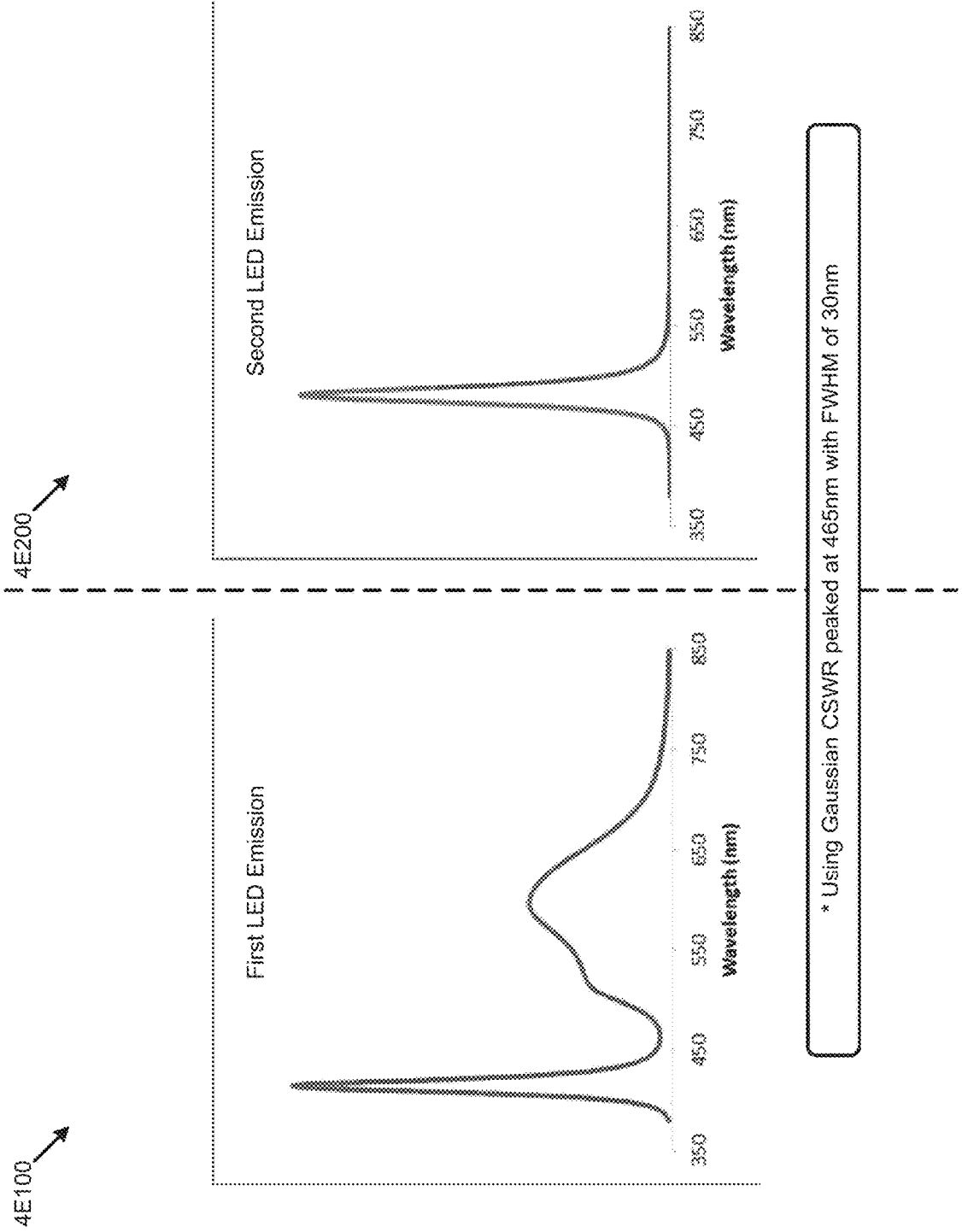

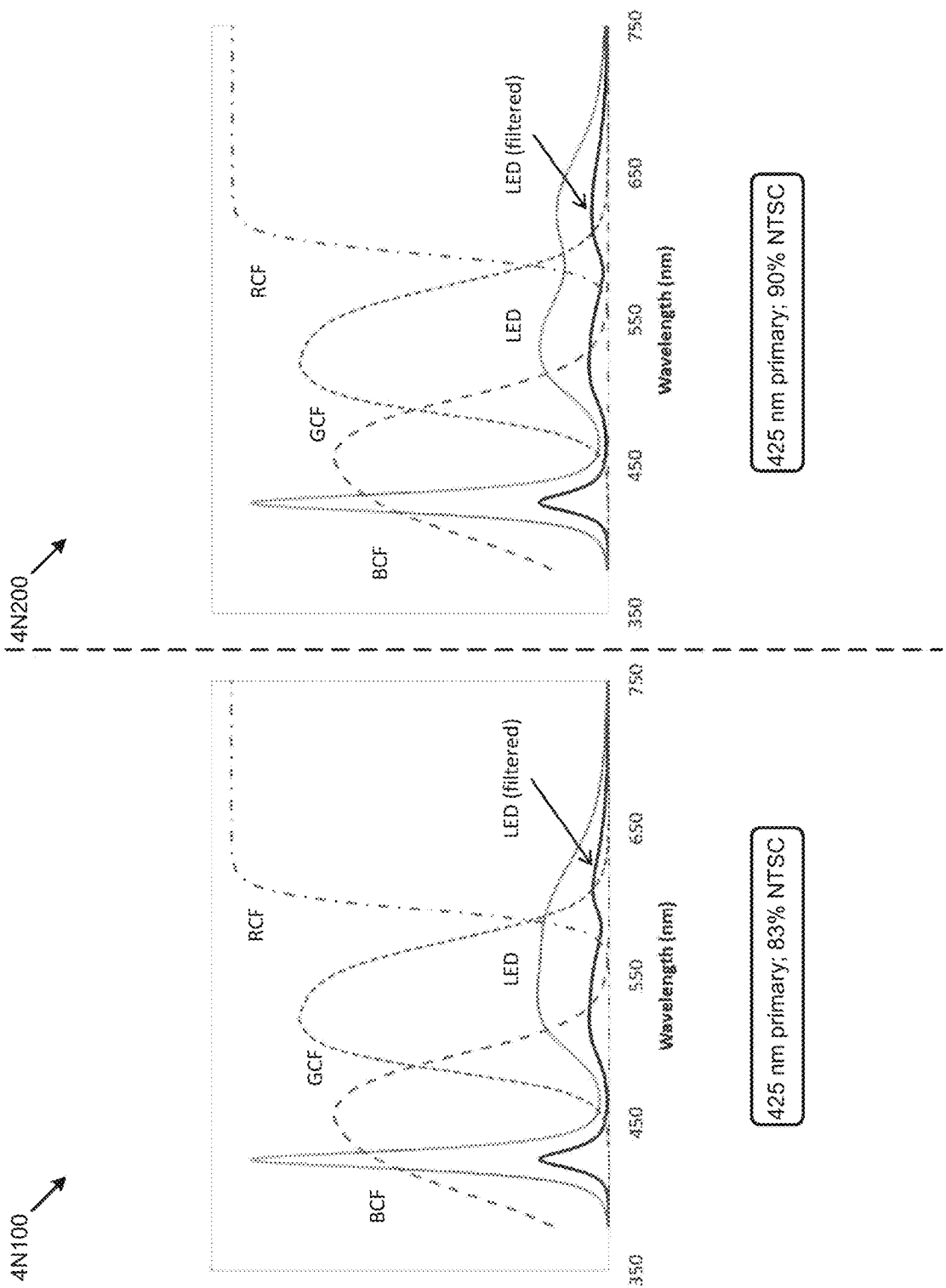

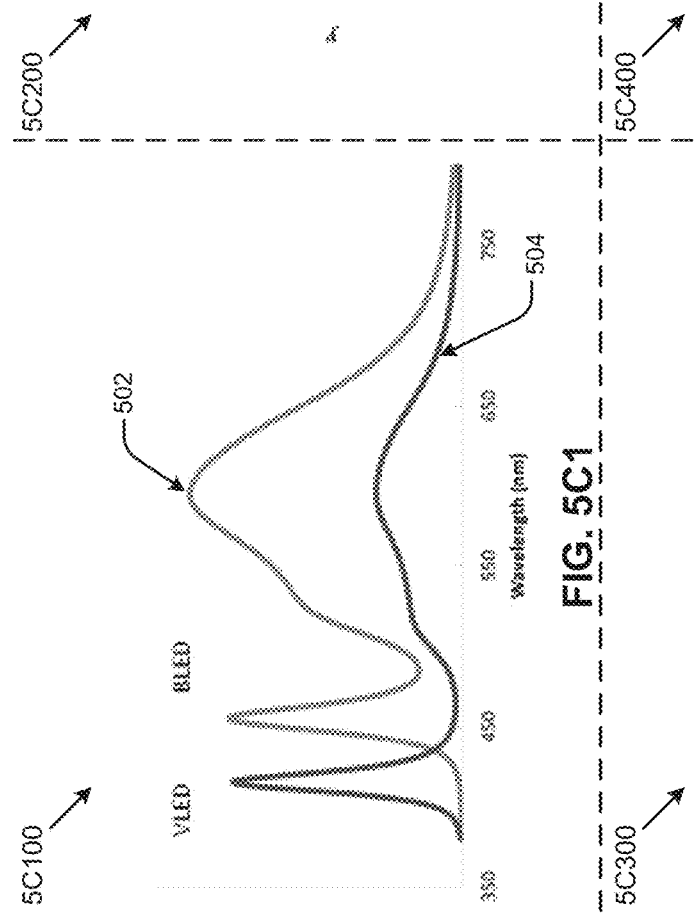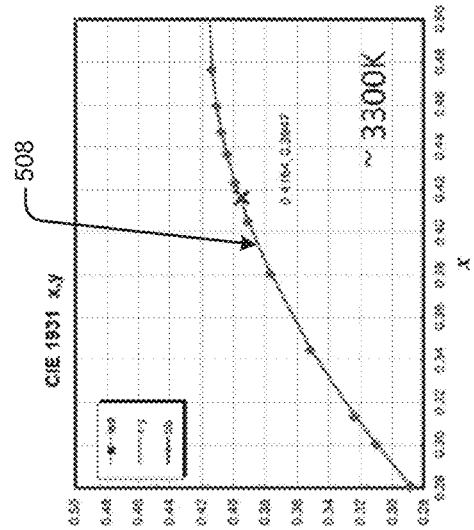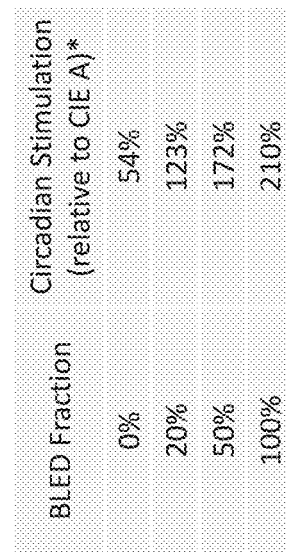
FIG. 5C1
FIG. 5C2
FIG. 5C3
FIG. 5C4

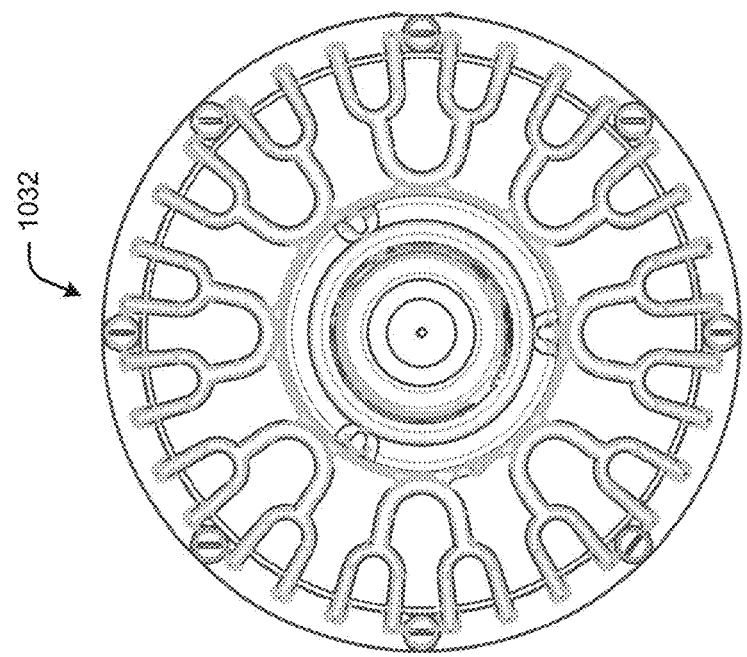
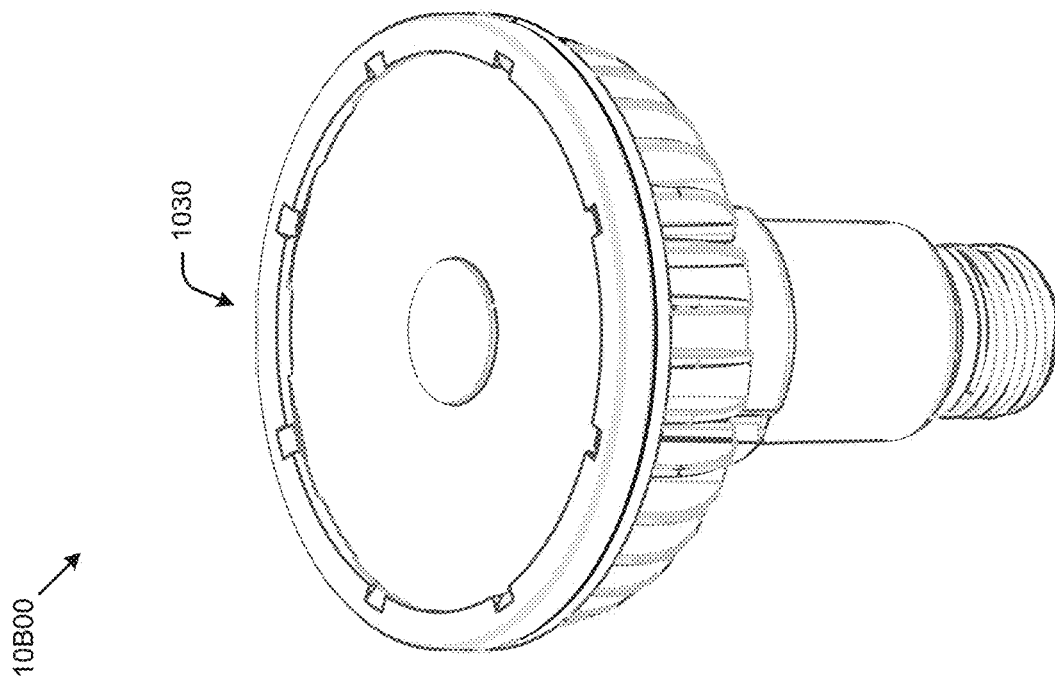
FIG. 10B

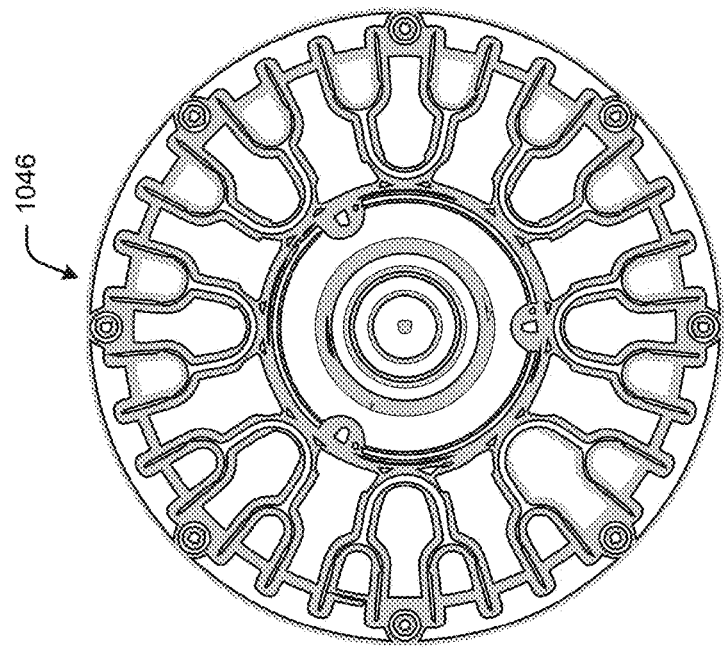
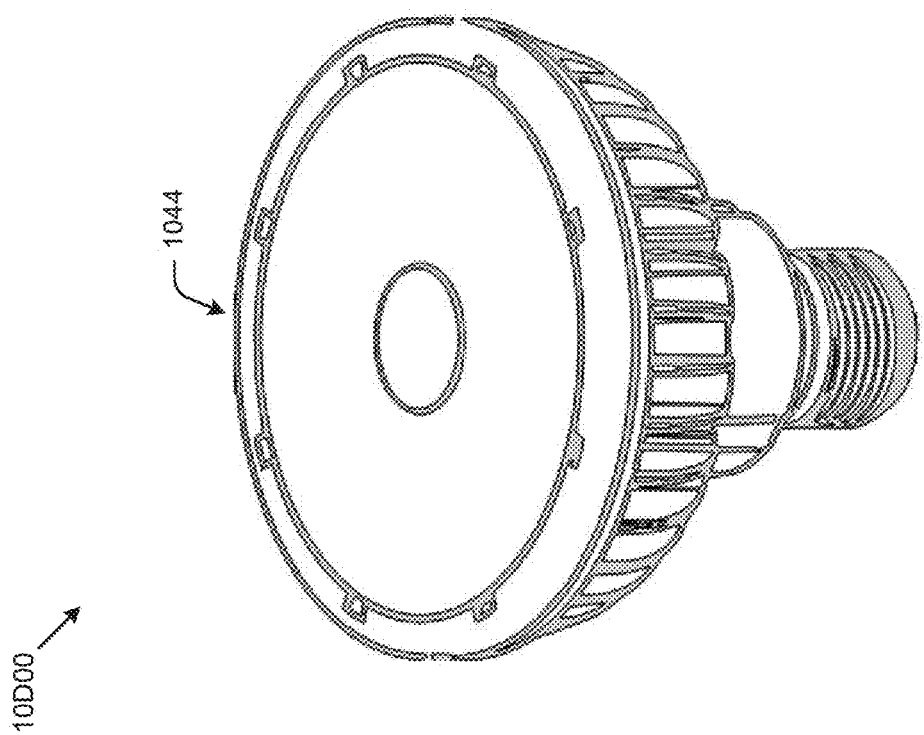
FIG. 10D

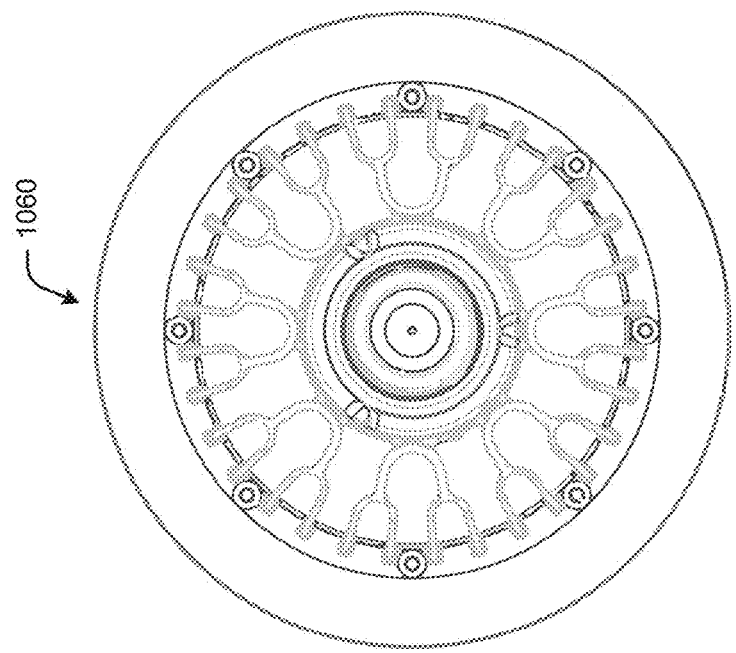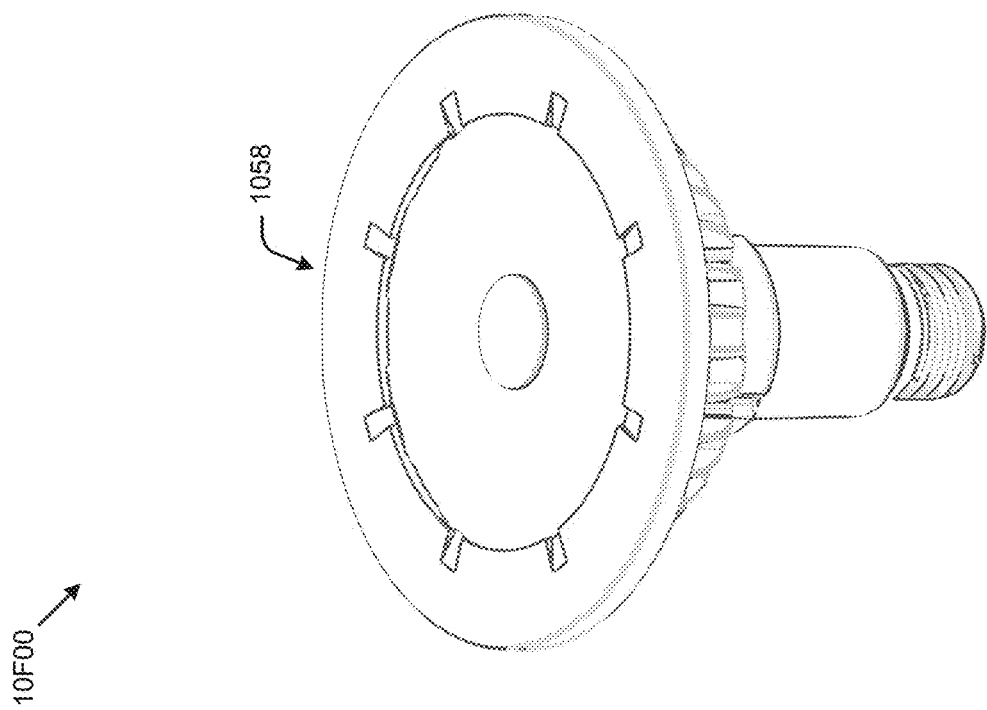
FIG. 10F

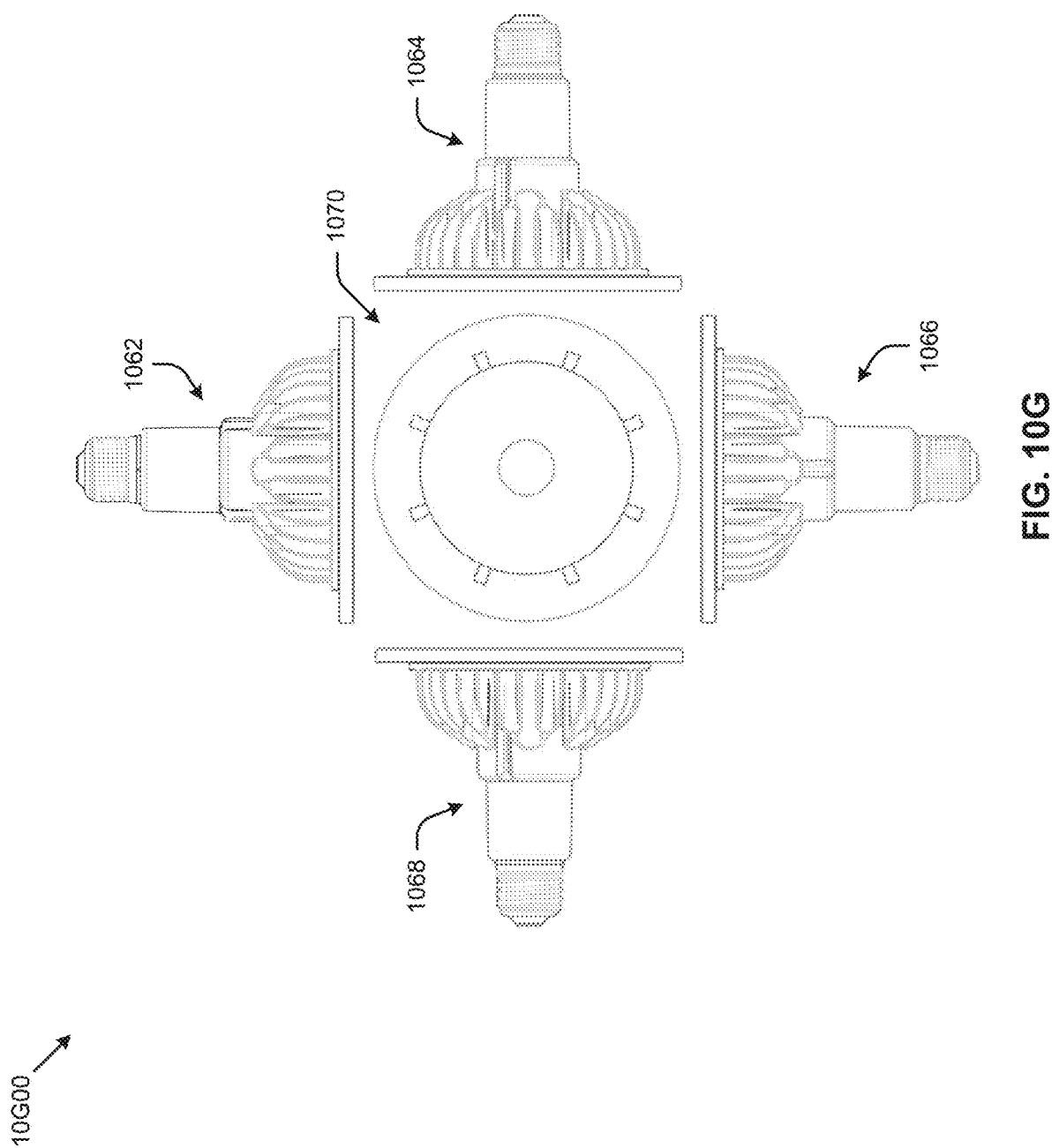

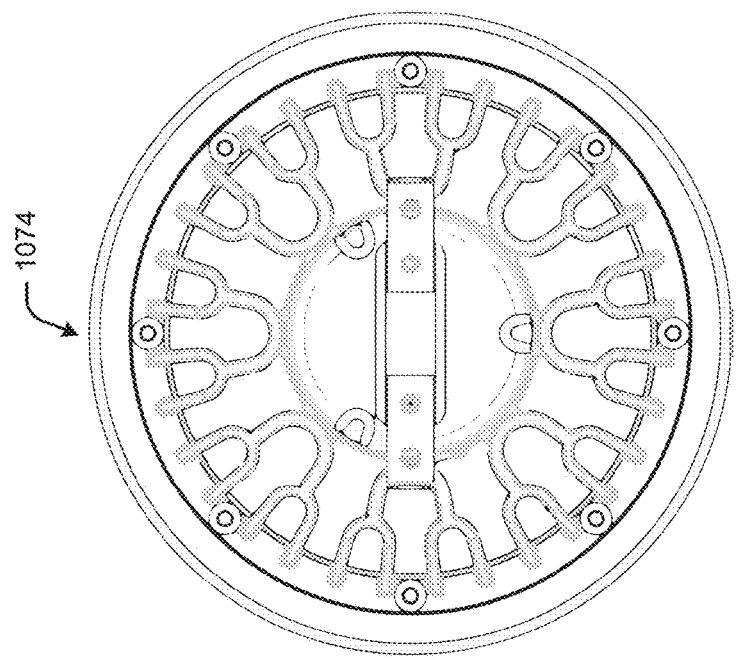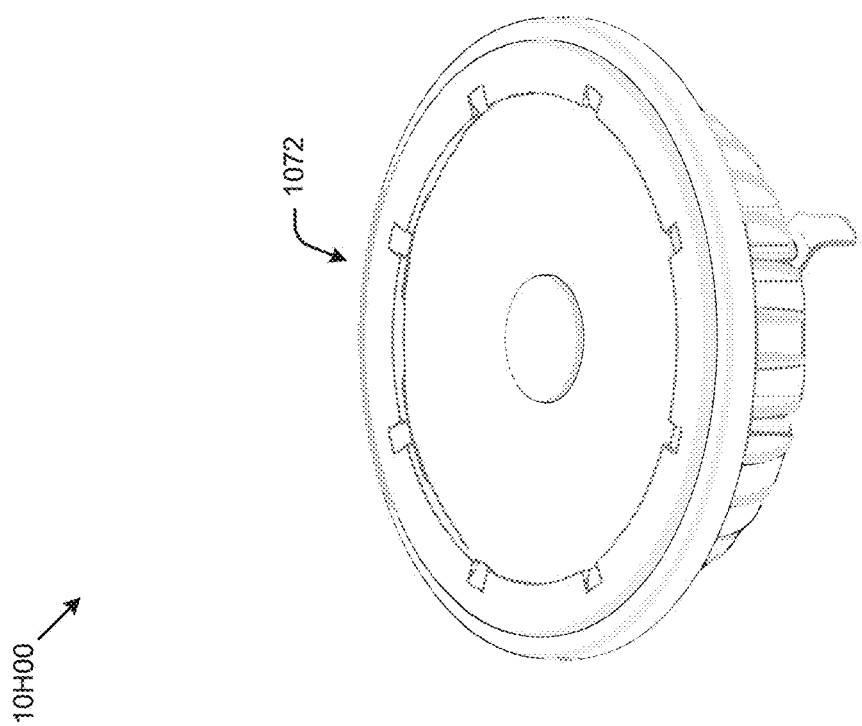
FIG. 10H

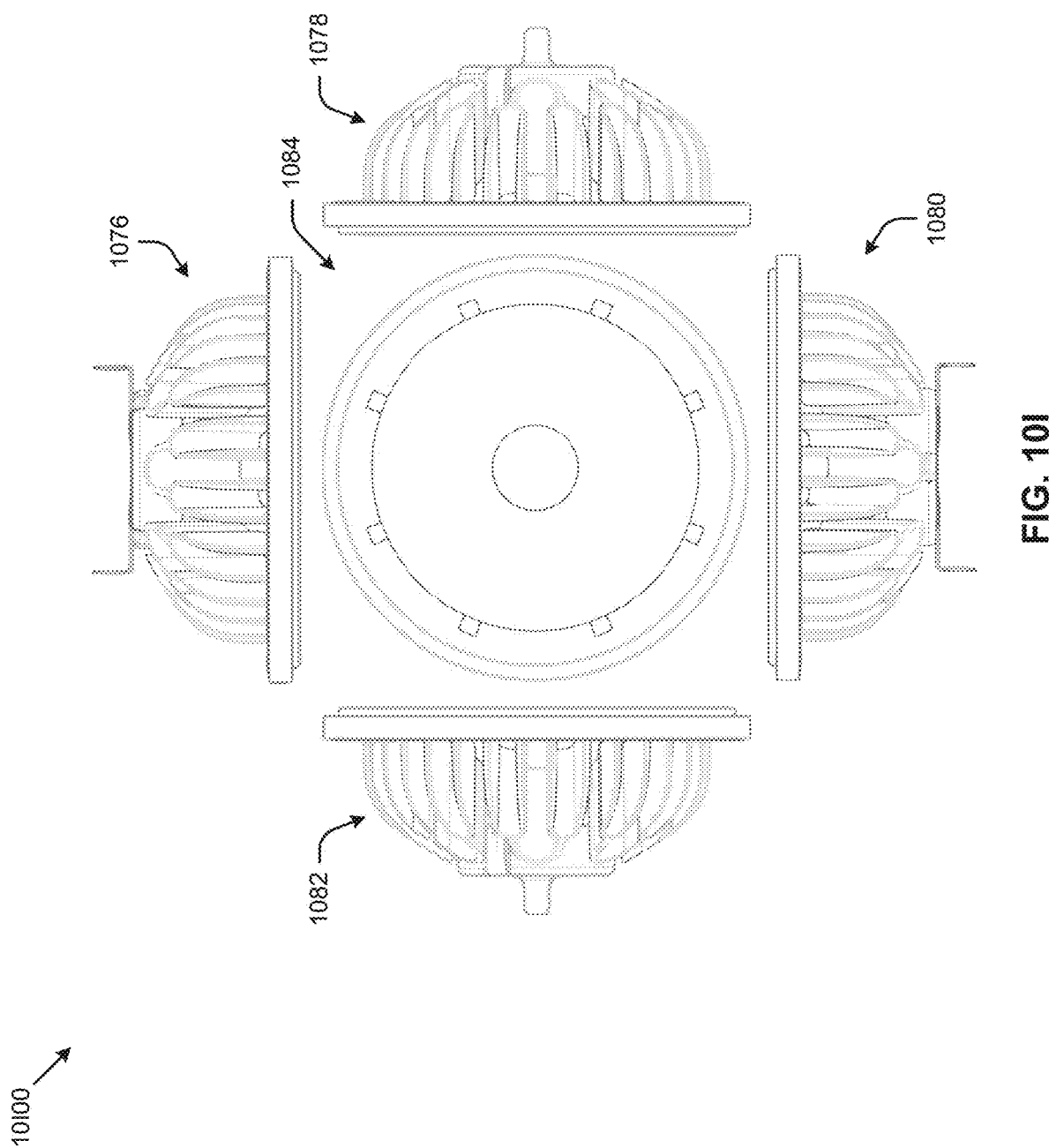

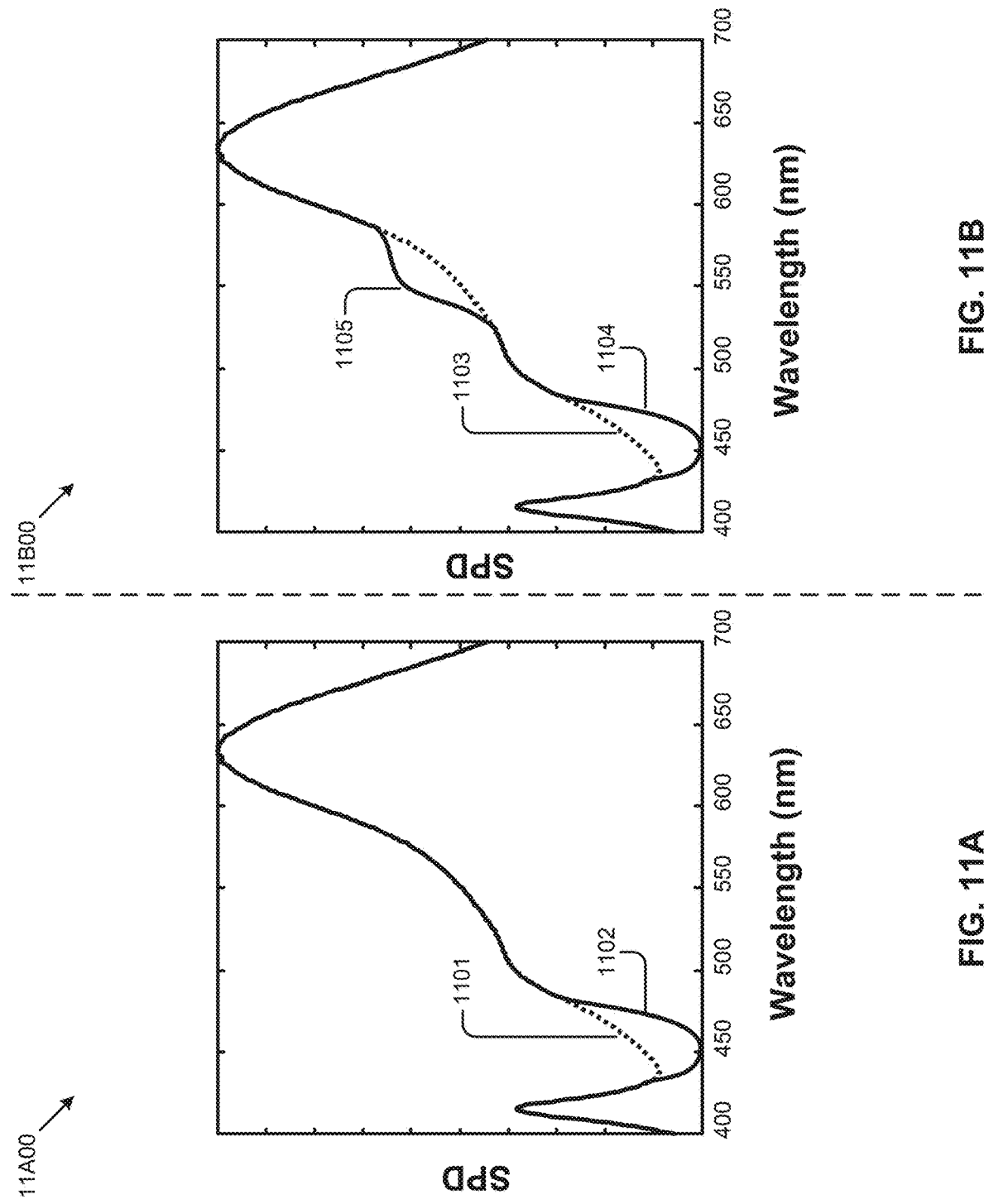

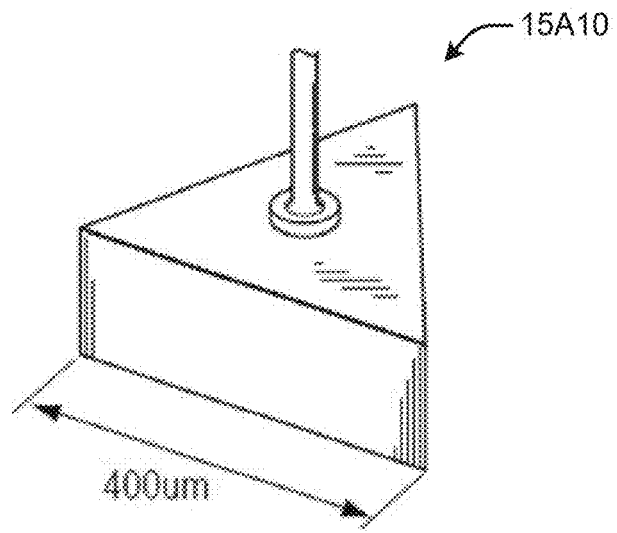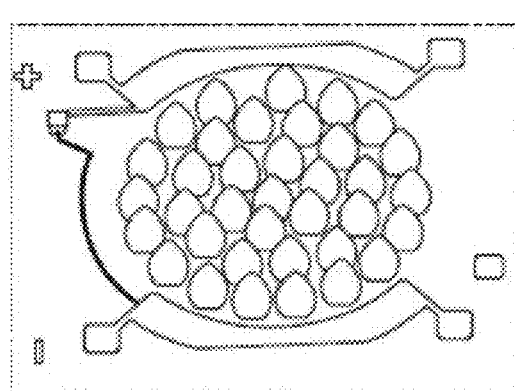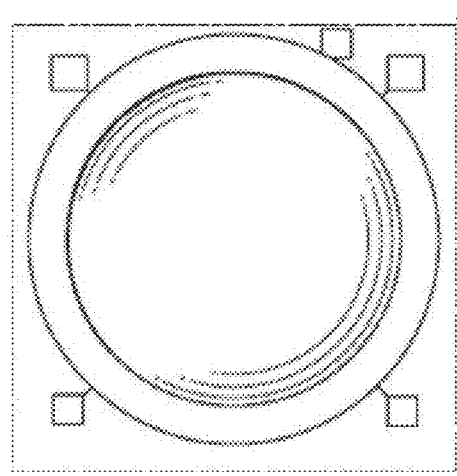
FIG. 15A

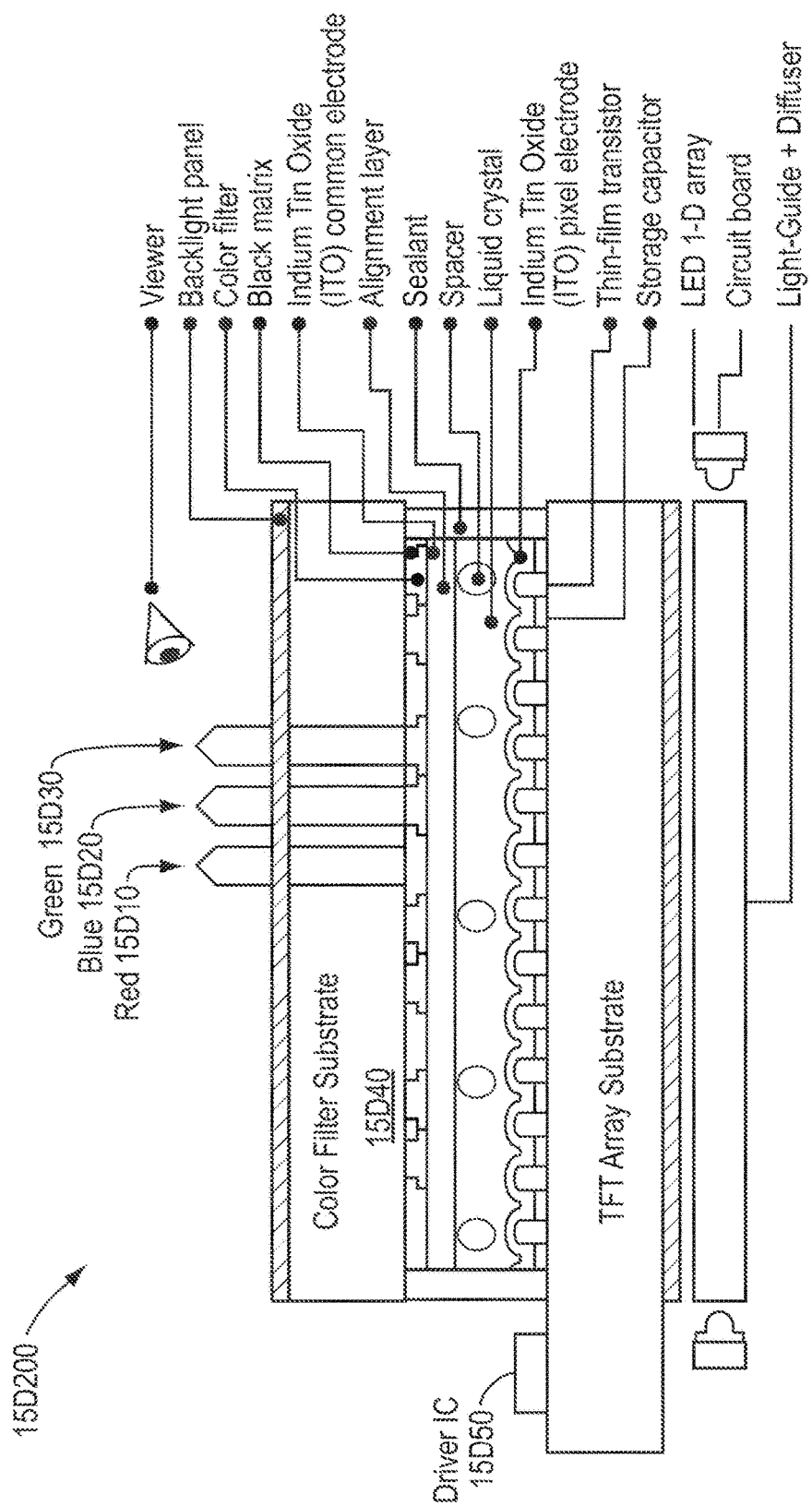
FIG. 15D Con't

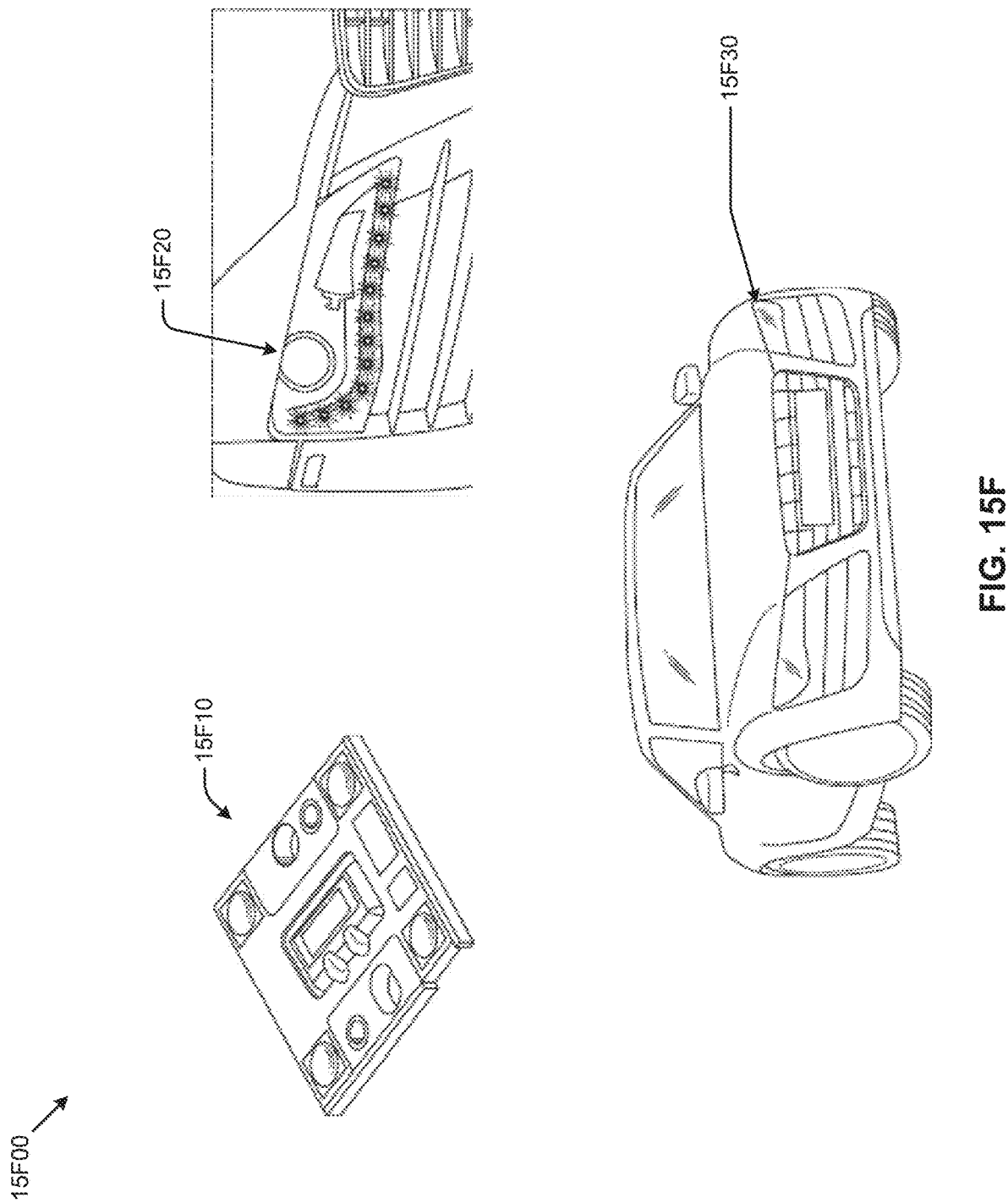

16A00

| | |
|---|---|
| SiOx | 99.9 |
| NbOx | 4.3 |
| SiOx | 305.2 |
| NbOx | 12.8 |
| SiOx | 286.3 |
| NbOx | 18.4 |
| SiOx | 134.8 |
| NbOx | 6.5 |
| SiOx | 136.5 |
| NbOx | 15.3 |
| SiOx | 132.8 |
| NbOx | 14.9 |
| SiOx | 130.7 |
| NbOx | 13.9 |
| SiOx | 128.4 |
| NbOx | 17.6 |
| SiOx | 127.4 |
| NbOx | 17.0 |
| SiOx | 128.2 |
| NbOx | 15.3 |
| SiOx | 127.7 |
| NbOx | 18.6 |
| SiOx | 126.3 |
| NbOx | 17.7 |
| SiOx | 125.9 |
| NbOx | 16.3 |
| SiOx | 125.3 |
| NbOx | 19.8 |
| SiOx | 126.1 |
| NbOx | 16.4 |
| SiOx | 128.2 |
| NbOx | 15.5 |
| SiOx | 127.7 |
| NbOx | 16.7 |
| SiOx | 127.4 |
| NbOx | 14.9 |
| SiOx | 128.1 |
| NbOx | 14.6 |
| SiOx | 124.3 |
| NbOx | 23.9 |
| SiOx | 268.5 |
| NbOx | 32.5 |
| SiOx | 260.0 |
| NbOx | 17.5 |
| SiOx | 155.5 |
| NbOx | 7.0 |
| SiOx | 39.7 |
| NbOx | 7.7 |
| SiOx | 117.9 |

FIG. 16A

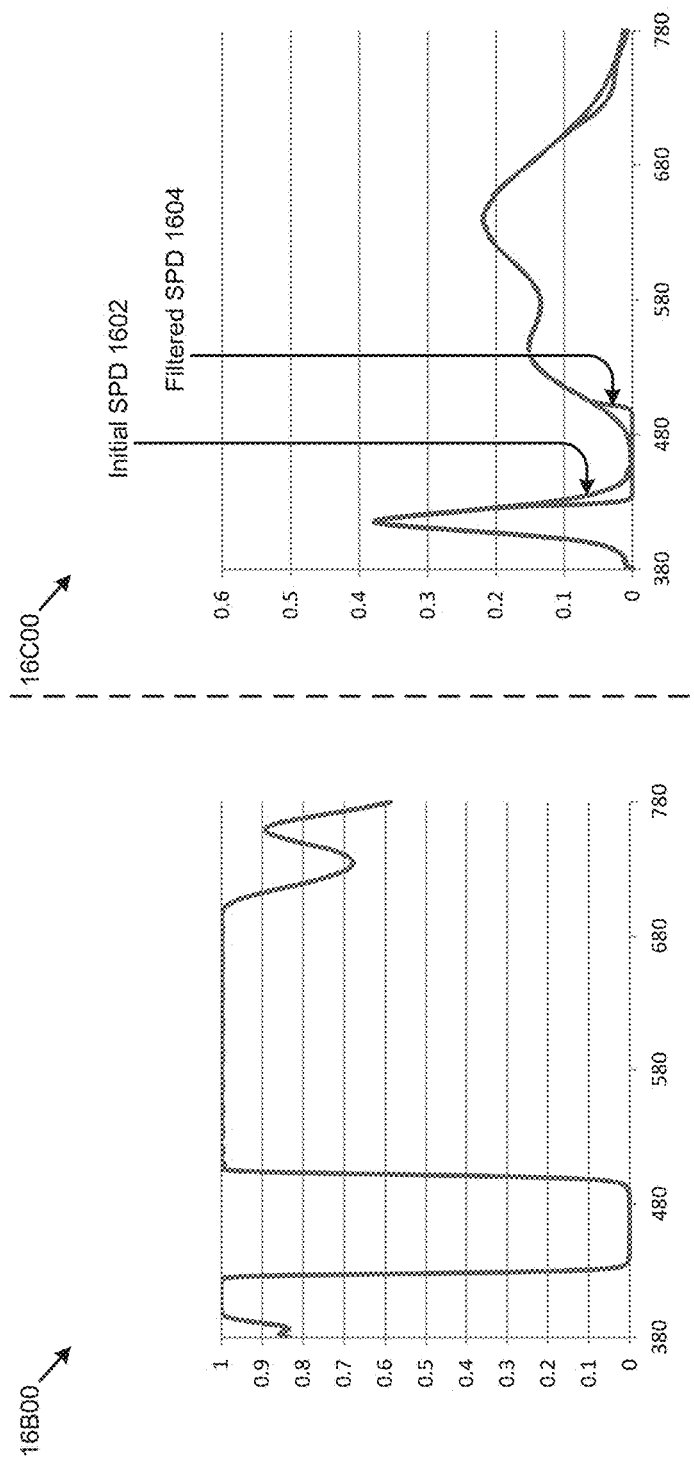

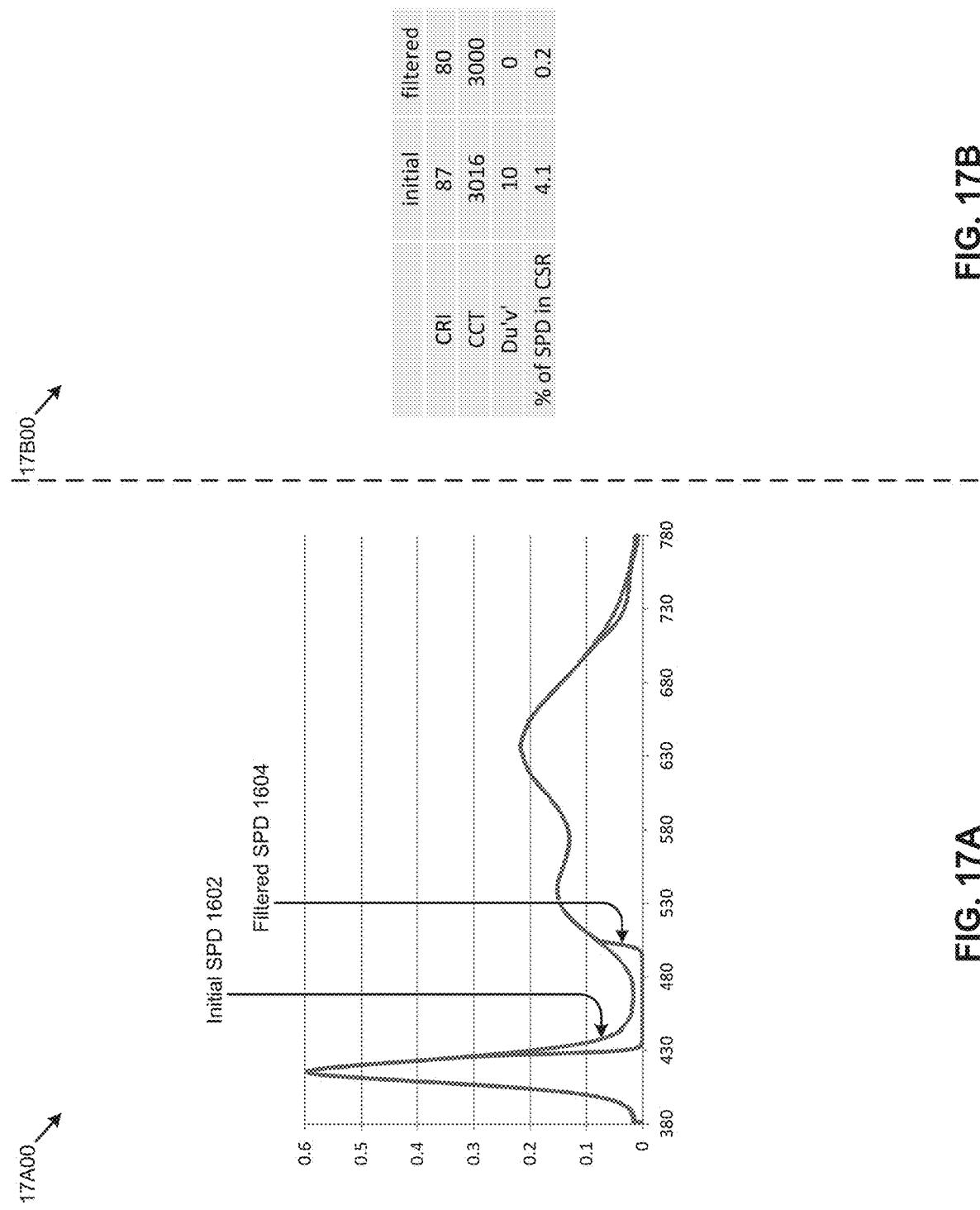

18A00

18B00

| Angle | 0 | 10 | 20 | 30 | 40 |
|---|---|---|---|---|---|
| Ra | 80 | 80 | 84 | 77 | 73 |
| CCT | 2861 | 2860 | 2839 | 2824 | 2874 |
| Du'v' | 7 | 9 | 17 | 22 | 24 |

| Angle | 0 | 10 | 20 | 30 | 40 |
|---|---|---|---|---|---|
| Ra | 79 | 79 | 80 | 81 | 81 |
| CCT | 2790 | 2788 | 2777 | 2793 | 2862 |
| Du'v' | 1 | 1 | 3 | 6 | 9 |

18E00

| | |
|---|---|
| NbOx | 13.96 |
| SiOx | 57.14 |
| NbOx | 5.21 |
| SiOx | 265.95 |
| NbOx | 6.37 |
| SiOx | 116.32 |
| NbOx | 3.06 |
| SiOx | 191.77 |
| NbOx | 4.37 |
| SiOx | 225.36 |
| NbOx | 0.3 |
| SiOx | 50.36 |
| NbOx | 157.43 |
| SiOx | 37.86 |
| NbOx | 89.64 |
| SiOx | 12.11 |
| NbOx | 77.94 |
| SiOx | 32.58 |
| NbOx | 79.23 |
| SiOx | 13.67 |
| NbOx | 85.54 |
| SiOx | 19.8 |
| NbOx | 51.62 |
| SiOx | 292.09 |
| NbOx | 11.71 |
| SiOx | 149.62 |
| NbOx | 3.22 |
| SiOx | 147.9 |
| NbOx | 10.92 |
| SiOx | 299.57 |
| NbOx | 46.13 |
| SiOx | 19.57 |
| NbOx | 89.5 |
| SiOx | 23.3 |
| NbOx | 84.93 |
| SiOx | 26.29 |
| NbOx | 77.96 |
| SiOx | 29.42 |
| NbOx | 77.9 |
| SiOx | 31.29 |
| NbOx | 79.94 |
| SiOx | 26.04 |
| NbOx | 82.79 |
| SiOx | 25.86 |
| NbOx | 82.15 |

| | |
|---|---|
| SiOx | 27.04 |
| NbOx | 79.81 |
| SiOx | 27.64 |
| NbOx | 80.58 |
| SiOx | 18.81 |
| NbOx | 87.5 |
| SiOx | 24.57 |
| NbOx | 96.92 |
| SiOx | 11.16 |
| NbOx | 70.58 |
| SiOx | 32.97 |
| NbOx | 57.88 |
| SiOx | 13.74 |
| NbOx | 37.56 |
| SiOx | 57.3 |
| NbOx | 13.65 |

FIG. 18E

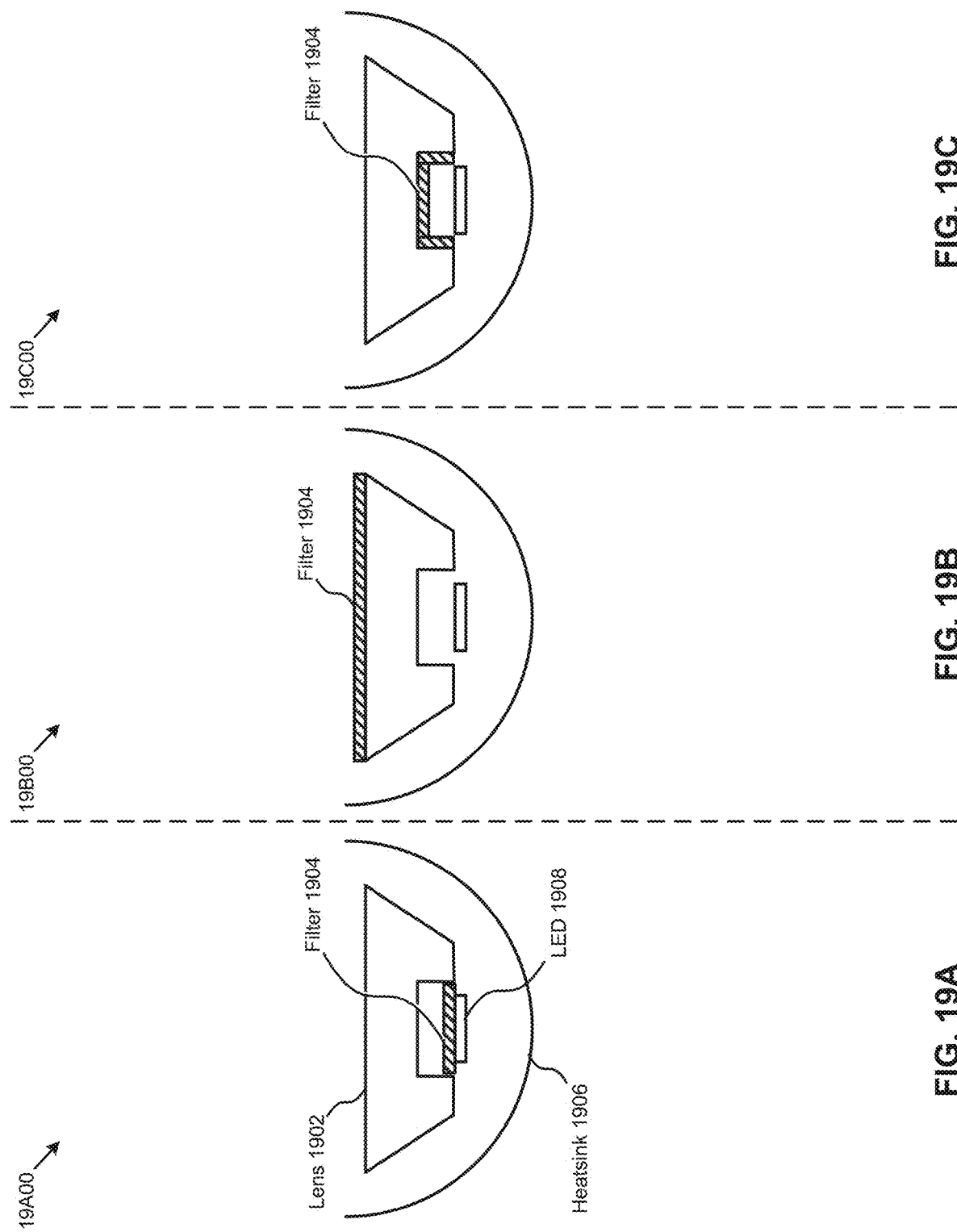

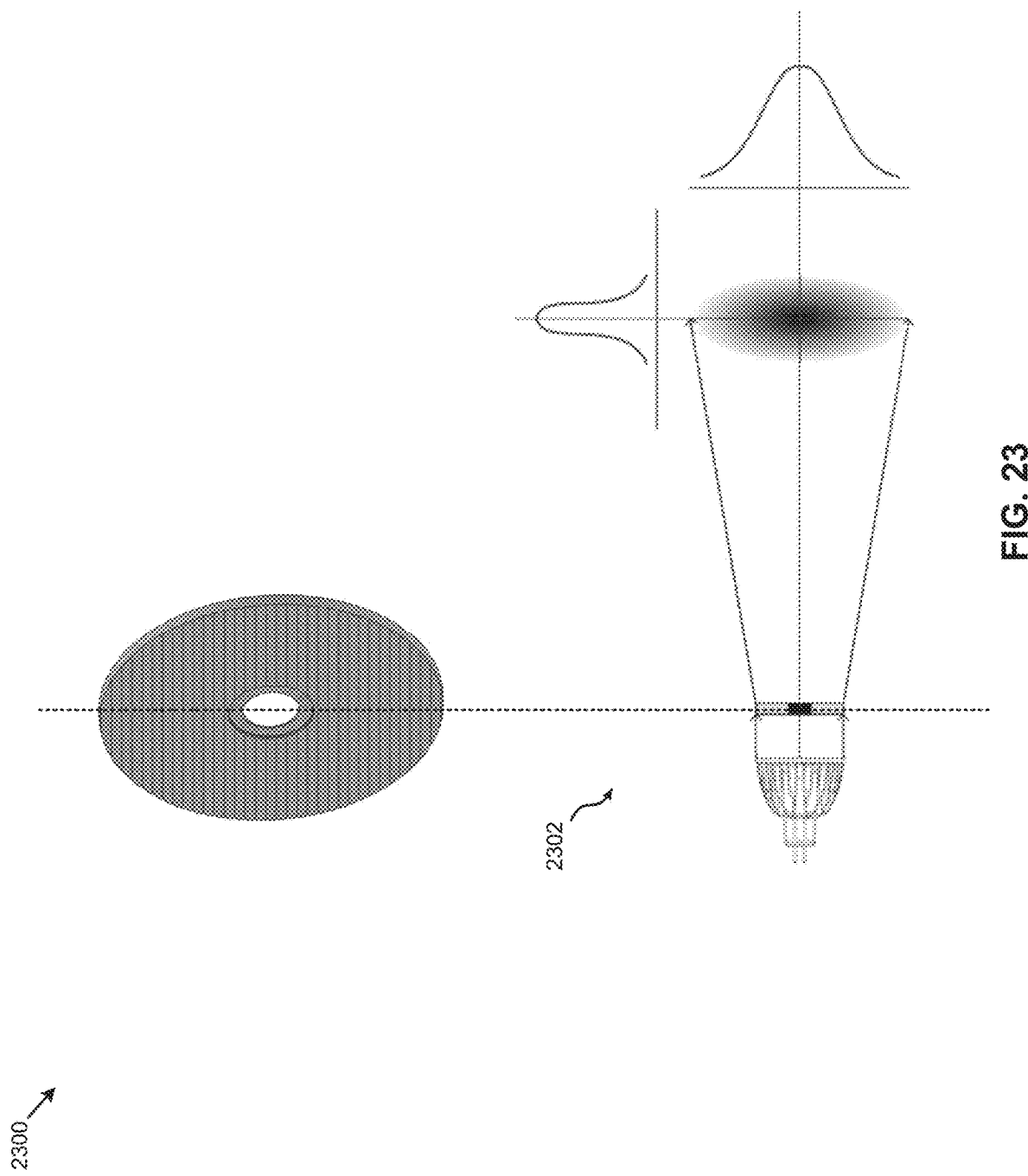

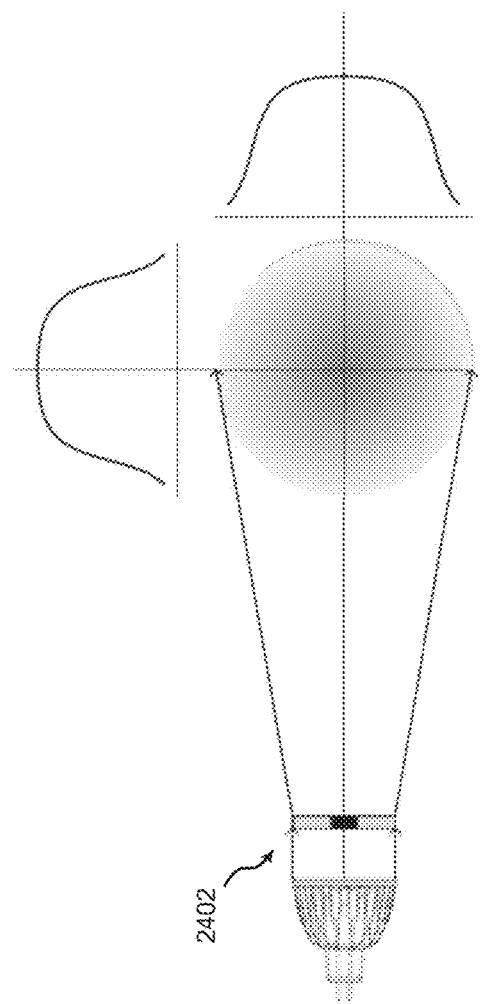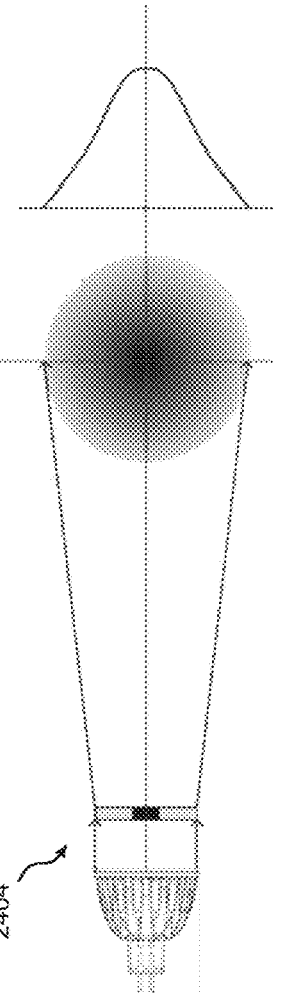
FIG. 24A
FIG. 24B

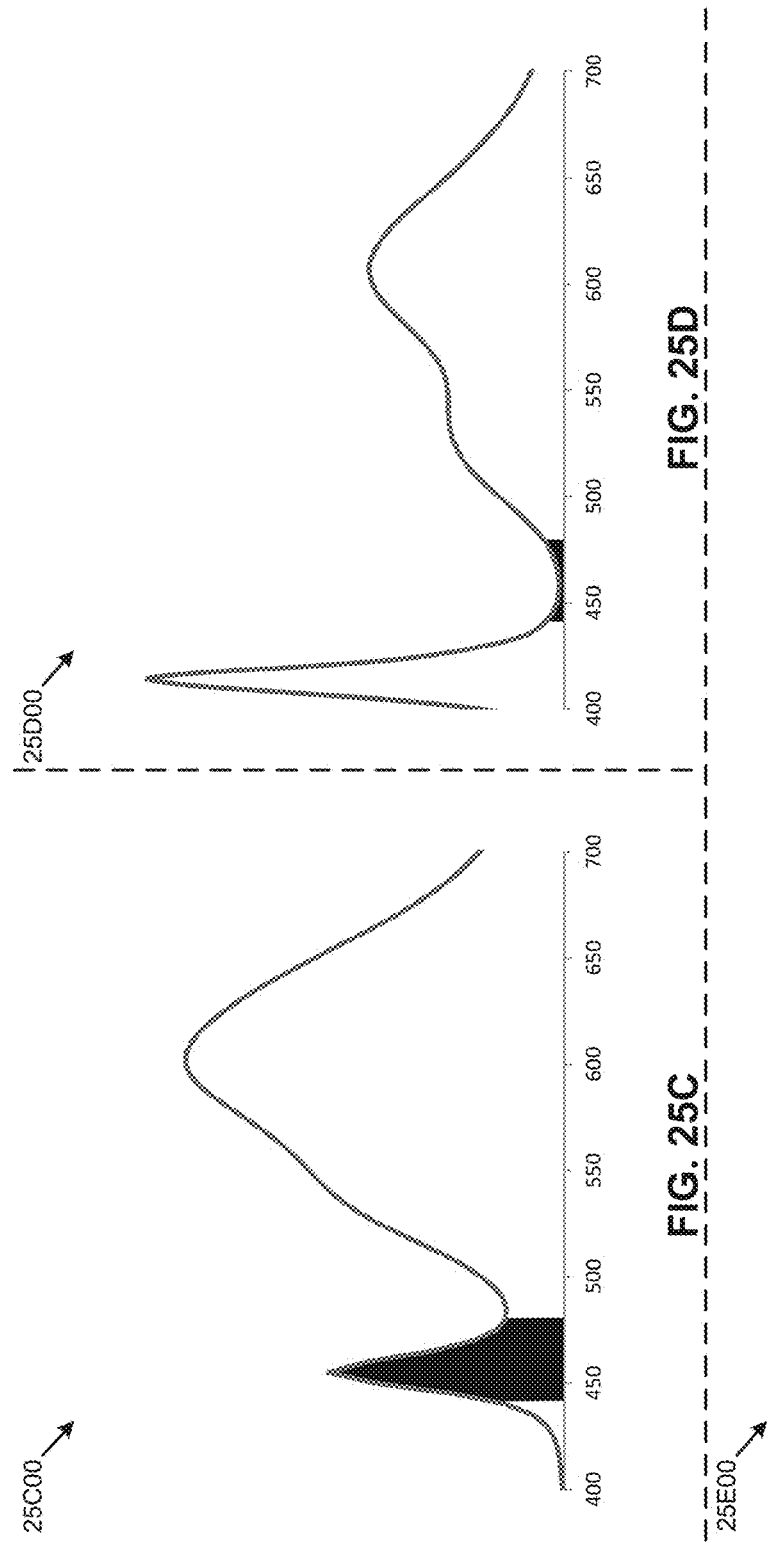

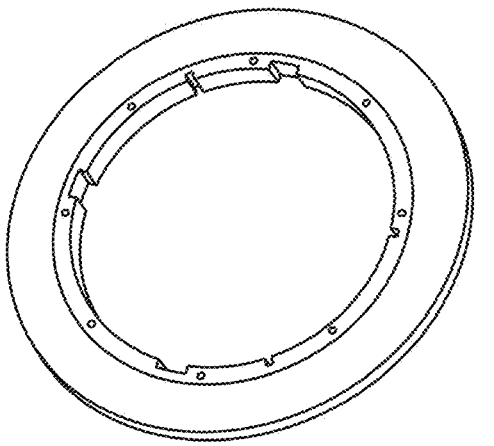
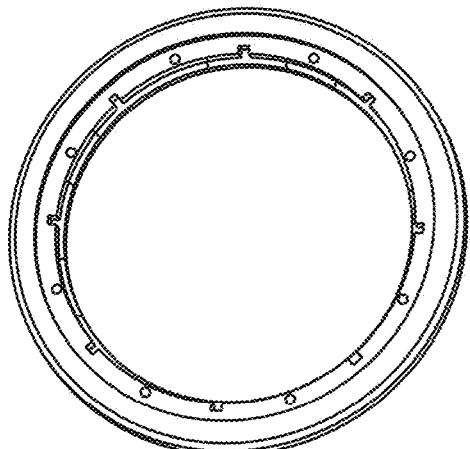
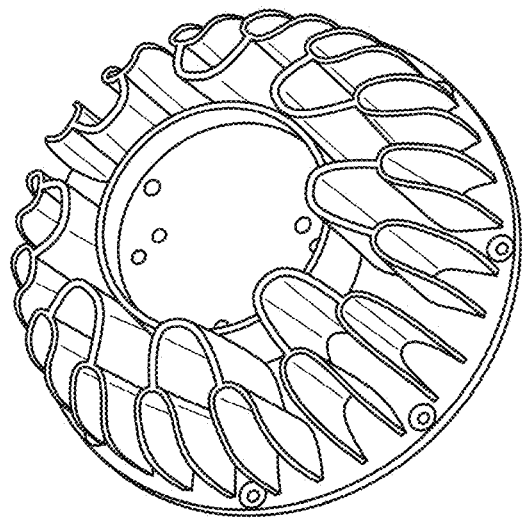
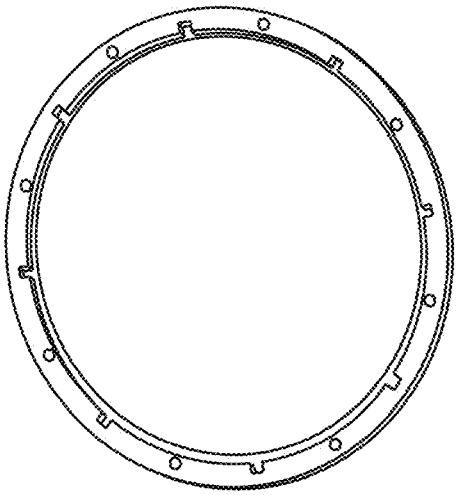
FIG. 26B

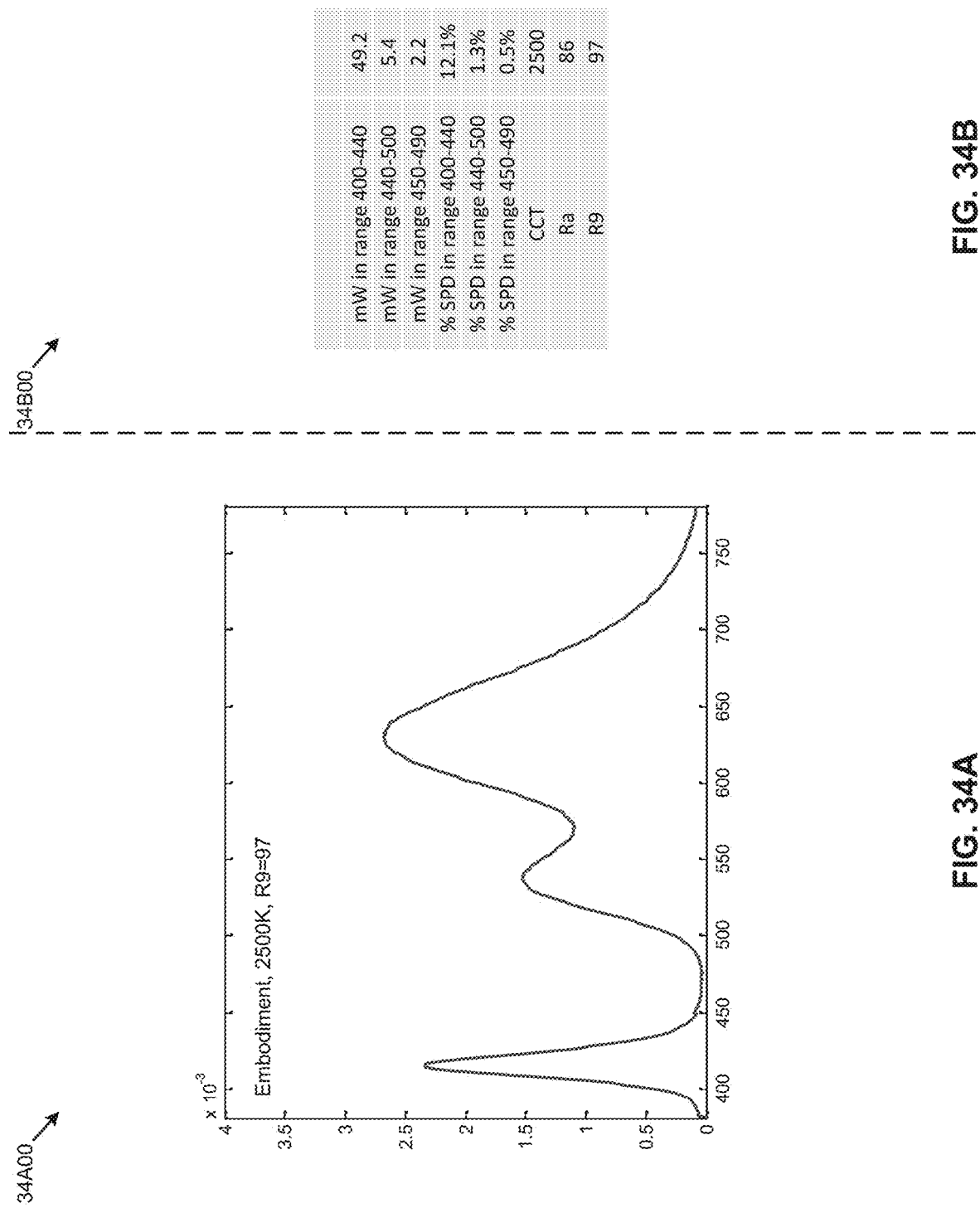

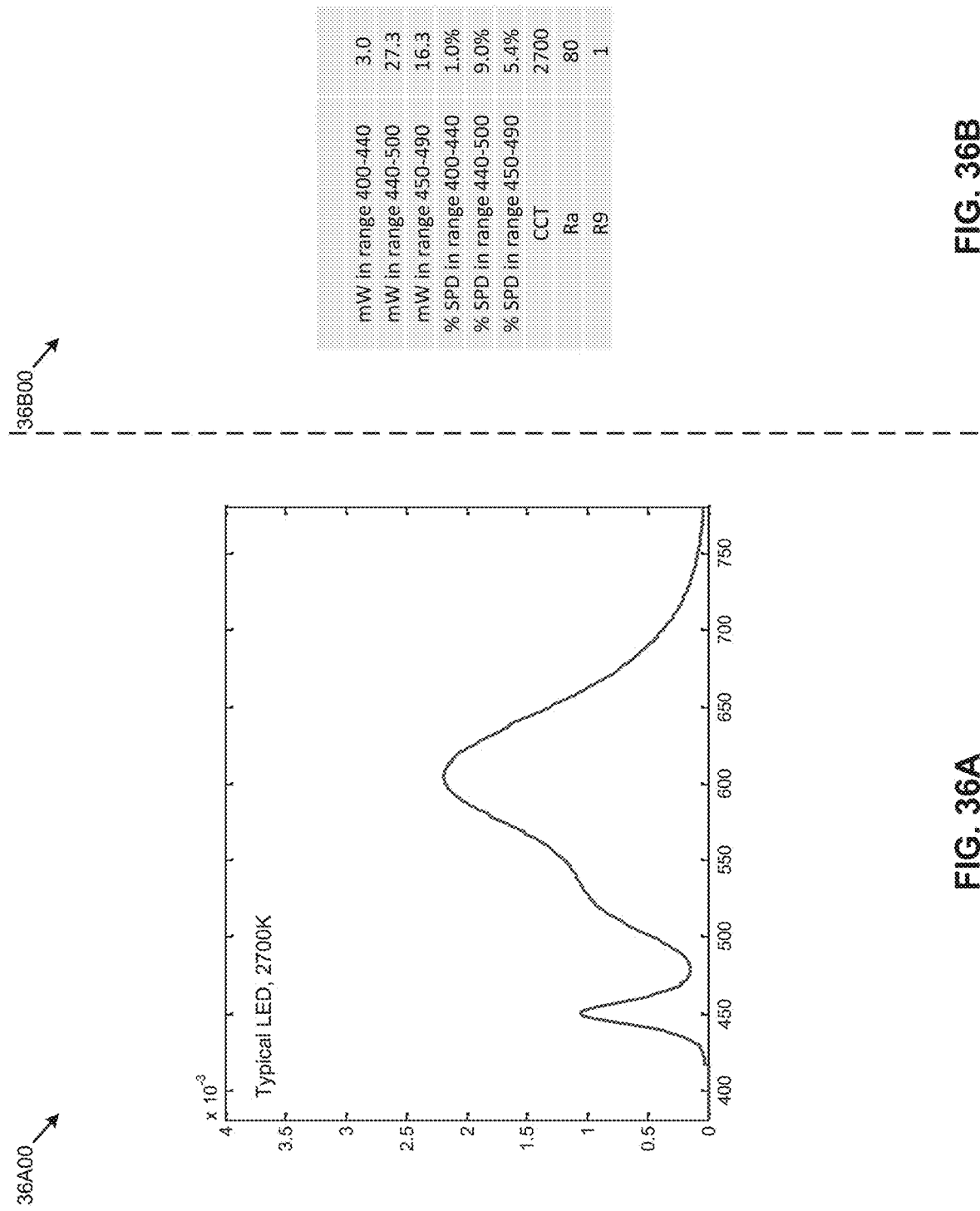

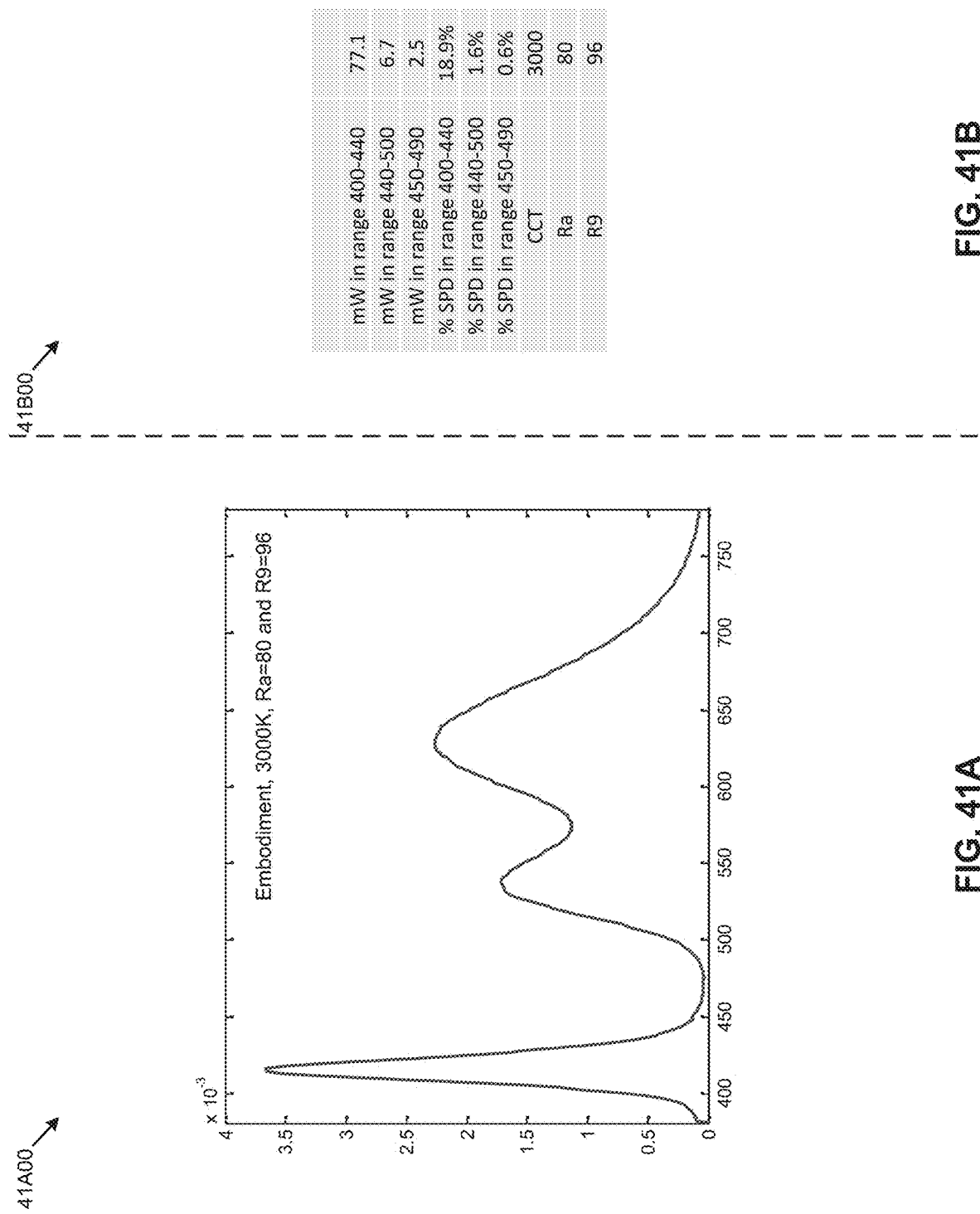

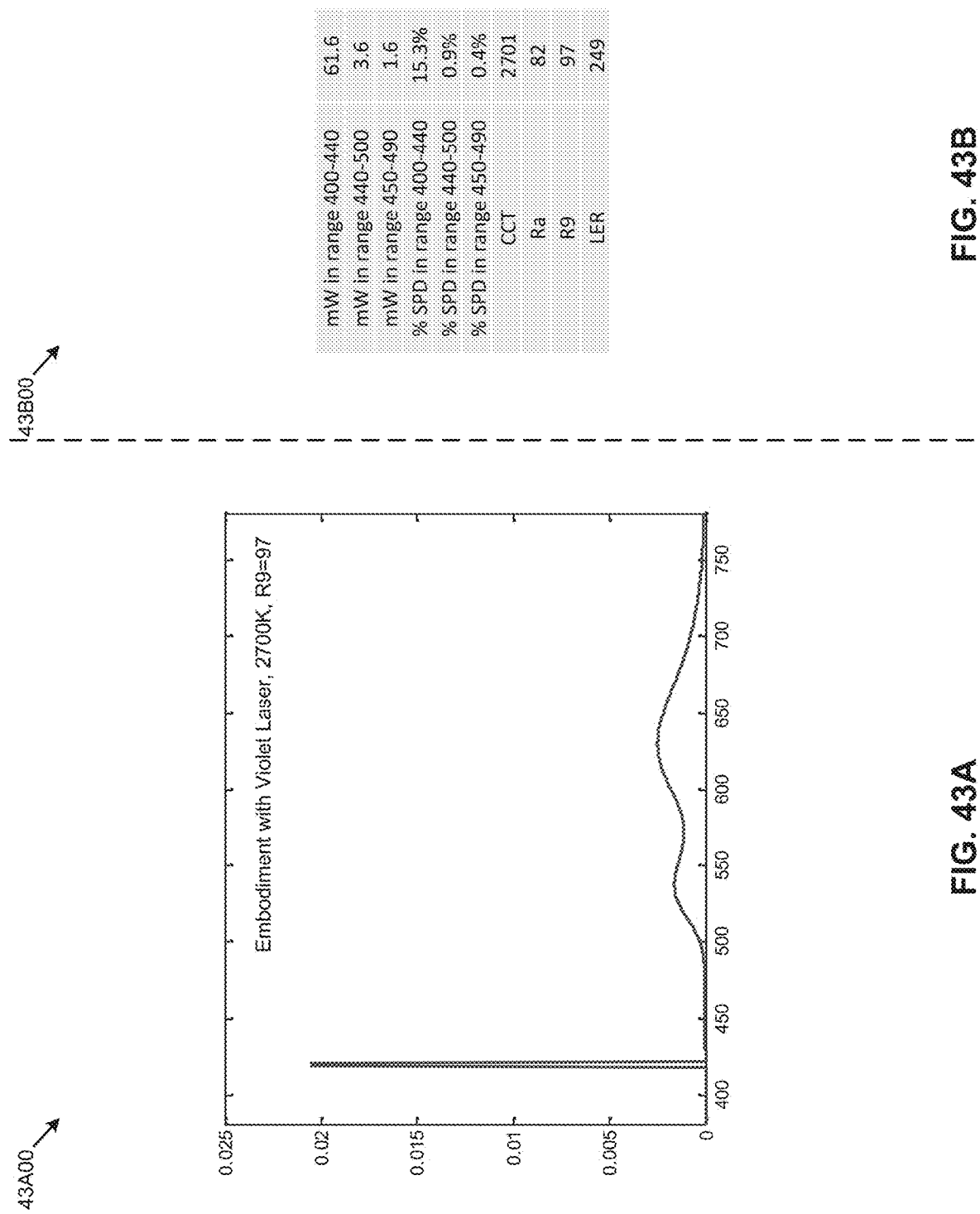

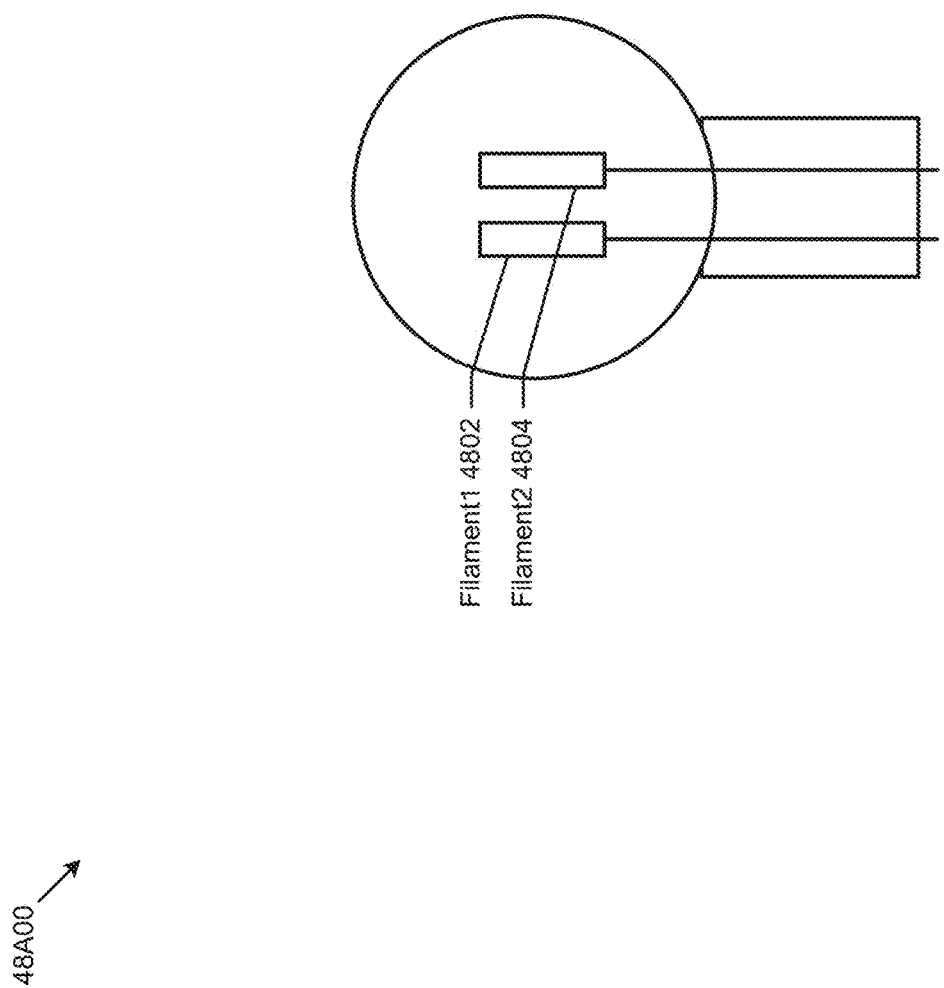

CIRCADIAN-FRIENDLY LED LIGHT SOURCES

RELATED APPLICATIONS

This application is a continuation of U.S. application Ser. No. 16/397,001, filed Apr. 29, 2019, which is a continuation of U.S. application Ser. No. 15/878,110, filed Jan. 23, 2018, which is a divisional of U.S. application Ser. No. 14/996,143 filed on Jan. 14, 2016, which is a continuation-in-part of U.S. application Ser. No. 14/316,685 filed on Jun. 26, 2014, entitled, "CIRCADIAN FRIENDLY LED LIGHT SOURCE", which is entitled to priority under 35 U.S.C. § 119(e) of U.S. Provisional Application No. 61/871,525 filed on Aug. 29, 2013; also Ser. No. 14/996,143 filed on Jan. 14, 2016 is a continuation-in-part of U.S. application Ser. No. 14/819,010 filed on Aug. 5, 2015, entitled, "FILTERS FOR CIRCADIAN LIGHTING", which is entitled to priority under 35 U.S.C. § 119(e) of U.S. Provisional Application No. 62/033,487 filed on Aug. 5, 2014, entitled, "FILTERS FOR CIRCADIAN LIGHTING", and Ser. No. 14/996,143 filed on Jan. 14, 2016 claims benefit under 35 U.S.C. § 119(e) to U.S. Provisional Application No. 62/103,472 filed on Jan. 14, 2015, entitled, "CIRCADIAN-FRIENDLY LED LIGHT SOURCES", each of which are incorporated by reference in their entireties.

FIELD

The disclosure relates to the field of illumination products and more particularly to apparatus and methods for providing circadian-friendly LED light sources.

BACKGROUND

Identification of non-visual photoreceptors in the human eye (so-called intrinsically photosensitive retinal ganglion cells, or "ipRGCs") linked to the circadian system has sparked considerable interest in the effects of various light spectra on health and amenity for human beings. High circadian stimulation may lead to positive effects such as resetting sleep patterns, boosting mood, increasing alertness and cognitive performance, and alleviating seasonal affective depression. However, mis-timed circadian stimulation can also be associated with disruption of the internal biological clock and melatonin suppression, and may be linked to illnesses such as cancer, heart disease, obesity and diabetes.

Circadian stimulation is associated with glucocorticoid elevation and melatonin suppression and is most sensitive to light in the blue wavelength regime. With the preponderance of light-emitting diode (LED) illumination products being based on blue-primary phosphor-converted white-emitting LEDs, the situation has developed that most LED-based illumination sources have higher levels of circadian stimulation than the traditional sources they are intended to replace.

Legacy techniques have been studied and in some cases techniques for dealing with circadian stimulation in lighting products have been published (e.g., see WO 2014165692 to Moore-Ede et al.), however such legacy techniques are deficient, at least in regards to uses of the herein-disclosed techniques to address lighting system design with respect to diurnal or circadian cycles In addition, illumination products are rarely tunable (other than mere dimming), and legacy illumination products fail to address the impact on humans with respect to diurnal or circadian cycles. Still worse, legacy illumination products that are ostensibly tunable fail to produce good color rendering throughout the tunable range.

What is needed is a technique or techniques for constructing illumination products in which light emission (e.g., LED light emission) can be controlled to provide varying levels of circadian stimulation while providing desirable light quality aspects such as correlated color temperature (CCT) and color rendering index (CRI). Also needed is an illumination system in which a first ratio and a second ratio of light emission are such that changing from the first ratio to the second ratio varies relative circadian stimulation while maintaining a CRI above 80 and maintaining the CCT within a prescribed range.

The aforementioned legacy technologies do not have the capabilities to implement a circadian-friendly LED light sources in an efficient manner. Therefore, there is a need for improved approaches.

SUMMARY

The following presents a simplified summary of the invention in order to provide a basic understanding of some aspects of the invention. This summary is not an extensive overview of the invention. It is not intended to identify key/critical elements of the invention or to delineate the scope of the invention. Its purpose is to present some concepts of the invention in a simplified form as a prelude to the more detailed description that is presented later.

Regarding human circadian system stimulation, positive benefits can be realized and the deleterious ones avoided by stimulating a circadian light cycle in a way similar to that which occurs in nature (sunlight action over the course of the day), i.e., bright illumination levels associated with high blue content in the morning and midday, and lower light levels and greatly reduced blue content in the evenings.

The embodiments disclosed herein describe how to make and use various combinations of different LED emission spectra, and how to make white light sources that can be tuned to cycle through ranges from high-circadian-stimulating light to less-circadian-stimulating light while maintaining reasonable color rendering (CRI>80 and R9>0) and white color point.

The various embodiments (e.g., lamps and displays) are tuned to emit light in cycles (e.g., diurnal cycles) that range from high-circadian-stimulating light to less-circadian-stimulating light.

In a first aspect, light sources are provided comprising at least one first LED emission source characterized by a first emission, and at least one second LED emission source characterized by a second emission; wherein the first emission and the second emission are configured to provide a first combined emission and a second combined emission, the first combined emission is characterized by a first SPD and fractions Fv1 and Fc1; the second combined emission is characterized by a second SPD and fractions Fv2 and Fc2; Fv1 represents the fraction of power of the first SPD in the wavelength range from 400 nm to 440 nm; Fc1 represents the fraction of power of the first SPD in the wavelength range from 440 nm to 500 nm; Fv2 represents the fraction of power of the second SPD in the wavelength range from 400 nm to 440 nm; Fc2 represents the fraction of power of the second SPD in the wavelength range from 440 nm to 500 nm; the first SPD and the second SPD have a color rendering index above 80; Fv1 is at least 0.05; Fc2 is at least 0.1; and Fc1 is less than Fc2 by at least 0.02.

In a second aspect, light sources are provided comprising an LED device configured to emit a primary emission; one or more wavelength conversion materials optically coupled to the primary emission; wherein a portion of the primary emission is absorbed by the wavelength conversion materials to produce a secondary emission; wherein a combination of the primary emission and the secondary emission produces white light characterized by an SPD having a CCT and a color rendering index; wherein at least 5% of the SPD power is in a wavelength range from 400 nm to 435 nm; wherein a circadian stimulation of the SPD is less than 80% of a circadian stimulation of a reference illuminant having the same color temperature; and wherein the white light is characterized by a color rendering index above 80.

In a third aspect, lighting systems are provided comprising an LED device configured to emit a primary emission characterized by a primary SPD; at least one phosphor optically coupled to the primary emission, wherein the at least one phosphor is characterized by saturable absorption within a blue-cyan wavelength region; wherein the LED device is configured to be controlled by a power signal configured to dim the primary emission; wherein at a first power level the system emits a first SPD characterized by a first fraction fc1 of spectral power in a wavelength range from 440 nm to 500 nm and a first CCT; wherein at a second power level the system emits a second SPD characterized by a second fraction fc2 of spectral power in a wavelength range from 440 nm to 500 nm and a second CCT; and wherein the second power level is less than the first power level and the second fraction fc2 is less than 80% of the first fraction fc1.

In a fourth aspect, light emissions having specific Circadian-friendly emission peaks are made using blends of selected wavelength-converting materials.

In a fifth aspect, a method is provided of using a lighting system to emit emitted light having a relatively high illuminance but a relatively low circadian stimulation, said light system having at least one solid-state lighting emitter, and at least a first and second additional light emitters for cooperating with said lighting emitter such that said emitted light is white light. The method comprises applying power to said lighting system thereby causing at least said light emitter and said first and second additional light emitters to emit said emitted light having a certain correlated color temperature (CCT), the lighting system being configured to produce an illuminance of about 50 lux to about 5000 lux, and a circadian stimulation no greater than about 50% of a reference circadian stimulation of a reference illuminant configured to produce an illuminance essentially the same as said predetermined illuminance and a CCT the same as said certain CCT.

In various embodiments of the above aspects or any other aspect of the invention delineated herein, circadian stimulation is no greater than about 20% of said reference circadian stimulation. In one embodiment, the light emitter comprises at least one light-emitting diode or one laser diode emitting having a peak wavelength in a range 400-430 nm, the first additional light emitter has an emission spectrum having a peak between 500 nm and 550 nm, and the second additional light emitter has an emission spectrum having a peak between 600 nm and 670 nm. In another embodiment, the emitted light is characterized by a spectral power distribution (SPD), wherein the SPD has a local minimum in a spectral region between 440 nm and 480 nm and a power in the SPD between 440 nm and 480 nm is less than 2% of a power of the SPD between 380 nm and 780 nm. In yet another embodiment, the emitted light has a CRI Ra higher than 80 and a CRI R9 higher than 0. In still another embodiment, the emitted light has a CRI R9 higher than 80. In another embodiment, the certain CCT is at least 2700K and a distance from the Planckian locus Duv which is smaller than +/−0.006. In yet another embodiment, the illuminance is a retinal illuminance. In still another embodiment, the first and second additional light emitters are phosphor light-converting materials. In another embodiment, the reference illuminant is a CIE CRI reference illuminant. In another embodiment, the method further comprises selecting a circadian action spectrum, and wherein said circadian stimulation is calculated as an integral of said SPD weighed by said circadian action spectrum. In yet another embodiment, the lighting system comprises no light emitting species having a peak emission at a wavelength in a range 440-490 nm.

In various embodiments of the above aspects or any other aspect of the invention delineated herein, the area under the SPD within a range of 440 nm and 480 nm is less than 0.5% of the area under the SPD within a range of 380 nm to 780 nm. In one embodiment, the SPD is characterized by a correlated color temperature (CCT) which is greater than or equal to 2700K. In another embodiment, an absolute distance from the Planckian locus (Duv) is less than 0.006. In yet another embodiment, the system comprises a general CRI index (Ra) is greater than or equal to 80. In still another embodiment, the system comprises a special CRI index #9 (R9) is greater than or equal to 0. In yet another embodiment, the first phosphor and the second phosphor are disposed in layers or in a pattern of small patches around the LED pump. In another embodiment, the system further comprises a filter substantially absorbing or reflecting light having a wavelength within a range of 430 nm to 490 nm. In one embodiment, the filter does not significantly affect a chromaticity of the emitted light.

BRIEF DESCRIPTION OF THE DRAWINGS

Those skilled in the art will understand that the drawings, described herein, are for illustration purposes only. The drawings are not intended to limit the scope of the present disclosure.

FIG. 4C shows emission of a first violet-pumped two-phosphor LED (right) and a second violet-pumped blue-phosphor LED (left), according to some embodiments.

FIG. 4E shows emission of a (right) first violet-pumped two-phosphor LED and a (left) second blue-emitting LED, according to some embodiments.

FIG. 4N shows embodiments for which the phosphor system is tuned to better work with a chosen primary peak emission wavelength, according to some embodiments.

FIGS. 5C1-5C4 show characteristics of two sets of LED-based sources that are controlled independently, according to some embodiments.

FIG. 10B depicts one embodiment of the present disclosure in the form of lamp applications, according to some embodiments.

FIG. 10D depicts one embodiment of the present disclosure in the form of lamp applications, according to some embodiments.

FIG. 10F depicts one embodiment of the present disclosure in the form of lamp applications, according to some embodiments.

FIG. 10G depicts one embodiment of the present disclosure in the form of lamp applications, according to some embodiments.

FIG. 10H depicts one embodiment of the present disclosure in the form of lamp applications, according to some embodiments.

FIG. 10I depicts one embodiment of the present disclosure in the form of lamp applications, according to some embodiments.

FIG. 11A shows an initial SPD of a white LED source, and a filtered SPD after blue light is blocked by a filter, according to some embodiments.

FIG. 11B shows an initial SPD of a white LED source and the converted SPD after blue light is absorbed by a "circadian phosphor" and converted to yellow light, according to some embodiments.

FIG. 15A depicts one embodiment of the present disclosure as can be applied toward lighting applications.

FIG. 15F depicts one embodiment of the present disclosure as can be applied toward lighting applications.

FIG. 16A shows an example using dielectric stacks and compares filtered SPDs under varying conditions, according to some embodiments.

FIG. 16B shows an example using dielectric stacks and compares filtered SPDs under varying conditions, according to some embodiments.

FIG. 16C shows an example using dielectric stacks and compares filtered SPDs under varying conditions, according to some embodiments.

FIG. 16D shows an example using dielectric stacks and compares filtered SPDs under varying conditions, according to some embodiments.

FIG. 17A shows an example using dielectric stacks and compares filtered SPDs under varying conditions, according to some embodiments.

FIG. 17B shows example using dielectric stacks and compares filtered SPDs under varying conditions, according to some embodiments.

FIG. 18E shows an example using dielectric stacks and compares filtered SPDs under varying conditions, according to some embodiments.

FIG. 19A shows an example using dielectric stacks and compares filtered SPDs under varying conditions, according to some embodiments.

FIG. 19B shows an example using dielectric stacks and compares filtered SPDs under varying conditions, according to some embodiments.

FIG. 19C shows examples using dielectric stacks and compares filtered SPDs under varying conditions, according to some embodiments.

FIG. 23 shows examples using dielectric stacks and compares filtered SPDs under varying conditions, according to some embodiments.

FIG. 24A shows an example using dielectric stacks and compares filtered SPDs under varying conditions, according to some embodiments.

FIG. 24B shows an example using dielectric stacks and compares filtered SPDs under varying conditions, according to some embodiments.

FIG. 25C shows an example using dielectric stacks and compares filtered SPDs under varying conditions, according to some embodiments.

FIG. 25D shows an example using dielectric stacks and compares filtered SPDs under varying conditions, according to some embodiments.

FIG. 25E shows an example using dielectric stacks and compares filtered SPDs under varying conditions, according to some embodiments.

FIG. 26B shows an example using dielectric stacks and compares filtered SPDs under varying conditions, according to some embodiments.

FIG. 34A compares experimental results to conventional LED spectra, according to some embodiments.

FIG. 34B compares experimental results to conventional LED spectra, according to some embodiments.

FIG. 36A compares experimental results to conventional LED spectra, according to some embodiments.

FIG. 36B compares experimental results to conventional LED spectra, according to some embodiments.

Figure 38B:
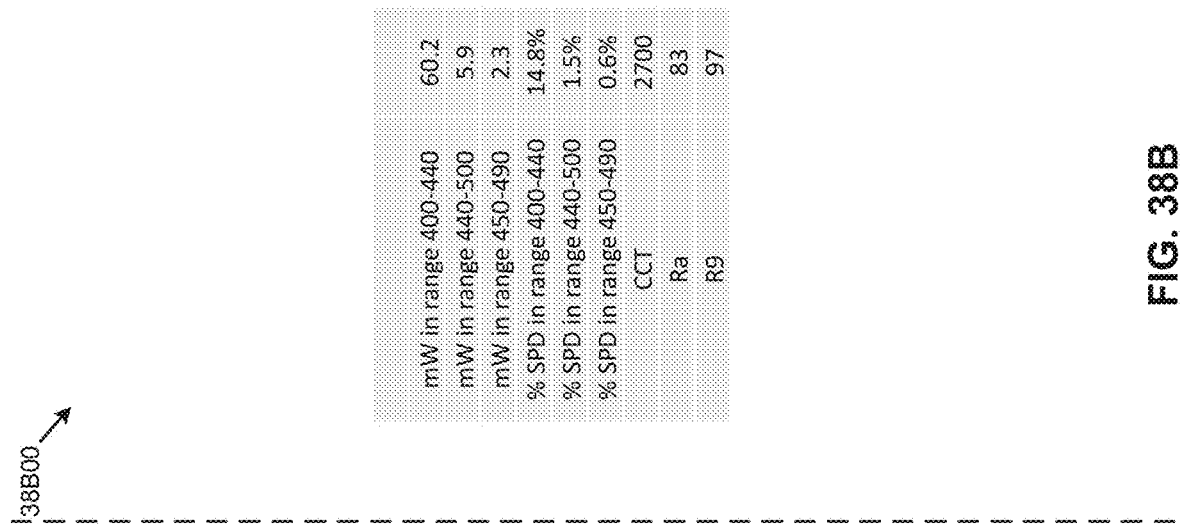
FIG. 38A compares experimental results to conventional LED spectra, according to some embodiments.
Figure 38A:
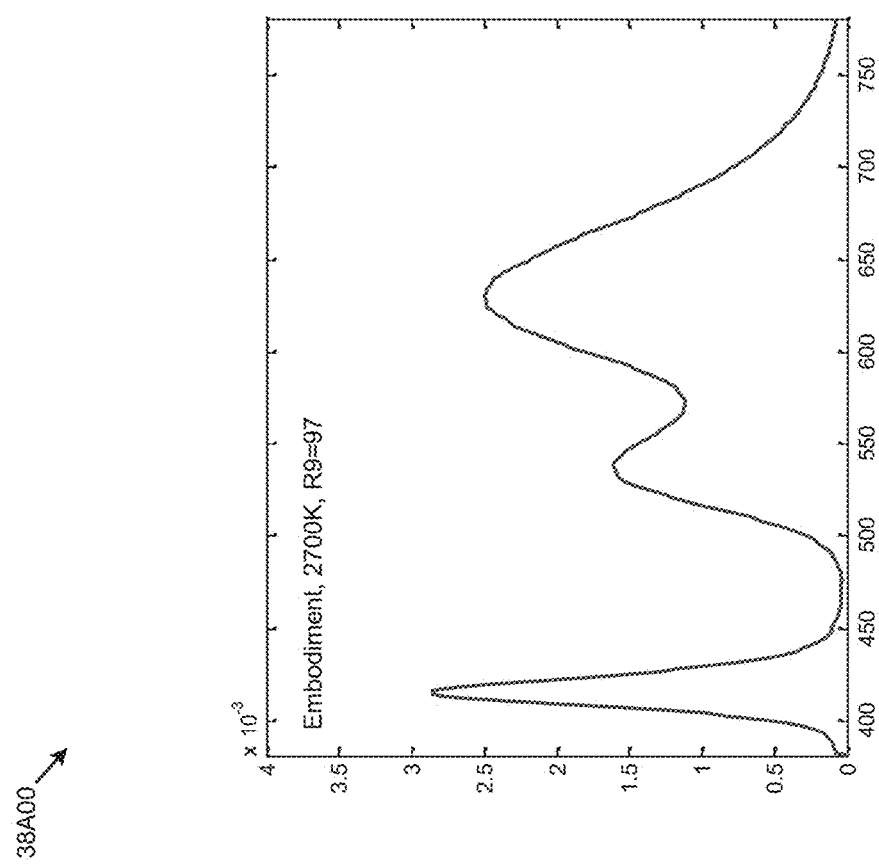

FIG. 38B compares experimental results to conventional LED spectra, according to some embodiments.

Figure 39B:
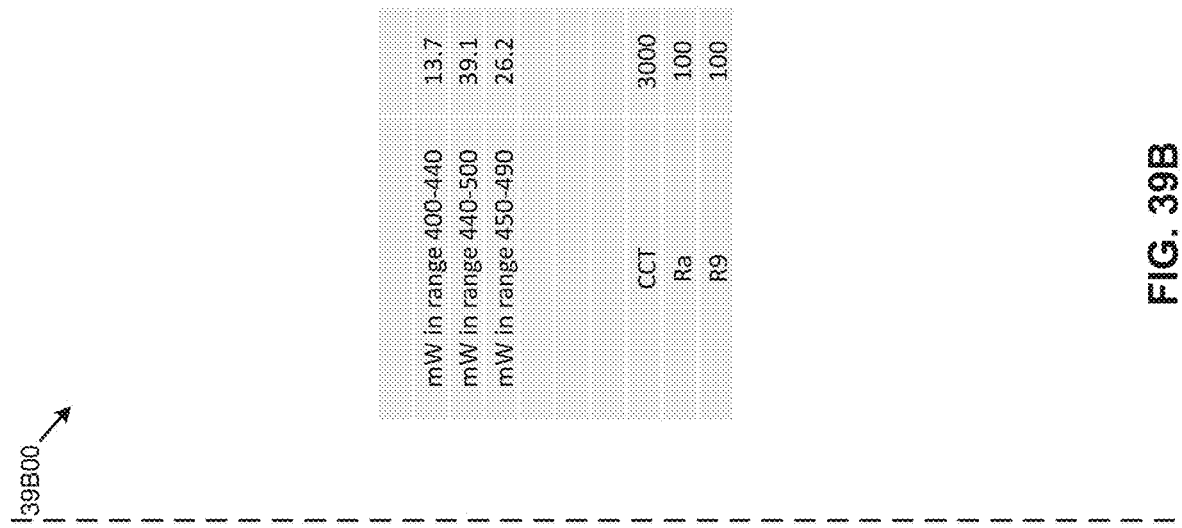
Figure 39A:
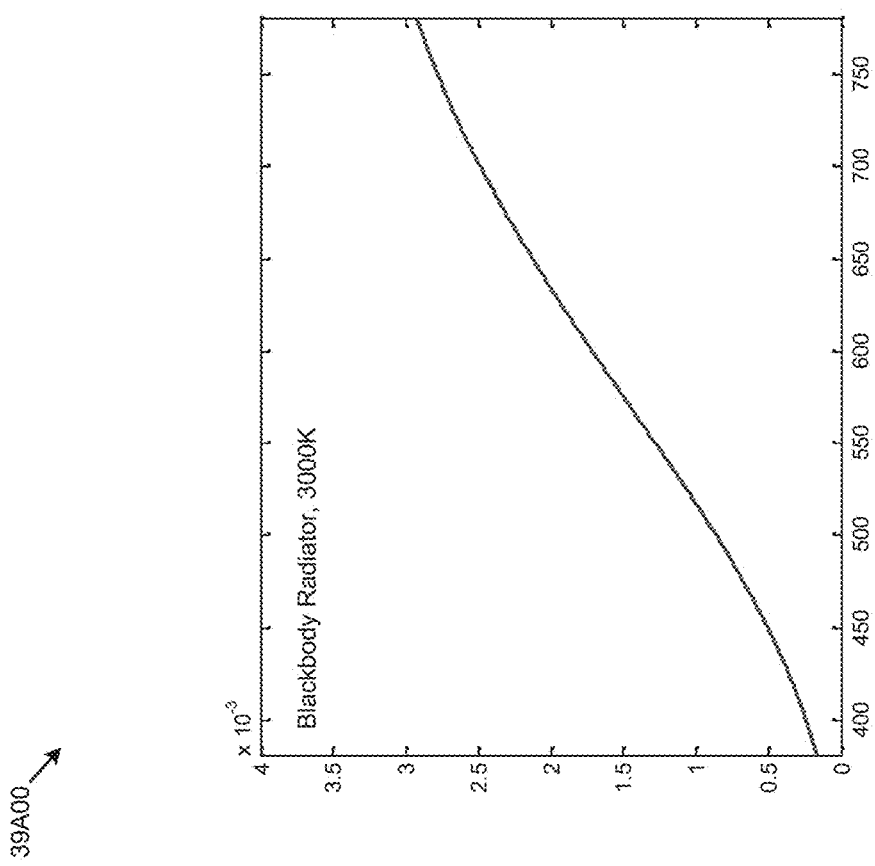

FIG. 39A compares experimental results to conventional LED spectra, according to some embodiments.

FIG. 39B compares experimental results to conventional LED spectra, according to some embodiments.

Figures 40A, 40B:
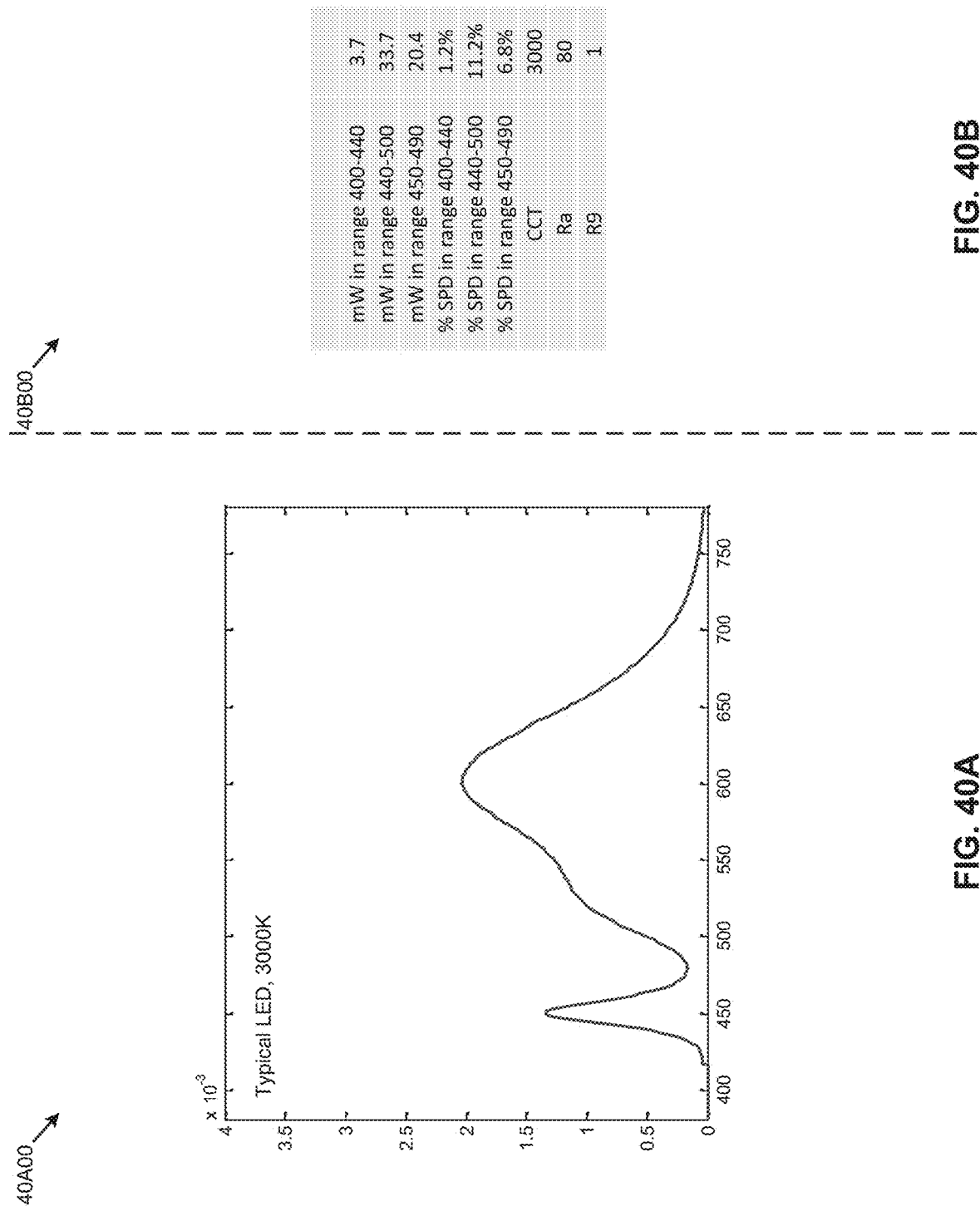

FIG. 40A compares experimental results to conventional LED spectra, according to some embodiments.

FIG. 40B compares experimental results to conventional LED spectra, according to some embodiments.

FIG. 41A compares experimental results to conventional LED spectra, according to some embodiments.

FIG. 41B compares experimental results to conventional LED spectra, according to some embodiments.

Figure 42B:
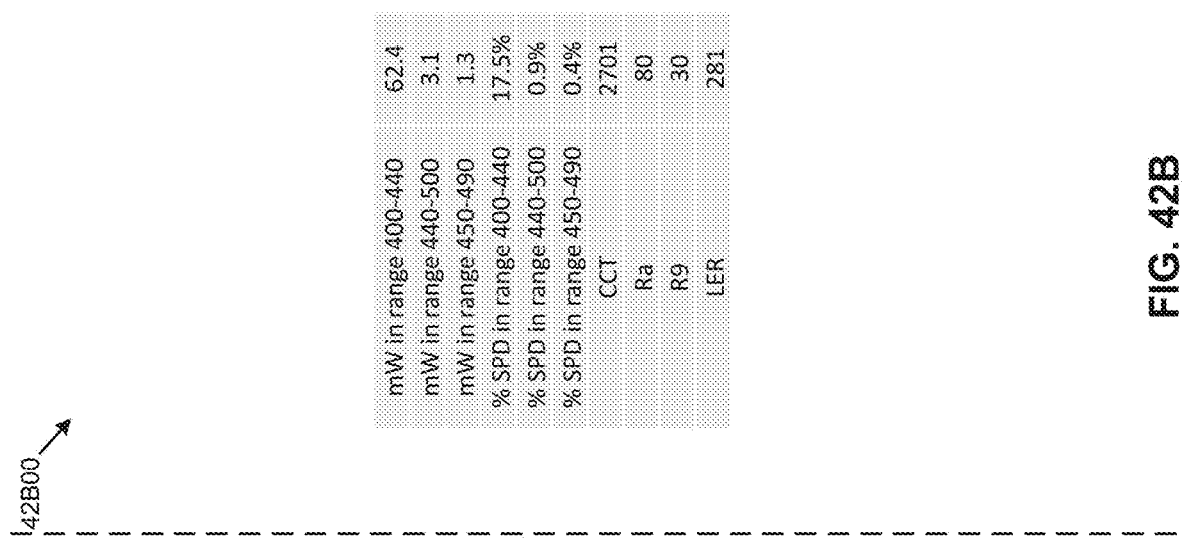
Figure 42A:
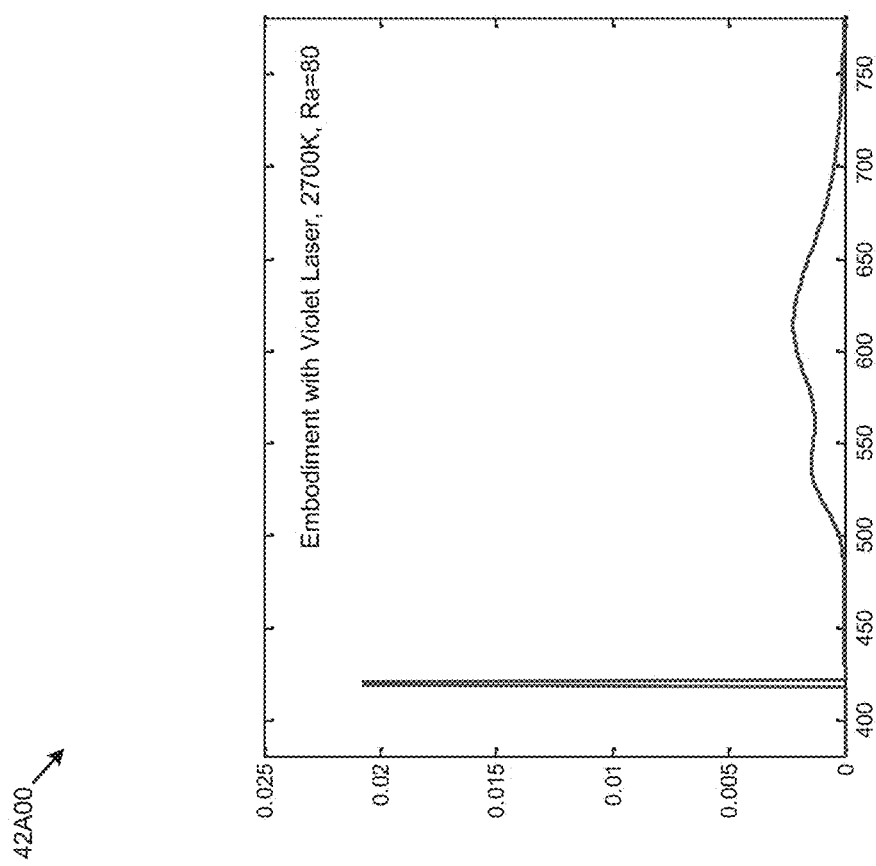

FIG. 42A compares experimental results to conventional LED spectra, according to some embodiments.

FIG. 42B compares experimental results to conventional LED spectra, according to some embodiments.

FIG. 43A compares experimental results to conventional LED spectra, according to some embodiments.

FIG. 43B compares experimental results to conventional LED spectra, according to some embodiments.

Figures 44A, 44B:
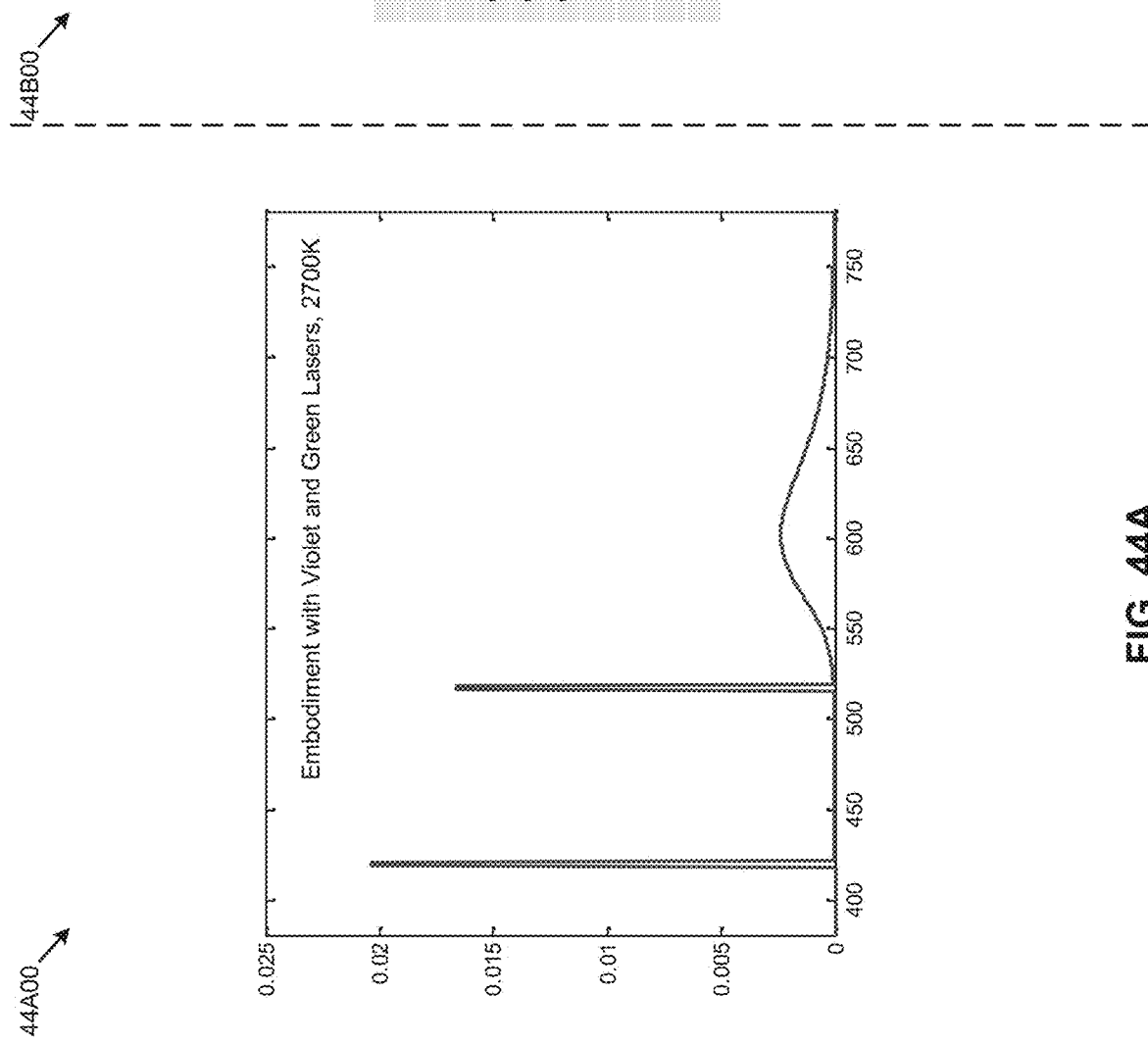

FIG. 44A compares experimental results to conventional LED spectra, according to some embodiments.

FIG. 44B compares experimental results to conventional LED spectra, according to some embodiments.

Figures 45A, 45B:
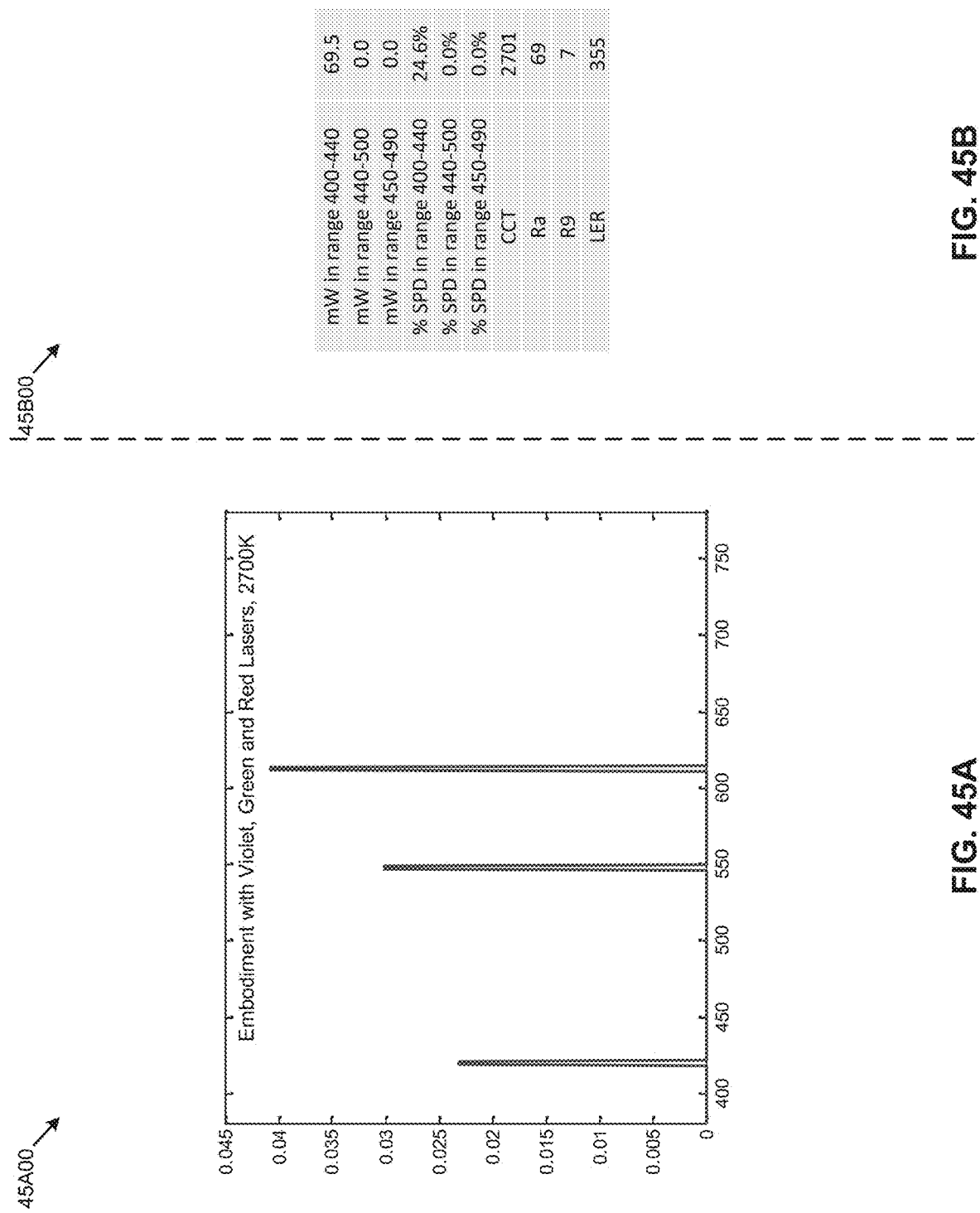

FIG. 45A compares experimental results to conventional LED spectra, according to some embodiments.

FIG. 45B compares experimental results to conventional LED spectra, according to some embodiments.

Figure 46:
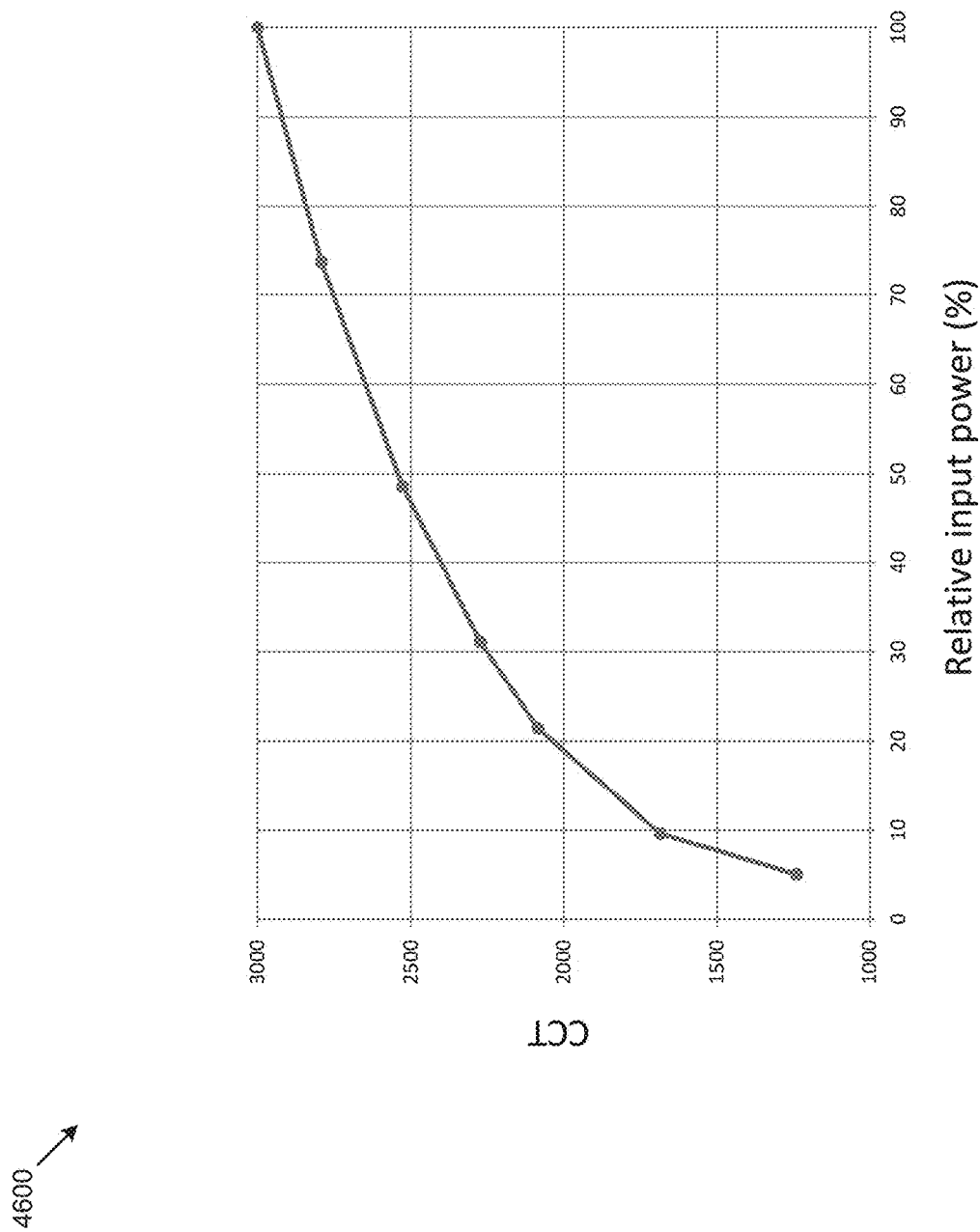

FIG. 46 depicts a CCT curve as it varies over input power, according to some embodiments.

Figure 47:
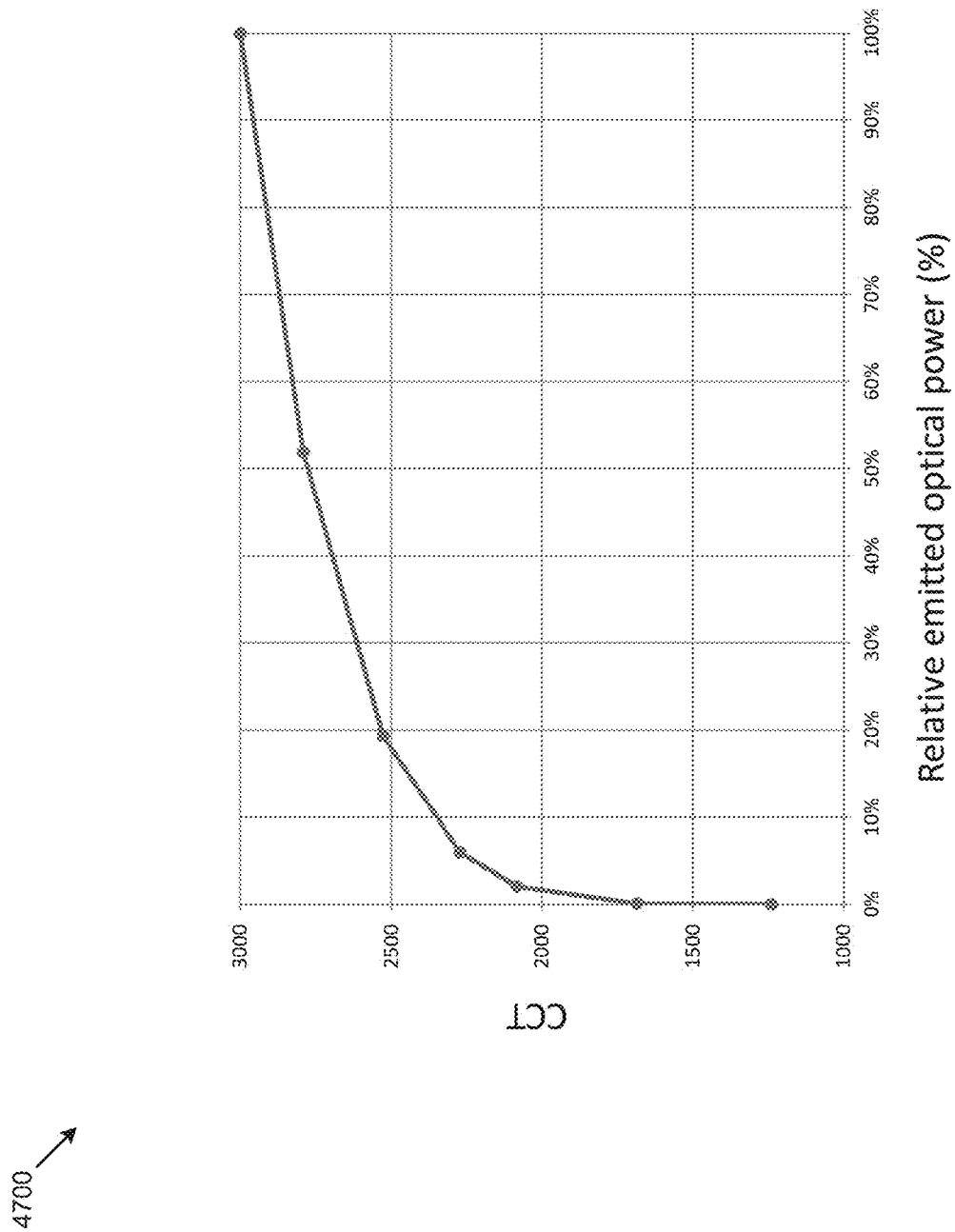

FIG. 47 depicts a CCT curve as it varies over input power, according to some embodiments.

FIG. 48A depicts various 3-way bulbs in an A-lamp form factor, according to some embodiments.

Figure 48B:
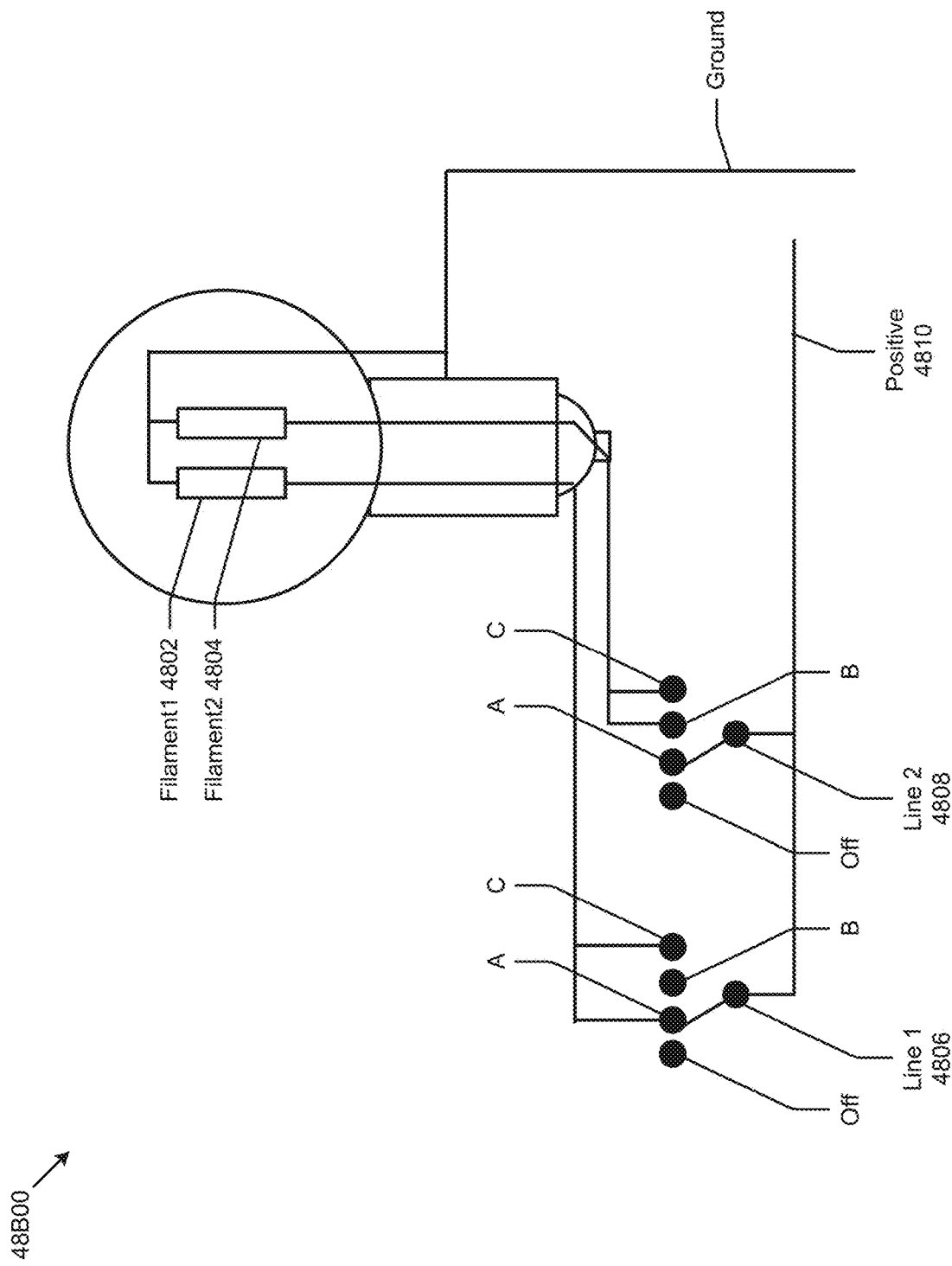

FIG. 48B depicts various 3-way bulbs in an A-lamp form factor, according to some embodiments.

Figure 48C:
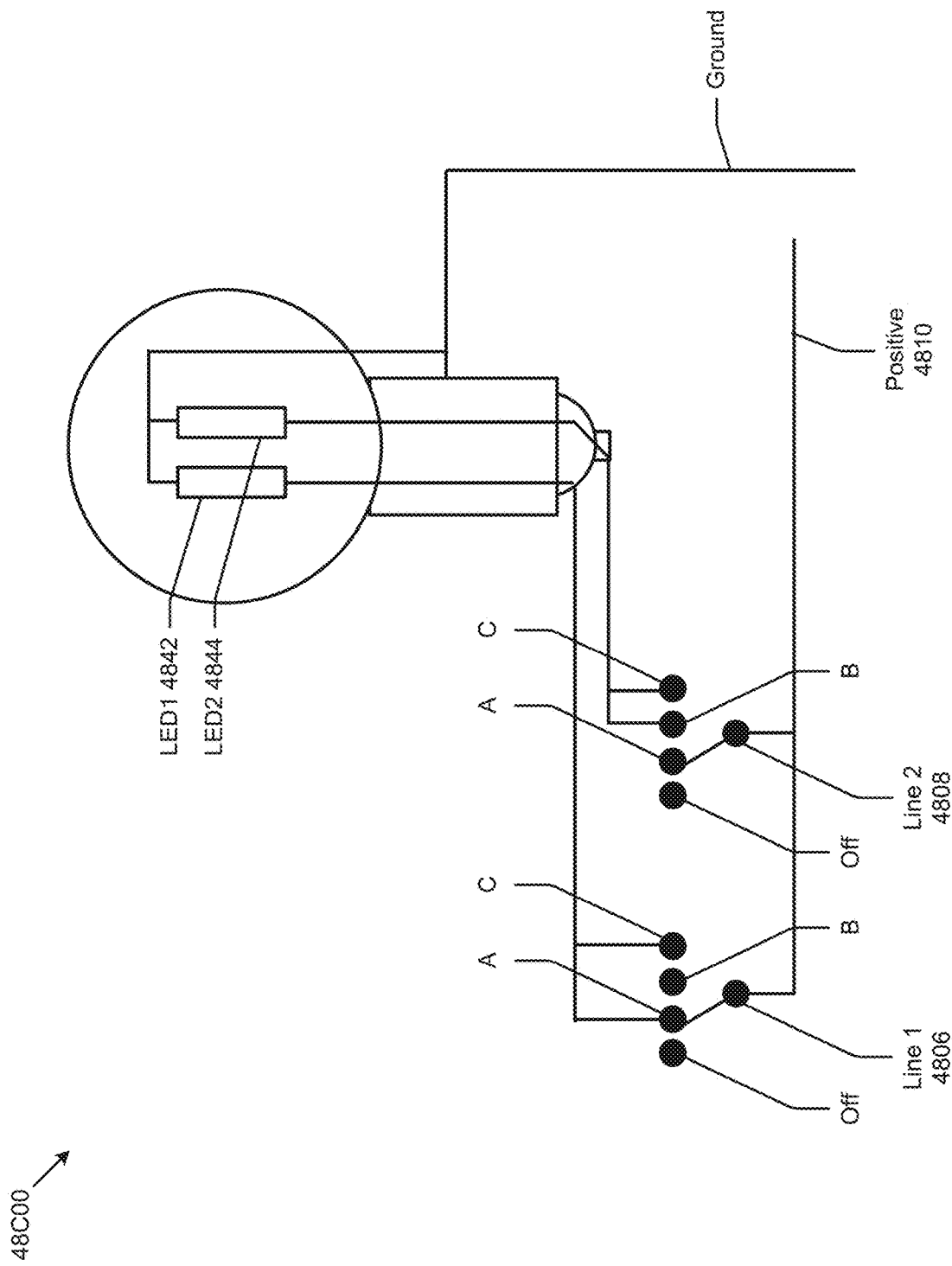

FIG. 48C depicts various 3-way bulbs in an A-lamp form factor, according to some embodiments.

Figure 48D:
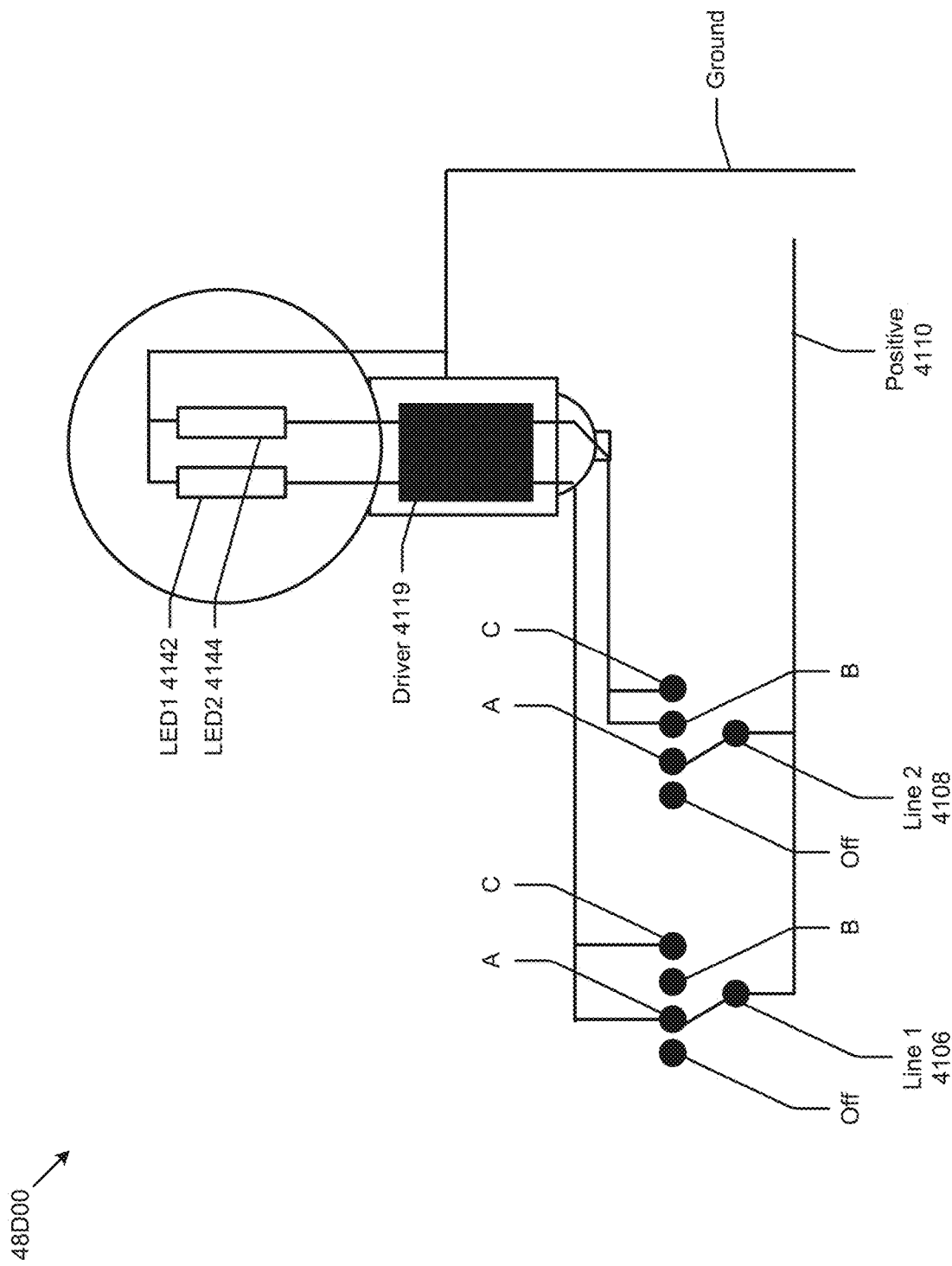

FIG. 48D depicts various 3-way bulbs in an A-lamp form factor, according to some embodiments.

Figure 48E:
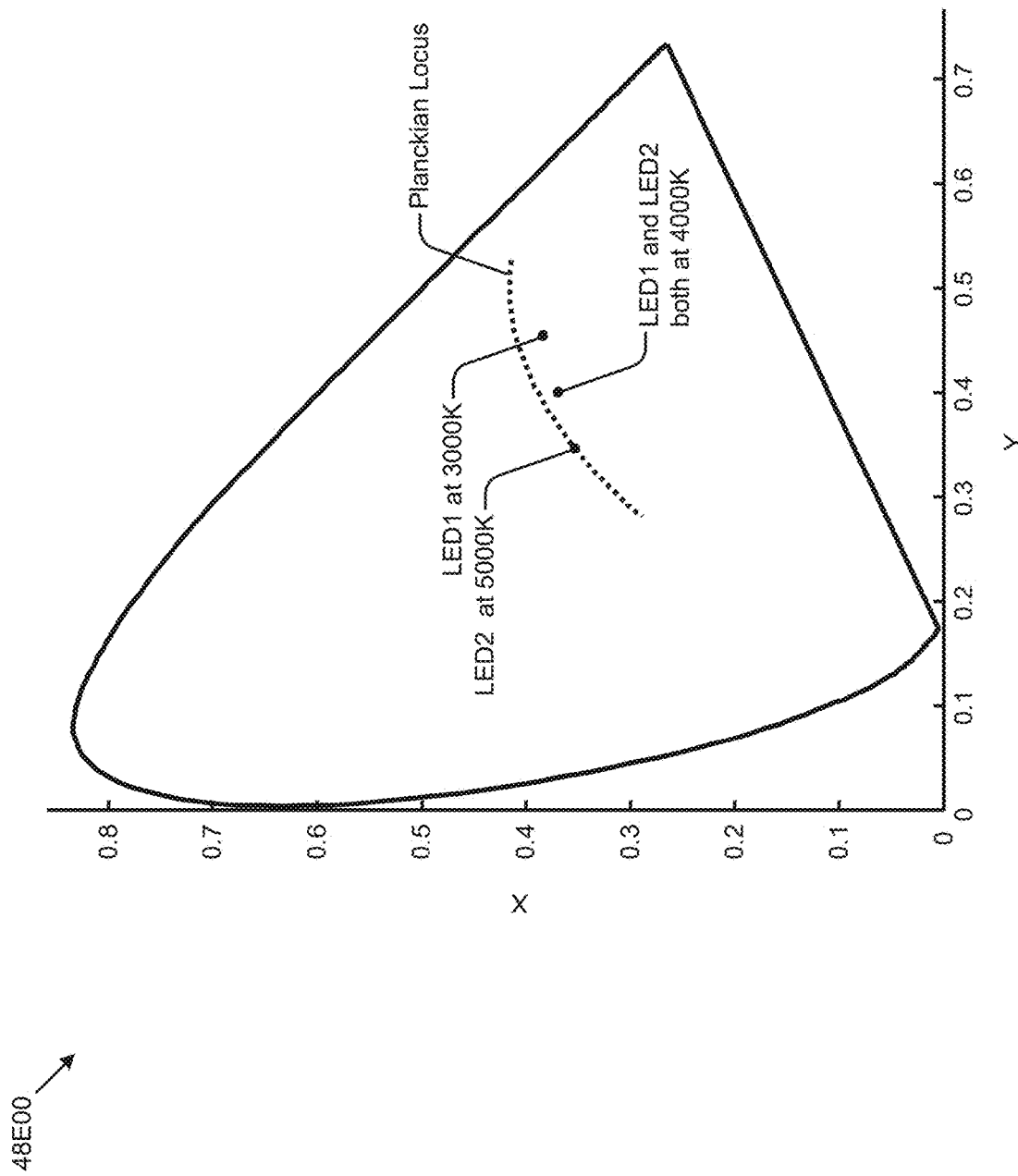

FIG. 48E depicts various 3-way bulbs in an A-lamp form factor, according to some embodiments.

Figure 49A:
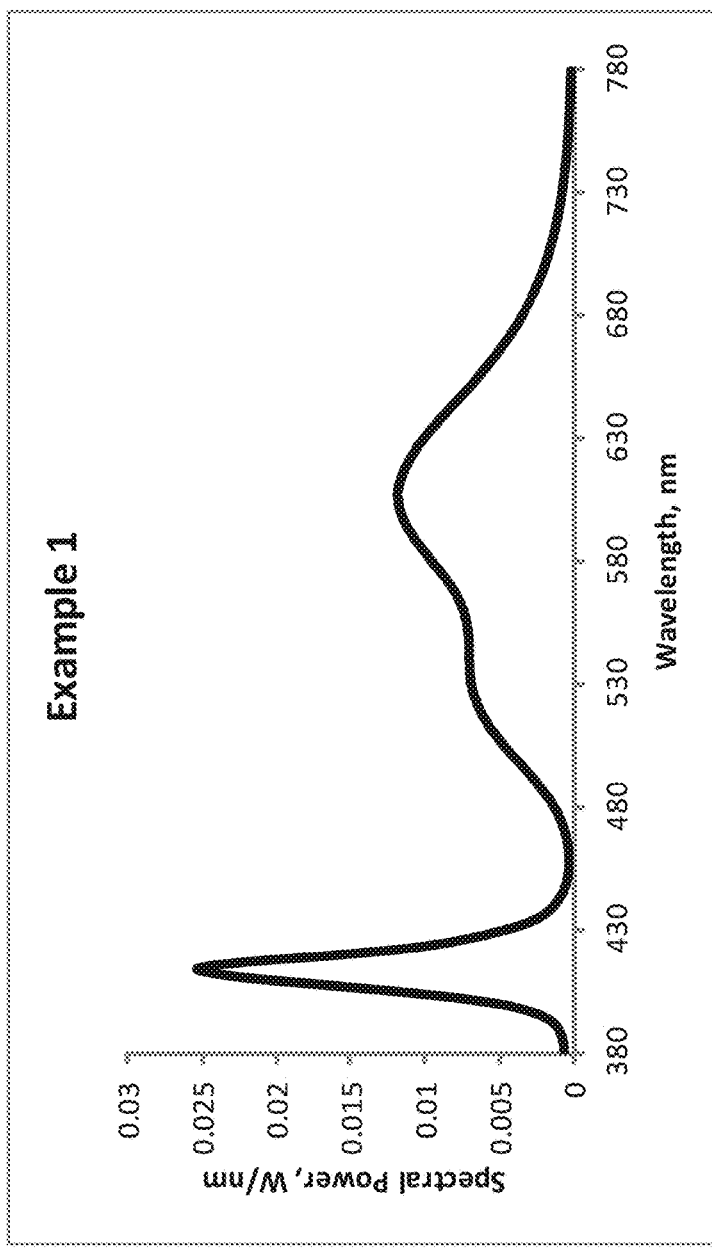

FIG. 49A depicts emission peaks using blends of selected wavelength-converting materials, according to some embodiments.

Figure 49B:
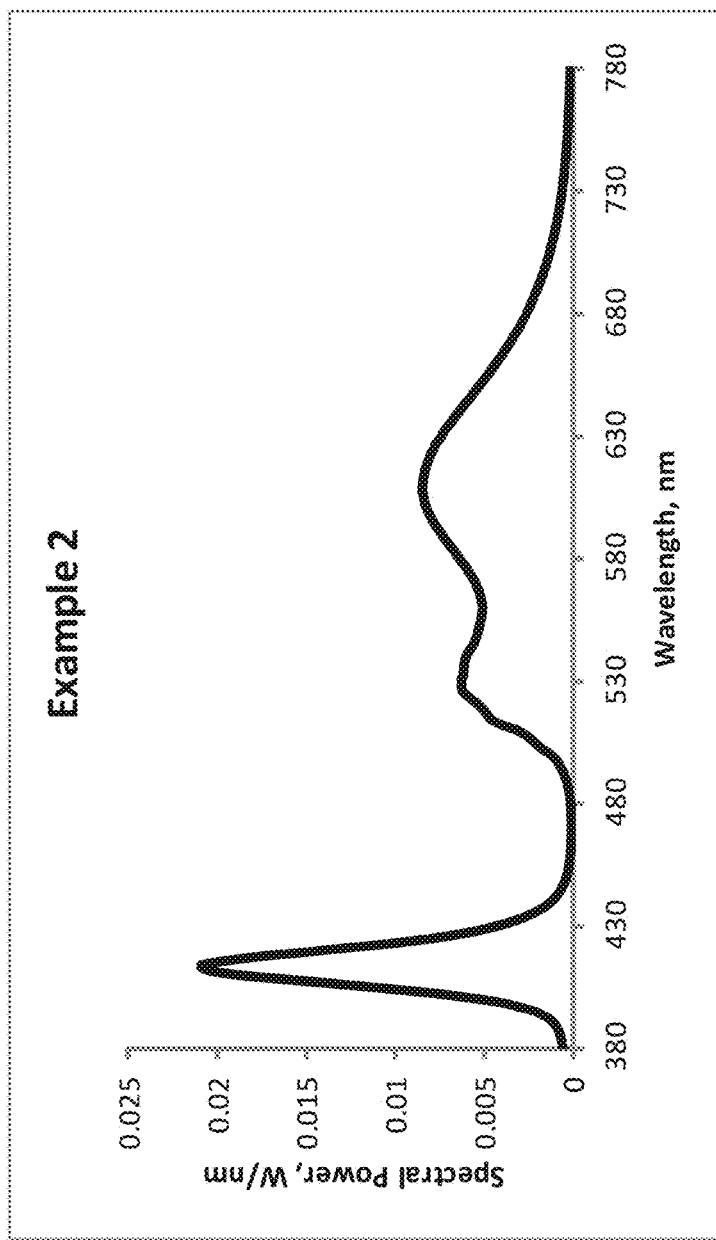

FIG. 49B depicts emission peaks using blends of selected wavelength-converting materials, according to some embodiments.

Figure 49C:
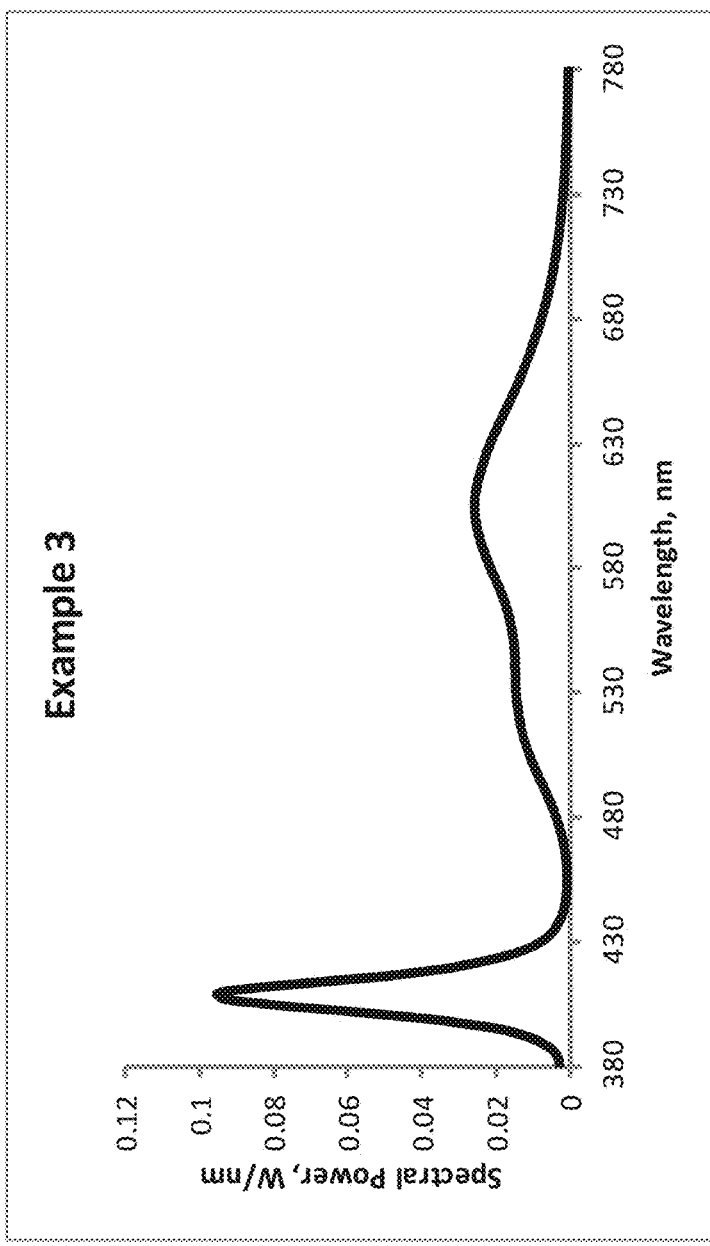

FIG. 49C depicts emission peaks using blends of selected wavelength-converting materials, according to some embodiments.

Figure 50A:
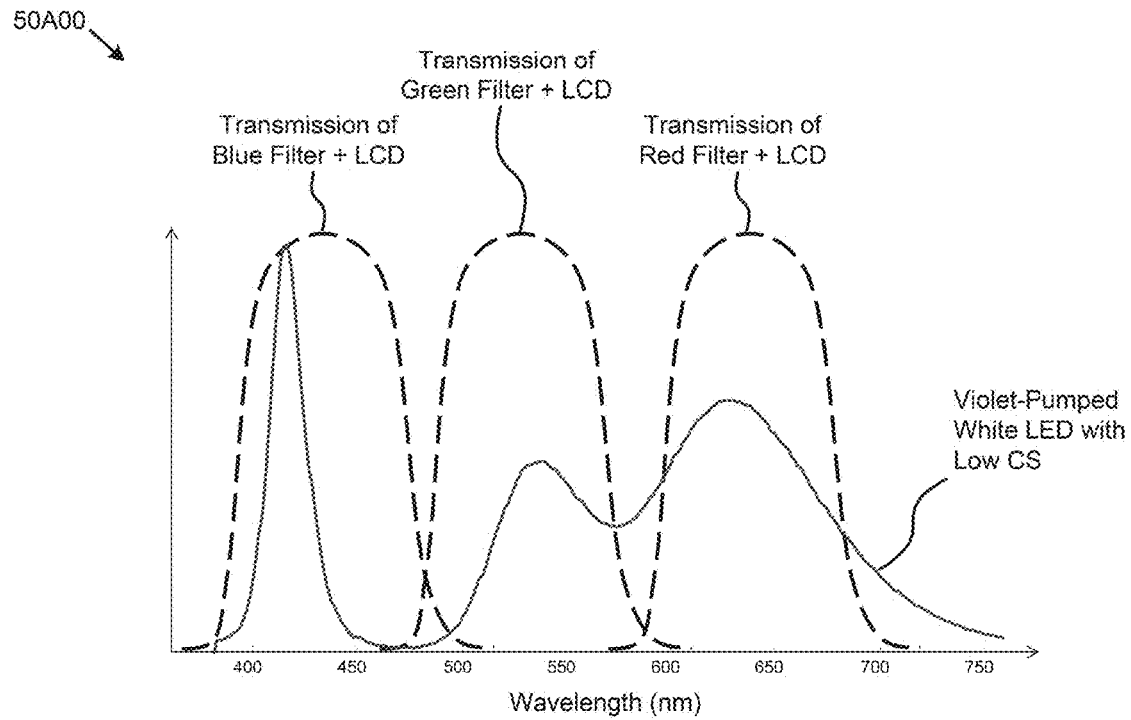

FIG. 50A illustrates characteristics of displays and components thereto, in accordance with some embodiments.

Figure 50B:
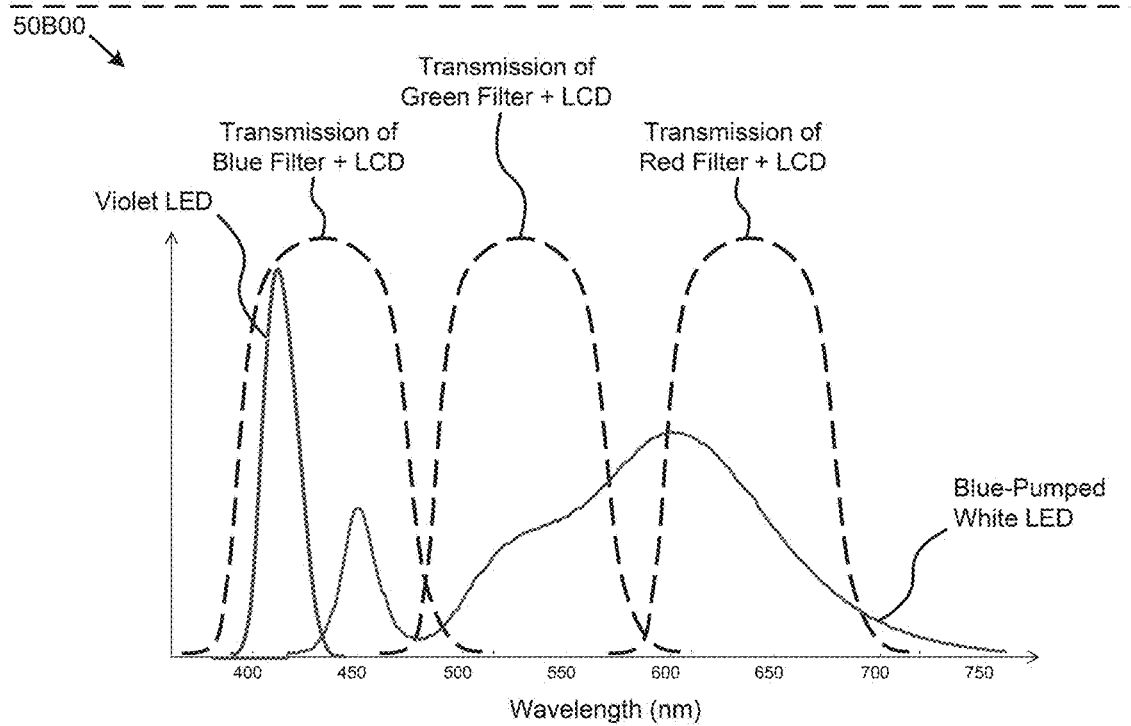

FIG. 50B illustrates characteristics of displays and components thereto, in accordance with some embodiments.

Figure 50C:
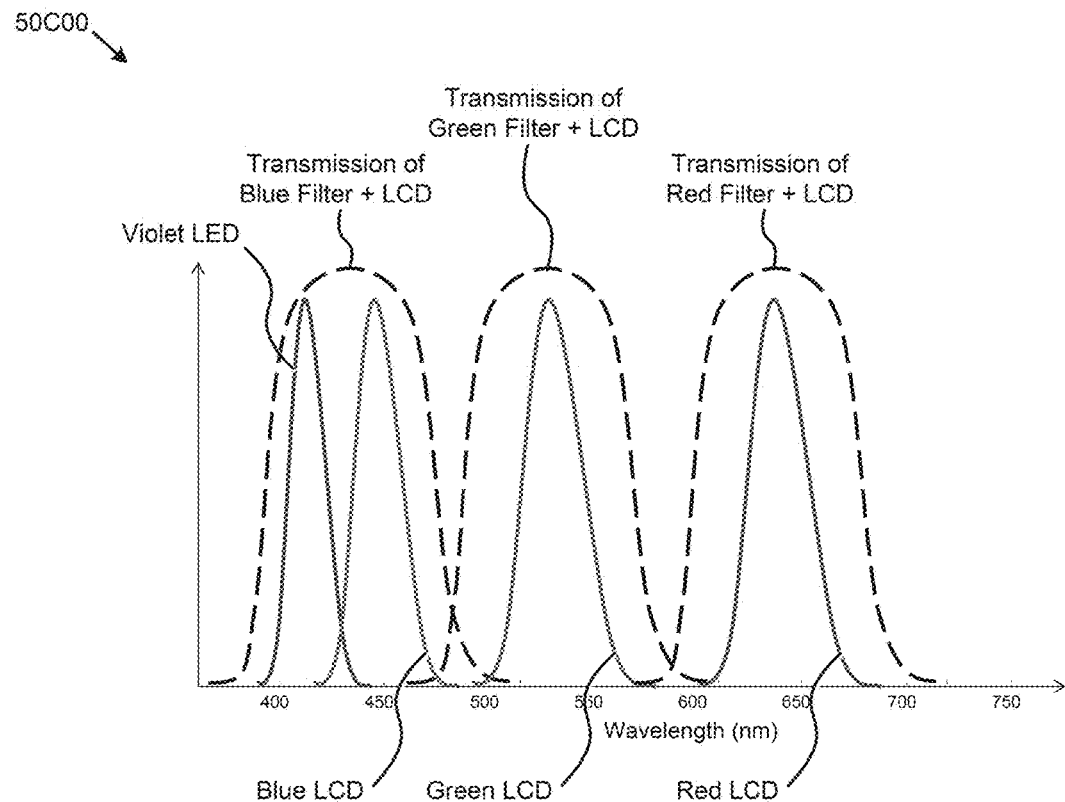

FIG. 50C illustrates characteristics of displays and components thereto, in accordance with some embodiments.

Figure 50D:
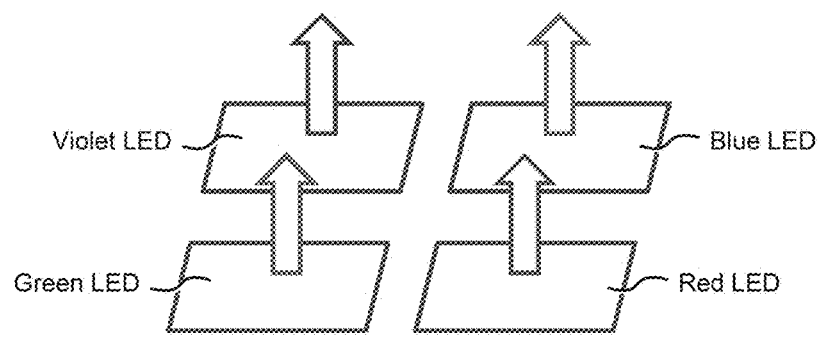

FIG. 50D illustrates characteristics of displays and components thereto, in accordance with some embodiments.

Figures 51A, 51B:
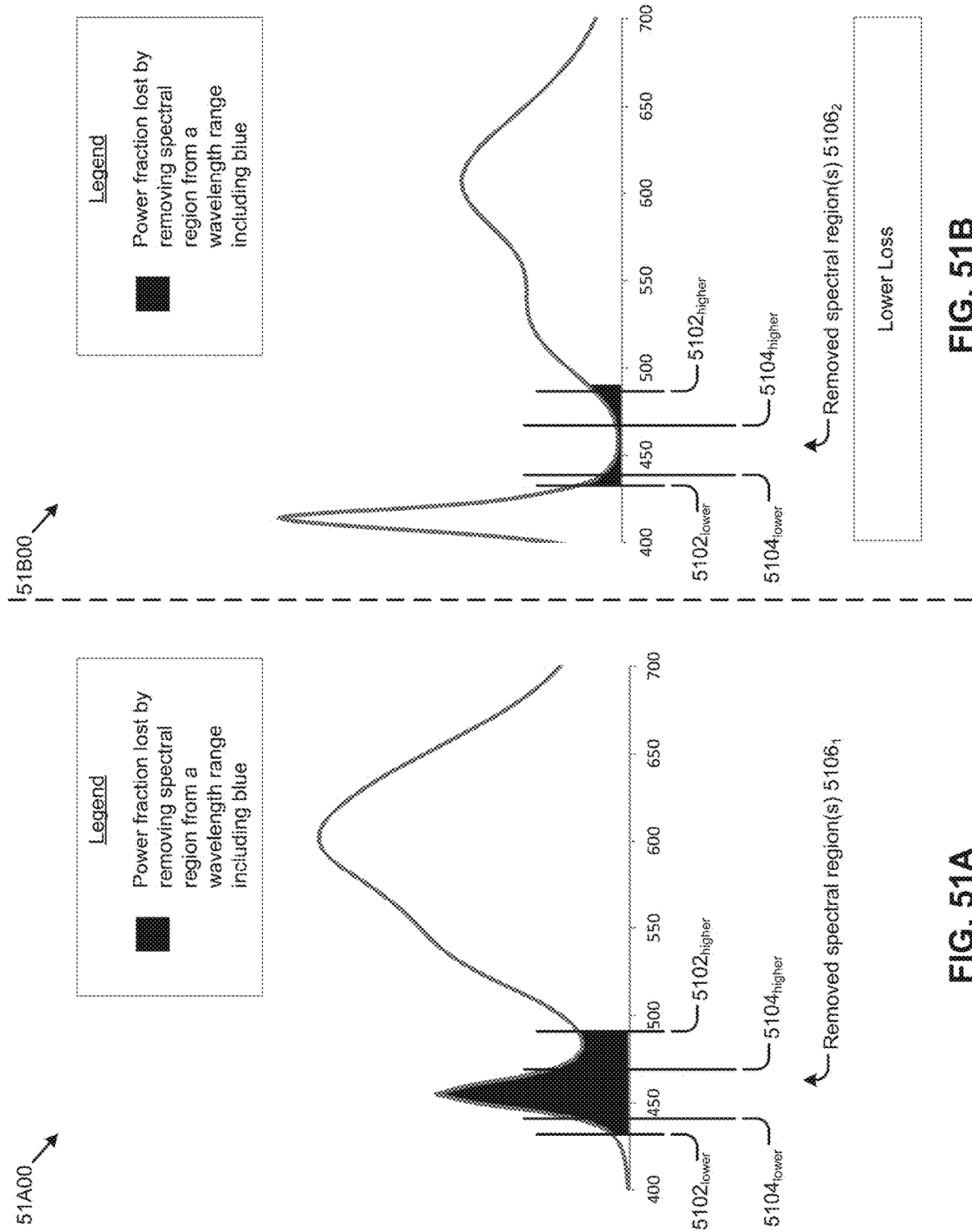

FIG. 51A illustrates reduced loss by providing a spectrum that already has only a small portion of radiation in the CSR.

FIG. 51B illustrates reduced loss by providing a spectrum that already has only a small portion of radiation in the CSR.

DETAILED DESCRIPTION

Reference is now made in detail to certain embodiments. The disclosed embodiments are not intended to be limiting of the claims.

Non-visual photoreceptors in the human eye (so-called intrinsically photosensitive retinal ganglion cells) are linked to the circadian system. While details of the circadian excitation band continue to evolve, a common consensus is that it the excitation band is peaked in the blue range at around 465 nm.

Figure 1A:
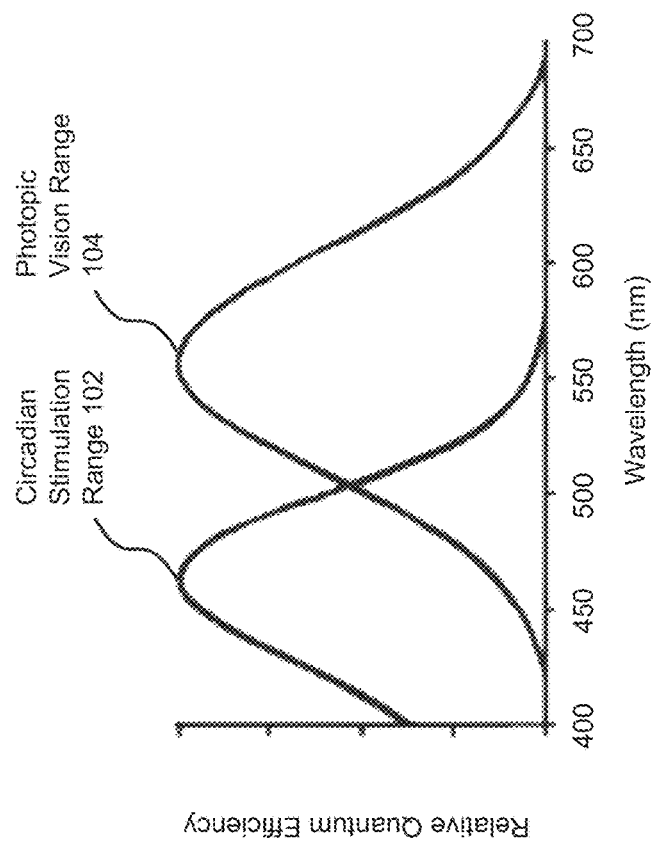
FIG. 1A is a diagram showing a circadian stimulation wavelength range as used to tune a circadian-friendly LED light source, according to some embodiments.

FIG. 1A is a diagram 1A00 showing a circadian stimulation wavelength range (CSWR) 102 as used to tune a circadian-friendly LED light source as presented by Brainard et al. in *The Journal of Neuroscience*, Aug. 15, 2001, 21(16):6405-6412 (Brainard), compared to the photopic vision range 104. With such a broad effective action spectrum, it appears there is little one can do to vary circadian stimulation for a white light source, other than varying the relative short-wavelength content, that is, the CCT. However, more recent work suggests that the relevant CSWR is in fact much narrower than presented in Brainard et al. For example, in Rahman et al., *Endocrinology*, Aug. 7, 2008, 149(12):6125-6135, it is shown that glucocorticoid elevation and melatonin suppression may be avoided by filtering blue light in a wavelength range of only 450 nm to 480 nm. This is significant because a narrower CSWR means there should be more flexibility in designing a white light source for desirable quality of light, while also controlling the amount of circadian stimulation. Further, it is noteworthy that Brainard et al. imposed a symmetric shape for their action spectrum when fitting experimental data; however, a careful analysis of the experimental points in FIG. 5 of Brainard et al. shows that the experimental response at short wavelength (e.g., 420 nm) is significantly lower than is obtained by the fitted curve. In other words, there is suggestive evidence that the CSWR is not well-known, especially at short wavelength, and may be narrower than is reported in some action spectra.

Depending on the details of the actual CSWR at short-wavelength, a variety of light sources with low circadian stimulation can be designed. Therefore it is possible to assume a CSWR and design a light source accordingly. Various embodiments of the invention do this, and illustrate how a light source can be optimized for a given assumed CSWR, for instance by optimizing the tradeoff between circadian stimulation and various aspects of quality of light (including CCT, chromaticity, absence of tint of the white point, and aspects of color rendition) and energy efficiency.

Circadian stimulation (CS) via ipRGCs for an illuminant with a spectral power distribution SPD as a function of wavelength, $\lambda$, can be modeled as:

$$CS = \frac{\int c(\lambda) SPD(\lambda) d\lambda}{\int SPD(\lambda) d\lambda}$$

where $c(\lambda)$ is the circadian stimulation spectrum. For two illuminants A and B of equal luminous flux (relevant for illumination applications), the relative Circadian Stimulation (CS) of A vs. B is:

$$\frac{CS_A}{CS_B} \cdot \frac{LE_B}{LE_A}$$

where LE is the lumen equivalent of the spectral power distribution.

Figure 1B:
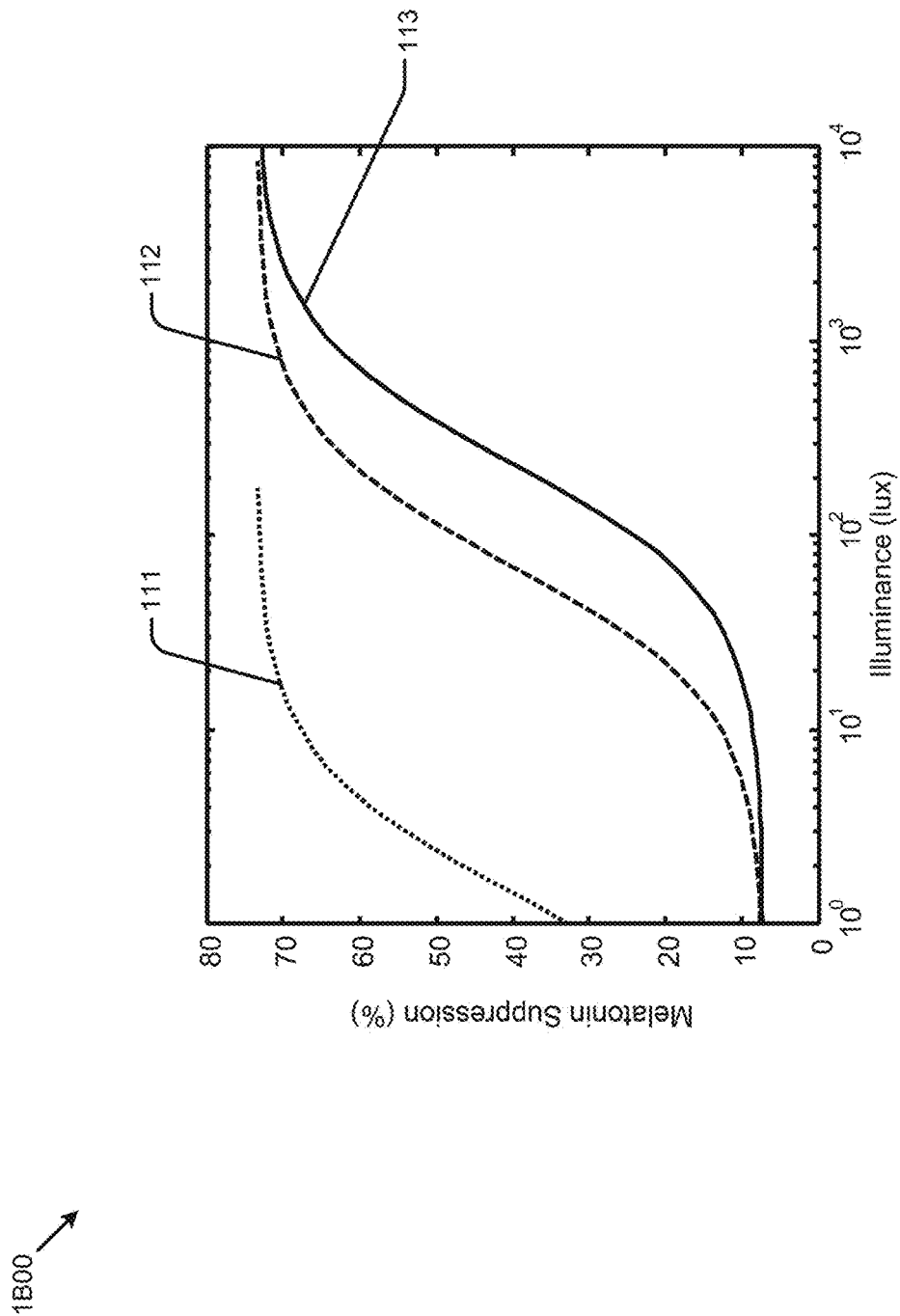
FIG. 1B shows how the impact of a light source on the circadian system scales against light intensity.

FIG. 1B shows how the impact of a light source on the circadian system scales against light intensity. The impact of a light source on the circadian system scales with relative CS, with light intensity (e.g., lux level), and with exposure time. One can combine the relative CS and the data from monochromatic stimuli disclosed by Brainard. One then obtains FIG. 1B which shows the melatonin suppression for various illuminances and for various light sources.

FIG. 1B shows melatonin suppression as a function of illuminance (lux) reaching the human eye, after a 90 min exposure. Curve 111 shows the response to monochromatic radiation at 460 nm, and is directly taken from Brainard. Curve 112 shows the response to standard illuminant D65. Curve 113 shows the response to illumination by standard illuminant A. Curves 112 and 113 are obtained by shifting curve 111, according to their relative CS.

FIG. 1B shows that for a common indoor residential lighting situation (300 lx under illuminant CIE A, representative of an incandescent lamp) melatonin suppression is significant: about 50% after 90 min. Thus, even in this common situation the circadian system can be impacted. For light sources with a larger relative CS than illuminant A, the effect can be stronger.

Figure 1C:
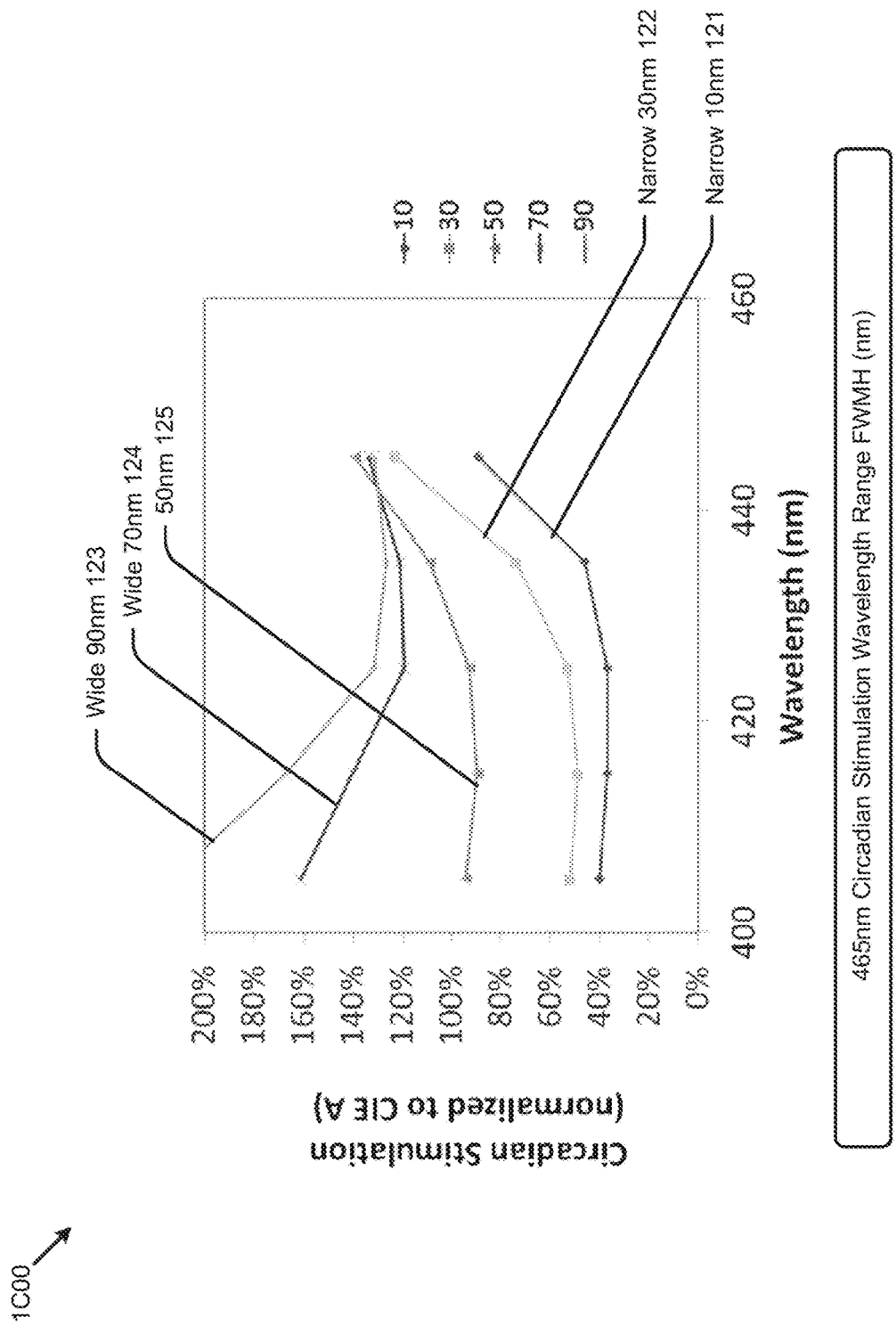
FIG. 1C shows a relative circadian stimulation for 3300K white light sources composed of a primary LED (varying from violet- to blue-emitting) combined with a green-emitting and red-emitting phosphor for different full-width half-maxima of circadian stimulation wavelength ranges peaked at 465 nm, according to some embodiments.
Figure 1D:
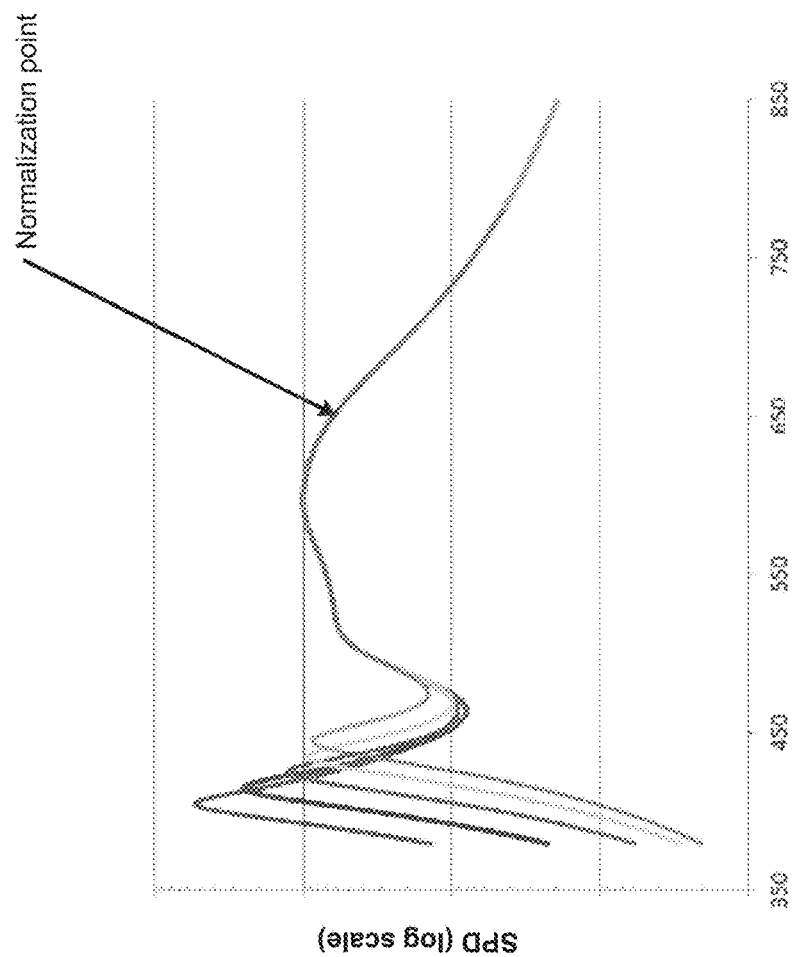
FIG. 1D shows SPDs for 3300K white light sources composed of a primary LED (varying from violet- to blue-emitting) combined with a green-emitting and red-emitting phosphor, normalized to emission at 600 nm according to some embodiments.

The following figures and text serve to compare the relative CS between various LED white light sources. FIG. 1C shows a relative circadian stimulation (CS) for 3300K white light sources composed of a primary LED (varying from violet- to blue-emitting) combined with a green-emitting and a red-emitting phosphor. In FIG. 1C, the x-axis is the center emission wavelength of the primary LED and the y-axis is the relative circadian stimulation (normalized to CIE A). The circadian stimulation is calculated assuming a circadian stimulation wavelength range peaked at 465 nm, with a Gaussian line shape and with various full-width half-maxima (from 10 nm to 90 nm) as labeled on the figure (see FIG. 1A). Regarding the phosphors used to obtain the white light source, suitable phosphors may be $Eu^{2+}$ doped materials. An example of a green-emitter is $BaSrSiO:Eu^{2+}$. An example of a red-emitter is $CaAlSiN:Eu^{2+}$. In FIG. 1C, the green and red emission peak wavelength/FWHM are 530/100 and 630/100, respectively. Other phosphors are also possible, as described below. In addition to phosphors, other wavelength down-converting materials may be used, such as organic materials or semiconductors such as nanoparticles otherwise known as "quantum dots". In other embodiments, the green and/or red emission may be provided by LEDs or by laser diodes (LDs). As shown in FIG. 1C, for wide CSWRs (e.g., wide 90 nm 123 and wide 70 nm 124) there is little primary LED wavelength sensitivity, or even a penalty as the wavelength gets too short. However, for narrower CSWRs (e.g., 10 nm 121 and 30 nm 122), there is a strong benefit to reducing the primary LED wavelength. For example, for a 30 nm FWHM CSWR 122, the relative CS for a violet (approximately 405 nm to approximately 425 nm) primary 3300K LED is about half that of the CIE A illuminant (2856K) 125. Thus, light source 122 is less circadian stimulating than many incandescent lamps, and dramatically less stimulating than a 445 nm (blue) based 3300K LED 123, which has a CS about 20% higher than CIE A. SPDs for various LED light source emissions including those of FIG. 1C are shown in FIG. 1D, normalized to emission at 600 nm. The SPDs are characterized, for example, by different violet content. For each SPD, CRI is maintained at 80 or higher and R9 is above zero (about 10).

Figure 1E:
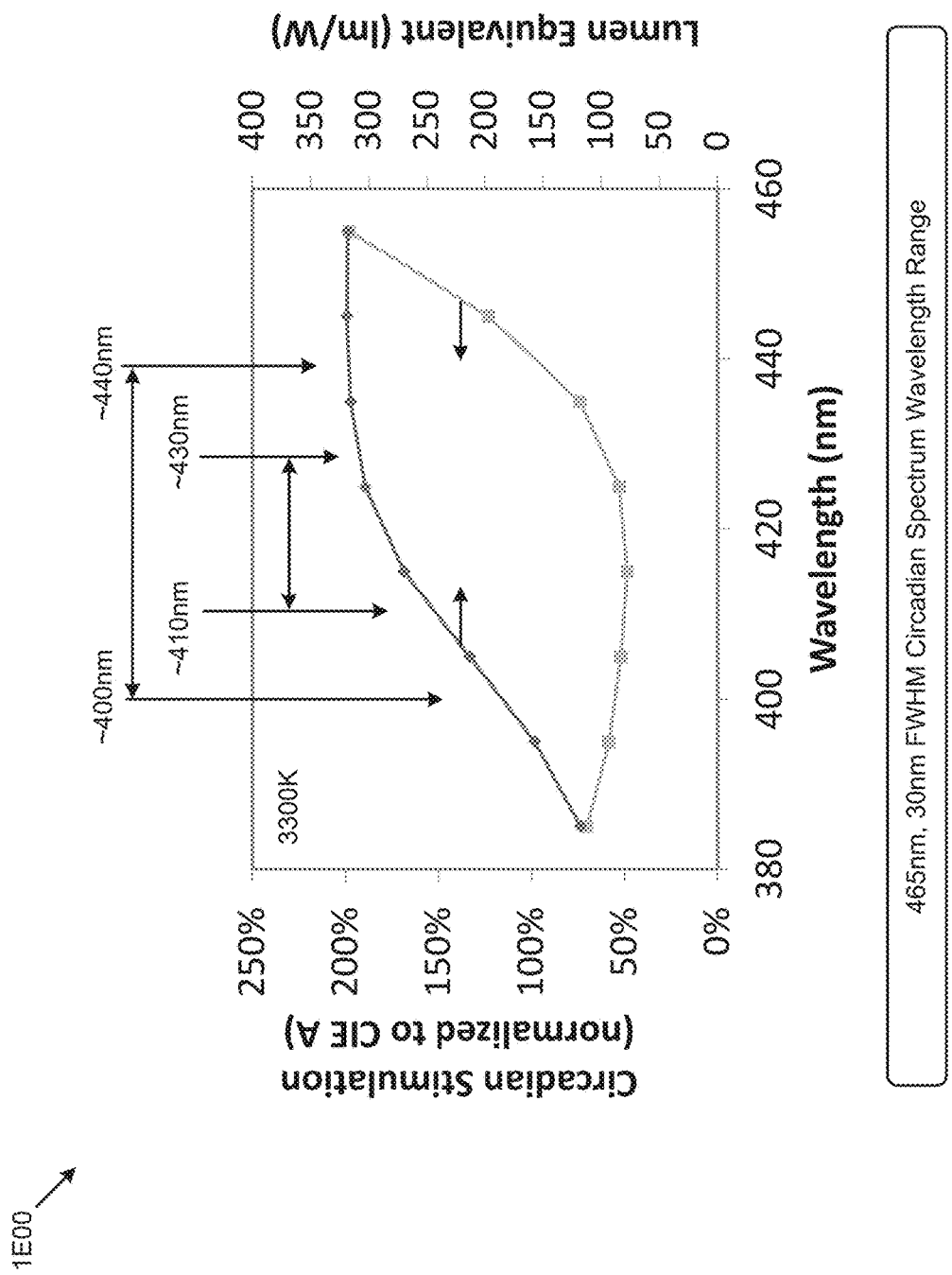
FIG. 1E shows the circadian stimulation for a two-phosphor based LED white light source at 3300K as a function of the primary LED emission peak wavelength, according to some embodiments.

Non- or weakly-circadian-stimulating light sources are desirable, for example, for evening illumination, in order to avoid glucocorticoid elevation and melatonin suppression, and thus prepare people for healthy sleep. Referring to the 30 nm FWHM CSWR of FIG. 1C, FIG. 1E shows the CS for a two-phosphor based LED white light source at 3300K as a function of the primary LED emission peak wavelength. For a 455 nm primary emission, the lumen equivalent (LE) of the SPD is high (about 320 lm/Wopt), but the CS is also high (about twice that of CIE A). As the primary LED peak wavelength is reduced below 455 nm, the CS falls dramatically. Further, as the primary LED peak wavelength is reduced below 420 nm, the LE also decreases. Thus, there is a range of primary LED peak emission wavelengths where the LE is still reasonably high, but the CS is reduced relative to CIE A. In particular, the wavelength range of 405 nm to 435 nm provides reduced CS and reasonable LE. A variety of standard LED sources with this CCT have a LE of about 300, therefore embodiments with an LE of about 200 or about 250 can be considered acceptable as they provide a much lower CS than standard sources.

Figure 1F:
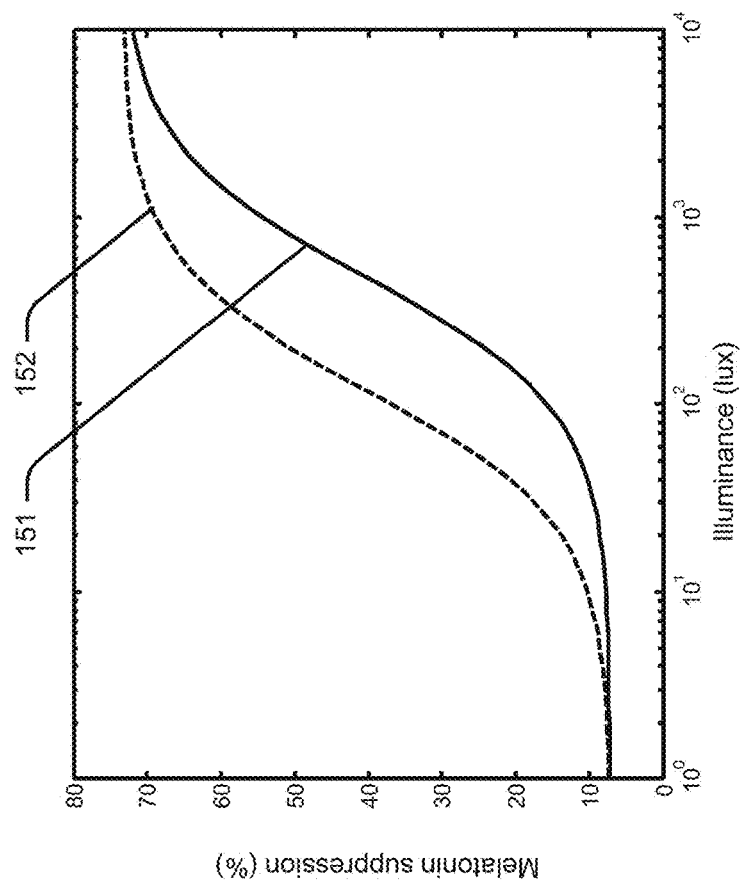
FIG. 1F shows predicted melatonin suppression versus illuminance at the eye level, for a 90 min exposure, according to some embodiments.

FIG. 1F further illustrates the advantage of such light sources. FIG. 1F shows predicted melatonin suppression versus illuminance at the eye level, for a 90 min exposure. Curve 1 corresponds to an LED source with 415 nm primary peak emission, and curve 2 corresponds to an LED source with 455 nm primary peak emission. Due to the lower relative CS, the 415 nm-primary LED induces less melatonin suppression. If the light level is dimmed to about 100 lux, the suppression becomes very small (less than 10% above the ceiling of the signal) whereas for the same illuminance under the 455 nm-primary LED, melatonin suppression is significant (about 40% in 90 min). Thus, the change in circadian stimulation has a relevant impact in a realistic environment.

In principle, another approach can be used to reduce the circadian stimulation of a light source: tuning the CCT of the light source—indeed, a warmer CCT generally leads to a lower relative CS. Various LED-based products provide this capability. However these products employ blue primary LEDs (peak emission wavelength range from about 445 nm to 460 nm). Therefore, even at low CCT, the relative CS remains fairly high (e.g., about twice that of illuminant CIE A for a 3000K LED source, as shown, for example, in FIG. 1C).

Therefore, careful choice of the emission wavelength of the primary LED and of the overall emission spectrum of the primary LED is important to significantly modulate CS.

Embodiments of various circadian-friendly LED white light sources can be configured such that the respective emission spectra can be tuned so as to simulate a circadian cycle in a more or less daily diurnal cycle.

Figure 2A:
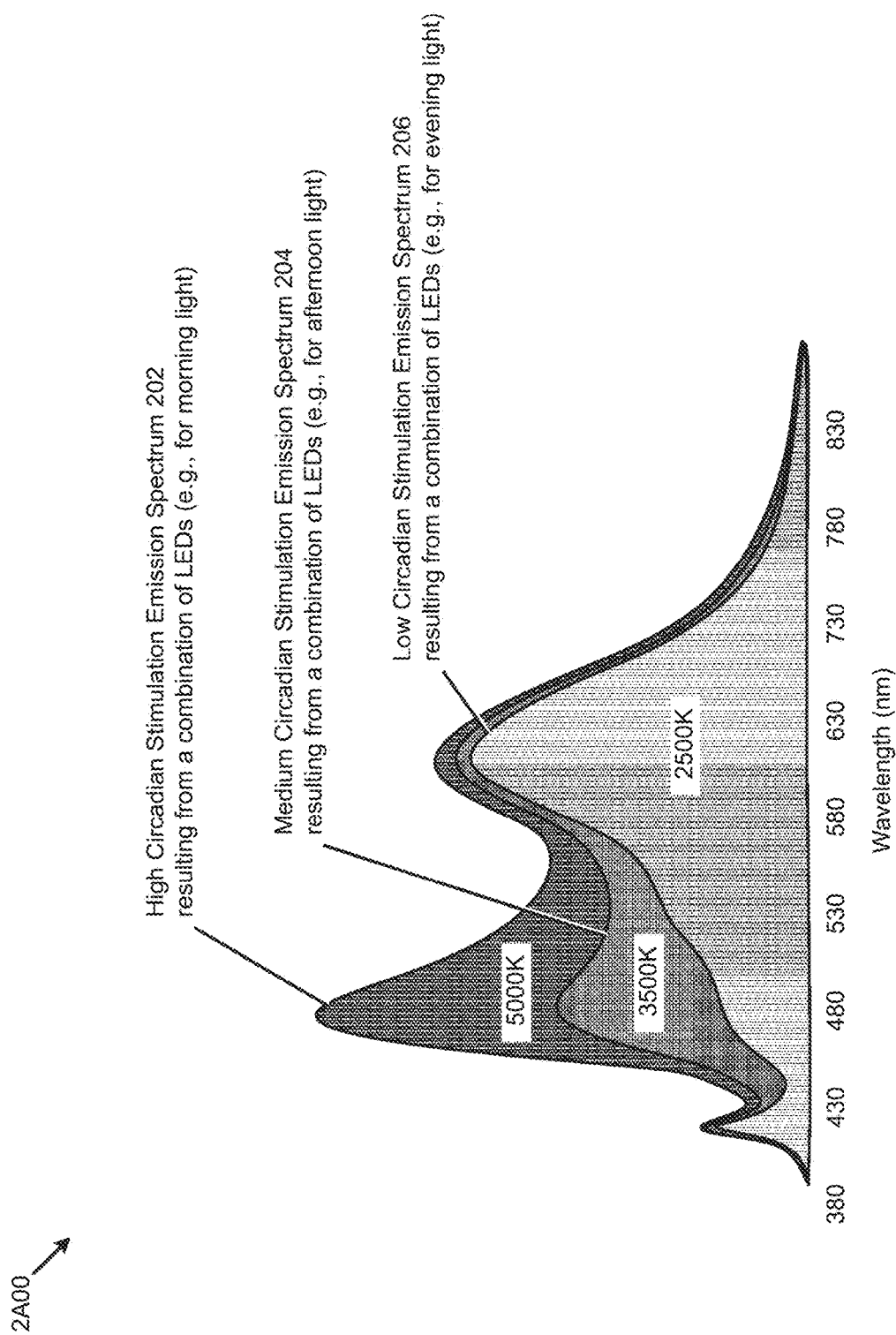
FIG. 2A shows spectral power distributions (SPDs) of various wavelength combinations as used in configuring a circadian-friendly LED light source, according to some embodiments.

FIG. 2A shows spectral power distributions (SPDs) of various wavelength combinations 2A00 as used in configuring a circadian-friendly LED white light source.

As shown in FIG. 2A, a stimulating blue peak is emitted for morning circadian stimulation (see curve 202). Another curve exhibits low circadian stimulation (see curve 206) for evenings, and a third curve (204) shows an intermediate option.

Figures 2B, 2C:
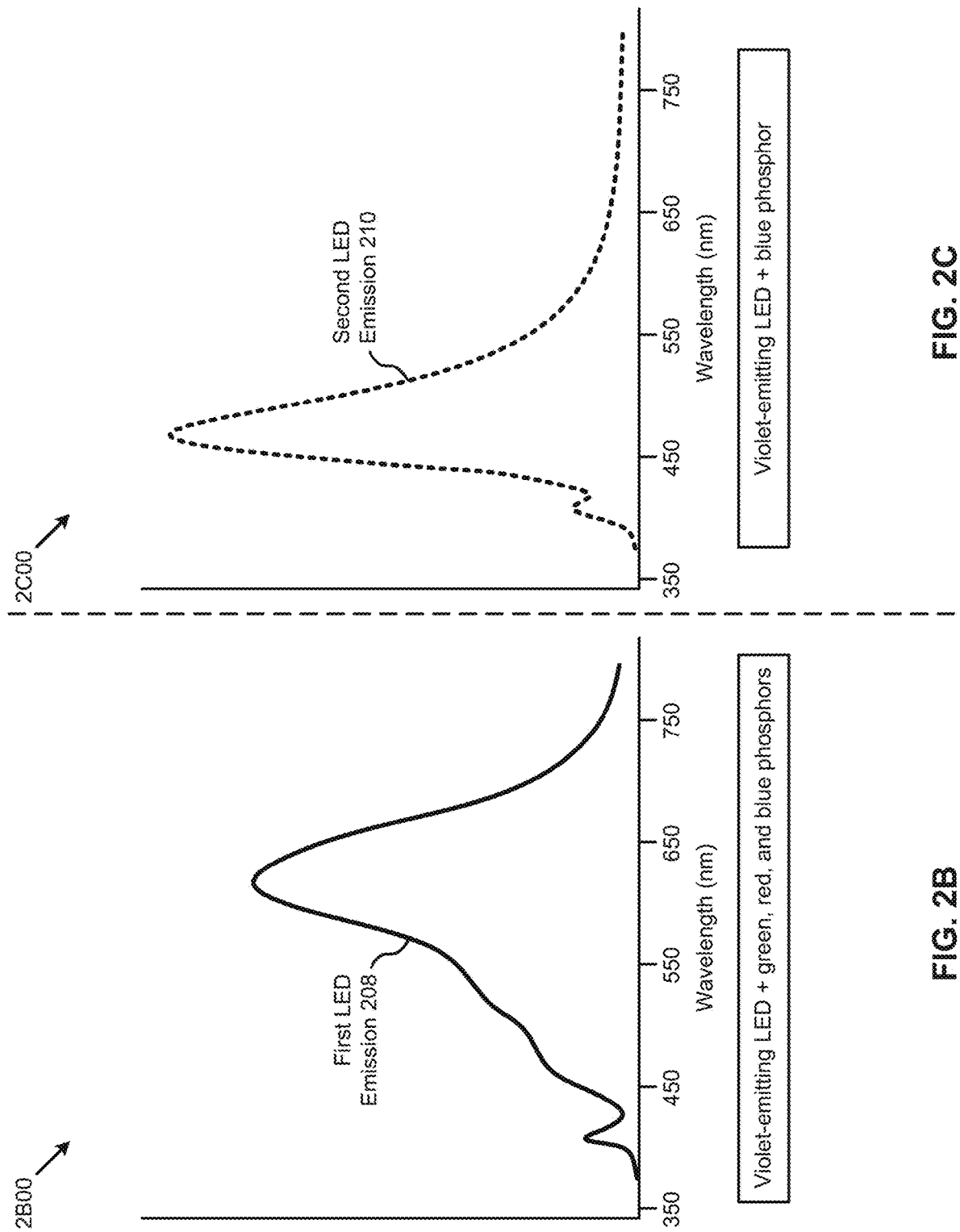
FIG. 2B shows an SPD corresponding to a first LED emission as used in configuring a circadian-friendly LED light source, according to some embodiments.
FIG. 2C shows an SPD corresponding to a second LED emission as used in configuring a circadian-friendly LED light source, according to some embodiments.

In certain embodiments, a circadian-friendly LED white light source (e.g., see luminaire of FIG. 4A and lamp of 6A and FIG. 6B) includes a first LED (see FIG. 2B) such as a violet (or UV) primary LED combined with a green, red, and (optional) blue phosphor to emit a spectrum 208 that is substantially a low-circadian-stimulating spectrum at a correlated color temperature (CCT) of 2500K (see spectrum of LED emissions 208 in FIG. 2B). Such an LED and phosphor combination can exhibit a reasonable white color point and can exhibit reasonable color rendering properties. Depending on the details such as the emission spectra of the primary LED and phosphors, it may not be necessary to combine a blue phosphor with a first LED.

For implementation of a circadian-friendly LED light source, a second LED (see FIG. 2C) can be added. The emission 210 (FIG. 2C) can be generated by using a second LED comprising, for example, a violet (or UV) LED to pump only a blue phosphor. The blue phosphor can be selected based on absorption characteristics of photons from the primary (violet or UV) LED: namely, is the blue phosphor can be chosen such that excitation can occur for moderate phosphor loading, such that the resulting system package efficiency is sufficient. Also, a blue phosphor can be selected based on the emission properties of the combination so as to combine with the first LED emission, thus shifting or tuning the chromaticity in a controlled manner (e.g., in a direction similar to increasing CCTs along the Planckian curve to maintain a white light appearance). In addition, a blue phosphor peak emission wavelength and FWHM can be selected to maintain specified color rendering properties even as the contribution of the second LED to the total spectrum (first and second LED combined) is increased (FIG. 2A). In some cases, the desired color rendering properties can be expressed as a CRI above 50, a CRI above 80, or in certain embodiments, a CRI above 90. Other metrics such as R9, another color fidelity metric, and/or a color gamut metric can also be employed. In some embodiments, a blue phosphor may be a mix of different phosphors, which, combined together, give the desired excitation and emission properties including the desired dominant wavelength of emission for spectral tuning as described herein.

For an SPD with a CCT of 2500K, the fraction of power in the spectral range from 400 nm to 440 nm is 0.03 and the fraction of power in the range from 440 nm to 500 nm is 0.06. For an SPD with a CCT of 5000K, the fraction of power in the spectral range from 400 nm to 440 nm is 0.02 and the fraction of power in the range from 440 nm to 500 nm is 0.20.

Figures 3A, 3B:
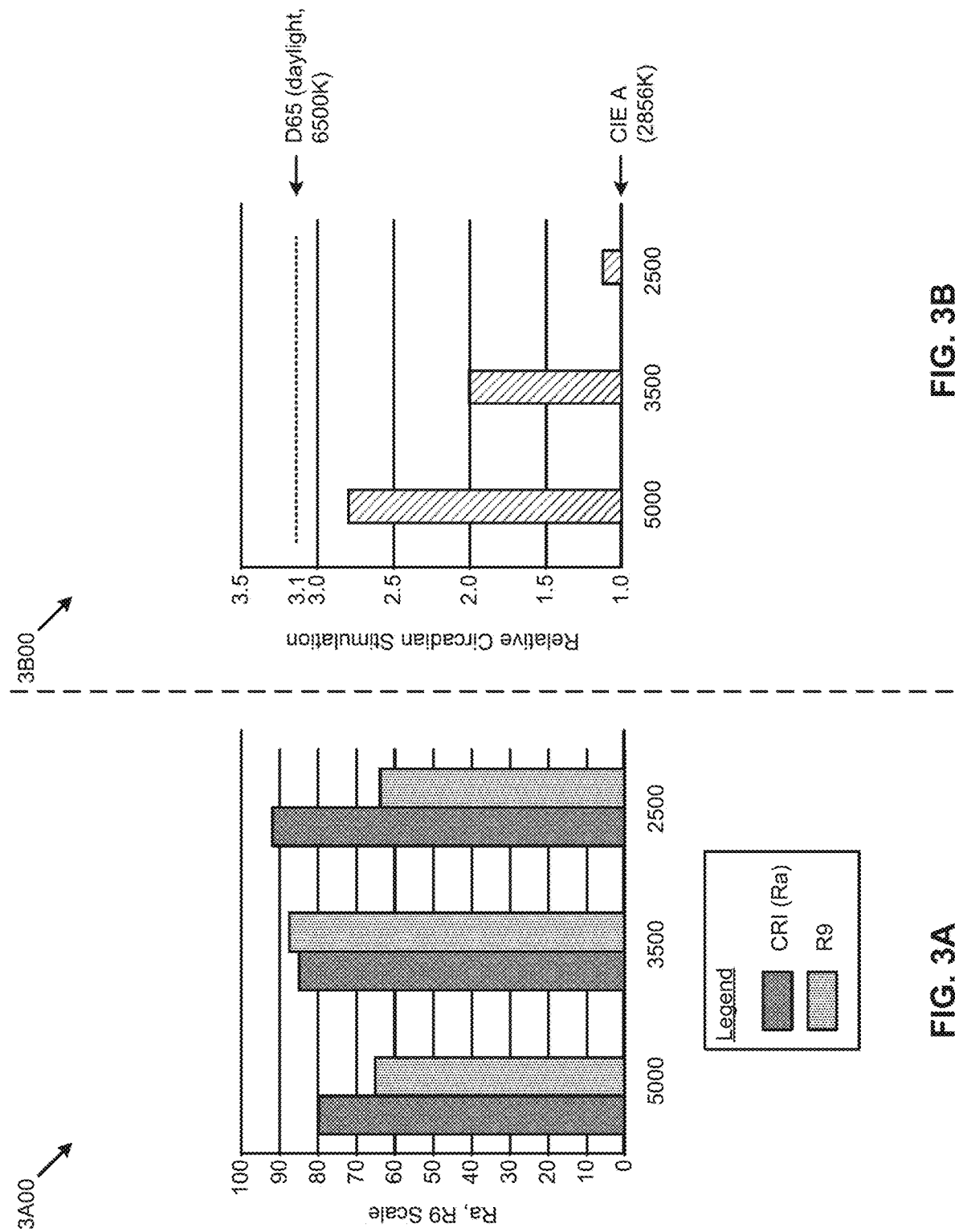
FIG. 3A is a chart showing color rendering properties exhibited by a circadian-friendly LED light source at three different color temperatures, according to some embodiments.
FIG. 3B is a chart showing relative circadian stimulation resulting from a circadian-friendly LED light source at three different color temperatures, according to some embodiments.

Certain color rendering properties for LED white light sources provided by the present disclosure at various LED temperatures are illustrated in FIG. 3A. The circadian stimulation (relative to a CIE A illuminant), based on a CSWR modeled after Brainard (102 in FIG. 1A, about 95 nm FWHM) is illustrated in FIG. 3B.

Certain embodiments use a blue phosphor characterized by a 477 nm peak emission wavelength and a FWHM of 80 nm. Such blue phosphors with a 477 nm peak emission wavelength represents only one embodiment and other embodiments use other phosphors and phosphor combinations. In particular, the phosphors and/or compositions of wavelength-conversion materials referred to in the present disclosure may comprise various wavelength-conversion materials.

Wavelength conversion materials can be crystalline (single or poly), ceramic or semiconductor particle phosphors, ceramic or semiconductor plate phosphors, organic or inorganic downconverters, upconverters (anti-stokes), nanoparticles and other materials which provide wavelength conversion. Major classes of downconverter phosphors used in solid-state lighting include garnets doped at least with $Ce^{3+}$; nitridosilicates, oxynitridosilicates or oxynitridoaluminosilicates doped at least with $Ce^{3+}$; chalcogenides doped at least with $Ce^{3+}$; silicates or fluorosilicates doped at least with $Eu^{2+}$; nitridosilicates, oxynitridosilicates, oxynitridoaluminosilicates or sialons doped at least with $Eu^{2+}$; carbidonitridosilicates or carbidooxynitridosilicates doped at least with $Eu^{2+}$; aluminates doped at least with $Eu^{2+}$. phosphates or apatites doped at least with $Eu^{2+}$; chalcogenides doped at least with $Eu^{2+}$; and oxides, oxyfluorides or complex fluorides doped at least with $Mn^{4+}$. Some specific examples are listed below:

$(Ba,Sr,Ca,Mg)_5(PO_4)_3(Cl,F,Br,OH):Eu^{2+}, Mn^{2+}$
$(Ca,Sr,Ba)_3MgSi_2O_8:Eu^{2+}, Mn^{2+}$
$(Ba,Sr,Ca)MgAl_{10}O_{17}:Eu^{2+}, Mn^{2+}$
$(Na,K,Rb,Cs)_2[(Si,Ge,Ti,Zr,Hf,Sn)F_6]:Mn^{4+}$
$(Mg,Ca,Zr,Ba,Zn)[(Si,Ge,Ti,Zr,Hf,Sn)F_6]:Mn^{4+}$
$(Mg,Ca,Sr,Ba,Zn)_2SiO_4:Eu^{2+}$
$(Sr,Ca,Ba)(Al,Ga)_2S_4:Eu^{2+}$
$(Ca,Sr)S:Eu^{2+},Ce^{3+}$
$(Y,Gd,Tb,La,Sm,Pr,Lu)_3(Sc,Al,Ga)_5O_{12}:Ce^{3+}$
$Eu_x(A1)_{6-z}(A2)_zO_yN_{8-z}(A3)_{2(x+z-y)}$, where $0 \le z \le 4.2$; $0 \le y \le z$; $0 < x \le 0.1$; A1 is Si, C, Ge, and/or Sn;

A2 is Al, B, Ga, and/or In; A3 is F, Cl, Br, and/or I.

The group:

$$Ca_{1-x}Al_{x-xy}Si_{1-x+xy}N_{2-x-xy}C_{xy}:A \tag{1}$$

$$Ca_{1-x-z}Na_zM(III)_{x-xy-z}Si_{1-x+xy+z}N_{2-x-xy}C_{xy}:A \tag{2}$$

$$M(II)_{1-x-z}M(I)_zM(III)_{x-xy-z}Si_{1-x+xy+z}N_{2-x-xy}C_{xy}:A \tag{3}$$

$$M(II)_{1-x-z}M(I)_zM(III)_{x-xy-z}Si_{1-x+xy+z}N_{2-x-xy-2w/3}C_{xy}O_{w-v/2}H_v:A \tag{4); and}$$

$$M(II)_{1-x-z}M(I)_zM(III)_{x-xy-z}Si_{1-x+xy+z}N_{2-x-xy-2w/3-v/3}C_{xy}O_wH_v:A \tag{4a},$$

wherein 0<x<1, 0<y<1, 0≤z<1, 0≤v<1, 0<w<1, x+z<1, x>xy+z, and 0<x−xy−z<1, M(II) is at least one divalent cation, M(I) is at least one monovalent cation, M(III) is at least one trivalent cation, H is at least one monovalent anion, and A is a luminescence activator doped in the crystal structure.

$Ce_x(Mg,Ca,Sr,Ba)_y(Sc,Y,La,Gd,Lu)_{1-x-y}Al(Si_{6-z+y}Al_{z-y})(N_{10-z}O_z)$ (where x,y<1, y≥0 and z~1)

$(Mg,Ca,Sr,Ba)(Y,Sc,Gd,Tb,La,Lu)_2S_4:Ce^{3+}$ $(Ba,Sr,Ca)_xSi_yN_z:Eu^{2+}$ (where 2x+4y=3z)

$(Y,Sc,Lu,Gd)_{2-n}Ca_nSi_4N_{6+n}C_{1-n}:Ce^{3+}$, (wherein 0≤n≤0.5)

$(Lu,Ca,Li,Mg,Y)$ alpha-SiAlON doped with $Eu^{2+}$ and/or $Ce^{3+}$ $(Ca,Sr,Ba)SiO_2N_2:Eu^{2+},Ce^{3+}$ $(Sr,Ca)AlSiN_3:Eu^{2+}$ $CaAlSi(ON)_3:Eu^{2+}$ $(Y,La,Lu)Si_3N_5:Ce^{3+}$ $(La,Y,Lu)_3Si_6N_{11}:Ce^{3+}$ $(Mg,Ca,Sr,Ba)(S,Se):Eu^{2+}$ $Sr[LiAl_3N_4]:Eu^{2+}$.

For purposes of the application, it is understood that when a phosphor has two or more dopant ions (i.e., those ions following the colon in the above phosphors), this is to mean that the phosphor has at least one (but not necessarily all) of those dopant ions within the material. That is, as understood by those skilled in the art, this type of notation means that the phosphor can include any or all of those specified ions as dopants in the formulation. Further, it is to be understood that nanoparticles, quantum dots, semiconductor particles, and other types of materials can be used as wavelength converting materials. The list above is representative and should not be taken to include all the materials that may be utilized within embodiments described herein.

More discussion of suitable phosphors for specific embodiments will be presented further in this application.

Embodiments of lamps can include any of the aforementioned wavelength conversion materials, and can exhibit various qualities of light characteristics. Some of such qualities of light characteristics are shown in FIG. 3A and FIG. 3B.

FIG. 3A is a color rendering chart 3A00 showing color rendering index (Ra) and red color rendering (R9) exhibited by a circadian-friendly LED white light source of FIG. 2A at three different color temperatures (e.g., 5000° K, 3500° K, and 2500° K).

When the first and second LED emissions are combined in comparable levels, a 5000K color point can be achieved with acceptable color rendering (Ra, R9 of 80, 65 respectively). Moreover, this emission spectrum can have a high relative circadian stimulation (as defined above) similar to that achieved with a D65 reference illuminant (daylight). When the second LED emission is reduced to a very low level (or turned off), the first LED emission dominates, and a low-circadian-stimulating spectrum is achieved at 2500K with Ra, R9 of 93, 65. At an intermediate point, a 3500K color temperature is provided with Ra, R9 of 85, 88 and a mid-level stimulation of the circadian system. Accordingly, this LED white light source can be used to achieve high-stimulating 5000K light in the morning, 3500K mid-stimulating illumination in the afternoon, and low-stimulating 2500K light in the evening, all while maintaining acceptable white light quality (Ra 80, R9>50). Total power to the first and second LEDs may be adjusted to provide the desired total illuminance levels.

FIG. 3B is a chart 3B00 showing relative circadian stimulation resulting from a circadian-friendly LED light source.

FIG. 3B shows the relative circadian stimulation of the circadian-friendly light source illustrated in FIG. 2A, using a 95 nm FWHM CSWR as modeled after Brainard. By combining both first and second LED emissions to achieve a color temperature of 5000K (202 in FIG. 2A), a very high circadian stimulating effect is achieved. As shown in FIG. 3B, at 5000K the relative circadian stimulation is approximately 2.8 times higher than that of the CIE A reference illuminant. This level of circadian stimulation is close to that achieved with an illuminant associated with daylight (e.g., D65 illuminant, as shown), which has a relative circadian stimulation 3.1 times higher than that of the CIE A reference illuminant. When the second LED is turned down (or off) so that the first LED emission dominates, the 2500K spectrum is achieved (206 in FIG. 2A), which has a very low circadian stimulation (within 10% of that of the CIE A reference illuminant). When the intensity of the first and second LED emission are comparable, an intermediate spectrum at 3500K is achieved (204 in FIG. 2A), which provides a relative circadian stimulation about two times higher than that of the CIE A reference illuminant.

The color may be changed dynamically (either continuously or stepwise) throughout the day, via a clock-controlled driving scheme. Or, the desired color point may be selected using a switching mechanism provided for the end user. Many other automatic and/or human-interface control schemes may be employed, such as power-line communication, Wi-Fi, Zigby, DALI, etc. Different target CCTs are also possible. It is expected that such a light source would have dramatic benefits for health and amenity compared to circadian-unfriendly light sources such as standard blue-based LEDs.

Figure 4A:
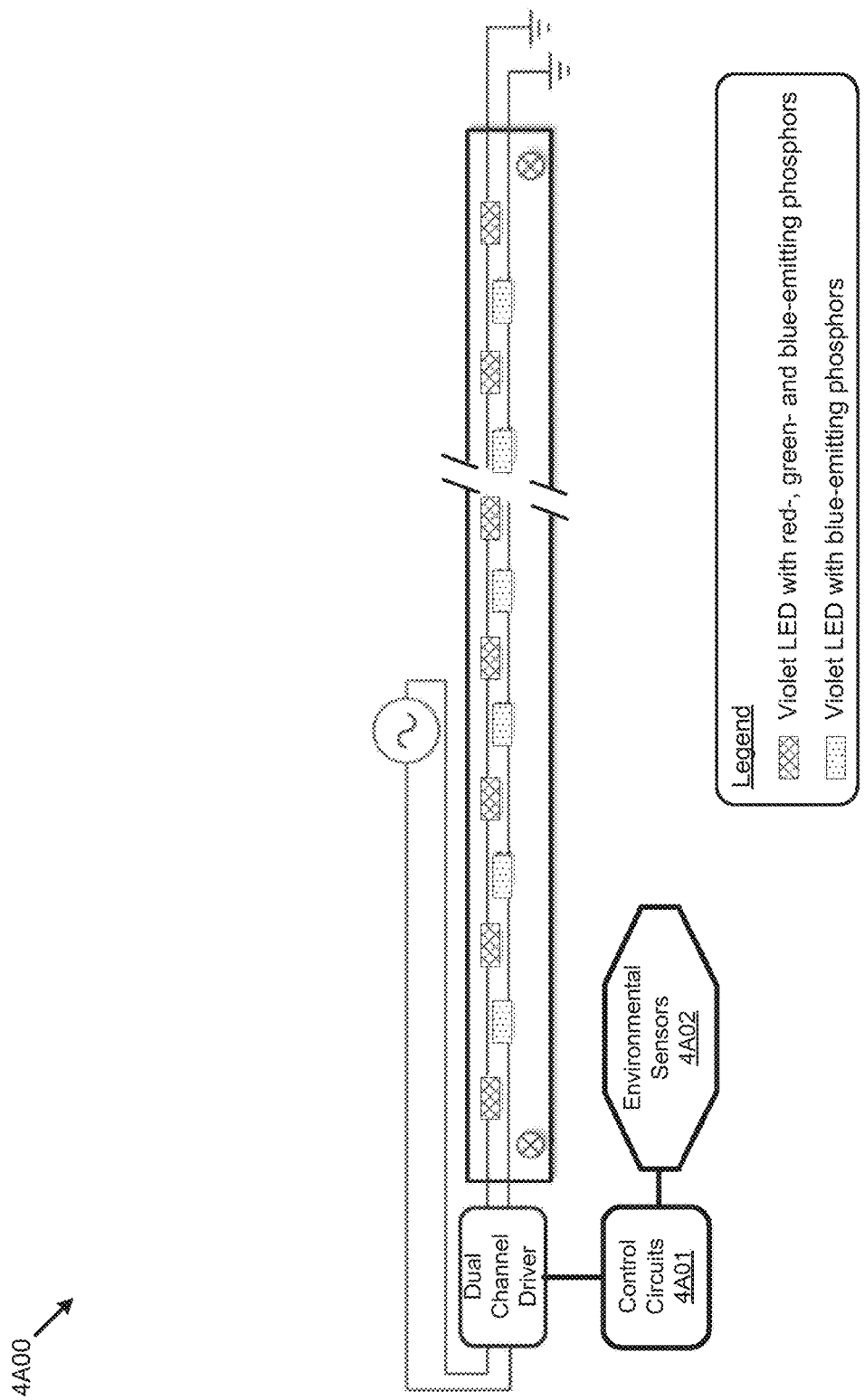
FIG. 4A shows an example of a light strip used to implement a white light source that is tunable based on measurable aspects and/or changes in the environment, according to some embodiments.

FIG. 4A shows an example of a light strip used to implement a white light source that is tunable based on measurable aspects (e.g., time of day) and/or changes in the environment. Such a white light source can be formed, for instance, by mixing at least two LED-based sources: e.g., a first using an appropriate mix one set of red-, green- and (optional) blue-emitting phosphors with violet-primary LEDs, and a second using either violet-pumped blue phosphor LEDs or blue-primary LEDs. The two sources can be mixed throughout a diurnal cycle to form a circadian-friendly LED white light source. Such a light strip may be used, for example, as a light engine for a linear troffer luminaire.

Figure 4B:
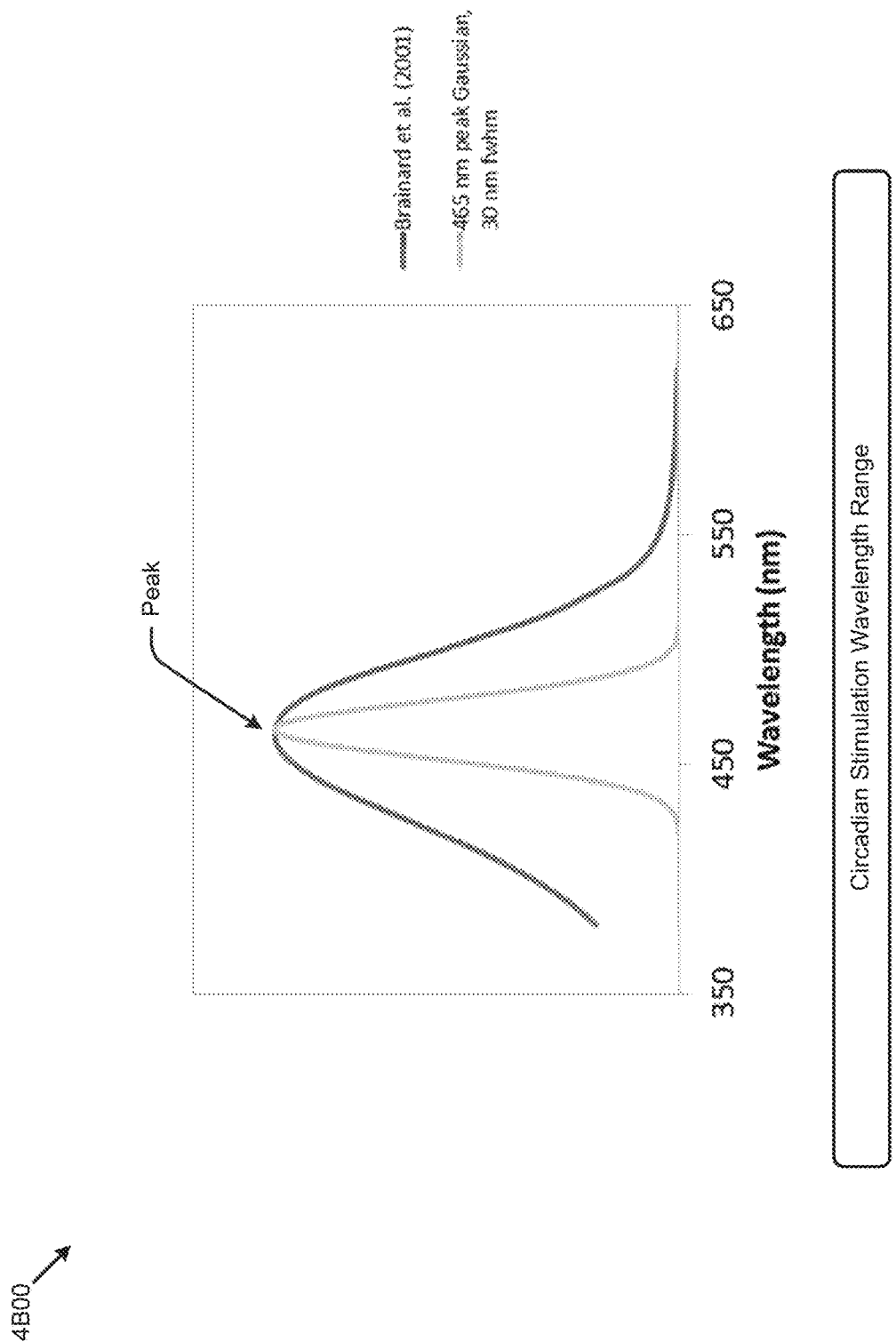
FIG. 4B shows a narrower band (Gaussian) circadian stimulation range with 30 nm full-width-half-maximum (FWHM) and peaked at 465 nm.

In other embodiments, the CSWR can be narrower than described by Brainard (curve 401 in FIG. 4B). For example, consider a 465 nm peak Gaussian CSWR with a FWHM of 30 nm as shown as curve 402 in FIG. 4B. For this narrower CSWR, it is possible to design LED white light sources having a CCT higher than that of CIE A, but with lower circadian stimulation.

Figure 4D:
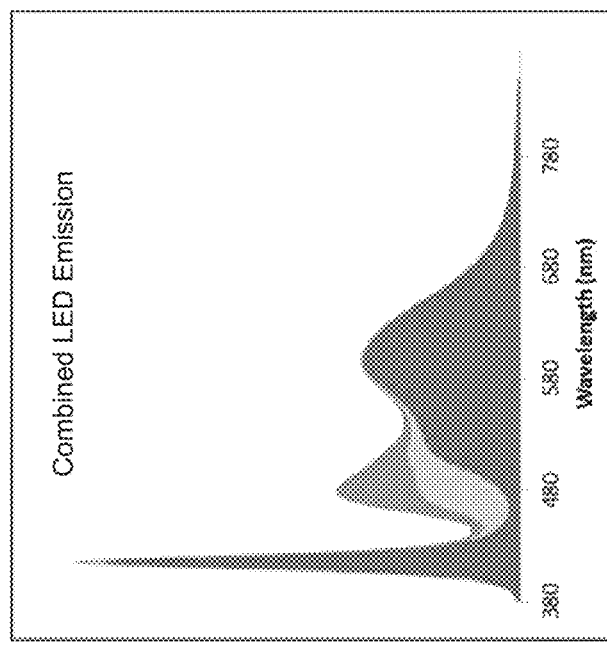
FIG. 4D shows the individual and combined LED-based emission spectra of FIG. 4C.

FIG. 4C shows a first LED emission 4C100 of a violet-primary LED pumping a green and red phosphor 403. This emission is at 3286K but has a CS 50% relative to CIE A. Thus, the LED white light source has a higher CCT than CIE A but a lower circadian stimulation. The second LED emission 4C200 (FIG. 4C) is a violet primary LED pumping a blue phosphor having a peak emission wavelength of 477 nm 404. The first and second LED-based emissions can be combined, as shown in FIG. 4D, to tune from about 5000K to about 3300K, varying the CS from about 300% to less than 50% that of CIE A, while maintaining a white point within 4 points of the Planckian, a CRI>80, and an R9>10, as shown in the table in FIG. 4D.

This change in CS can also be quantified by considering the relative spectral content (e.g., fraction of the SPD) in specific spectral ranges. Two ranges of interest are the relative spectral content in the 'violet-blue' (VB) range 400 nm to 440 nm and in the 'blue-cyan' (BC) range 440 nm to 500 nm. The former range is relatively less circadian-stimulating, and the latter range is relatively more circadian-stimulating. The table in FIG. 4D shows the relative spectral content for these wavelength ranges. When tuning from 5000K to 3300K, the fraction of total SPD power in the VB range increases slightly (from 0.19 to 0.23) whereas the fraction in the BC range decreases significantly (from 0.20 to 0.05). This re-apportioning of the spectral content from the BC range to the VB range contributes to the low CS of the 3300K SPD. Also, note that the presence of violet light enables the SPD to remain on-Planckian.

It is an unexpected result that it is possible to design a SPD having a small amount of blue light (to reduce the CS significantly against a standard light source, such as illuminant A) while also retaining good properties: high CRI and R9, chromaticity on-Planckian, good LER. Indeed it is conventionally believed that the presence of blue light is necessary to achieve on-Planckian white balance, and that the use of violet light instead of blue light has a prohibitive impact on LER.

In certain embodiments, having a large fraction Fv of the SPD in the VB range or a small fraction Fc in the BC range corresponds to a low CS, and vice-versa. For example, an SPD characterized by a Fc>0.1 may have a high stimulation, and an SPD characterized by a Fc<0.06 and Fv>0.05 may have a low stimulation. Similarly, an SPD characterized by a Fc/Fv>0.5 may have relatively high stimulation, and an SPD characterized by a Fc/Fv>1 may have a high stimulation. An SPD characterized by a Fc/Fv<0.4 may have a relatively low stimulation and an SPD characterized by a Fc/Fv<0.2 may have a low stimulation. These ranges correspond to certain embodiments of LED white light sources provided by the present disclosure, including those of FIGS. 4A-4N and FIGS. 5A-5C.

Therefore, the CS can, in general, be proportional to the ratio Fc/Fv, with higher values being associated with greater circadian stimulation. CS can also, in general, be proportional to the Fc content. Furthermore, in certain embodiments, increasing the VB content of a LED white light source will decrease the BC content, and conversely increasing the BS will result in reduced VB content.

Fv and Fc represent the fraction of power in the SPD within either the VB wavelength range or the BC wavelength range, respectively. For example, where the total power in the SPD is 1, when 10% of the power in the SPD is in the VB wavelength range, Fv is 0.1; and when 10% of the power of the SPD is in the BC wavelength range, Fc is 0.1.

In certain embodiments, Fv is less than 0.2, less than 0.15, less than 0.1, less than 0.08, and in certain embodiments, less than 0.05.

In certain embodiments, Fv is greater than 0.2, greater than 0.15, greater than 0.1, greater than 0.08, and in certain embodiments, greater than 0.05.

In certain embodiments, Fc is less than 0.2, less than 0.15, less than 0.1, less than 0.08 and in certain embodiments, less than 0.05.

In certain embodiments, Fc is greater than 0.2, greater than 0.15, greater than 0.1, greater than 0.08, and in certain embodiments, greater than 0.05.

Various combinations of Fv and Fc can be provided consistent with providing a LED white light source of the present disclosure. It is significant that using the devices and methods provided by the present disclosure, Fv, i.e., the spectral content in the VB range from 400 nm to 440 nm can be controlled to provide a desired white light emission and maintain desired attributes such as CCT, CRI, Ra, Duv, and others. Use of violet emitting LEDs and select phosphors, and optionally additional LEDs emitting at other wavelengths, provide the ability to more accurately control the content in the VB range from 400 nm to 440 nm.

In certain embodiments, Fc/Fv is from 0.1 to 1, from 0.1 to 0.8, from 0.1 to 0.6, and in certain embodiments, from 0.1 to 0.4.

In certain embodiments, Fc/Fv is less than 0.1, less than 0.2, less than 0.3, less than 0.4, less than 0.5, and in certain embodiments, less than 0.6.

In certain embodiments, Fc/Fv is from 0.5 to 1.5, from 0.5 to 1.3, from 0.5 to 1.1, and in certain embodiments, from 0.5 to 0.9.

In certain embodiments, Fc/Fv is greater than 0.5, greater than 0.6, greater than 0.7, greater than 0.8, greater than 0.9, and in certain embodiments, greater than 1.

It should be appreciated that it is not trivial to obtain the high quality of light demonstrated by the embodiments of the present disclosure. Although one can reduce the CS of a light source by simply removing all (or most) of the blue and cyan emission—without supplementing it with violet radiation, the resultant color rendering index would be poor because of the absence of short-wavelength light in the spectrum. Furthermore, it can be difficult to maintain the chromaticity of a source near-Planckian (resulting in a source with a low CCT and/or a greenish tint). In contrast, embodiments of the present disclosure balance the amount of blue and violet light and thereby facilitate modulating the CS while maintaining high quality of light (e.g., CRI, Ra, Duv).

Figure 4F:
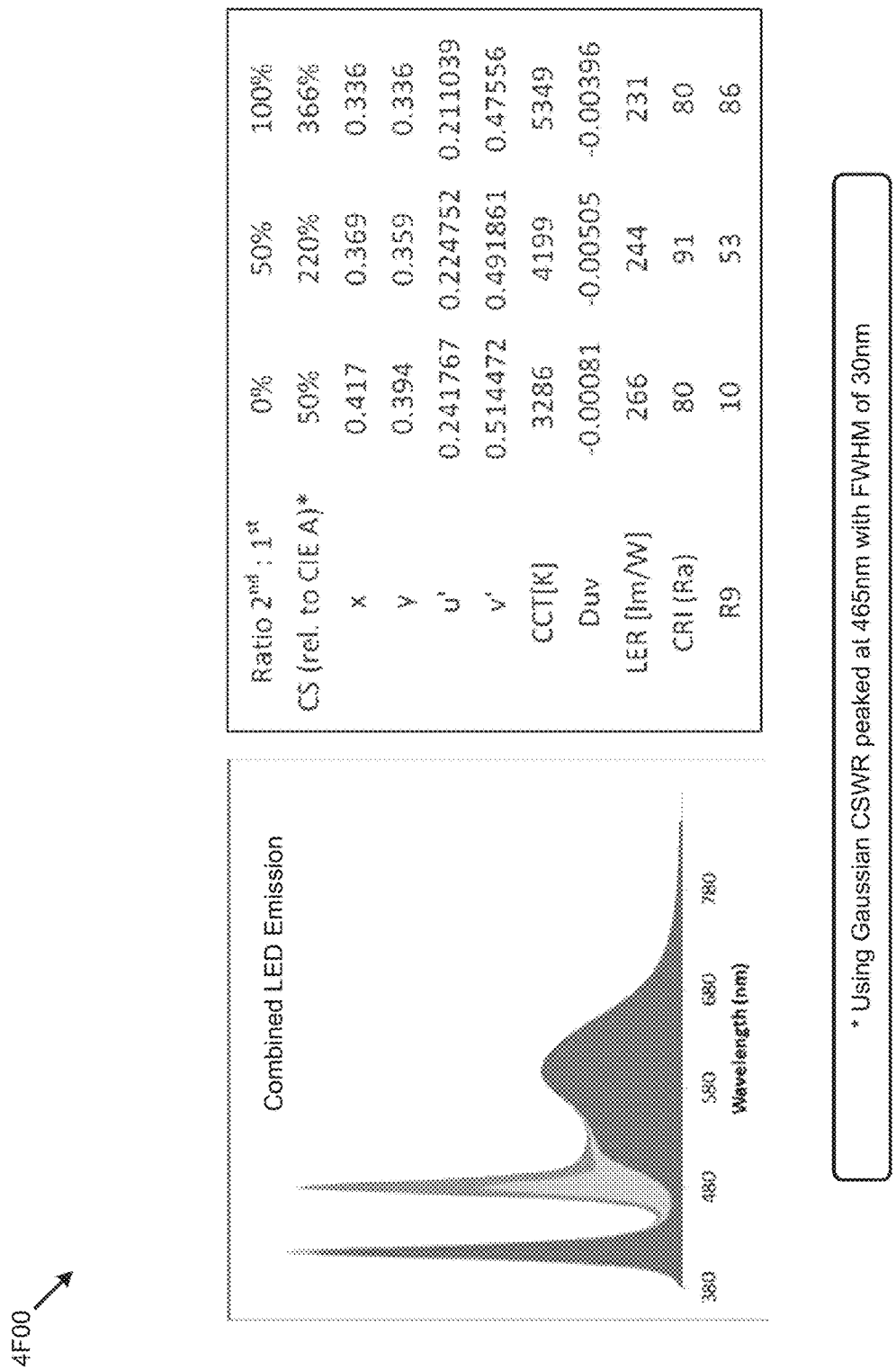
FIG. 4F shows the individual and combined LED-based emission spectra of FIG. 4D.

It is possible for a second LED emission to use a primary blue-emitting LED with a suitable dominant wavelength to tune along the Planckian. For example, as shown in FIG. 4E, an about 480 nm peak emission LED may be used in place of the blue-phosphor-based LED of FIG. 4C. FIG. 4E shows an emission spectrum of a first LED-based source 420 and FIG. 4E shows a spectrum 421 of a blue-emitting LED. By combining the emissions shown in FIG. 4E, a similar effect is achieved as shown by the combined spectrum 422 in FIG., with slight differences in color properties and levels of circadian stimulation, as shown in the table in FIG. 4F.

Figure 4G:
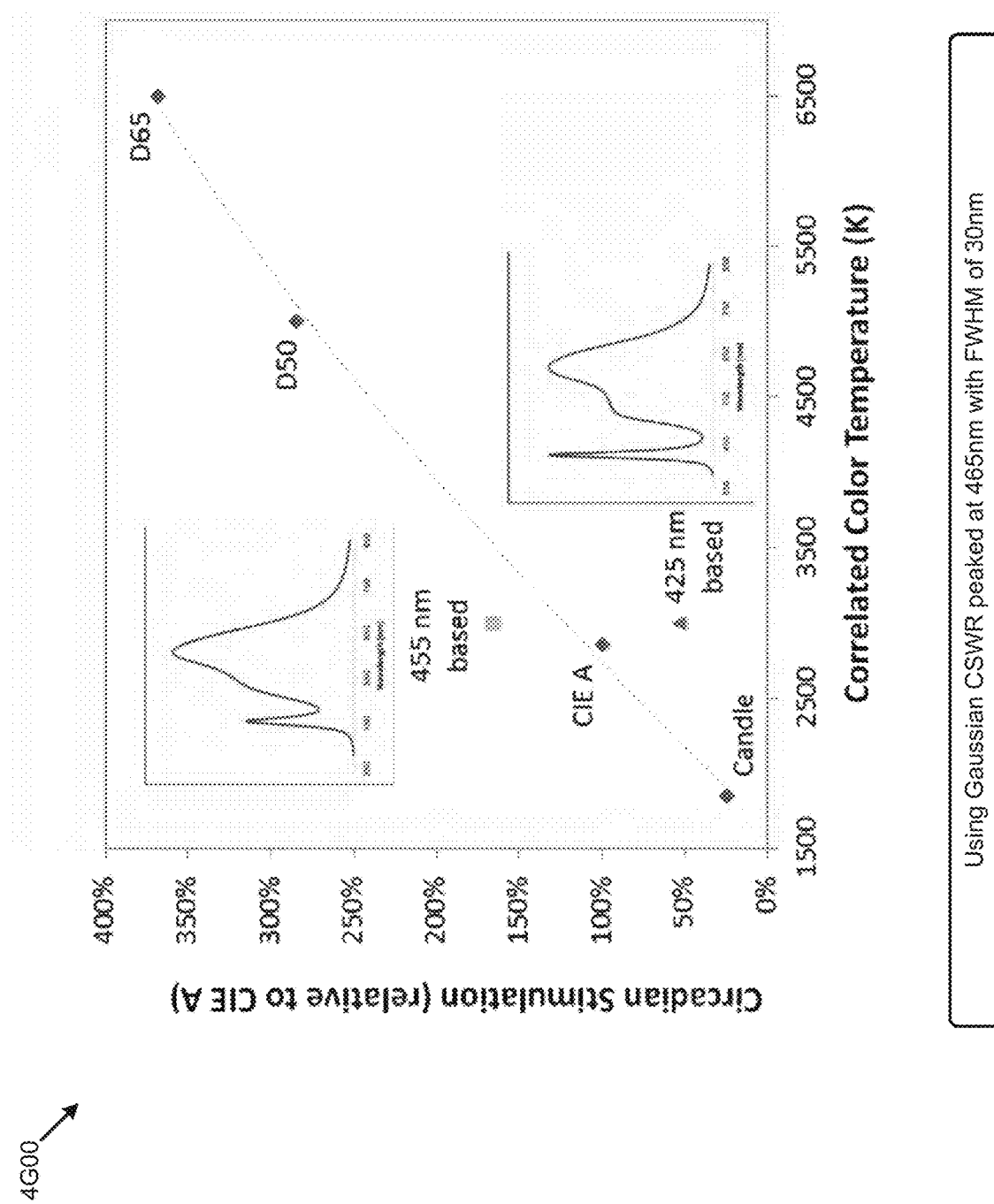
FIG. 4G shows circadian stimulation as a function of color temperature for certain light sources.

In the case of a 465 nm peak Gaussian CSWR with a FWHM of 30 nm, it is illustrative to compare the relative CS for common light sources with LED white light sources provided by the present disclosure. FIG. 4G shows the CS (normalized to that for CIE A) as a function of color temperature for common light sources such as candlelight (1850K), CIE A (2856K), D50 phase daylight (5000K), and D65 phase daylight (6500K). The CS varies from about 25% (candlelight) to almost four times (D65) that of CIE A. Also plotted are the CS for a 455 nm blue primary LED two-phosphor 3000K LED, and that for a 425 nm violet primary LED two-phosphor 3000K LED. The difference in circadian stimulation is remarkable, with that for the 455 nm-based LED white light source being more than 1.5-times higher than that of CIE A, and more than three times that of the 425 nm-based LED white light source. It is worth noting that $Ce^{3+}$ garnet phosphors (e.g., "YAG") are not highly absorbing in the violet, so for the 425 nm-based LED it may be desirable to use a Eu$^{2+}$ phosphor for the green, as well as for the red, emissions.

Figure 4H:
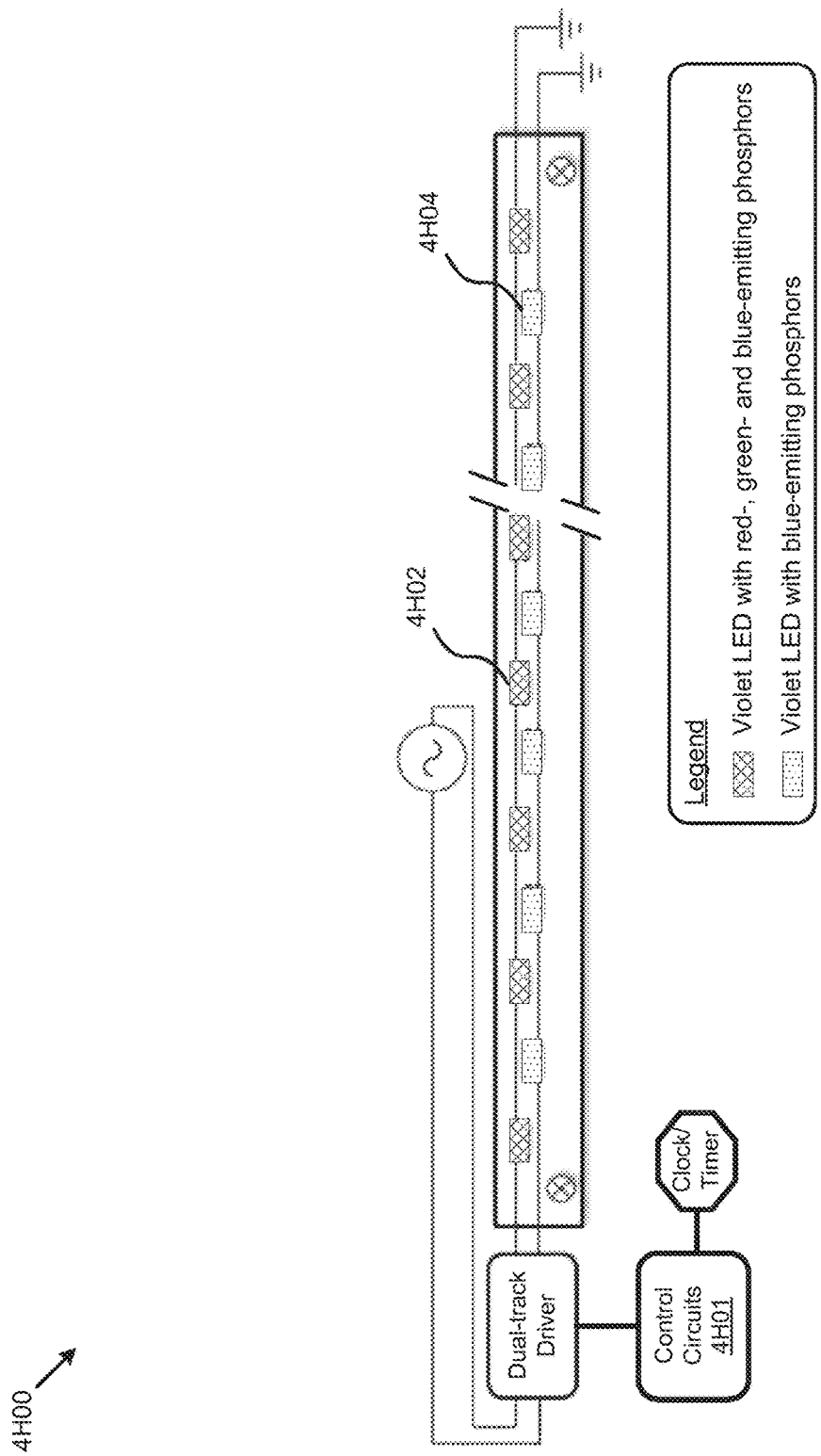
FIG. 4H shows a light strip having two different sets of LED-based emitters and a clock/timer, control circuits, and a driver to control the ratio of emissions of the two different sets of LED-based emitters to implement a circadian-friendly LED white light source, according to some embodiments.

FIG. 4H shows light strip having two different sets of LED-based emitters and a clock/timer, control circuits 4H01, and a driver to control the ratio of emissions of the two different sets of LED-based emitters to implement a circadian-friendly LED white light source, according to some embodiments.

As shown, a first group of violet-primary LEDs with an appropriate mix of red-, green- and (optionally) blue-emitting phosphors 4H02 can be combined with a second group of violet-primary LEDs with blue phosphors, or blue-primary LEDs, 4H04.

The first and second groups of LED-based emitters may be contained in separate packages, and the light combined with mixing optics, or the LED-based emitters may be incorporated into a single package, such as a s chip-on-board (COB) package (e.g., see the arrangement of FIG. 8) and/or linear COB packages. COB packages can be used in a lamp assembly as is shown in FIG. 6A and FIG. 6B.

In addition, although the above embodiments describe two-channel tuning methods to provide varying levels of circadian stimulation while maintaining a high quality of light, which can be useful to minimize cost and complexity, it is possible to use three or more channels using the devices and concepts provided disclosure. More channels offer more degrees of freedom in terms of light source selection, and tuning for arbitrary (e.g., non-linear) curves in chromaticity space, but at the cost of higher levels of complexity in terms of luminaire design, LED procurement, mixing, and control.

In addition to the elements shown in FIG. 4H one or more light mixing optics (not shown) may be used to mix the LED emissions first group and second group to provide a uniform or other desired light color appearance. Still further, secondary optics can be used to achieve a desired light distribution pattern.

The foregoing discussion is focused on lighting systems and benefits resulting from a reduced CS. However, display systems can also benefit from a reduced CS.

Figure 4I:
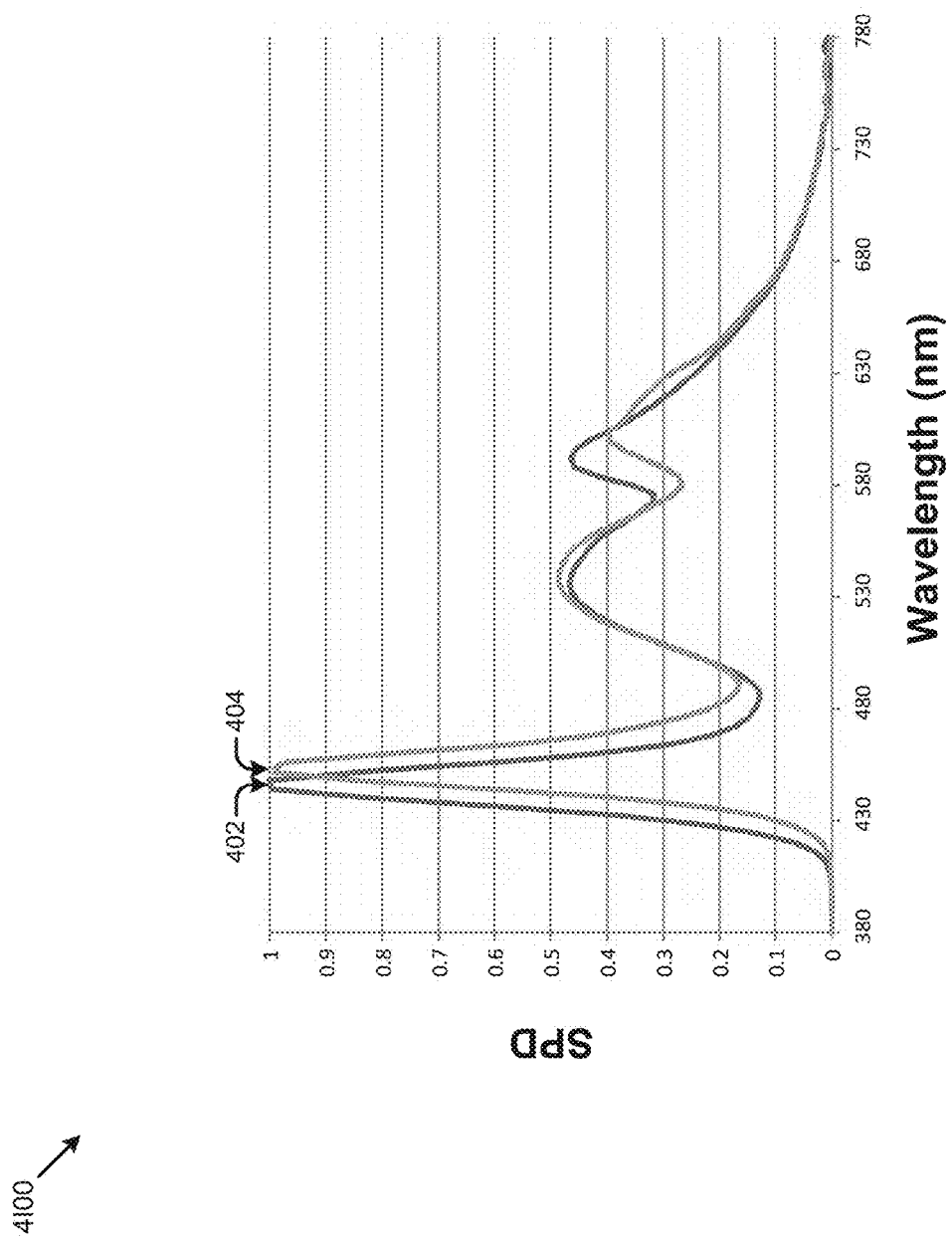
FIG. 4I shows measured SPDs for two display systems with a white screen, according to some embodiments.
Figure 15B:
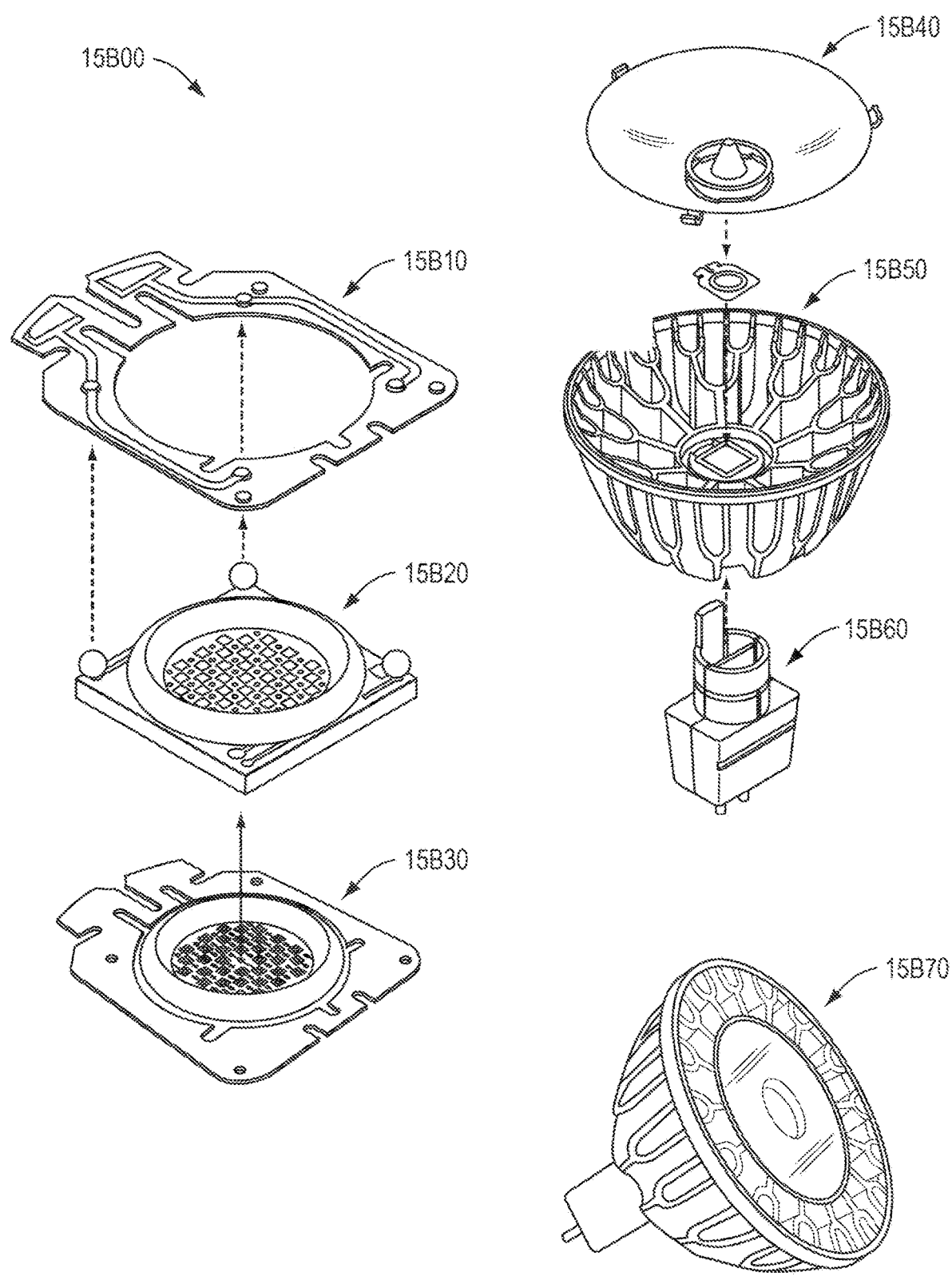
FIG. 15B depicts one embodiment of the present disclosure as can be applied toward lighting applications.
Figure 15C:
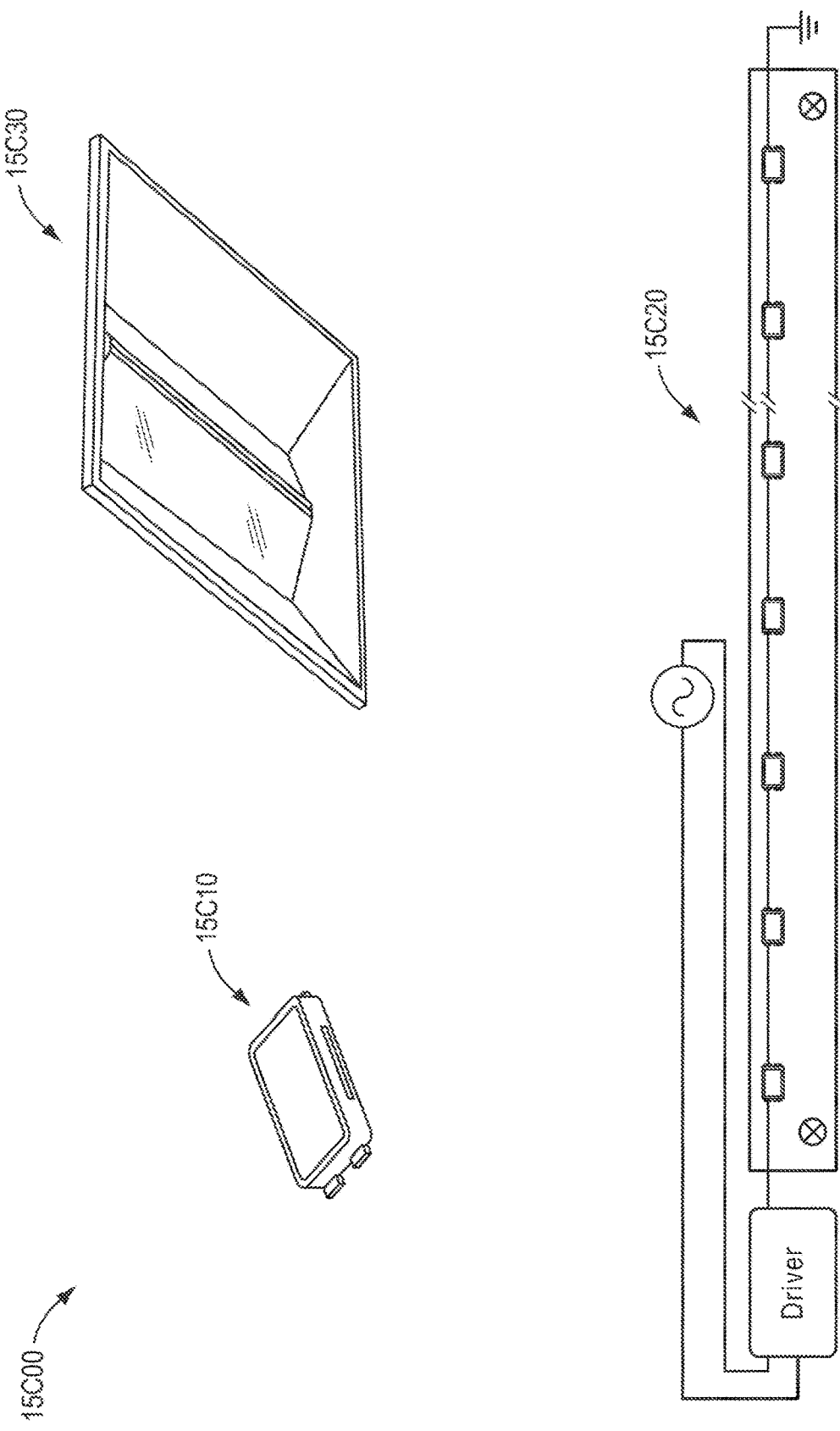
FIG. 15C depicts one embodiment of the present disclosure as can be applied toward lighting applications.
Figure 15D:
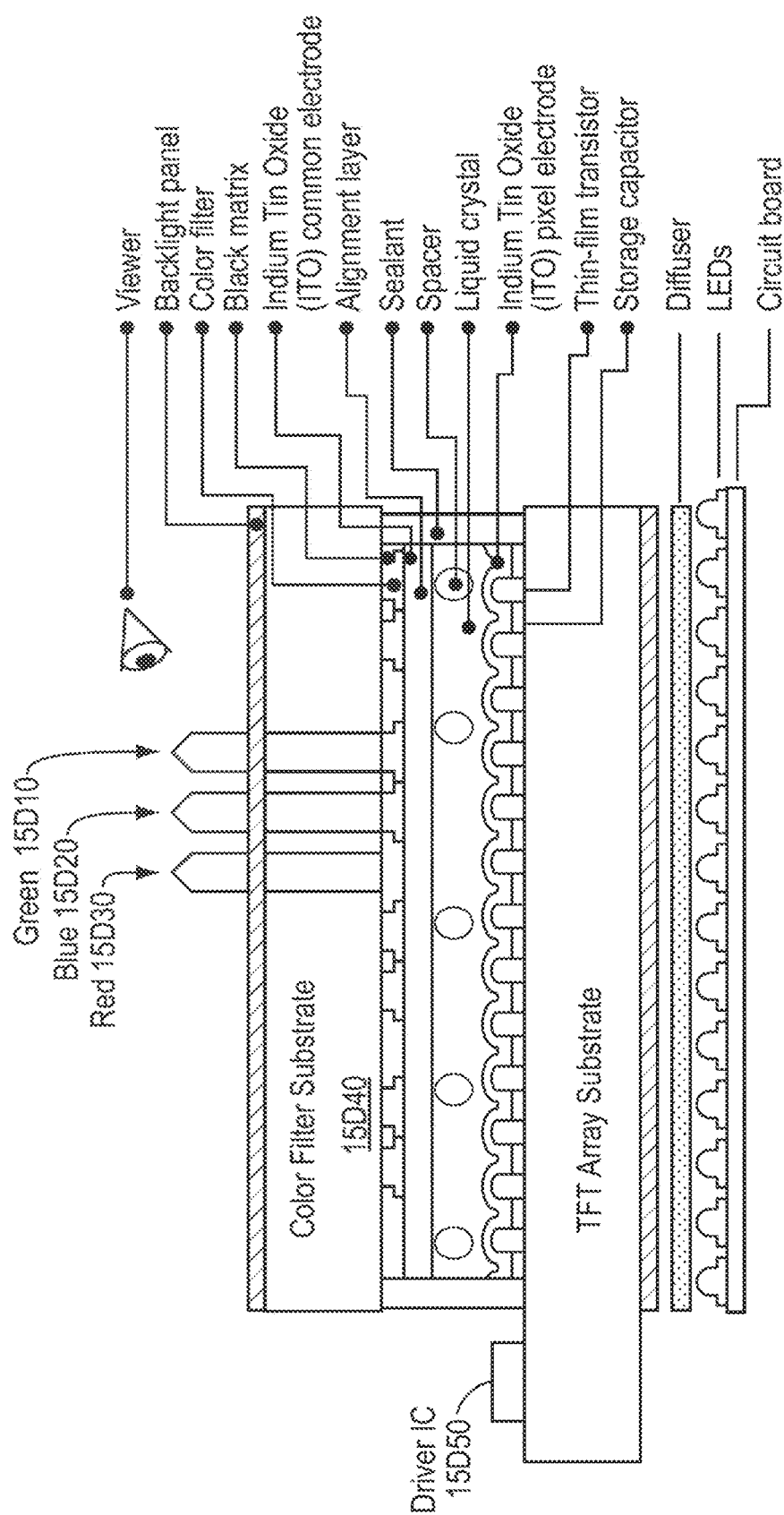
FIG. 15D depicts one embodiment of the present disclosure as can be applied toward lighting applications.
Figure 15E:
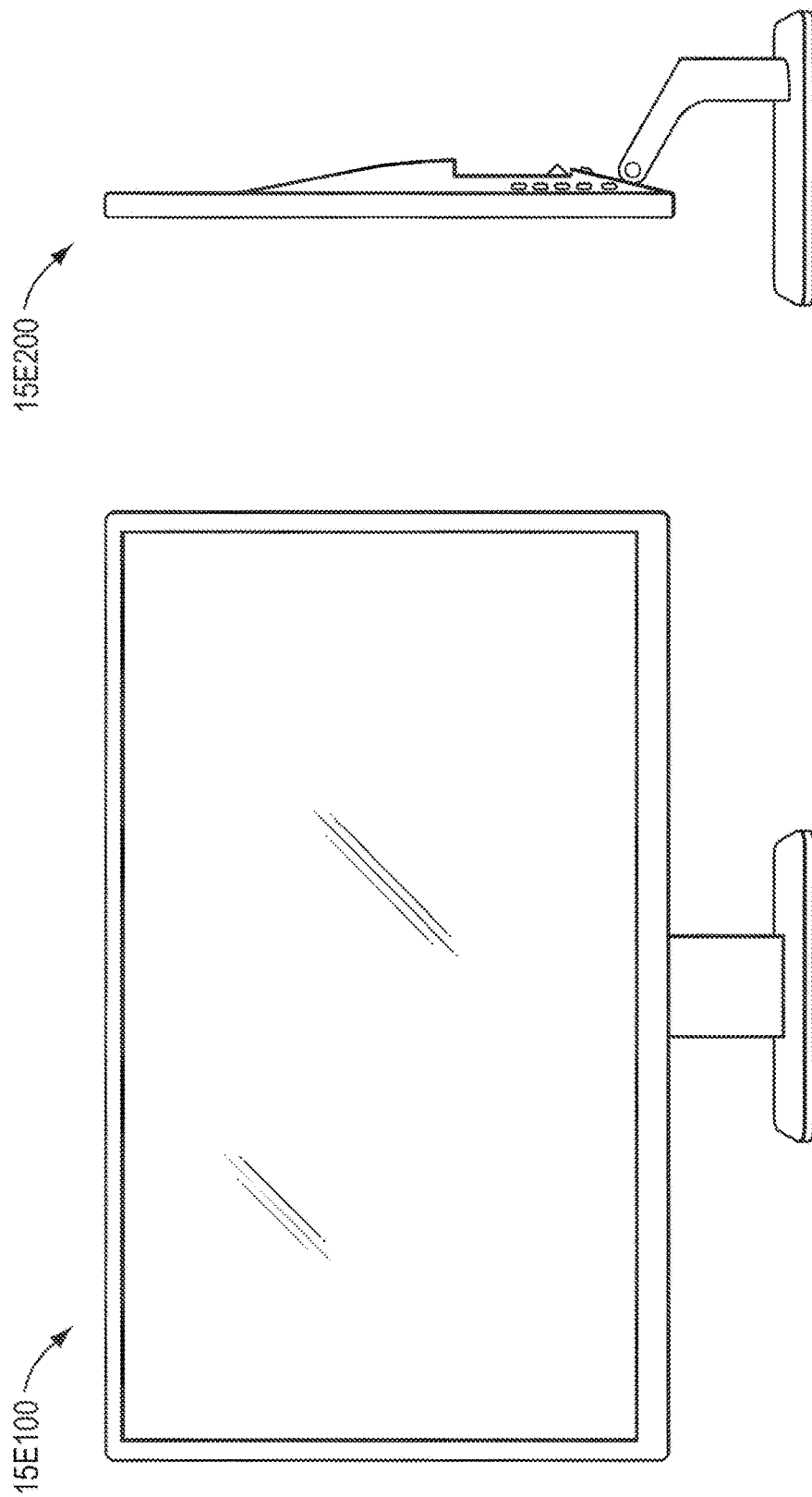
FIG. 15E depicts one embodiment of the present disclosure as can be applied toward lighting applications.

FIG. 4I shows measured SPDs 4100 for two display systems with a white screen—a laptop screen 402 and a smartphone screen 404. Examples of other display systems are illustrated in FIGS. 15D through 15E. Both displays shown in FIG. 4I have CCTs of about 6500K, which is typical for display screens. Both are lit by blue-primary LEDs and the emission spectra are characterized by a large blue peak. The relative circadian stimulation is about 330% for the laptop and about 470% for the phone screen.

Figure 4J:
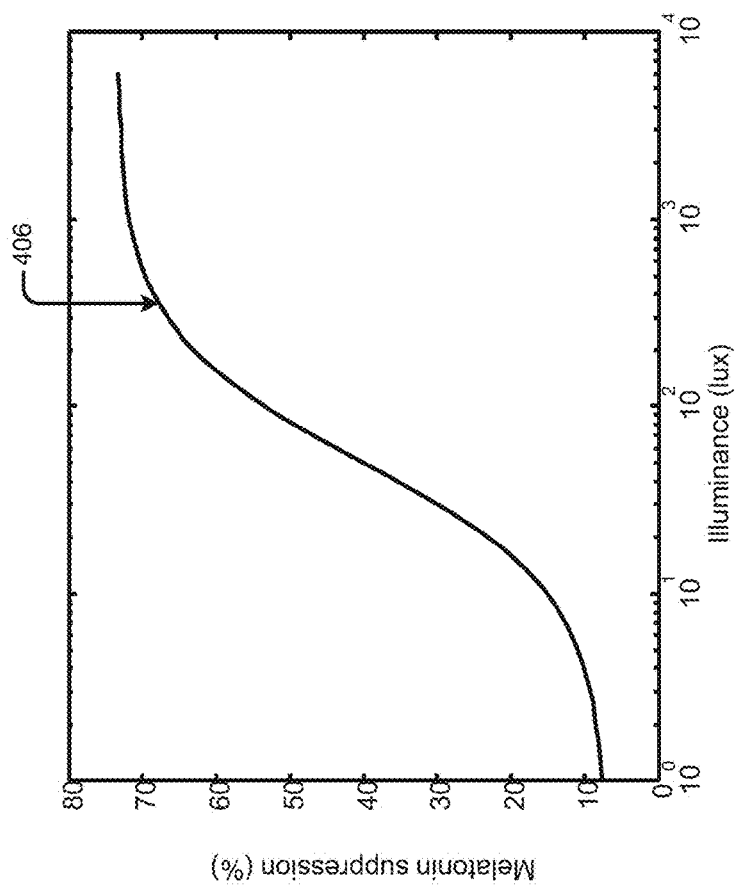
FIG. 4J shows predicted melatonin suppression, according to some embodiments.

FIG. 4J shows the predicted melatonin suppression 406 (after 90 min exposure to a white screen of a smartphone) versus luminance for the smartphone screen. In practice, luminance levels for displays can be high—one hundred to several hundreds of lux in some cases (for instance if the device is held close to the face). Therefore, the net impact on the circadian system can be significant and can disrupt sleep patterns, even for a relatively short exposure time.

For display applications, there are already software solutions that aim at reducing circadian disruption. For instance, software such as "f.lux" can adapt the CCT of the screen with time: during the day, the CCT is about 6500K, but as the night falls the CCT is 'warmed' to about 3400K.

Figure 4K:
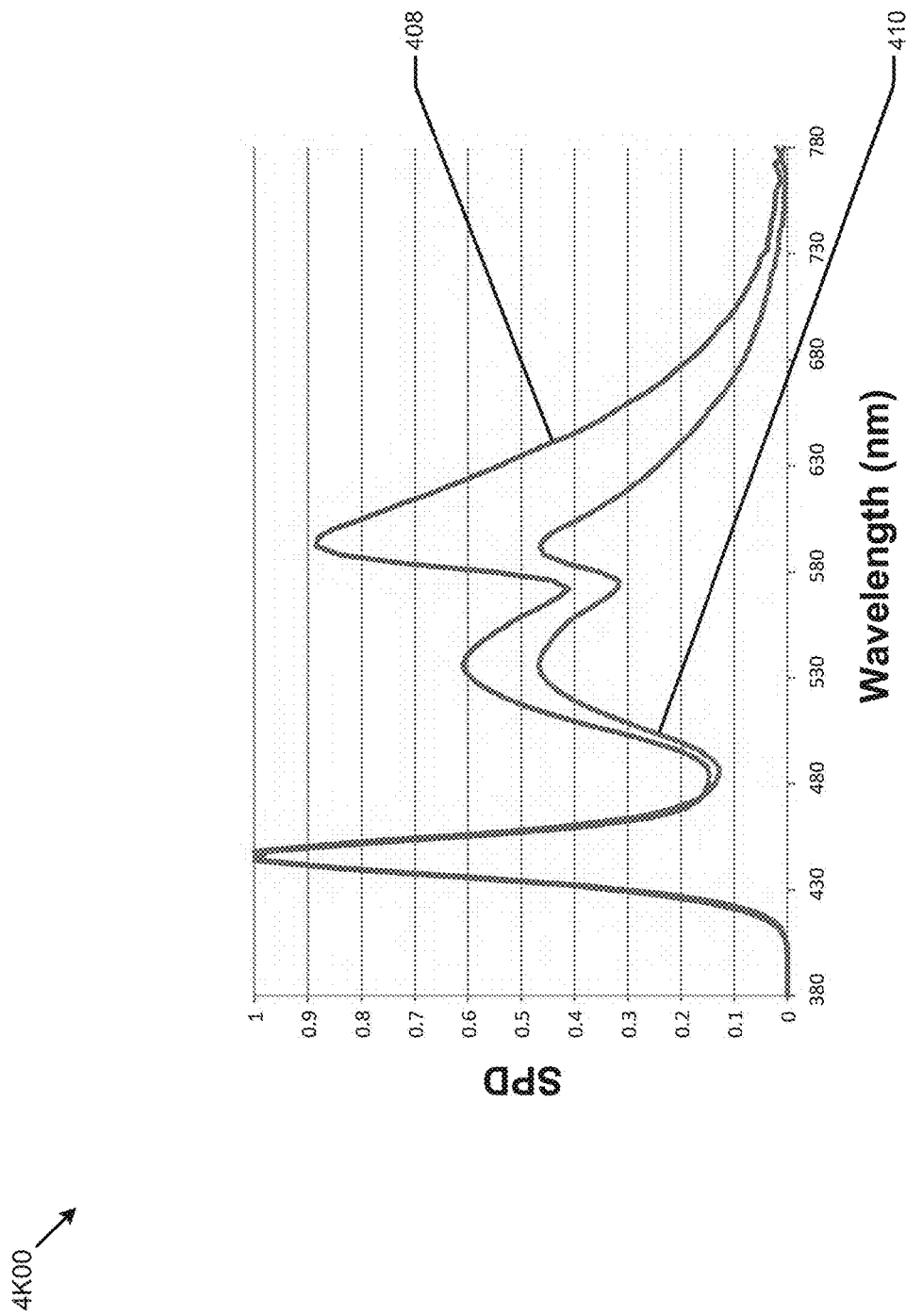
FIG. 4K shows an example of a spectrum emitted by a white screen, according to some embodiments.

FIG. 4K shows an example of a spectrum emitted by a white screen using this software: curve 410 is for the standard emission (6500K) and curve 408 is for the warmed emission (about 3400K nominally).

The reduction in CCT is beneficial because the relative circadian stimulation is less at lower CCT. Namely, the relative circadian stimulation is about 330% for the standard emission and about 210% for the warmed screen (assuming equal luminance), relative to illuminant A. While this is an improvement, stimulation is still high for the warmed screen due to the use of blue-pump LEDs. Also, it can be useful to reduce CS while still achieving the more typical electronic display white center point (typically 6000K to 7000K).

Therefore, as with lighting systems, a careful choice of the emission wavelength and profile of the primary LED and of the overall SPD is important to obtain a display system with a low circadian stimulation.

Figure 4L:
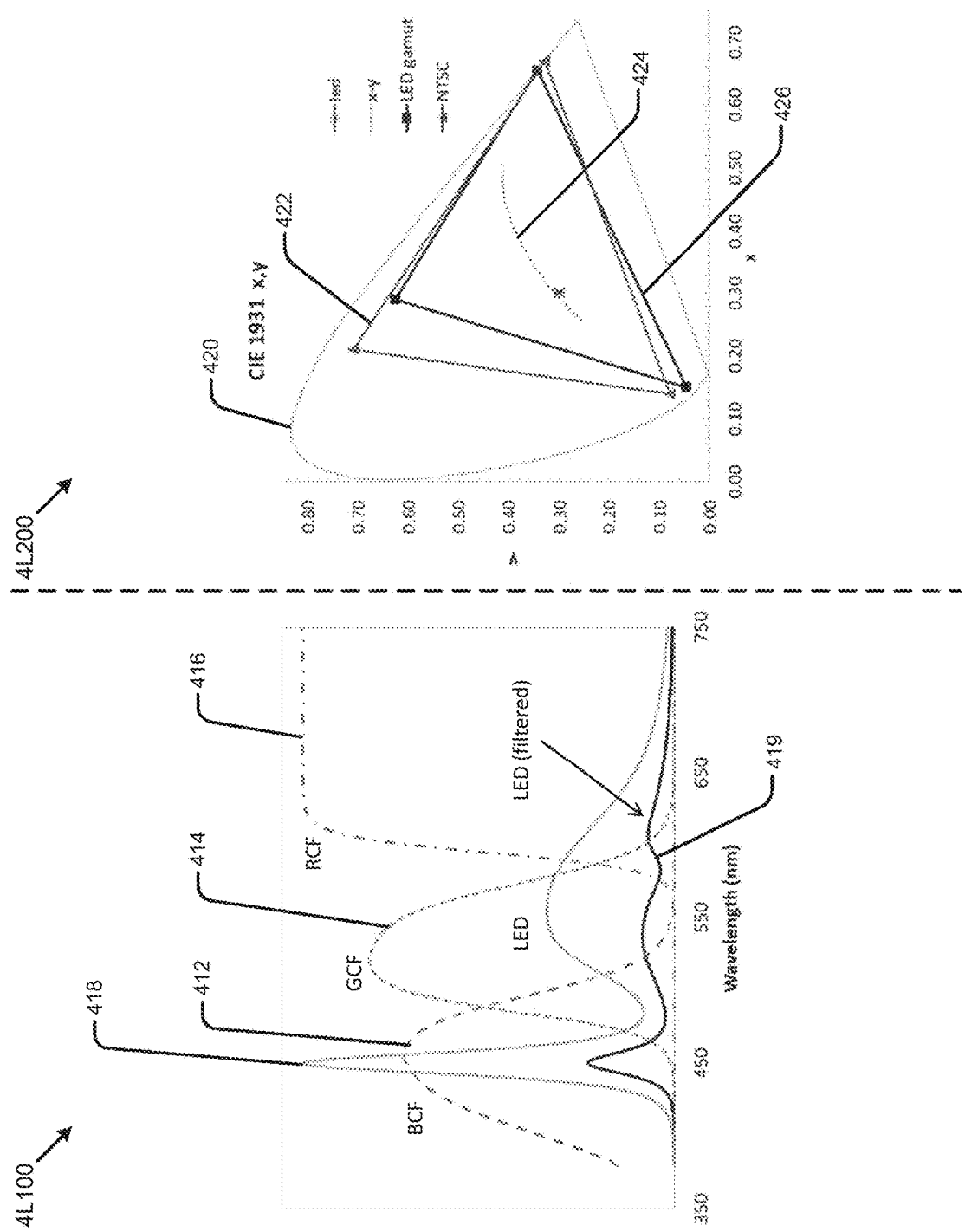
FIG. 4L illustrates relevant spectra for a typical LED-lit liquid crystal display, according to some embodiments.

FIG. 4L illustrates relevant spectra for typical LED-lit liquid crystal displays (LCD), which are used in many applications including televisions, monitors, laptop and notebook computers, gaming systems, and portable devices such as tablets, phones, MP3 players, etc. FIG. 4L shows spectra for a blue color filter 412, a green color filter 414, and a red color filter 416 (collectively, CFs) which are employed in conjunction with an LCD display to control color. A typical LED spectrum (e.g., LED spectrum 418) is a blue primary-based LED pumping a yellow (and/or red) emitting phosphor system. Filtering by the red, green and blue filters results in a transmitted spectrum, for example, a white transmitted spectrum 419 if all three filters fully transmit. A typical color gamut of this system (shown as triangle 426 in FIG. 4L) is limited in the green and red, and covers an area in x-y chromaticity space of about 79% with respect to the National Television System Committee gamut standard 422 (NTSC, 1953). As discussed above, such an LED-based source (with a primary peak wavelength typically in the 440 nm to 460 nm range) is inherently highly circadian stimulating, which can be undesirable especially for viewing in the evenings and nighttime. FIG. 4L also shows the Planckian locus 424 and the boundaries of the (xy) colorspace 420.

Figure 4M:
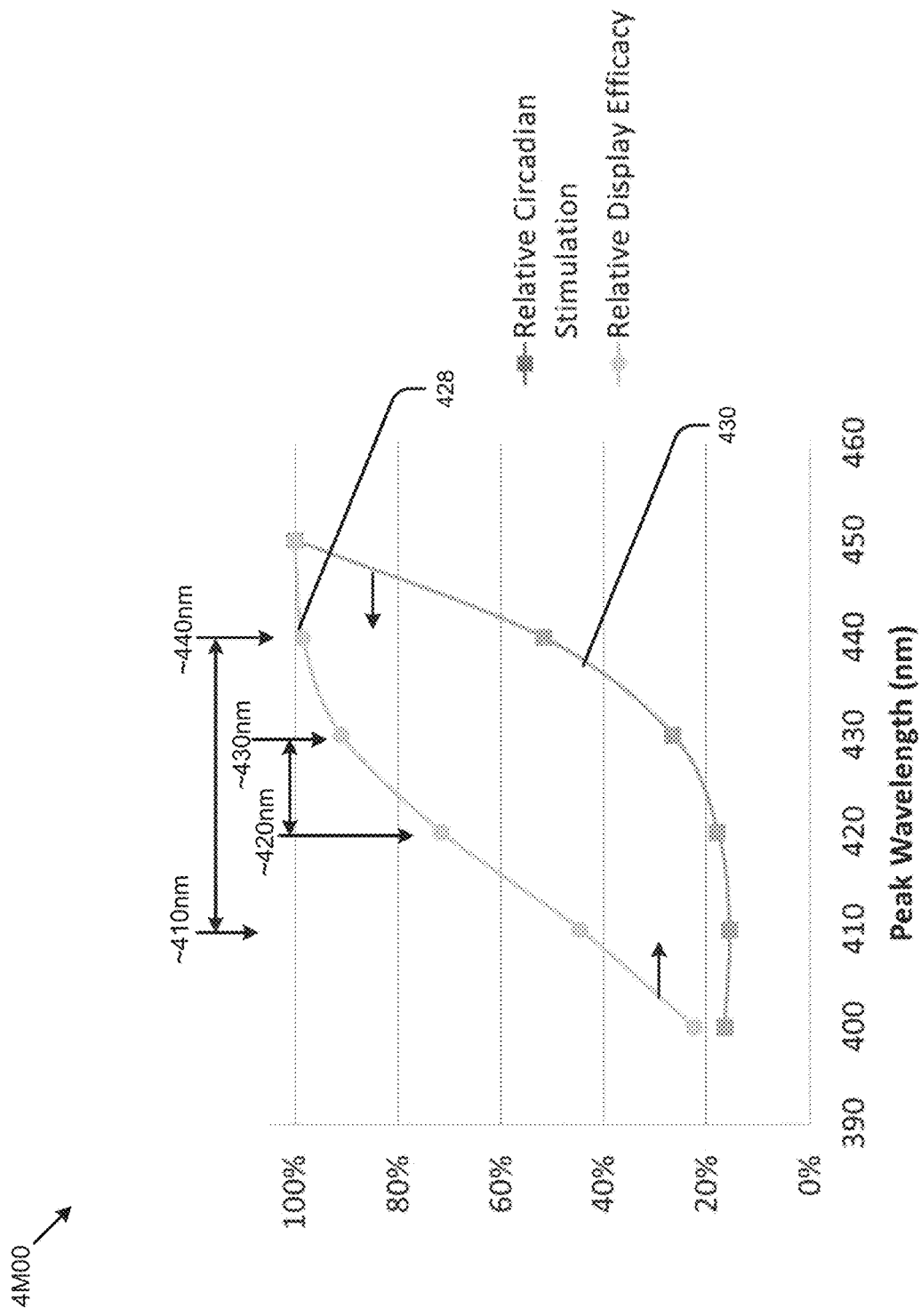
FIG. 4M shows calculated relative circadian stimulation and relative display efficacy.

FIG. 4M shows the calculated relative CS (curve 430) and relative display efficacy (curve 428) as the "blue" LED primary peak wavelength is decreased (using the same phosphor emission, while maintaining the same display white color point), using a 465 nm peak Gaussian CSWR with a FWHM of 30 nm. For peak wavelengths less than 440 nm, there is a significant drop in CS, which reaches a minimum at about 410 nm. The efficacy reduces also, but more slowly with decreasing peak wavelength, suggesting an optimum peak wavelength range between 410 nm and 440 nm or between 420 nm to 430 nm for a reduced-CS display.

FIG. 4N shows embodiments for which the phosphor system is tuned to better work with a chosen primary peak emission wavelength of 425 nm. In FIG. 4N, 83% NTSC is achieved using phosphors with peak/FWHM (emission) of 530 nm/85 nm and 605 nm/80 nm, with only about a 10% efficacy penalty compare to a 450 nm-based source achieving 79% NTSC. In FIG. 4N, 90% NTSC is achieved using phosphors with peak/FWHM (emission) of 530 nm/85 nm and 630 nm/80 nm, with only about a 20% efficacy penalty compare to a 450 nm-based source achieving 79% NTSC. One skilled in the art can identify different combinations of phosphors to achieve the desired balance of color gamut and efficacy. Use of a 425 nm wavelength primary LED can reduce CS by about five times, which is extremely significant. Referring to FIG. 4J, a five times reduction for a 100 lux display would reduce melatonin suppression from about 50% to about 20% for a 90 minute exposure.

Application of the present disclosure is not limited to displays based on LCDs. Direct-view LED displays have been demonstrated, using both organic and inorganic LEDs. In these displays individual pixels are made up of active LEDs, which include blue, green, and red emitters and are selectively controlled. Based on embodiments of the present disclosure, the "blue" emitters may be tuned to shorter wavelengths to reduce CS as described. In certain embodiments, using a 465 nm peak Gaussian CSWR with a FWHM of 30 nm, an optimum peak wavelength range for the "blue" emitter can be between 410 nm and 440 nm, or between 420 nm and 430 nm, can be chosen for a reduced-CS display.

It is also possible to mix longer and shorter wavelength primary "blue" LEDs in order to have displays in which CS can be controlled. For example, it may be desirable to have high CS stimulation in the morning (e.g., 440 nm to 460 nm primary "blue") that shifts to shorter wavelength (e.g., 420 nm to 430 nm) during the evening. This can be done by including two sets of primary "blue" LEDs in the display and can be implemented in both LCD and direct-view LED-based displays.

In some cases the color point (or more generally the spectrum) of the embodiments can be tuned automatically in response to behavior or actions of the end user. Examples of such trigger events include the presence of the end user in a room (or a part of the room) for a given amount of time, the movement of the user across the space, the user's general level of activity, specific words or gestures, and/or actions on a device (a smartphone for instance). Such responses may be employed to match the spectrum to the condition of the user (for instance, lower the circadian cycle when the user becomes sleepy or prepares for sleep) or to modify the condition of the user (e.g., detect sleepiness and increase circadian stimulation to lessen it). In some cases, the response can be determined by the user's behavior in combination with other measurable conditions or cues such as time of the day, weather and/or changing weather, amount of outdoor light, etc. In some cases, the cues can be obtained from another "smart" system (another appliance, a smartphone, or other electronic device) which monitors the user's behavior—the cues can then be communicated over a network (wired or wireless) between said smart system and the lighting system, such as a network enabled by a smart-home hub. In some cases the cues relate to the user's past behavior, such as the time the user woke up or his past sleep pattern, which has been recorded by a system such as the user's smart phone.

In some cases, a response can be predetermined by the manufacturer of the system so that a given set of cues leads to a deterministic response. In other cases, the lighting system "learns" from the user. For instance, in a teaching phase, the user (or another person) manually tunes the spectrum. The system learns to associate these settings with specific cues and the tuning is then performed automatically in response to the cues, (e.g., rather than being triggered manually). Learning can be achieved by a variety of machine-learning techniques known to those skilled in the art, such as via a neural network and/or using Bayesian inference.

A specific example of the previous scenario is as follows: The user follows a routine (e.g., a series of actions performed repeatedly with some periodicity) a few hours before going to bed. Such a routine might include leaving the dining table, brushing his teeth, watching TV etc. Cues of this routine are collected by various appliances (TV, toothbrush, motion sensors) and communicated with the lighting system through a wireless protocol. In the teaching phase, the user also tunes the spectrum of the lighting system to reduce circadian stimulation—for example, the user the lighting system to a non-stimulating setting a few hours before going to bed. Once the system has associated these settings with one or more cues of the routine, and with an approximate hour, the tuning occurs automatically to help reduce the circadian response before the user goes to bed. Conversely, tuning can also occur in the morning to stimulate the circadian system.

Such automated behavior can be used for a variety of light-emitting systems—including lighting appliances per se, and for display systems (e.g., TV and computer screens, tablets, phones, etc.). Such lighting systems may for instance adapt their spectrum to reduce circadian stimulation a given time before the user goes to bed. In the case of display systems, the change in LED spectrum may be combined with software changes (such as the screen's color point) in order to further reduce circadian stimulation. Such automated behavior can be implemented in a wide variety of lighting situations. Strictly as one example, a light strip can be fitted with sensors to take-in and/or learn from measurable aspects and/or changes in the environment, and in response, tune circadian-friendly emissions.

While the previous examples assumed a domestic setting, such embodiments with automatic or 'smart' tuning can be used in other contexts such as in a professional context. For example, in an office setting, the lighting system may adapt to monitor used activity and increase CS accordingly; or the CS may be increased in the morning, reduced near the end of the work day, or adapted to complement the outside lighting conditions (which could vary with weather and season). System tuning may follow a simple timing scheme or also take into account the workers' behavior. Embodiments may also be used in other contexts where sleep pattern is affected, including night-shift worker facilities, long-range travel (such as airplane flights), care facilities for the elderly.

Further, in various cases, the intensity of the light emitted by the system may be tuned together with its spectrum to further influence CS. For instance, the intensity may be dimmed as the spectrum is tuned for lower CS. In the case of a display, the luminance of the display may be dimmed and its CS may be lowered if the ambient light in the room decreases—this can be detected by a simple light sensor connected to the display.

Figure 5A:
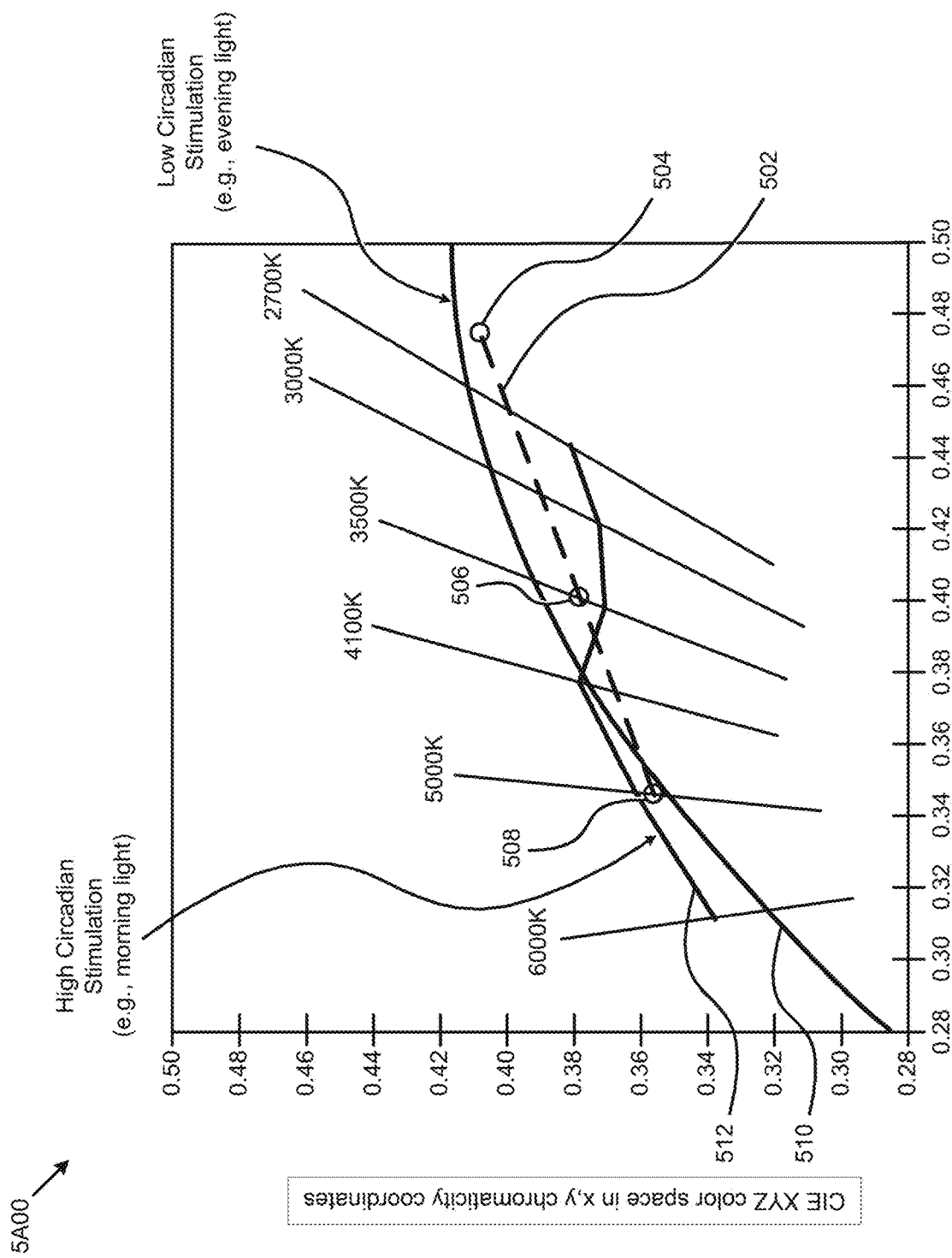
FIG. 5A is a chart showing a linear chromaticity curve in x-y chromaticity space as produced by a circadian-friendly LED light source, according to some embodiments.

FIG. 5A is a chart 5A00 showing a linear chromaticity curve 502 produced by a circadian-friendly LED white light source in x-y chromaticity space. FIG. 5A also shows the Planckian loci 510 and minimum-hue-shift curve 512 as described by Rea and Freyssinier, Color Research and Application 38, 82-92 (2013).

The Planckian loci form a curve in chromaticity space, leading to the popular notion that a linear dual-track tunability cannot properly replicate white emission across a wide range of color temperatures. However, recent psycho-physical experiments show that the definition of "white" may deviate from the Planckian curve. In particular, subjects tend to observe less tint for color points below the Planckian loci.

This observation has two ramifications: 1) a person's perception of "white" is somewhat arbitrary, and 2) tinting below the Planckian curve may not only be acceptable, but perhaps preferred. Opening up this region in chromaticity space allows for the engineering of dual-channel tunable white emission. The chromaticities for the three color temperatures described for a circadian friendly light-source (FIG. 2A) are shown (e.g., see point 504, point 506, and point 508) superimposed on the Planckian loci and the "minimum-hue-shift" points. Based on the arguments above, these three color points (and those in between) can provide an acceptable white appearance, as well as good color rendering properties.

Again this is not trivial to achieve because the most obvious way to reduce the CS of a light source is to remove blue or cyan light, thus shifting the chromaticity above the Planckian (and away from the preferred chromaticity curve 502 shown in FIG. 5A).

Figure 5B:
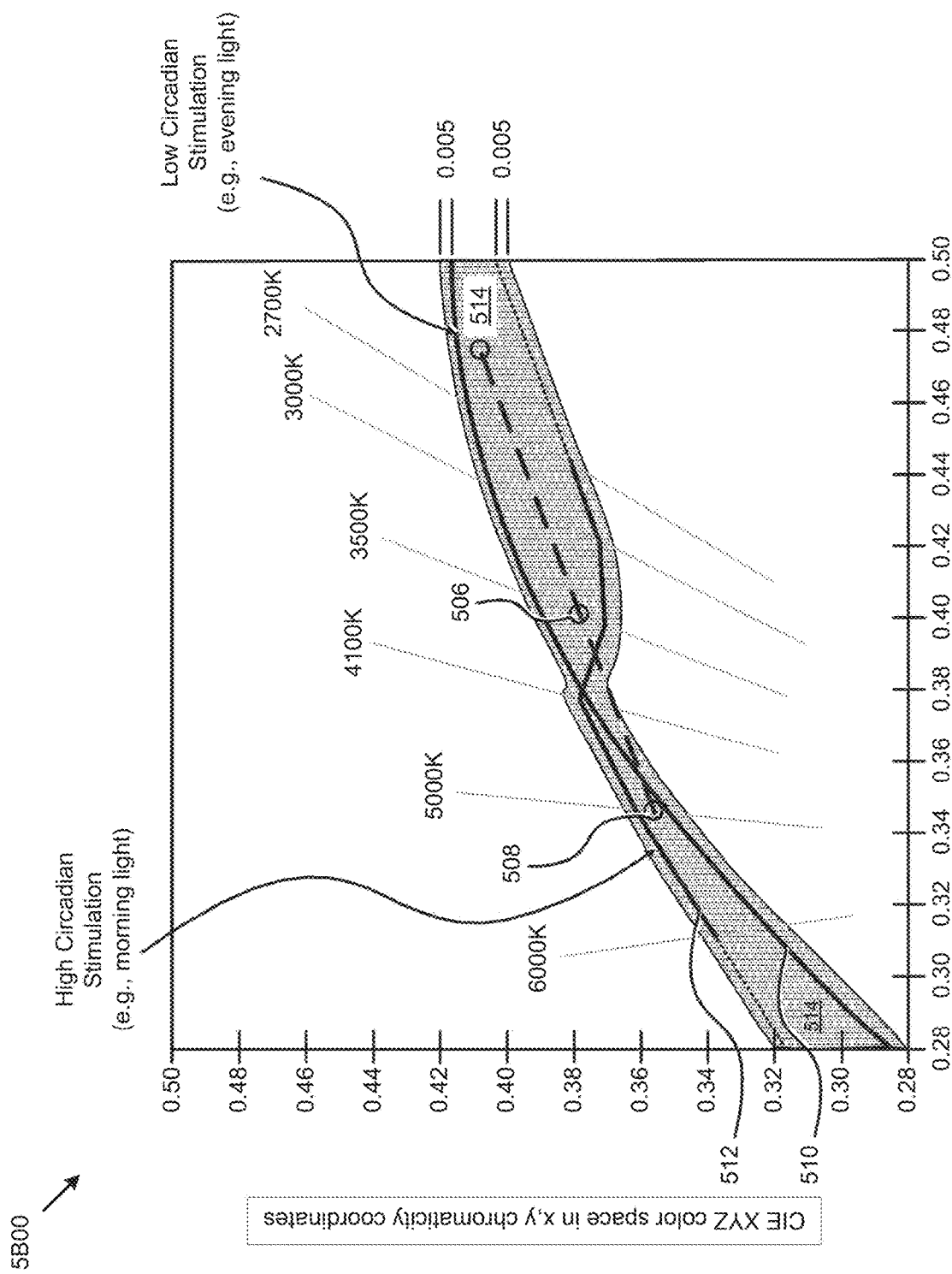
FIG. 5B is a chart showing the shape of a white light bounding region as produced by a circadian-friendly LED light source, according to some embodiments.

FIG. 5B is a chart 5B00 showing the shape of a white light bounding region 514 as produced by a circadian-friendly LED white light source, according to some embodiments. The white light bounding region 514 is taken as the range limits of the Planckian loci 510 and "minimum-hue-shift" curves, inclusive of a ±0.005 border region in x-y chromaticity space.

As shown in FIG. 5B, the white light bounding region is highlighted with hatching. In particular, the hatched region 514 represents varying ratios of color mixing, and bounds of a white light region.

In yet other embodiments, the change in circadian stimulation is not associated with a change in CCT or chromaticity. This can be useful in situations for which a given CCT (e.g., 3000K or 6500K) is desired at all times, but the stimulation should vary through the day. This can be useful for lighting applications and for display applications, where CS may be changed without the user being aware in a change in illumination. Such embodiments may, for example, be achieved by combining two LED-based tracks emitting light with a CCT of 3000K. One track can have a large relative circadian stimulation, and the other can have a low circadian stimulation. More specifically, the first track may include blue pump LEDs and phosphors and the second track may include violet LEDs and phosphors. As disclosed herein, the emission spectrum from each track can also be designed to provide high quality of light (e.g., a CRI above 80). In such systems, it may be desirable to design the spectra such than their chromaticities are similar perceptually rather than nominally. Alternatively, it may be desirable to compute the chromaticities with suitable color matching functions (CMFs) such as the 1964 CMFs or other modern CMFs, rather than the conventional 1931 2 degree CMFs. This is because the predictions of the 1931 2 degree CMFs are sometimes poorly representative of user perception. In addition, chromaticity calculations may be performed for a given demographic group (e.g., taking into account the reduction of sensitivity to short-wavelength light for elderly users).

Such embodiments, with a stable CCT, are illustrated in FIG. 5C, in which two sets of LED-based sources are controlled independently: (1) a blue primary based LED white source at 3300K with CRI about 80 and R9 greater than 0 ("BLED" 502), and (2) a violet primary based LED white source at 3300K with CRI about 80 and R9 greater than 0 ("VLED" 504). When the BLED devices are on and the VLED off, the circadian stimulation is high (210% of CIE A). Alternatively, When the VLED devices are on and the BLED off, the circadian stimulation is low (54% of CIE A). In mixed combinations, the circadian stimulation varies between these two levels; however, the chromaticity is nominally unchanged. In other embodiments the primary blue LEDs could be replaced by blue phosphors pumped by shorter wavelength LEDs. FIG. 5C2 shows the CIE 508 for an LED-based white light source described above and FIG. 5C3 shows an example of the combined VLED and BLED spectrum 506. The CS for representative BLED fractions is provided in FIG. 5C4.

Here again, the change in CS can also be related to a change in relative spectral content (e.g., fraction of the SPD) Fv in the 'violet-blue' (VB) range 400 nm to 440 nm and Fc in the 'blue-cyan' (BC) range 440 nm to 500 nm. Referring to FIG. 5C1, for SPD 502, Fv=0.01 and Fc=0.14 and for SPD 504 Fv=0.24 and Fc=0.05.

In certain embodiments, an LED emission source is characterized by a color rendering index above 80; a Fv of at least 0.01, at least 0.05, at least 0.1, at least 0.15, at least 0.2, and in certain embodiments, at least 0.25; and an Fc of at least 0.01, at least 0.05, at least 0.1, at least 0.15 at least 0.2, at least 0.25, at most 0.01, at most 0.05, at most 0.10, at most 0.15, at most 0.20 or at most 0.25; or a combination of any of the foregoing.

Figure 6:
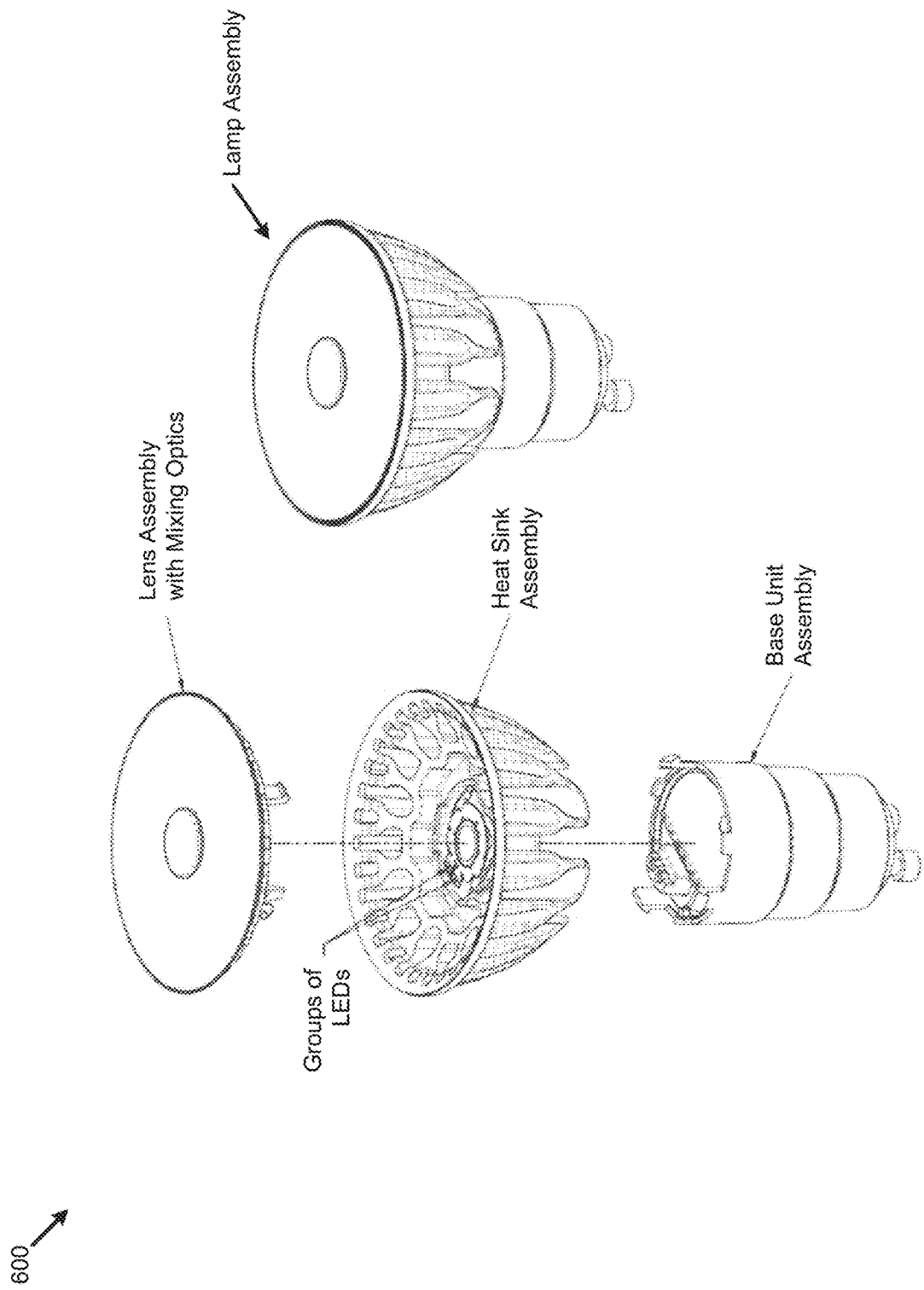
FIG. 6 shows an exploded view of an assembly view of an LED lamp forming a circadian-friendly LED light source, according to some embodiments.

FIG. 6 shows an exploded view 600 of an assembly view 6B00 of an LED lamp forming a circadian-friendly LED light source.

As shown in FIG. 6, the exploded view 600 includes a GU10 (10 mm "twist-lock") base for connecting to a 120/230-volt source. Such an embodiment can be used as an MR16 halogen light replacement 6B00 for the 35/50 watt halogen lamps in use since the mid-2000s.

The lamp shown in FIG. 6 is merely one embodiment of a lamp that conforms to fit with any one or more of a set of mechanical and electrical standards.

The list above is representative and is not intended to include all the standards or form factors that may be utilized with embodiments described herein.

Figure 7:
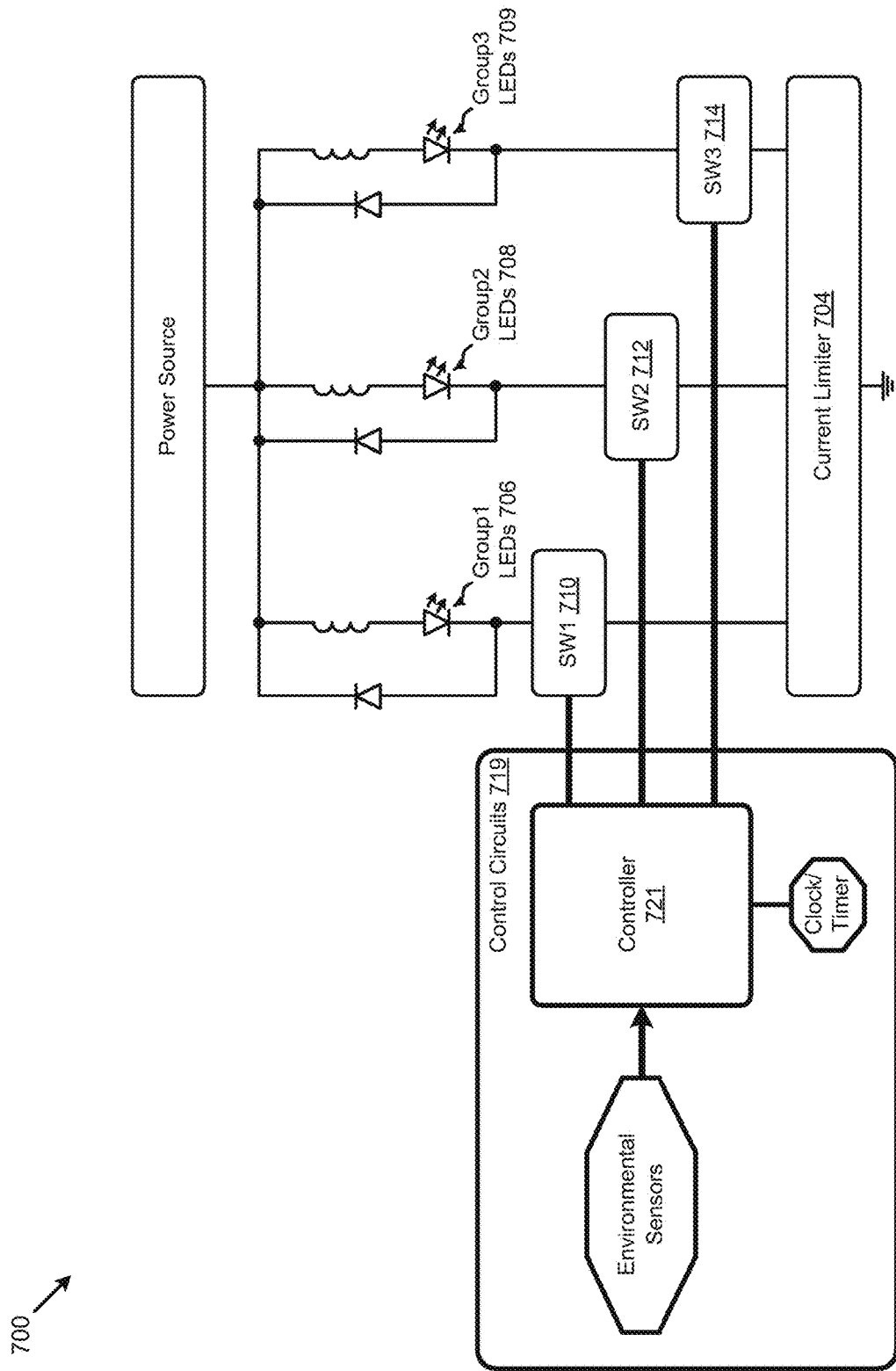
FIG. 7 shows a schematic of a multi-track driver control system as used in an LED lamp employing a circadian-friendly LED light source, according to some embodiments.

FIG. 7 shows a schematic of a multi-track driver control system as used in an LED lamp employing a circadian-friendly LED light source. As shown in FIG. 7, the emission of multiple strings of LEDs is separately varied such that the ratio of output of one string with respect to another string is varied according to a time-based function. For example, the clock/timer can model the sunrise and sunset timings over a 24-hour period, and during the 24 hour period, a violet emitting LED with blue phosphor can be attenuated in afternoon and evening hours. In dual track systems, a linear chromaticity curve 502 can be implemented. With three or more tracks (e.g., the shown three groups of LEDs) non-linear chromaticity curves can be enabled. Suitable driver control systems are disclosed in U.S. Application No. 62/026,899 filed on Jun. 25, 2014, which is incorporated by reference in its entirety.

Control circuits (e.g., control modules) can employ any known-in-the-art techniques, including current limiting based on current or voltage sensing, and/or current limiting based on temperature sensing. More specifically, one or more current limiters (e.g., current limiter 704) can be controlled by any known techniques. The controller and/or current limiters in turn can modulate the current flowing to any individual groups of LEDs (e.g., Group1 LEDs 706, Group2 LEDs 708, GroupN LEDs 709, etc.), which current flowing to any individual groups can be individually increased or decreased using FETs or switches (e.g., SW1 710, SW2 712, SW3 714, etc.). The shown control circuits 719 comprise environmental sensors, and a clock/timer, each of which provide inputs to controller 721, which in turn serves to modulate the current flowing to any individual groups of LEDs (e.g., Group1 LEDs 706, Group2 LEDs 708, GroupN LEDs 709, etc.).

Figure 8:
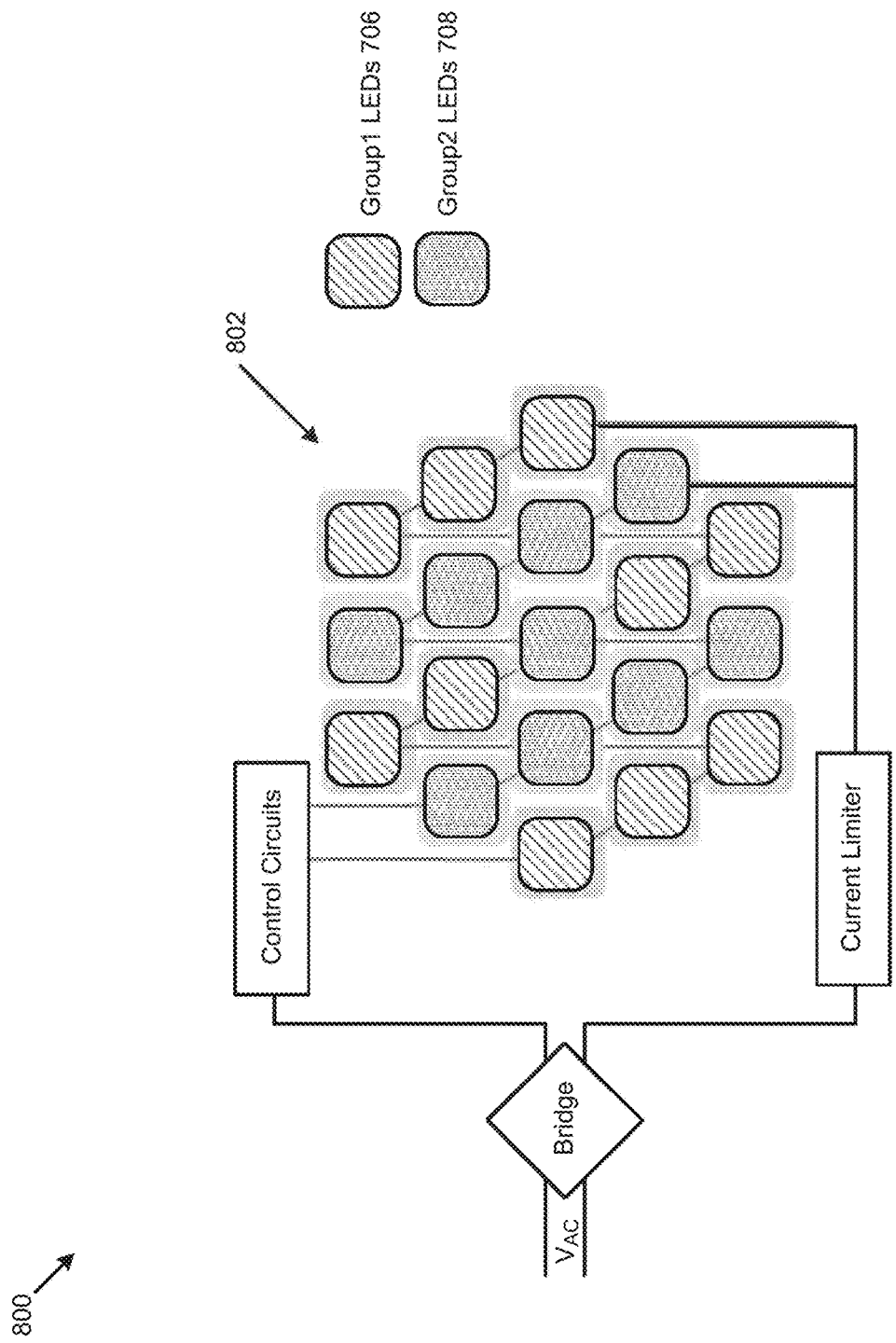
FIG. 8 shows two strings of LEDs in an intermixed physical arrangement to form a two-channel, circadian-friendly arrangement as used in an LED lamp, according to some embodiments.

FIG. 8 shows two strings of LEDs in an intermixed physical arrangement 802 to form a two-channel, circadian-friendly arrangement 800 as used in an LED lamp. As shown, the control circuits can employ any known-in-the-art techniques to independently modulate the current flowing to either of the shown groups of LEDs (e.g., Group1 LEDs 706, Group2 LEDs 708).

Each of the Group1 LEDs, and Group2 LEDs comprise individual patterned-phosphor chips so that the circadian-friendly source may be condensed into a compact area, for example, for directional lighting. A mixing optic can be included to mix the two types of LED light emissions (e.g., for homogeneity). The arrangement shown is illustrative and other arrangements are suitable. Techniques for patterning phosphors are disclosed in U.S. Pat. No. 9,761,763, which is incorporated by reference in its entirety.

In some embodiments of the invention, the LEDs from Groups 1 and 2 are optically isolated from each other. For instance, an optical barrier (which may be a reflective element, or an optical element such as a lens) is positioned between the LEDs from Groups 1 and 2. Thus, the radiation emitted by Group 1 LEDs does not significantly impinge on the Group 2 LEDs, and vice-versa. For instance, in some embodiments, less than 10% (or less than 1%) of the radiation emitted by Group 1 LEDs impinges on Group 2 LEDs, and vice-versa. This may be desirable in some embodiments where cross-pumping between the LEDs is not desirable. For instance, in some embodiments Group 1 LEDs emit an SPD with little blue light having relatively low circadian stimulation and Group 2 emits an SPD with more blue light having relatively high circadian stimulation; in such embodiments it may be undesirable that radiation from Group 1 LEDs optically excite Group 2 LEDs, as this may result in luminescence from Group 2 LEDs even though the Group 2 LEDs are not electrically injected (thus leading to an unwanted presence of blue light in the emitted SPD). Likewise, the optical design of the system, including its optics, may be designed so that there is little optical cross-excitation between Group 1 and Group 2 LEDs. One skilled in the art may achieve this by designing the optical system while taking into account reflection and scattering of light emitted by Groups 1 and 2.

More generally, in embodiments having more than one Group of LEDs emitting distinct SPDs, it may be desirable to design the system so that optical cross-excitation between Groups is minimized.

Another embodiment of the invention includes circadian-friendly directional light sources.

In some embodiments of the invention, directional light sources are implemented with a multiple-optic approach. A directional optic is attached to each LED emitter. The LED emitter may be small (it may have a characteristic lateral dimension of less than 2 mm, less than 1 mm, less than 500 um, less than 100 um). A directional micro-optic is configured to capture the light from each LED emitter. The LEDs may be separated optically by an optical blocking element. In some embodiments the directional optics are configured above the LED emitters; in others, the directional optics are configured around the LED emitters, thus capturing and directing lateral light emitted by the sides of the LED emitters. The directional optics may produce directional light beams, with the beam from all emitters blending in the far-field pattern. In some embodiments, each emitter consists of a pump LED and wavelength-converting materials. In some embodiments, Group 1 LEDs emit an SPD with little blue light having relatively low circadian stimulation and Group 2 emits an SPD with more blue light having relatively high circadian stimulation. Thus, by separately driving the LEDs of Groups 1 and 2, the emitted light can switch from a low excitation circadian-friendly mode to a circadian-entraining mode. In some embodiments, the pump LEDs of at least one Group are violet emitters. In some embodiments, the pump LEDs of the circadian-entraining Group are blue LEDs. Some embodiments comprise more than two Groups; for instance they may contain a direct green or a direct red LED. In various embodiments, the layout of the LEDs and the optics are configured to obtain a desired beam, for instance a beam with homogeneous chromaticity.

Figure 9A:
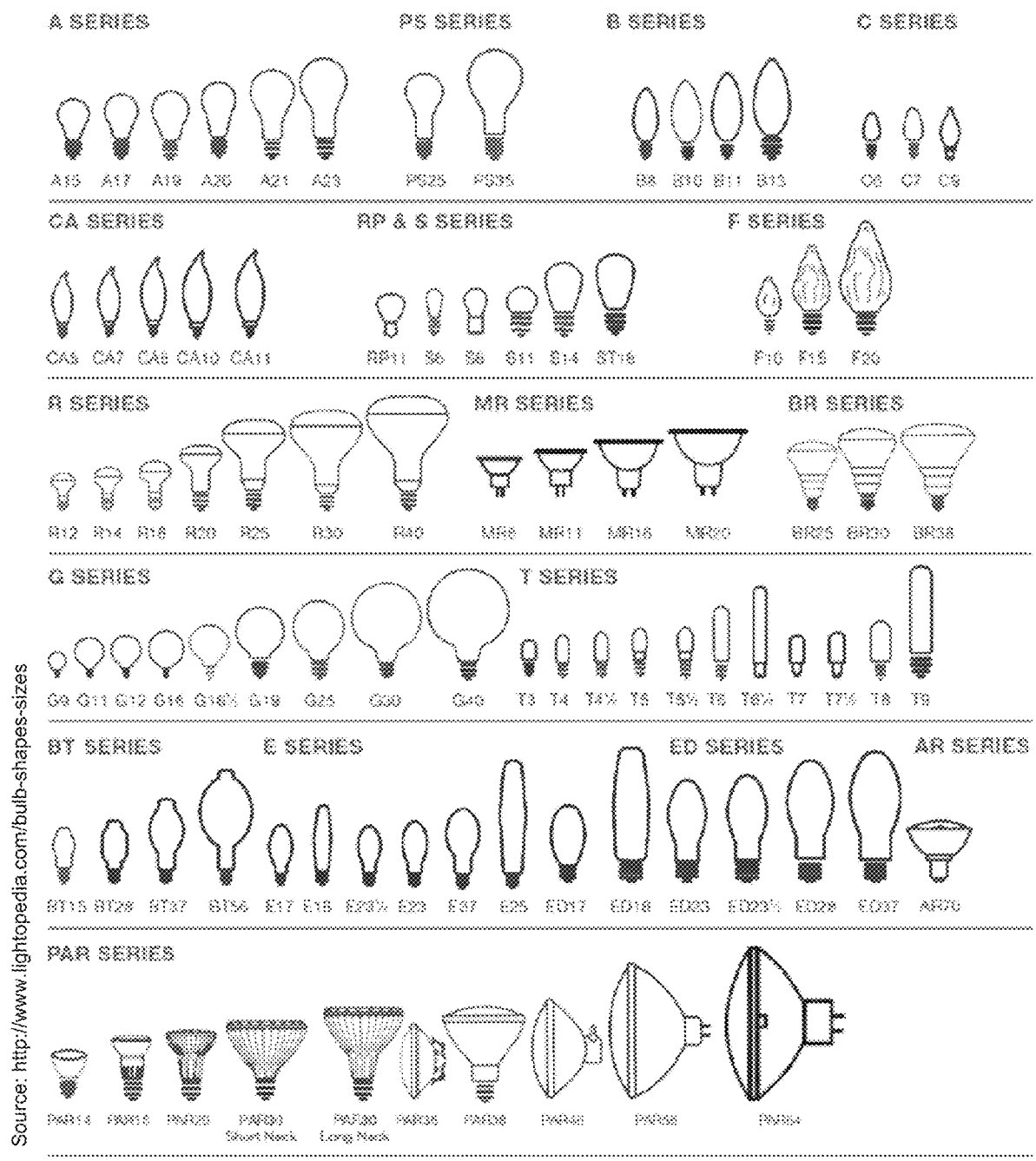
FIG. 9A presents a selection of lamp shapes corresponding to various standards, according to some embodiments.
Figure 9B:
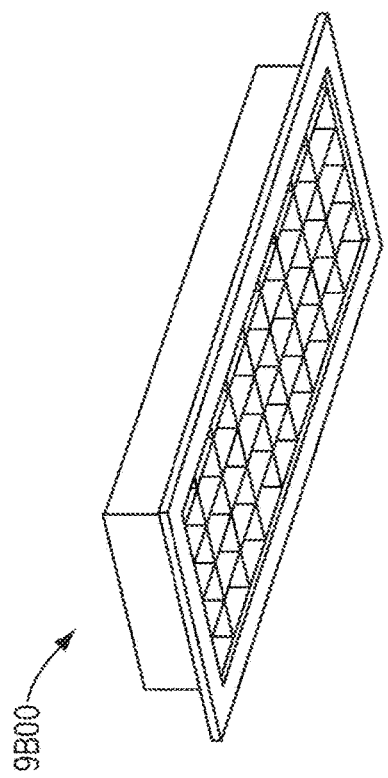
FIG. 9B presents one selection of troffers corresponding to various shapes, according to some embodiments.
Figure 9C:
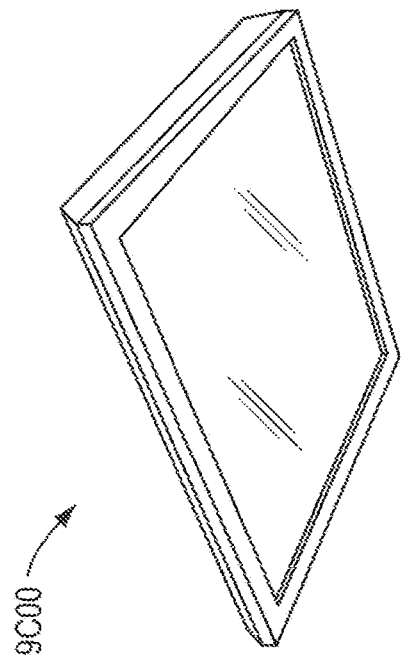
FIG. 9C presents one selection of troffers corresponding to various shapes, according to some embodiments.
Figure 9D:
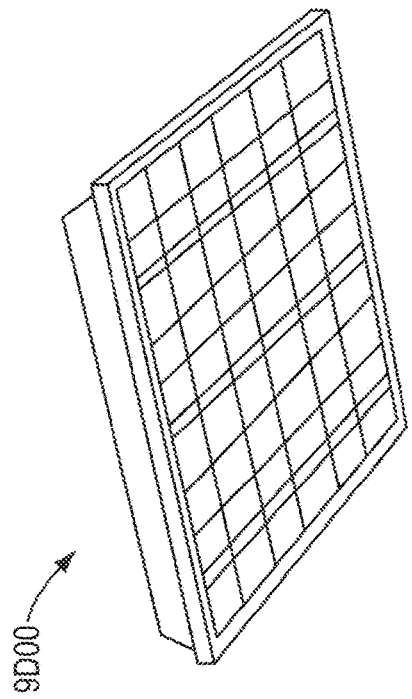
FIG. 9D presents one selection of troffers corresponding to various shapes, according to some embodiments.
Figure 9E:
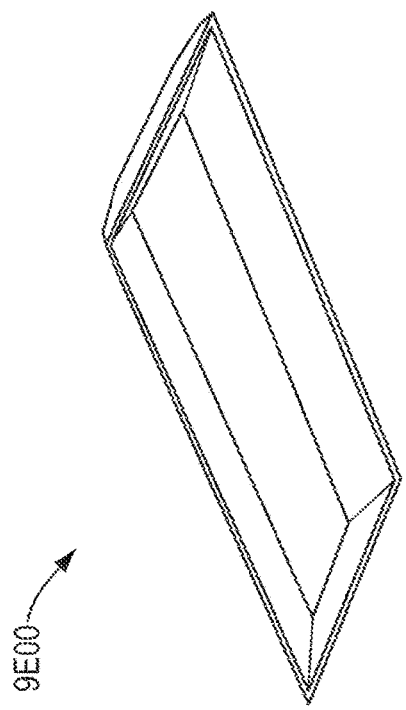
FIG. 9E presents one selection of troffers corresponding to various shapes, according to some embodiments.
Figure 9F:
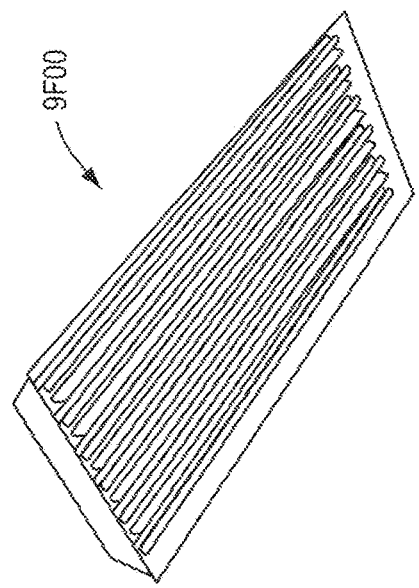
FIG. 9F presents one selection of troffers corresponding to various shapes, according to some embodiments.
Figure 9G:
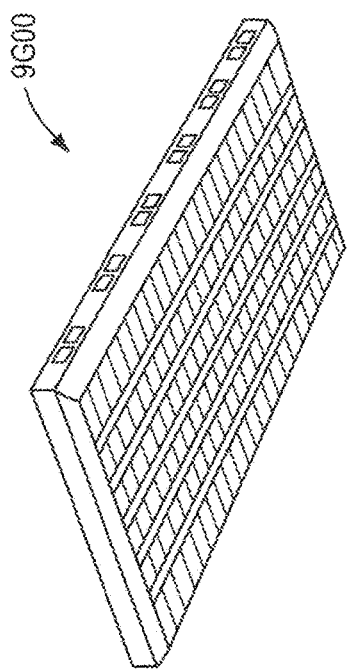
FIG. 9G presents one selection of troffers corresponding to various shapes, according to some embodiments.
Figure 9H:
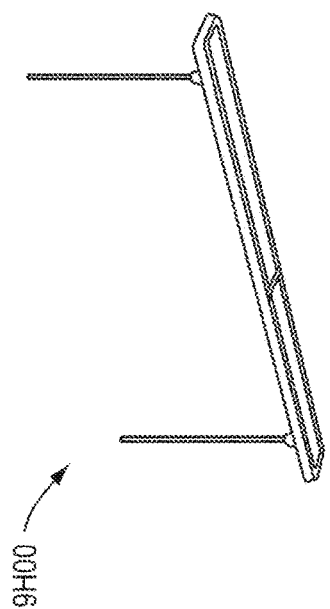
FIG. 9H presents one selection of troffers corresponding to various shapes, according to some embodiments.
Figure 9I:
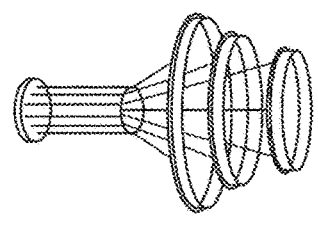
FIG. 9I presents one selection of troffers corresponding to various shapes, according to some embodiments.

FIG. 9A presents a selection of lamp shapes corresponding to known-in-the-art standards. The aforementioned lamps are merely selected embodiments of lamps that conform to fit with any one or more of a set of mechanical and electrical standards. Table 1 gives standards (see "Designation") and corresponding characteristics.

TABLE 1

| Designation | Base Diameter (Crest of thread) | Name | IEC 60061-1 Standard Sheet |
|---|---|---|---|
| E05 | 05 mm | Lilliput Edison Screw (LES) | 7004-25 |
| E10 | 10 mm | Miniature Edison Screw (MES) | 7004-22 |
| E11 | 11 mm | Mini-Candelabra Edison Screw (mini-can) | (7004-06-1) |
| E12 | 12 mm | Candelabra Edison Screw (CES) | 7004-28 |
| E14 | 14 mm | Small Edison Screw (SES) | 7004-23 |
| E17 | 17 mm | Intermediate Edison Screw (IES) | 7004-26 |
| E26 | 26 mm | [Medium] (one-inch) Edison Screw (ES or MES) | 7004-21A-2 |
| E27 | 27 mm | [Medium] Edison Screw (ES) | 7004-21 |
| E29 | 29 mm | [Addendum] Edison Screw (ES) | |
| E39 | 39 mm | Single-contact (Mogul) Giant Edison Screw (GES) | 7004-24-A1 |
| E40 | 40 mm | (Mogul) Giant Edison Screw (GES) | 7004-24 |

Additionally, the base member of a lamp can be of any form factor configured to support electrical connections, which electrical connections can conform to any of a set of types or standards. For example Table 2 gives standards (see "Type") and corresponding characteristics, including mechanical spacing between a first pin (e.g., a power pin) and a second pin (e.g., a ground pin).

TABLE 2

| Type | Standard | Pin center to center | Pin Diameter | Usage |
|---|---|---|---|---|
| G4 | IEC 60061-1 (7004-72) | 4.0 mm | 0.65-0.75 mm | MR11 and other small halogens of 5/10/20 watt and 6/12 volt |
| GU4 | IEC 60061-1 (7004-108) | 4.0 mm | 0.95-1.05 mm | |
| GY4 | IEC 60061-1 (7004-72A) | 4.0 mm | 0.65-0.75 mm | |
| GZ4 | IEC 60061-1 (7004-64) | 4.0 mm | 0.95-1.05 mm | |

TABLE 2-continued

| Type | Standard | Pin center to center | Pin Diameter | Usage |
|---|---|---|---|---|
| G5 | IEC 60061-1 (7004-52-5) | 5 mm | | T4 and T5 fluorescent tubes |
| G5.3 | IEC 60061-1 (7004-73) | 5.33 mm | 1.47-1.65 mm | |
| G5.3-4.8 | IEC 60061-1 (7004-126-1) | | | |
| GU5.3 | IEC 60061-1 (7004-109) | 5.33 mm | 1.45-1.6 mm | |
| GX5.3 | IEC 60061-1 (7004-73A) | 5.33 mm | 1.45-1.6 mm | MR16 and other small halogens of 20/35/50 watt and 12/24 volt |
| GY5.3 | IEC 60061-1 (7004-73B) | 5.33 mm | | |
| G6.35 | IEC 60061-1 (7004-59) | 6.35 mm | 0.95-1.05 mm | |
| GX6.35 | IEC 60061-1 (7004-59) | 6.35 mm | 0.95-1.05 mm | |
| GY6.35 | IEC 60061-1 (7004-59) | 6.35 mm | 1.2-1.3 mm | Halogen 100 W 120 V |
| GZ6.35 | IEC 60061-1 (7004-59A) | 6.35 mm | 0.95-1.05 mm | |
| G8 | | 8.0 mm | | Halogen 100 W 120 V |
| GY8.6 | | 8.6 mm | | Halogen 100 W 120 V |
| G9 | IEC 60061-1 (7004-129) | 9.0 mm | | Halogen 120 V (US)/230 V (EU) |
| G9.5 | | 9.5 mm | 3.10-3.25 mm | Common for theatre use, several variants |
| GU10 | | 10 mm | | Twist-lock 120/230-volt MR16 halogen lighting of 35/50 watt, since mid-2000s |
| G12 | | 12.0 mm | 2.35 mm | Used in theatre and single-end metal halide lamps |
| G13 | | 12.7 mm | | T8 and T12 fluorescent tubes |
| G23 | | 23 mm | 2 mm | |
| GU24 | | 24 mm | | Twist-lock for self-ballasted compact fluorescents, since 2000s |
| G38 | | 38 mm | | Mostly used for high-wattage theatre lamps |
| GX53 | | 53 mm | | Twist-lock for puck-shaped under-cabinet compact fluorescents, since 2000s |

The list above is representative and should not be taken to include all the standards or form factors that may be utilized within embodiments described herein.

FIG. 9B through FIG. 9I present selections of troffers corresponding to various shapes (e.g., substantially square, substantially rectangular) and installation configurations (e.g., recessed, flush mounted, hanging, etc.). Combinations of the foregoing multi-track driver control system (see FIG. 7), and strings of LEDs in an intermixed physical arrangement (see FIG. 8) can be used with the exemplary troffers and/or with any sorts of general illumination fixtures.

Other luminaires such as suspended luminaires may emit light upward rather than downward, or may emit light in both directions.

FIG. 10A through FIG. 10I depict embodiments of the present disclosure in the form of lamp applications. In these lamp applications, one or more light emitting diodes are used in lamps and fixtures. Such lamps and fixtures include replacement and/or retro-fit directional lighting fixtures.

Figure 10A:
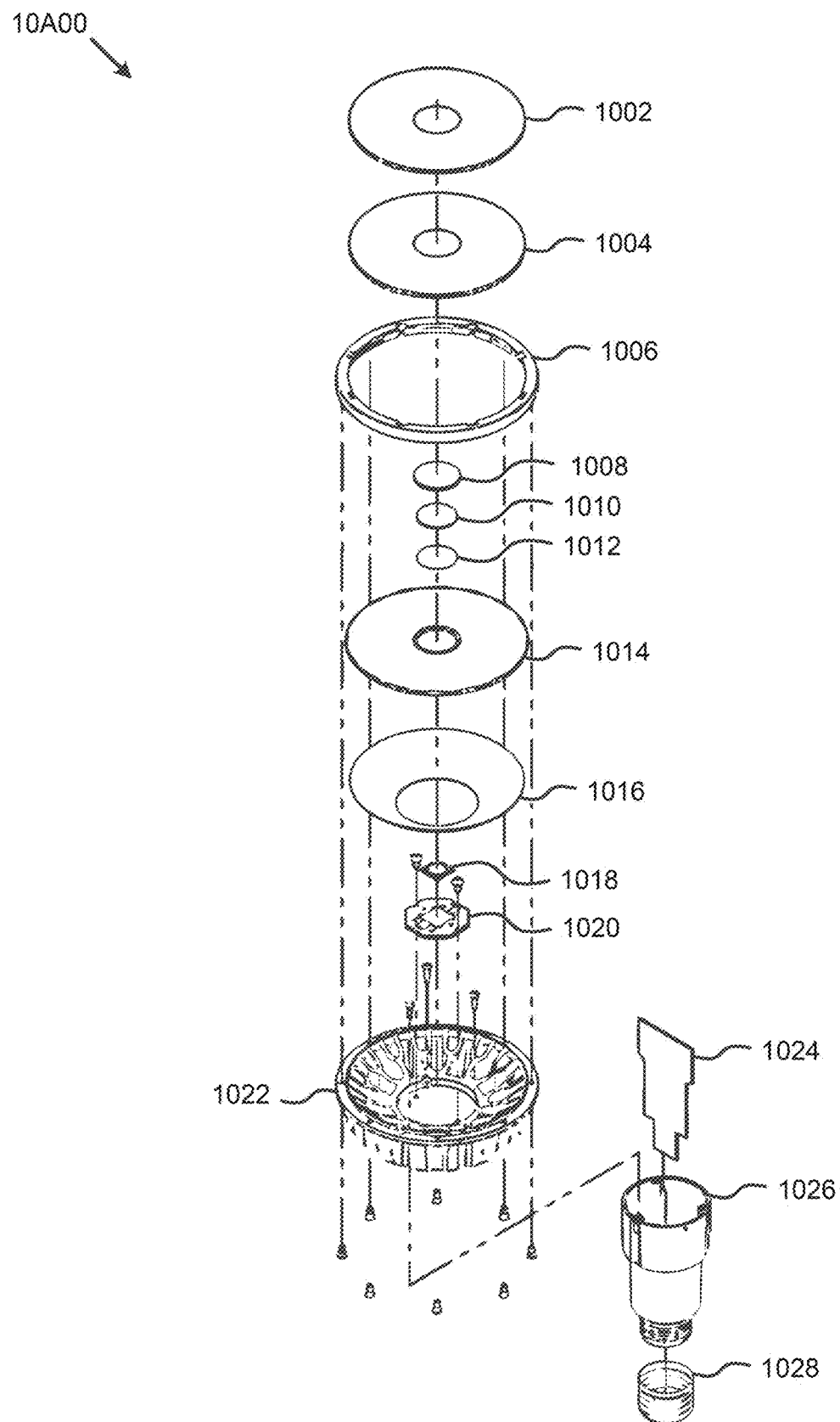
FIG. 10A depicts one embodiment of the present disclosure in the form of lamp applications, according to some embodiments.
Figure 10C:
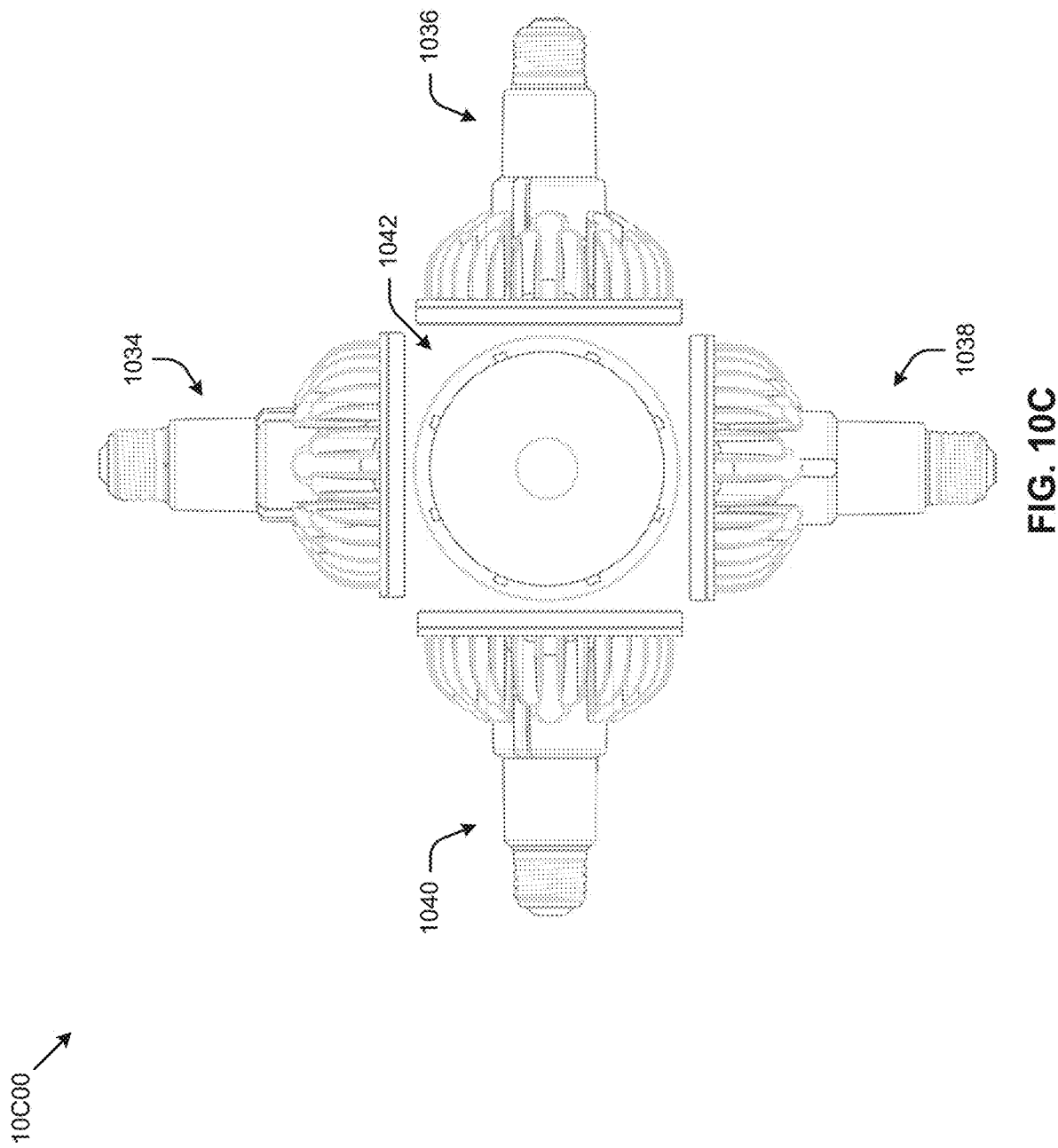
FIG. 10C depicts one embodiment of the present disclosure in the form of lamp applications, according to some embodiments.
Figure 10E:
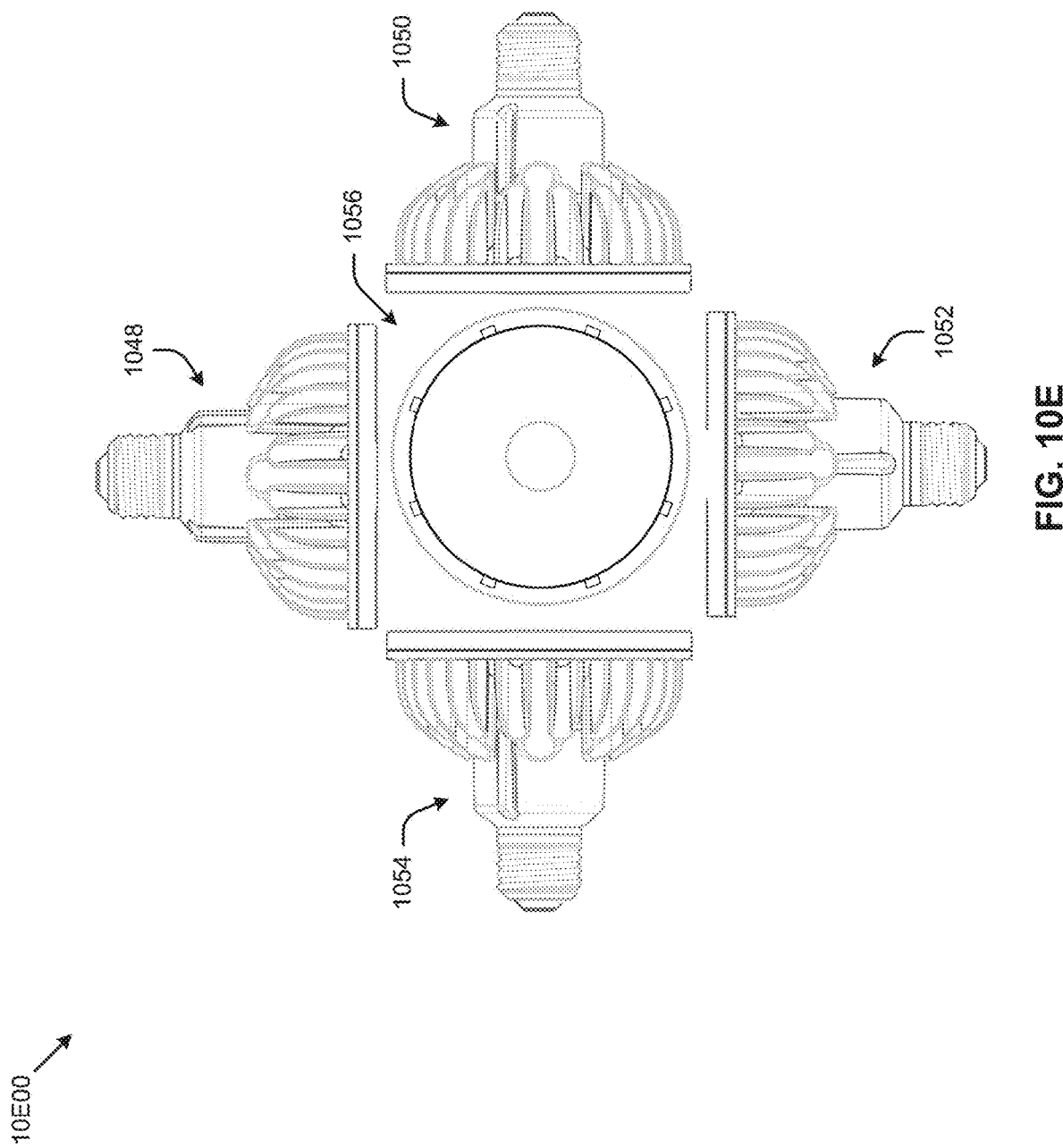
FIG. 10E depicts one embodiment of the present disclosure in the form of lamp applications, according to some embodiments.

In some embodiments, aspects of the present disclosure can be used in an assembly. As shown in FIG. 10A, the assembly comprises:
  a screw cap 1028
  a driver housing 1026
  a driver board 1024
  a heatsink 1022
  a metal-core printed circuit board 1020
  an LED light source 1018
  a dust shield 1016
  a lens 1014
  a reflector disc 1012
  a magnet 1010
  a magnet cap 1008
  a trim ring 1006
  a first accessory 1004
  a second accessory 1002

The components of assembly 10A00 may be described in substantial detail. Some components are 'active components' and some are 'passive' components, and can be variously-described based on the particular component's impact to the overall design, and/or impact(s) to the objective optimization function. A component can be described using a CAD/CAM drawing or model, and the CAD/CAM model can be analyzed so as to extract figures of merit as may pertain to e particular component's impact to the overall design, and/or impact(s) to the objective optimization function. Strictly as one example, a CAD/CAM model of a trim ring is provided in a model corresponding to the drawing of FIG. 10A2.

The components of the assembly 10B100 and assembly 10B200 can be fitted together to form a lamp. FIG. 10B1 depicts a perspective view 1030 and FIG. 10B2 depicts a top view 1032 of such a lamp. As shown in FIG. 10B1 and FIG. 10B2, the lamp 10B100 and 10B200 comports to a form factor known as PAR30L. The PAR30L form factor is further depicted by the principal views (e.g., left 1040, right 1036, back 1034, front 1038 and top 1042) given in array 10C00 of FIG. 10C.

The components of the assembly 10D100 and assembly 10D200 can be fitted together to form a lamp. FIG. 10D1 depicts a perspective view 1044 and FIG. 10D2 depicts a top view 1046 of such a lamp. As shown in FIG. 10D1 and in FIG. 10D2, the lamp 10D100 and 10D200 comports to a form factor known as PAR30S. The PAR30S form factor is further depicted by the principal views (e.g., left 1054, right 1050, back 1048, front 1052 and top 1056) given in array 10E00 of FIG. 10E.

The components of the assembly 10A00 can be fitted together to form a lamp. FIG. 10F1 depicts a perspective view 1058 and FIG. 10F2 depicts a top view 1060 of such a lamp. As shown in FIG. 10F1 and FIG. 10F2, the lamp 10F100 and 10F200 comports to a form factor known as PAR38. The PAR38 form factor is further depicted by the principal views (e.g., left 1068, right 1064, back 1062, front 1066 and top 1070) given in array 10G00 of FIG. 10G.

The components of the assembly 10A00 can be fitted together to form a lamp. FIG. 10H1 depicts a perspective view 1072 and FIG. 10H2 depicts a top view 1074 of such a lamp. As shown in FIG. 10H1 and FIG. 10H2, the lamp 10H100 and 10H200 comports to a form factor known as PAR111. The PAR111 form factor is further depicted by the principal views (e.g., left 1082, right 1078, back 1076, front 1080 and top 1084) given in array 10I00 of FIG. 10I.

In addition to uses of the aforementioned lamps and lamp shapes, filters or so-called 'circadian phosphors' can be employed.

Various implementations can be considered to alter an SPD's impact on the circadian system. As discussed above, it is possible to use a multiple-channel system including violet-pump and blue-pump LEDs and to balance the contribution of both channels. Besides, it is possible to physically block a given spectral range (such as the blue, cyan or violet region)—for instance by using absorbing or reflecting filters which may be fixed or moving. Filters offer the advantage that a substantial amount of light (or even all the light) can be blocked in a given spectral range, which may be of importance. For instance, it may be desirable to block nearly all the light in the blue-cyan range (or in a more specific range) to obtain a very low circadian stimulation—this is because standard spectra (such as a dimmed filament lamp) still have a fair amount of circadian stimulation. Such filters may for instance be dichroic reflective filters or absorbing filters including dye filters in a matrix (glass, plastic or other)

The specific design of a dichroic filter will be exemplified further in this document.

Another option, however, is to use a light-converting material in the system with a carefully chosen absorption range. For instance, one may include a phosphor which absorbs blue light and down-converts it to green or red light. This approach may be desirable because it enables one to remove a substantial amount of light in the absorption range like a blocking approach would, but with higher system efficiency since the radiation is converted to another wavelength rather than merely being blocked. For simplicity, this phosphor is called the 'circadian phosphor', since its absorption has an impact on the circadian action of the light source.

FIG. 11A and FIG. 11B contrasts the two approaches. FIG. 11A shows the initial SPD of a white LED source 1101 and the filtered SPD 1102 after blue light is blocked by a filter. The filtered SPD 1102 can be used in many embodiments, as it has a low amount of blue light, which can reduce disruption of the circadian system; furthermore the width and general shape of the filter may be designed to control this effect. However, filtering induces a penalty in efficiency because the filtered light is lost.

FIG. 11B shows the initial SPD of a white LED source 1103 and the converted SPD 1104 after blue light is absorbed by a "circadian phosphor" and converted to yellow light 1105. In this case, the same desirable effect on the circadian system is obtained, but the impact on efficiency is lessened thanks to the conversion of blue light. Here again, various aspects of the approach can be controlled through design, such as the position and amplitude of the absorption dip, which absorption dip can be controlled through the choice and amount of phosphor, and the position and amplitude of the luminescence. For instance, the absorption may be chosen to substantially block blue light but to allow some violet light transmission.

The circadian phosphor may be static, in which case the emitted SPD does not vary, or it may be on a moving part in order to control the SPD dynamically. The moving part may be a plate containing the phosphor, which can be moved mechanically in and out of the path of light emission of the system.

In FIG. 11A and FIG. 11B, the embodiments are designed to remove light in the range 440 nm to 460 nm. By choosing other filters or other phosphors this range can be tuned—for instance the range 450 nm to 480 nm, or another range, can be targeted and the spectral power in the range reduced. In some embodiments, a specific circadian action spectrum is assumed and the SPD is designed to have a low amount of light in the range where the action spectrum is high.

In yet another embodiment, the circadian phosphor shows a saturation behavior: it absorbs light at low flux, but absorption saturates at high flux. Such an approach is illustrated in FIG. 12 through FIG. 14.

Figure 12:
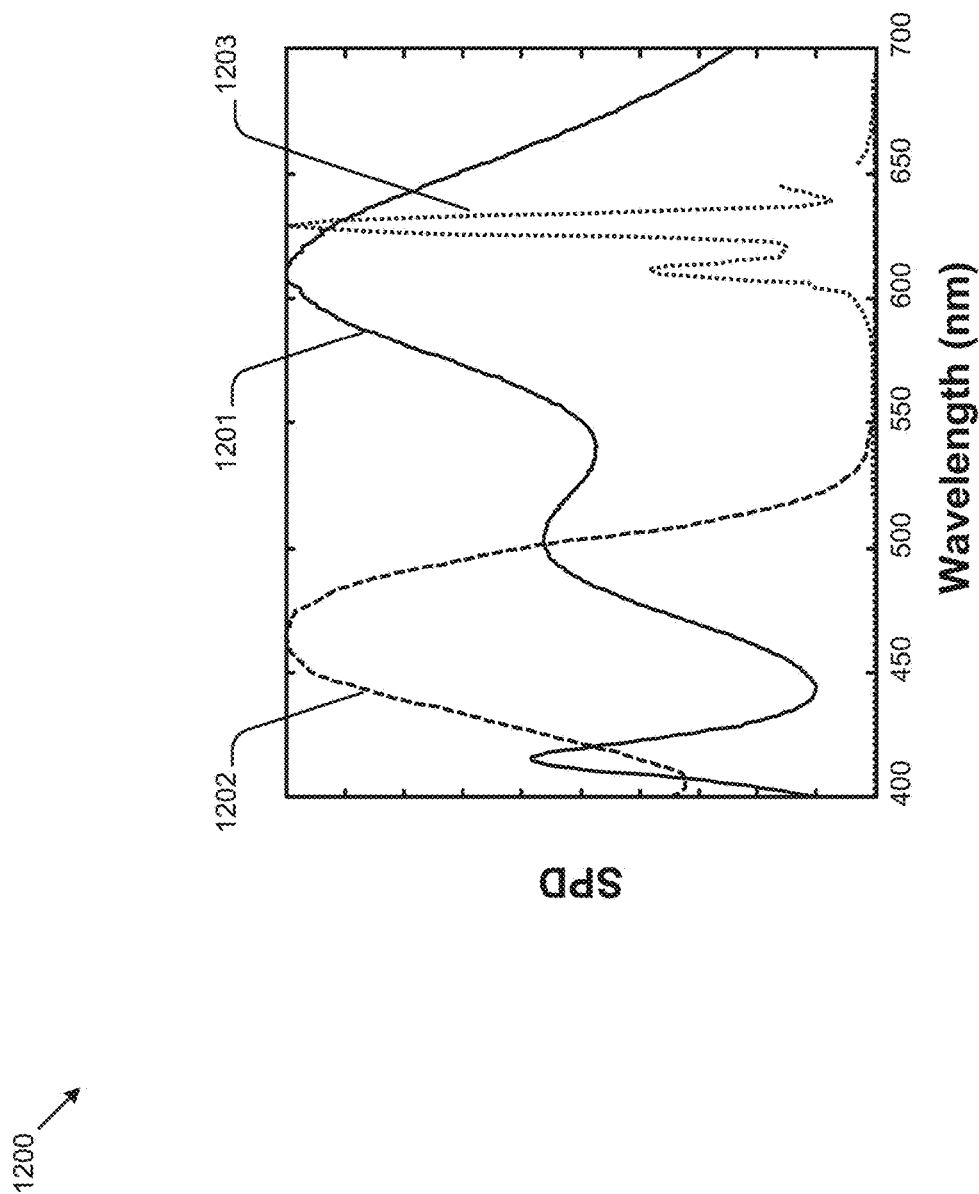
FIG. 12 shows an emission spectrum of a white LED light source with a CCT of 3000K and a CRI of about 90, and the emission and absorption spectra of a saturable red phosphor, according to some embodiments.

FIG. 12 shows various spectra. Spectrum 1201 is an emission spectrum of a white LED source with a CCT of 3000K and a CRI of about 90. This spectrum may be obtained by combining a violet-pump LED and several phosphors (e.g., a green phosphor, a red phosphor and possibly a blue phosphor). Curve 1202 is the absorption spectrum of a saturable red circadian phosphor and curve 1203 is the corresponding luminescence spectrum. Spectrum 1202 and spectrum 1203 can be obtained, for instance, with Mn-doped phosphors such as $K_2[TiF_6]$: $Mn^{4+}$.

Figure 13:
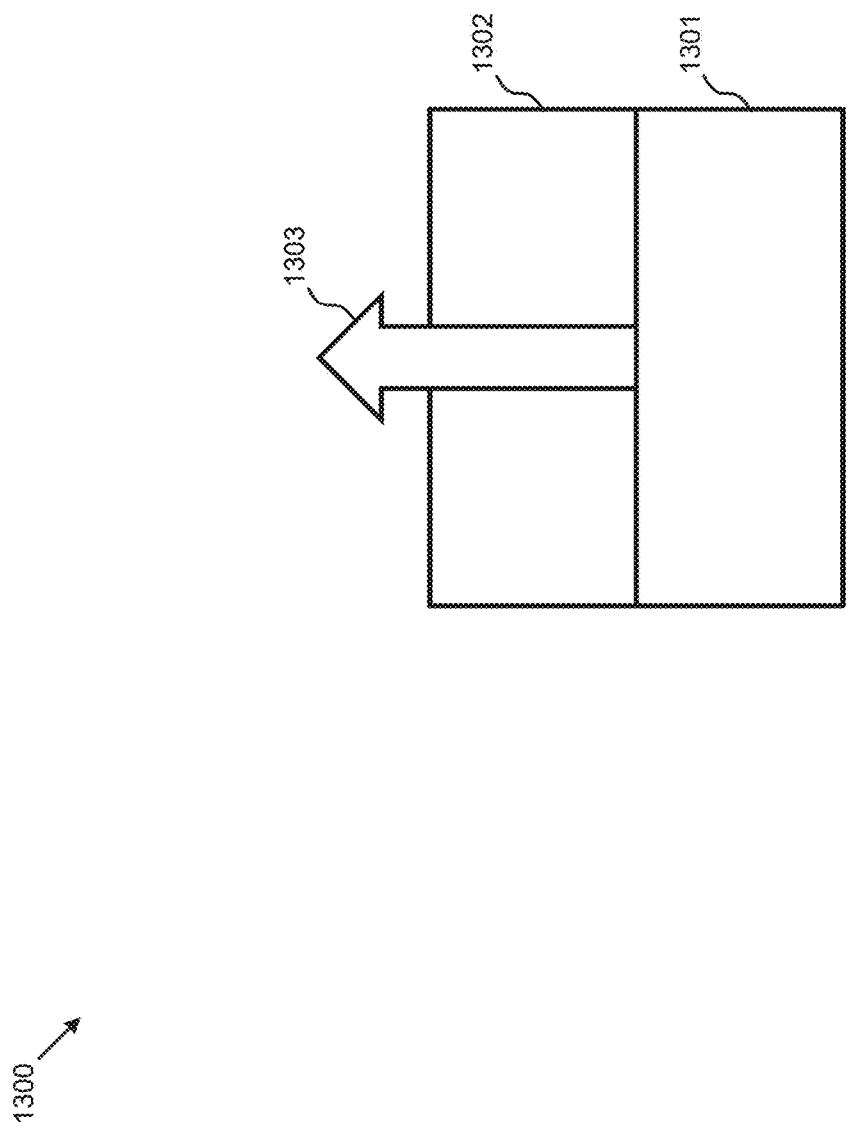
FIG. 13 shows a possible way to combine such a white LED light source with such a saturable phosphor, according to some embodiments.

FIG. 13 shows a possible way to combine such a white LED source and such a saturable phosphor. In FIG. 13, the saturable circadian phosphor 1302 is placed above the LED source 1301 so that the white light emitted by the device 1303 can be absorbed by the circadian phosphor. Various other configurations are also possible—for instance, the circadian phosphor may be mixed with the phosphors of the white LED or may be in a remote configuration.

Figures 14A, 14B:
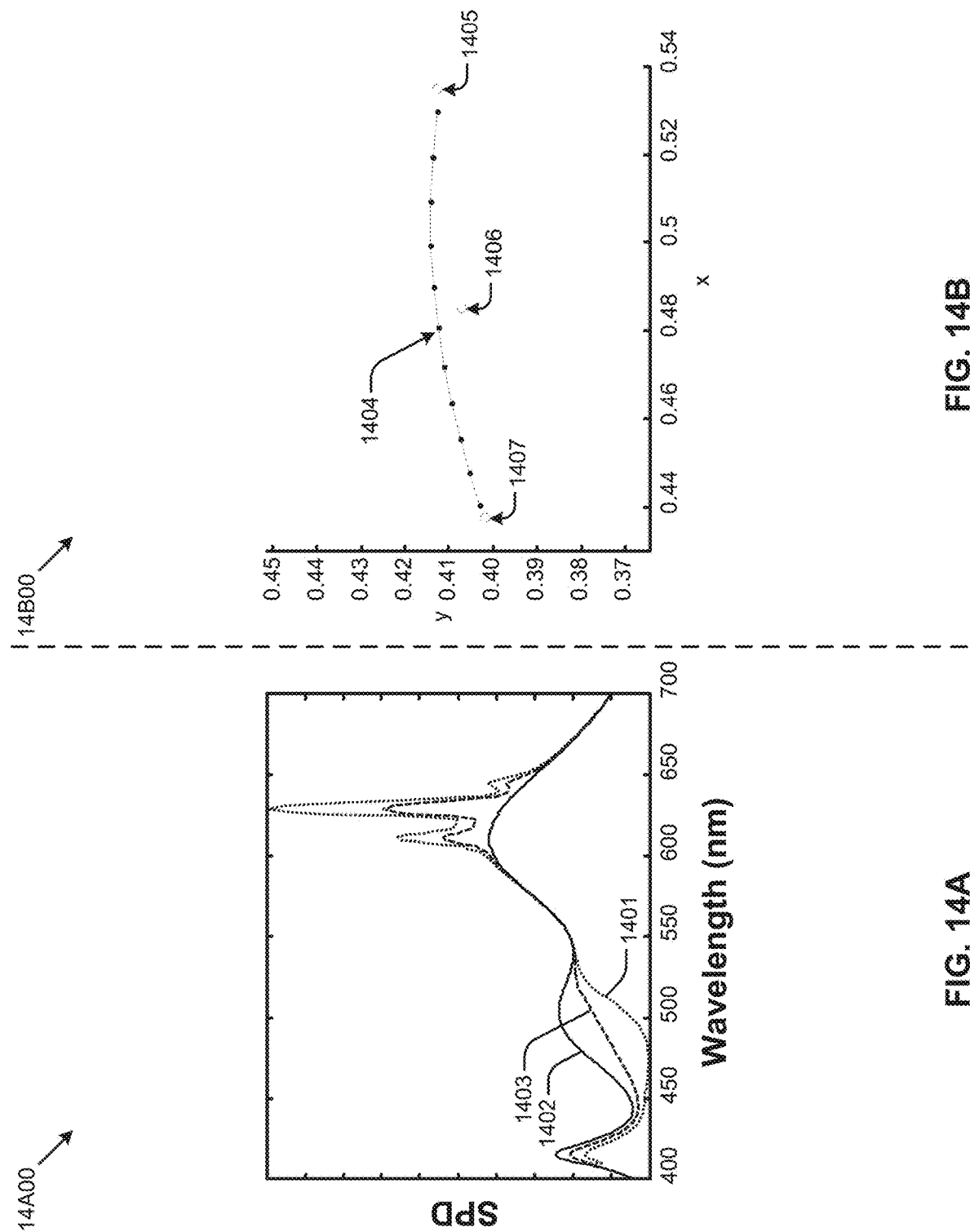
FIG. 14A shows the resulting spectral properties of the system shown in FIG. 13, according to some embodiments.
FIG. 14B shows the resulting colorimetric properties of the system shown in FIG. 13, according to some embodiments.

FIG. 14A and FIG. 14B show the resulting spectral and colorimetric properties of the system shown in FIG. 13. FIG. 14A shows the spectrum emitted by the system at various LED drive currents. At low drive current the saturable phosphor is not saturated and absorbs most of the light in its absorption range (e.g., blue-cyan light), resulting in spectrum 1401. At higher drive current the phosphor absorption is partially saturated and part of the blue-cyan light is transmitted, resulting in spectrum 1402. At even higher drive current the phosphor absorption is fully saturated, and the original spectrum of the white LED 1403 is emitted with very little perturbation from the circadian phosphor. FIG. 14B shows the corresponding chromaticity in (x, y) space for each drive current. At low drive current the CCT is about 2000K 1405, at higher drive current it is about 2500K 1406 and at the highest drive current it is about 3000K 1407. In all cases, the chromaticity is close to the Planckian locus 1404.

The embodiments of FIG. 12 through FIG. 14 achieve several desirable properties. At high drive current (e.g., see curve 1402), the embodiments behave like a conventional halogen retrofit with a high CRI (e.g., the circadian stimulation is 128% relative to standard illuminant A). As the current is reduced (e.g., see curves 1403 and 1401), the chromaticity shifts toward lower CCT (from 1407 to 1406 to 1405) thus emulating the behavior of a dimmed halogen or incandescent lamp. In addition, the spectrum is modified so that circadian stimulation decreases; at the lowest drive condition there is very little radiation in the range 440 nm to 490 nm (e.g., see curve 1401) and therefore very low stimulation of the circadian system (the circadian stimulation is only 8% relative to standard illuminant A).

As in other embodiments, the properties of the SPDs shown in FIG. 14A can be characterized by their relative fraction of power Fv in the range 400 nm to 440 nm and the fraction of power Fc in the range 440 nm to 500 nm. For SPD 1401, Fv=0.06 and Fc=0.01; for SPD 1402, Fv=0.08 and Fc=0.12. The value of Fc is especially low for SPD 1401, which can be associated with a very low circadian stimulation. This is in contrast to typical LED sources where a substantial fraction of power is in the range 440 nm to 500 nm (even for low-CCT sources with a CCT below 2700K).

While sources of varying CCT are known in the art and can be useful to modulate circadian stimulation, this embodiment has superior properties. The circadian stimulation is extremely low at low drive conditions: it is indeed lower than what is achieved with conventional LED sources, which employ a blue pump LED, or even by dimming of a conventional incandescent/halogen lamp. For example, a dimmed filament lamp emitting a blackbody spectrum with a CCT of 2000K still has a circadian stimulation of about 54% relative to illuminant A. Furthermore the present embodiment is 'passive' in that it doesn't require multiple channel drivers to modulate the spectrum. Therefore, such an embodiment may be integrated to a retrofit lamp or more generally a lighting system in absence of any advanced control circuits. In some such cases standard dimming switches provides the needed control.

In this embodiment, the presence of a violet pump is of importance since the violet light enables the chromaticity to be near-Planckian at low drive current, even in the absence of blue-cyan light.

Various aspects of this embodiment can be advantageously controlled. For instance, the optical properties of the pump LED can be varied, and the selection of phosphors can be varied, and the relative loading of phosphors can be varied to accomplish an optimization objective. The optimization criteria may include the CRI of the source at various dimming levels, its chromaticity and various dimming level, and metrics related to its circadian impact at various dimming levels. Strictly as one example, optimization criteria may include aspects of an integrated circadian action spectrum. The loading of the circadian phosphor can be chosen so that its saturation occurs at a desired drive, such as, for instance, 10% dimming. In other embodiments, more than one circadian phosphor is used.

In other embodiment, the white LED is obtained by multiple LED chips, such as uses of a violet LED, a green LED and a red LED rather than a phosphor-converted LED. In other embodiments, the chromaticity of the source does not follow the Planckian locus—it may for instance be below the Planckian locus, which is sometimes associated with a preferred perception as already discussed.

Embodiments may be integrated to various systems. This includes lighting systems (e.g., lamps, troffers and others) and non-lighting systems (e.g., display applications).

FIG. 15A1 through FIG. 15I depict embodiments of the present disclosure as can be applied toward lighting applications. In these embodiments, as shown in FIGS. 15A1-15A3, one or more light-emitting diodes 15A10, as taught by this disclosure, can be mounted on a submount or package to provide an electrical interconnection. As shown in FIGS. 15B1-15B3 a submount or package can be a ceramic, oxide, nitride, semiconductor, metal, or combination thereof that includes an electrical interconnection capability 15A20 for the various LEDs. The submount or package can be mounted to a heatsink member 15B50 via a thermal interface. The LEDs can be configured to produce a desired emission spectrum, either by mixing primary emissions from various LEDs, or by having the LEDs photo-excite wavelength down-conversion materials such as phosphors, semiconductors, or semiconductor nanoparticles ("quantum dots"), or a combination of any of the foregoing.

The total light emitting surface (LES) of the LEDs and any down-conversion materials can form a light source 15A30. One or more light sources can be interconnected into an array 15B20, which in turn is in electrical contact with connectors 15B10 and brought into an assembly 15B30. One or more lens elements 15B40 can be optically coupled to the light source. The lens design and properties can be selected so that the desired directional beam pattern for a lighting product is achieved for a given LES. The directional lighting product may be an LED module, a retrofit lamp 15B70, or a lighting fixture 15C30. In the case of a retrofit lamp, an electronic driver can be provided with a surrounding member 15B60, the driver to condition electrical power from an external source to render it suitable for the LED light source. The driver can be integrated into the retrofit lamp. In the case of a fixture, an electronic driver is provided which conditions electrical power from an external source to make it suitable for the LED light source, with the driver either integrated into the fixture or provided externally to the fixture. In the case of a module, an electronic driver can be provided to condition electrical power from an external source to render it suitable for the LED light source, with the driver either integrated into the module or provided externally to the module. Examples of suitable external power sources include mains AC (e.g., 120 Vrms AC or 240 Vrms AC), low-voltage AC (e.g., 12 VAC), and low-voltage DC (e.g., 12 VDC). In the case of retrofit lamps, the entire lighting product may be designed to fit standard form factors (e.g., ANSI form factors). Examples of retrofit lamp products include LED-based MR16, PAR16, PAR20, PAR30, PAR38, BR30, A19 and various other lamp types. Examples of fixtures include replacements for halogen-based and ceramic metal halide-based directional lighting fixtures.

In some embodiments, the present disclosure can be applied to non-directional lighting applications. In these embodiments, one or more light-emitting diodes (LEDs), as taught by the disclosure, can be mounted on a submount or package to provide an electrical interconnection. The submount or package can be, for example, a ceramic, oxide, nitride, semiconductor, metal, or combination of any of the foregoing that includes electrical interconnection capability for the various LEDs. The submount or package can be mounted to a heatsink member via a thermal interface. The LEDs can be configured to produce a desired emission spectrum, either by mixing primary emissions from various LEDs, or by having the LEDs photo-excite wavelength down-conversion materials such as phosphors, semiconductors, or semiconductor nanoparticles ("quantum dots"), or a combination thereof. The LEDs can be distributed to provide a desired shape of the light source. For example, one common shape is a linear light source for replacement of conventional fluorescent linear tube lamps. One or more optical elements can be coupled to the LEDs to provide a desired non-directional light distribution. The non-directional lighting product may be an LED module, a retrofit lamp, or a lighting fixture. In the case of a retrofit lamp, an electronic driver can be provided to condition electrical power from an external source to render it suitable for the LED light source, with the driver integrated into the retrofit lamp. In the case of a fixture, an electronic driver is provided to condition electrical power from an external source to render it suitable for the LED light source, with the driver either integrated into the fixture or provided externally to the fixture. In the case of a module, an electronic driver can be provided to condition electrical power from an external source to render it suitable for the LED light source, with the driver either integrated into the module or provided externally to the module. Examples of external power sources include mains AC (e.g., 120 Vrms AC or 240 Vrms AC), low-voltage AC (e.g., 12 VAC), and low-voltage DC (e.g., 12 VDC). In the case of retrofit lamps, the entire lighting product may be designed to fit standard form factors (e.g., ANSI form factors). Examples of non-directional lighting products are shown in FIG. 15C1, FIG. 15C2, and FIG. 15C3. Such a lighting fixture can include replacements for fluorescent-based troffer luminaires 15C30. In this embodiment, LEDs are mechanically secured into a package 15C10, and multiple packages are arranged into a suitable shape such as linear array 15C20.

Some embodiments of the present disclosure can be applied to backlighting for flat panel display applications. In these embodiments, one or more light-emitting diodes (LEDs), as taught by this disclosure, can be mounted on a submount or package to provide an electrical interconnection. The submount or package can be a ceramic, oxide, nitride, semiconductor, metal, or combination of any of the foregoing that include electrical interconnection capability for the various LEDs. The submount or package can be mounted to a heatsink member via a thermal interface. The LEDs can be configured to produce a desired emission spectrum, either by mixing primary emissions from various LEDs, or by having the LEDs photo-excite wavelength down-conversion materials such as phosphors, semiconductors, or semiconductor nanoparticles ("quantum dots"), or a combination of any of the foregoing. The LEDs can be distributed to provide a desired shape of the light source. One common shape is a linear light source. The light source can be optically coupled to a lightguide for the backlight. This can be achieved by coupling at the edge of the lightguide (edge-lit), or by coupling light from behind the lightguide (direct-lit). The lightguide distributes light uniformly toward a controllable display such as a liquid crystal display (LCD) panel. The display converts the LED light into desired images based on electrical control of light transmission and its color. One way to control the color is by use of filters (e.g., color filter substrate 15D40). Alternatively, multiple LEDs may be used and driven in pulsed mode to sequence the desired primary emission colors (e.g., using a red LED 15D30, a green LED 15D10, and a blue LED 15D20). Optional brightness-enhancing films may be included in the backlight "stack". The brightness-enhancing films narrow the flat panel display emission to increase brightness at the expense of the observer-viewing angle. An electronic driver can be provided to condition electrical power from an external source to render it suitable for the LED light source for backlighting, including any color sequencing or brightness variation per LED location (e.g., one-dimensional or two-dimensional dimming). Examples of external power sources include mains AC (e.g., 120 Vrms AC or 240 Vrms AC), low-voltage AC (e.g., 12 VAC), and low-voltage DC (e.g., 12 VDC). Examples of backlighting products are shown in FIG. 15D and FIG. 15E.

Some embodiments of the present disclosure can be applied to automotive forward lighting applications, as shown in FIGS. 15F1-15F (e.g., see the example of an automotive forward lighting product 15F30). In these embodiments, one or more light-emitting diodes (LEDs) can be mounted on a submount or on a rigid or semi-rigid package 15F10 to provide an electrical interconnection. The submount or package can be a ceramic, oxide, nitride, semiconductor, metal, or combination thereof, that include electrical interconnection capability for the various LEDs. The submount or package can be mounted to a heatsink member via a thermal interface. The LEDs can be configured to produce a desired emission spectrum, either by mixing primary emission from various LEDs, or by having the LEDs photo-excite wavelength down-conversion materials such as phosphors, semiconductors, or semiconductor nanoparticles ("quantum dots"), or a combination of any of the foregoing. The total light emitting surface (LES) of the LEDs and any down-conversion materials form a light source. One or more lens elements 15F20 can be optically coupled to the light source. The lens design and properties can be selected to produce a desired directional beam pattern for an automotive forward lighting application for a given LED. An electronic driver can be provided to condition electrical power from an external source to render it suitable for the LED light source. Power sources for automotive applications include low-voltage DC (e.g., 12 VDC). An LED light source may perform a high-beam function, a low-beam function, a side-beam function, or any combination thereof.

Figure 15G:
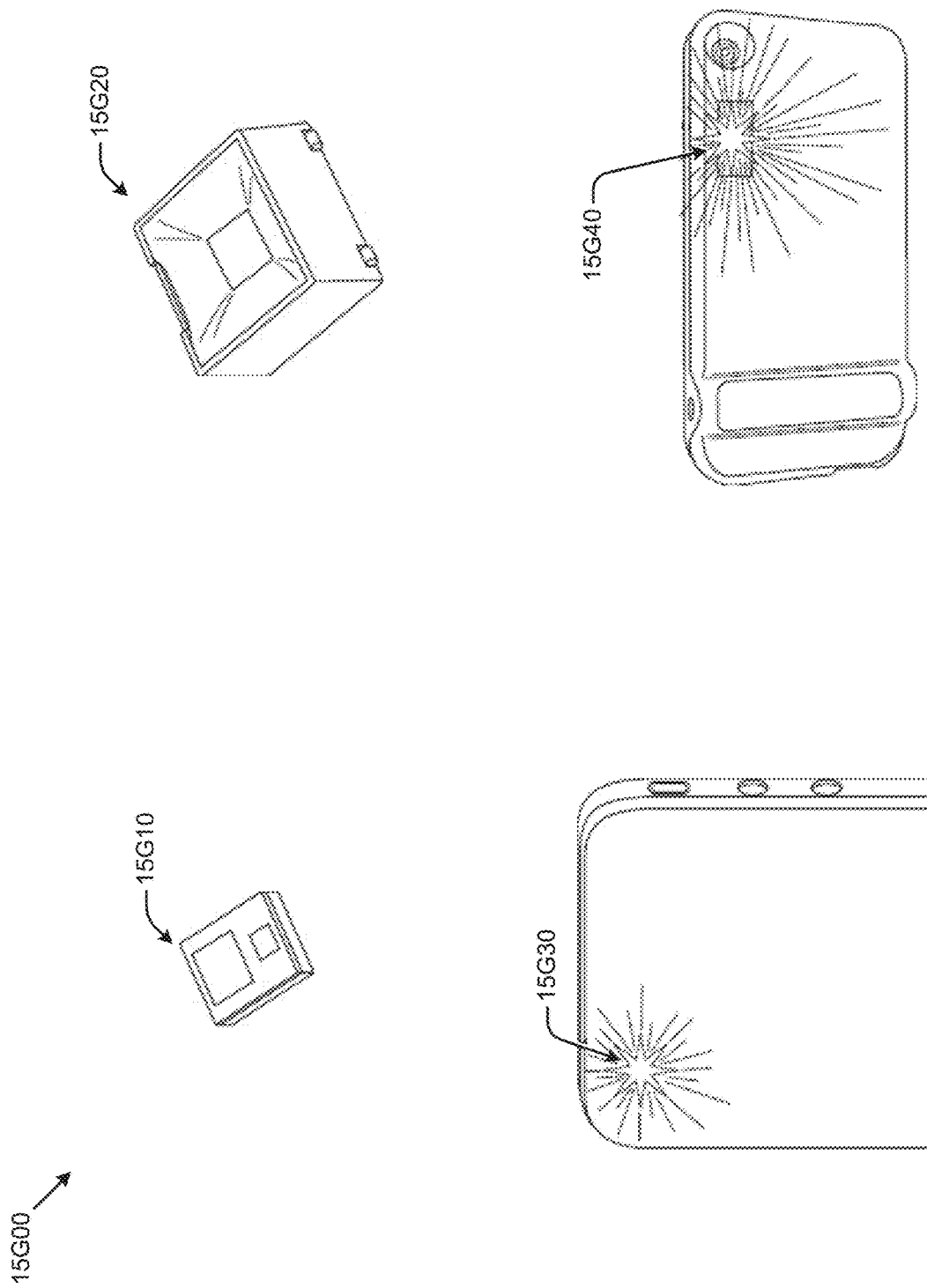
FIG. 15G depicts one embodiment of the present disclosure as can be applied toward lighting applications.

Certain embodiments of the present disclosure can be applied to digital imaging applications such as illumination for mobile phone and digital still cameras (e.g., see FIGS. 15G1-15G4). In these embodiments, one or more light-emitting diodes (LEDs), as taught by the disclosure, can be mounted on a submount or package 15G10 to provide an electrical interconnection. The submount or package can be, for example, a ceramic, oxide, nitride, semiconductor, metal, or combination of any of the foregoing that include electrical interconnection capability for the various LEDs. The submount or package can be mounted to a circuit board member and fitted with or into a mounting package 15G20. The LEDs can be configured to produce a desired emission spectrum, either by mixing primary emission from various LEDs, or by having the LEDs photo-excite wavelength down-conversion materials such as phosphors, semiconductors, or semiconductor nanoparticles ("quantum dots"), or a combination thereof. The total light emitting surface (LES) of the LEDs and any down-conversion materials form a light source. One or more lens elements can be optically coupled to the light source. The lens design and properties can be selected so that the desired directional beam pattern for an imaging application is achieved for a given LES. An electronic driver can be provided to condition electrical power from an external source to render it suitable for the LED light source. Examples of suitable external power sources for imaging applications include low-voltage DC (e.g., 5

VDC). An LED light source may perform a low-intensity function 15G30, a high-intensity function 15G40, or any combination thereof.

Figure 15H:
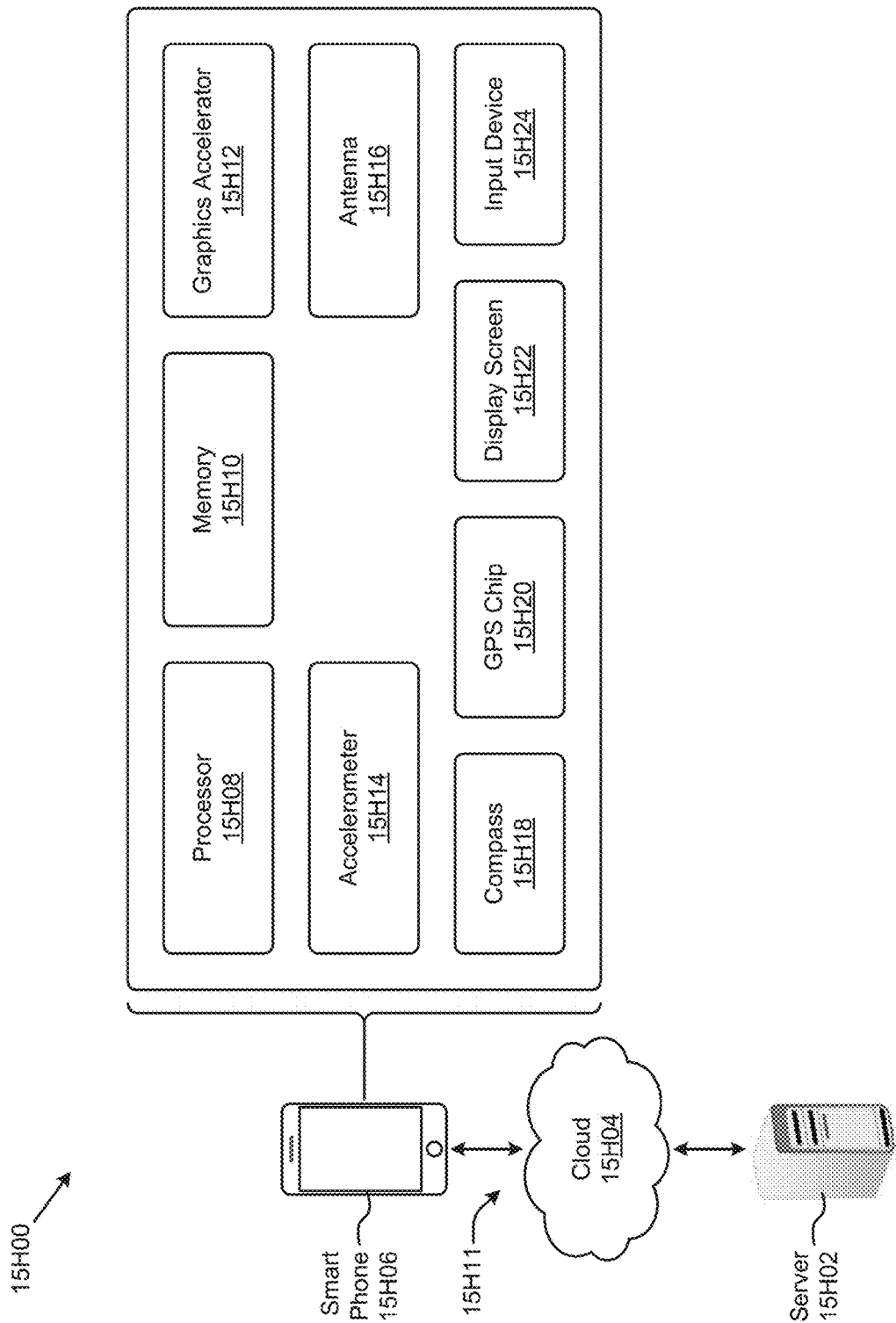
FIG. 15H depicts one embodiment of the present disclosure as can be applied toward lighting applications.

Some embodiments of the present disclosure can be applied to mobile terminal applications. FIG. 15H is a diagram illustrating a mobile terminal (see smart phone architecture 15H00). As shown, the smart phone 15H06 includes a housing, display screen, and interface device, which may include a button, microphone, and/or touch screen. In certain embodiments, a phone has a high resolution camera device, which can be used in various modes. An example of a smart phone can be an iPhone from Apple Inc. of Cupertino, Calif. Alternatively, a smart phone can be a Galaxy from Samsung, or others.

In an example, the smart phone may include one or more of the following features (which are found in an iPhone 4 from Apple Inc., although there can be variations), see www.apple.com:

GSM model: UMTS/HSDPA/HSUPA (850, 900, 1900, 2100 MHz); GSM/EDGE (850, 900, 1800, 1900 MHz)
CDMA model: CDMA EV-DO Rev. A (800, 1900 MHz)
802.11b/g/n Wi-Fi (802.11n 2.4 GHz only)
Bluetooth 2.1+EDR wireless technology
Assisted GPS
Digital compass
Wi-Fi
Cellular
Retina display
3.5-inch (diagonal) widescreen multi-touch display
800:1 contrast ratio (typical)
500 cd/m2 max brightness (typical)
Fingerprint-resistant oleophobic coating on front and back
Support for display of multiple languages and characters simultaneously
5-megapixel iSight camera
Video recording, HD (720p) up to 30 frames per second with audio
VGA-quality photos and video at up to 30 frames per second with the front camera
Tap to focus video or still images
LED flash
Photo and video geotagging
Built-in rechargeable lithium-ion battery
Charging via USB to computer system or power adapter
Talk time: Up to 20 hours on 3G, up to 14 hours on 2G (GSM)
Standby time: Up to 300 hours
Internet use: Up to 6 hours on 3G, up to 10 hours on Wi-Fi
Video playback: Up to 10 hours
Audio playback: Up to 40 hours
Frequency response: 20 Hz to 22,000 Hz
Audio formats supported: AAC (8 to 320 Kbps), protected AAC (from iTunes Store), HE-AAC, MP3 (8 to 320 Kbps), MP3 VBR, audible (formats 2, 3, 4, audible enhanced audio, AAX, and AAX+), Apple lossless, AIFF, and WAV
User-configurable maximum volume limit
Video out support with Apple digital AV adapter or Apple VGA adapter; 576p and 480p with Apple component AV cable; 576i and 480i with Apple composite AV cable (cables sold separately)
Video formats supported: H.264 video up to 1080p, 30 frames per second, main profile Level 3.1 with AAC-LC audio up to 160 Kbps, 48 kHz, stereo audio in .m4v, .mp4, and .mov file formats; MPEG-4 video up to 2.5 Mbps, 640 by 480 pixels, 30 frames per second, simple profile with AAC-LC audio up to 160 Kbps per channel, 48 kHz, stereo audio in .m4v, .mp4, and .mov file formats; motion JPEG (M-JPEG) up to 35 Mbps, 1280 by1020 pixels, 30 frames per second, audio in ulaw, PCM stereo audio in .avi file format
Three-axis gyro
Accelerometer
Proximity sensor
Ambient light sensor, etc.

Embodiments of the present disclosure may be used with other electronic devices. Examples of suitable electronic devices include a portable electronic device such as a media player, a cellular phone, a personal data organizer, or the like. In such embodiments, a portable electronic device may include a combination of the functionalities of such devices. In addition, an electronic device may allow a user to connect to and communicate through the Internet or through other networks such as local or wide area networks. For example, a portable electronic device may allow a user to access the internet and to communicate using e-mail, text messaging, instant messaging, or using other forms of electronic communication. By way of example, the electronic device may be similar to an iPod having a display screen or an iPhone available from Apple Inc.

In certain embodiments, a device may be powered by one or more rechargeable and/or replaceable batteries. Such embodiments may be highly portable, allowing a user to carry the electronic device while traveling, working, exercising, and so forth. In this manner, and depending on the functionalities provided by the electronic device, a user may listen to music, play games or video, record video or take pictures, place and receive telephone calls, communicate with others, control other devices (e.g., via remote control and/or Bluetooth functionality), and so forth while moving freely with the device. In addition, the device may be sized such that it fits relatively easily into a pocket or the hand of the user. While certain embodiments of the present disclosure are described with respect to portable electronic devices, it should be noted that the presently disclosed techniques may be applicable to a wide array of other, less portable, electronic devices and systems that are configured to render graphical data such as a desktop computer.

As shown, FIG. 15H includes a system diagram with a smart phone that includes an LED according to an embodiment of the present disclosure. The smart phone 15H06 is configured to communicate with a server 15H02 in electronic communication with any forms of handheld electronic devices. Illustrative examples of such handheld electronic devices can include functional components such as a processor 15H08, memory 15H10, graphics accelerator 15H12, accelerometer 15H14, communications interface 15H11 (possibly including an antenna 15H16), compass 15H18, GPS chip 15H20, display screen 15H22, and an input device 15H24. Each device is not limited to the illustrated components. The components may be hardware, software or a combination of both.

In some examples, instructions can be input to the handheld electronic device through an input device 15H24 that instructs the processor 15H08 to execute functions in an electronic imaging application. One potential instruction can be to generate an abstract of a captured image of a portion of a human user. In that case the processor 15H08 instructs the communications interface 15H11 to communicate with the server 15H02 (e.g., possibly through or using a cloud 15H04) and transfer data (e.g., image data). The data is transferred by the communications interface 15H11 and either processed by the processor 15H08 immediately after image capture or stored in memory 15H10 for later use, or both. The processor 15H08 also receives information regarding the display screen's attributes, and can calculate the orientation of the device, e.g., using information from an accelerometer 15H14 and/or other external data such as compass headings from a compass 15H18, or GPS location from a GPS chip 15H20, and the processor then uses the information to determine an orientation in which to display the image depending upon the example.

The captured image can be rendered by the processor 15H08, by a graphics accelerator 15H12, or by a combination of the two. In some embodiments, the processor can be the graphics accelerator 15H12. The image can first be stored in memory 15H10 or, if available, the memory can be directly associated with the graphics accelerator 15H12. The methods described herein can be implemented by the processor 15H08, the graphics accelerator 15H12, or a combination of the two to create the image and related abstract. An image or abstract can be displayed on the display screen 15H22.

Figure 15I:
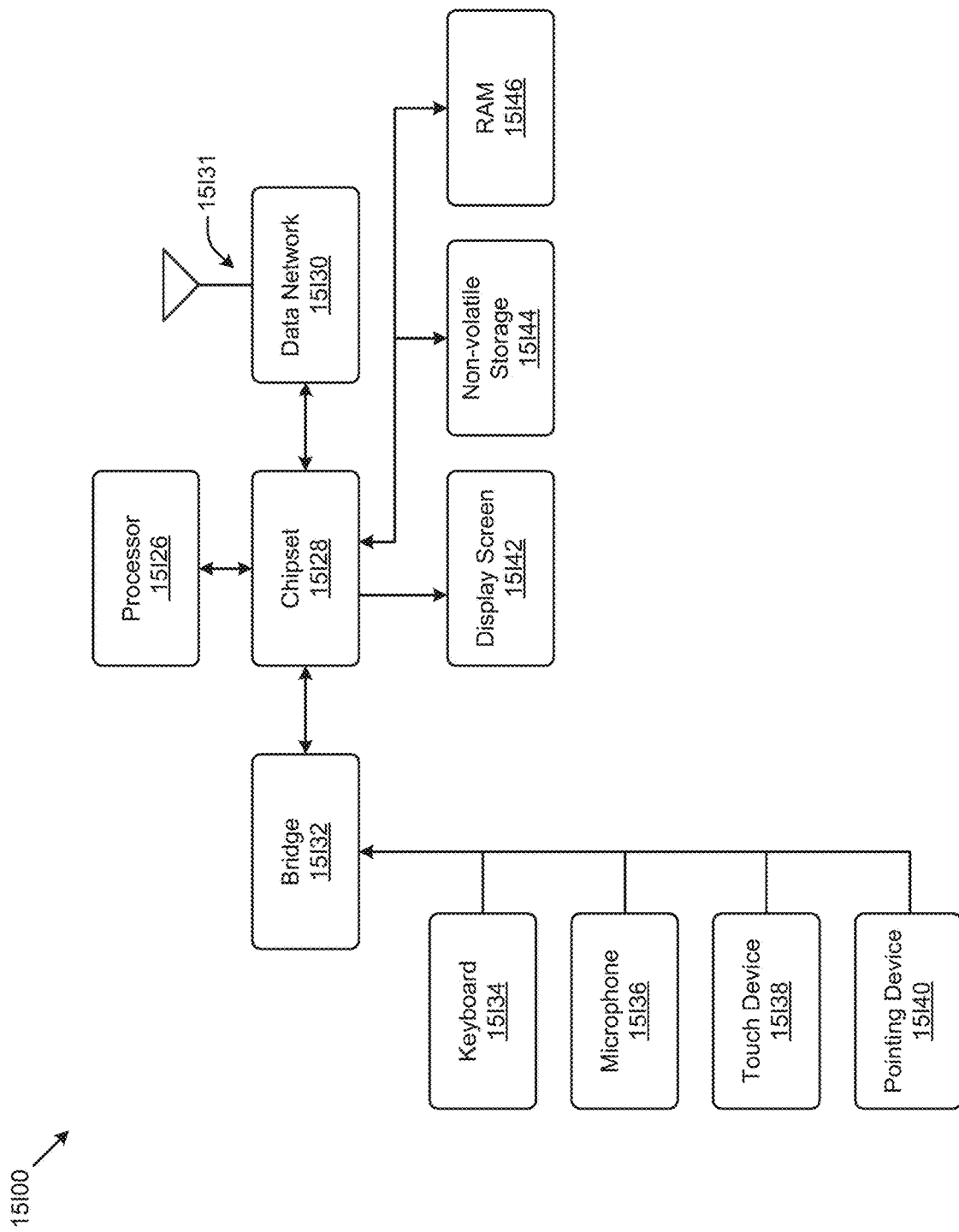
FIG. 15I depicts one embodiment of the present disclosure as can be applied toward lighting applications.

FIG. 15I depicts an interconnection of components in an electronic device 15100. Examples of electronic devices include an enclosure or housing, a display, user input structures, and input/output connectors in addition to the aforementioned interconnection of components. The enclosure may be formed from plastic, metal, composite materials, or other suitable materials, or any combination thereof. The enclosure may protect the interior components of the electronic device from physical damage, and may also shield the interior components from electromagnetic interference (EMI).

The display may be a liquid crystal display (LCD), a light emitting diode (LED) based display, an organic light emitting diode (OLED) based display, or some other suitable display. In accordance with certain embodiments of the present disclosure, the display may display a user interface and various other images such as logos, avatars, photos, album art, and the like. Additionally, in certain embodiments, a display may include a touch screen through which a user may interact with the user interface. The display may also include various functions and/or system indicators to provide feedback to a user such as power status, call status, memory status, or the like. These indicators may be incorporated into the user interface displayed on the display.

In certain embodiments, one or more of the user input structures can be configured to control the device such as by controlling a mode of operation, an output level, an output type, etc. For instance, the user input structures may include a button to turn the device on or off. Further, the user input structures may allow a user to interact with the user interface on the display. Embodiments of the portable electronic device may include any number of user input structures including buttons, switches, a control pad, a scroll wheel, or any other suitable input structures. The user input structures may work with the user interface displayed on the device to control functions of the device and/or any interfaces or devices connected to or used by the device. For example, the user input structures may allow a user to navigate a displayed user interface or to return such a displayed user interface to a default or home screen.

Certain device may also include various input and output ports to allow connection of additional devices. For example, a port may be a headphone jack that provides for the connection of headphones. Additionally, a port may have both input and output capabilities to provide for the connection of a headset (e.g., a headphone and microphone combination). Embodiments of the present disclosure may include any number of input and/or output ports such as headphone and headset jacks, universal serial bus (USB) ports, IEEE-1394 ports, and AC and/or DC power connectors. Further, a device may use the input and output ports to connect to and send or receive data with any other device such as other portable electronic devices, personal computers, printers, or the like. For example, in one embodiment, the device may connect to a personal computer via an IEEE-1394 connection to send and receive data files such as media files.

The depiction of an electronic device 15100 encompasses a smart phone system diagram according to an embodiment of the present disclosure. The depiction of an electronic device 15100 illustrates computer hardware, software, and firmware that can be used to implement the disclosures above. The shown system includes a processor 15126, which is representative of any number of physically and/or logically distinct resources capable of executing software, firmware, and hardware configured to perform identified computations. A processor 15126 communicates with a chipset 15128 that can control input to and output from processor 15126. In this example, chipset 15128 outputs information to display screen 15142 and can read and write information to non-volatile storage 15144, which can include magnetic media and solid state media, and/or other non-transitory media, for example. Chipset 15128 can also read data from and write data to RAM 15146. A bridge 15132 for interfacing with a variety of user interface components can be provided for interfacing with chipset 15128. Such user interface components can include a keyboard 15134, a microphone 15136, touch-detection-and-processing circuitry 15138, a pointing device 15140 such as a mouse, and so on. In general, inputs to the system can come from any of a variety of machine-generated and/or human-generated sources.

Chipset 15128 also can interface with one or more data network interfaces 15130 that can have different physical interfaces. Such data network interfaces 15130 can include interfaces for wired and wireless local area networks, for broadband wireless networks, as well as personal area networks. Some applications of the methods for generating, displaying and using the GUI disclosed herein can include receiving data over a physical interface 15131 or be generated by the machine itself by a processor 15126 analyzing data stored in non-volatile storage 15144 and/or in memory or RAM 15146. Further, the machine can receive inputs from a user via devices such as a keyboard 15134, microphone 15136, touch-detection-and-processing circuitry 15138, and pointing device 15140 and execute appropriate functions such as browsing functions by interpreting these inputs using processor 15126.

Filtering Based on Clinical Measurements

Assessing the impact of a light-emitting system on the circadian cycle may be performed in a variety of ways, including using medical or clinical trials. In such trials, various physiological signals related to the circadian cycle may be monitored for subjects exposed to the light-emitting system. For instance, it is possible to measure the melatonin suppression in the saliva or blood of the subjects. Other physiological signals, including various hormones, may be measured from saliva or blood samples or in other tests. Such protocols are known to those skilled in the art and are discussed in scientific publications. A specific physiological response (such as the level of a specific hormone) may be targeted in such tests, especially for responses known to correlate to a specific medical condition and/or a condition known or believed to be associated with the spectral content of light.

For instance, Brainard discloses a protocol for measuring the melatonin suppression under light exposure. Some steps of the protocol are as follows.

Subjects with normal vision are selected.

At midnight, the subjects enter a dimly lit room, their pupils are dilated and they wait for a period of 2 hrs.

A blood sample if taken.

The subjects are exposed to the test light for 90 min, and a second blood sample is taken.

The melatonin content in the blood samples is determined, and the relative decrease in melatonin compared to that in a control experiment (e.g., no light exposure).

Other testing protocols can be found in various publications such as, for example, in West et al.; in "Blue light from light-emitting diodes elicits a dose-dependent suppression of melatonin in humans" J. Appl. Physiol. 110, 619-626 (2011)).

It can be appreciated that the disclosed techniques can be applied to lighting or display systems based on light emitting diodes and/or based on laser diode devices.

In certain embodiments provided by the present disclosure, light sources comprise at least one first LED emission source characterized by a first emission; and at least one second LED emission source characterized by a second emission; wherein the first emission and the second emission are configured to provide a first combined emission and a second combined emission; the first combined emission is characterized by a first SPD and fractions Fv1 and Fc1; the second combined emission is characterized by a second SPD and fractions Fv2 and Fc2; Fv1 represents the fraction of power of the first SPD in the wavelength range from 400 nm to 440 nm; Fc1 represents the fraction of power of the first SPD in the wavelength range from 440 nm to 500 nm; Fv2 represents the fraction of power of the second SPD in the wavelength range from 400 nm to 440 nm; Fc2 represents the fraction of power of the second SPD in the wavelength range from 440 nm to 500 nm; the first SPD and the second SPD have a color rendering index above 80; Fv1 is at least 0.05; Fc2 is at least 0.1; and Fc1 is less than Fc2 by at least 0.02. Other values are possible for Fc1, Fc2, Fv1, and Fv2, such as 0.001, 0.005, 0.01, 0.05, 0.1, 0.2, or greater and any value inbetween.

In certain embodiments of a light source, the first combined emission is characterized by a first circadian stimulation; the second combined emission is characterized by a second circadian stimulation; and the second circadian stimulation is at least twice the first circadian stimulation.

In certain embodiments of a light source, the first LED emission source comprises at least one LED characterized by a peak emission in the range 405 nm to 430 nm.

In certain embodiments of a light source, the first emission and the second emission are configured to provide a third combined emission; the third combined emission is characterized by a third SPD, a fraction Fv3, a fraction Fc3, and a third circadian stimulation; Fv3 represents the fraction of power of the third SPD in the wavelength range from 400 nm to 440 nm; Fc3 represents the fraction of power of the third SPD in the wavelength range from 440 nm to 500 nm; the third SPD has a coloring rendering index above 80; and the first circadian stimulation and the third circadian stimulation are different.

In certain embodiments of a light source, the second emission comprises blue emission from a wavelength downconversion material.

In certain embodiments of a light source, the second emission comprises direct blue emission from an LED.

In certain embodiments of a light source, one of the combined emissions induces a circadian stimulation similar to a circadian stimulation of a D65 reference illuminant.

In certain embodiments of a light source, one of the combined emissions induces a circadian stimulation that is less than a circadian stimulation of a CIE A reference illuminant.

In certain embodiments of a light source, the at least one first LED emission source and the at least one second LED emission source are configured in an intermixed physical arrangement.

In certain embodiments of a light source, each of the first SPD and the second SPD is characterized by a chromaticity within the white light bounding region 514 of FIG. 5B.

In certain embodiments of a light source, each of the first SPD and the second SPD is characterized by a chromaticity bounded by ±0.005 of a Planckian loci and by ±0.005 of a minimum-hue-shift curve in a CIE chromaticity diagram.

In certain embodiments of a light source, each of the first SPD and the second SPD is characterized by a chromaticity within +/−five Du'v' points of a Planckian loci.

In certain embodiments of a light source, exposure of a subject to the second SPD with an illuminance of 100 lx for ninety minutes results in a suppression of blood melatonin concentration in the subject of at least 20%.

In certain embodiments of a light source, exposure of a subject to the first SPD with an illuminance of 100 lx for ninety minutes results in a suppression blood melatonin concentration in the subject of at most 20%.

In certain embodiments of a light source, Fc1 is at most 0.06

In certain embodiments, a display system comprises a first LED emission source characterized by a first emission; and a display configured to emit a first SPD characterized by a first fraction Fv1 of power in the range 400 nm to 435 nm; wherein, the display system is characterized by a color gamut of at least 70% of NTSC; the first SPD is substantially white with a CCT in a range from 3000K to 9000K; and Fv1 is at least 0.05.

In certain embodiments of a display system, the display comprises an emission spectrum characterized by a circadian stimulation that is less than a circadian stimulation of a reference illuminant having the same CCT.

In certain embodiments of a display system, the display system further comprises a color filter set and a liquid crystal display.

In certain embodiments of a display system, the first SPD is characterized by a peak in the wavelength range from 400 nm to 435 nm at a wavelength w; the color filter set comprises a blue filter characterized by a maximum transmission Tm, and by a transmission Tw at wavelength w; and Tw/Tm>0.8.

In certain embodiments, a display system further comprises a second LED emission source characterized by a second emission, wherein a ratio of the first emission and the second emission are configured to be adjusted to change a circadian stimulation.

In certain embodiments of a display system, the display system is configured for use with a TV, desktop PC, notebook PC, laptop PC, tablet, smartphone, MP3 player.

In certain embodiments of a display system, less than 5% of the power of the first SPD is in a wavelength range from 440 nm to 500 nm.

In certain embodiments, a light source comprises an LED device configured to emit a primary emission; one or more wavelength conversion materials optically coupled to the primary emission; wherein a portion of the primary emission is absorbed by the wavelength conversion materials to produce a secondary emission; wherein a combination of the primary emission and the secondary emission produces white light characterized by an SPD having a CCT and a color rendering index; wherein at least 5% of the SPD is in a wavelength range from 400 nm to 435 nm; wherein a circadian stimulation of the SPD is less than 80% of a circadian stimulation of a reference illuminant having the same color temperature; and wherein the white light is characterized by a color rendering index above 80.

In certain embodiments, of a light source, the primary emission is characterized by a peak wavelength between 405 nm and 425 nm.

In certain embodiments, a lighting system comprises an LED device configured to emit a primary emission characterized by a primary SPD; at least one phosphor optically coupled to the primary emission, wherein the at least one phosphor is characterized by saturable absorption within a blue-cyan wavelength region; wherein the LED device is configured to be controlled by a power signal configured to dim the primary emission; wherein at a first power level the system emits a first SPD characterized by a first fraction fc1 of spectral power in a wavelength range from 440 nm to 500 nm and a first CCT; wherein at a second power level the system emits a second SPD characterized by a second fraction fc2 of spectral power in a wavelength range from 440 nm to 500 nm and a second CCT; and wherein the second power level is less than the first power level and the second fraction fc2 is less than 80% of the first fraction fc1.

In certain embodiments of a lighting system, the second CCT is at least 500K less than the first CCT.

In certain embodiments of a lighting system, at least 5% of the primary SPD is in a wavelength range from 400 nm to 435 nm.

Some embodiments make use of filters. For instance, one or more filters can be employed in order to remove radiation that would cause circadian stimulation. Considerations with respect to such filters are discussed herein-below. In these discussions, the acronym CS is used to refer to circadian stimulation and the acronym CSR is used to refer to the circadian spectral range of maximal stimulation.

The disclosure herein shows how the combination of violet LEDs and properly-chosen phosphors enabled a reduction of CS by an order of magnitude or more as compared to conventional light sources. Such a dramatic reduction can be achieved by removing radiation in the CSR. In some cases it is desirable to further reduce the CS, for instance by two orders of magnitude or more. For instance, this is the case in an environment where there is a large illuminance (such as several hundreds or thousands of lux). Indeed, in this case the circadian response is "saturated". As one example, melatonin suppression can be measured and deemed complete after 90 minutes. Reducing the CS by only one order of magnitude still yields significant suppression. In some cases, it is difficult to attain such low levels of CS by combining a violet LED and conventional phosphors because the violet LED and the yellow/green phosphor have residual emission tails in the CSR.

Further reduction of CS can be obtained by the use of filters that remove radiation in the CSR. However, the filters should be designed such that the resulting quality of light is still acceptable. It is possible to substantially filter out any light below say 500 nm, thus achieving low CS, however that spectrum would be observed as a very undesirable quality of light (e.g., in terms of chromaticity and CRI)—for instance, it would likely have a pronounced yellow tint. For quality or light reasons, it is desirable to maintain a chromaticity on-Planckian or near-Planckian, and a CRI of 80 or above. The following discussions provide further details of practical implementation of reduced CS embodiments.

The following discussions use a simplified figure of merit for circadian stimulation. In particular, the fraction of the SPD in the CSR is considered. For the sake of teaching how to make and use these embodiments, consider the range 430-490 nm as the CSR in the following illustrations. The discussion can easily be adapted to other ranges (or to more complex responses, such as an action spectrum with a given shape in a given spectral range). For illustration, a conventional blue-pumped LED with a CCT of 3000K and a CRI of 80 has about 12% of its power in the CSR.

FIG. 16A through FIG. 21B present techniques for making and using circadian filters, according to certain specifications. Using various techniques, notch filters can be designed to block light in a selected wavelength range, while providing high transmission in other ranges. For instance, it is common to stack multilayers of materials with varying optical indices to obtain notch filters. A common choice is a SiOx/NbOx stack (of course other materials can be considered, such as TiOx, TaOx, etc.). These stacks can be designed by optical software, using a relevant figure of merit such as low transmission in the CSR.

The depictions of FIG. 16A through FIG. 16D show such an example. FIG. 16A describes a dielectric stack deposited on a glass substrate (materials and thicknesses in nm). FIG. 16B shows the corresponding transmission curve. FIG. 16C shows how the initial SPD of a light source is modified into a filtered SPD when the filter is placed in front of it. FIG. 16D indicates corresponding colorimetric properties of the initial spectrum and of the filtered spectrum.

In this example, the initial spectrum is targeted to be on-Planckian at 3000K. The filter induces a slight chromatic shift (approximately 7 Du'v' points). The CRI is maintained at 80. The effect on chromatic shift and CRI is moderate because the initial spectrum already had relatively little radiation in the CSR. Despite this modest effect on chromaticity, the reduction of power portion (e.g., percentage) in the CSR is substantial (more than tenfold). In comparison to a standard blue-pumped LED with the same CCT and CRI, the reduction in power in the CSR is sixty times. Other filter designs can achieve further reduction, or provide reduction in a different wavelength range as desired.

In various cases, one may want to design a filter such that the filtered SPD is on-Planckian. This can be achieved by starting from an off-Planckian initial SPD so that the chromatic shift of the filter brings the SPD on-Planckian. This is achievable by selecting the right choice and amount of phosphors to achieve a given chromaticity after filtering. FIG. 17A and FIG. 17B illustrates this. Here the dielectric filter is the same as in the FIG. 16 series, but the initial SPD has been tuned so that the filtered SPD would be on-Planckian. FIG. 17A shows the initial SPD and the filtered SPD. FIG. 17B shows the corresponding colorimetric properties. Here again, the filtered SPD has an order of magnitude less power in the CSR than the initial SPD.

One design technique starts with an on-Planckian light source and constructs a filter which has the proper transmission at all wavelengths to maintain the initial SPD's chromaticity. Also note that in the foregoing, the initial SPDs have little radiation in the CSR, therefore the filtering has a very small impact on the system's efficiency, which is desirable. Further, one may take into account the transmission and absorption of various other elements in the optical system (lenses, reflectors, etc) such that the final spectrum emitted by the system, taking into account the transmission of the whole system (including the filter), is on-Planckian or at a selected chromaticity. Taking such transmissions into account is well-known in the art.

Dichroic filters are especially suited when the light source is fairly directional, because transmission usually varies with angle. Therefore dichroic filters can be easily adapted to narrow-beam light sources. For instance dichroic filters can be used in conjunction with a spot lamp (such as a 40, a 100 or a 200 spot). Such dichroic filters may be added to any existing light source. As discussed above, the filter can be designed to maintain the chromaticity of the light source (and other properties such as CRI, etc.). In some embodiments, the spot lamp can be converted between a circadian-stimulating source and a circadian-friendly source by addition of the filter. This filter can be combined with a diffuser to obtain a wider beam angle.

Figures 18A, 18B:
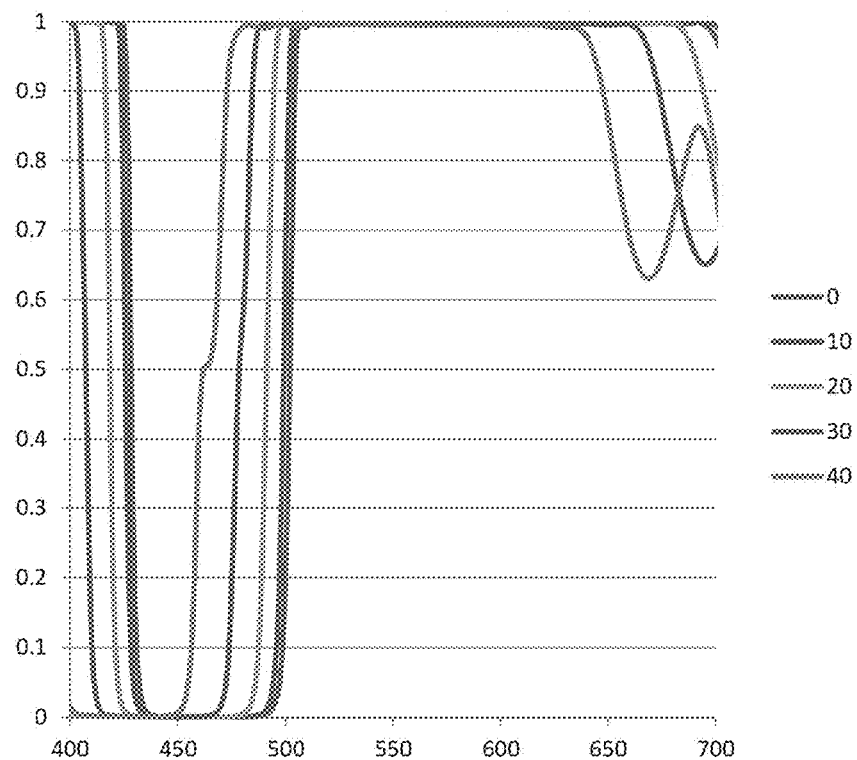
FIG. 18A shows an example using dielectric stacks and compares filtered SPDs under varying conditions, according to some embodiments.
FIG. 18B shows an example using dielectric stacks and compares filtered SPDs under varying conditions, according to some embodiments.

In other cases one may want to use a non-directional light source. FIGS. 18A and 18B show the effect of incidence angle for the filter of FIG. 16B coupled to the initial spectrum of FIG. 16C. FIG. 18A shows the transmission versus angle for the filter of the FIG. 16 series. The stop band shifts with incidence angle, as is typical in dichroic stacks. Table 18B shows how resulting colorimetric quantities can vary with angle. The CRI and Du'v' vary rather strongly between 0° and 40°. Thus this filter would be suitable for a 100 beam angle, but less so for a 40° beam angle.

Figures 18C, 18D:
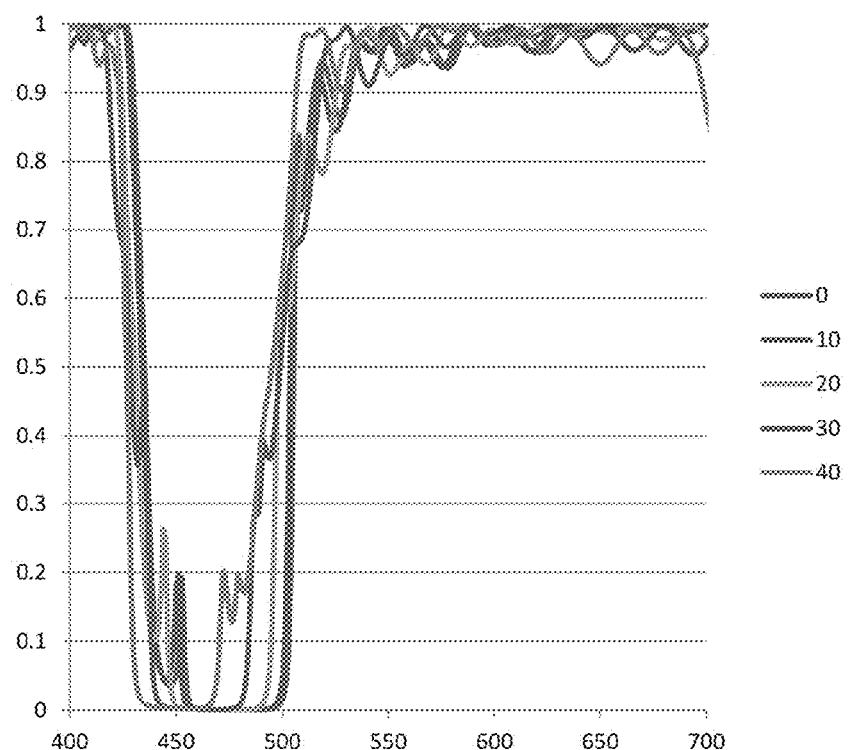
FIG. 18C shows an example using dielectric stacks and compares filtered SPDs under varying conditions, according to some embodiments.
FIG. 18D shows an example using dielectric stacks and compares filtered SPDs under varying conditions, according to some embodiments.

By applying design techniques to the foregoing observations, the filtering may be adapted to lessen this angular variation. This can be achieved by designing a dichroic stack where the figure of merit has low angular variation. FIGS. 18C-18D show such an embodiment.

In particular, FIG. 18C shows the transmission versus angle for a dichroic filter that has been designed for low transmission in the CSR for angles between 0° and 40°. The corresponding table (FIG. 18D) shows that the colorimetric quantities (Ra, cct, Du'v') show less variation with angle than previous embodiments (using the same initial spectrum of FIG. 16C).

FIG. 18E shows the corresponding stack's details (materials and thicknesses in nm). The total thickness of the filter depicted in embodiment 18E00 is less than 4 um. Further improvements could be achieved by allowing a thicker filter.

For non-directional light sources, another approach is to use a filter which is inherently non-directional, for instance an absorbing filter. Many exiting color filters (such as commercial polyester filters) incorporate dyes with absorption in the CSR. Use of such a filter yields angle-independent absorption. In some embodiments, the filter and the SPD are designed in conjunction, in order to obtain a desired chromaticity for the filtered spectrum (with the same procedure used in FIG. 2).

In some cases the system has a mechanical component such that the filter can be moved in various directions relative to the light source, and such movement can be performed manually or automatically (or both). For instance, the filter may be moved in and out of the beam of the light source to control filtering of the spectrum.

In the case of a lighting application, the filter can be placed at various positions in the system. FIG. 19A through 19C shows cross-sections of spot lamps with a lens 1902, an LED 1908, a heatsink 1096, and a filter 1904 placed at various positions in the system. For instance, the filter may be placed on top of the LED module (see FIG. 19A), at the exit port of the lens (see FIG. 19B) or at the entrance port of the lens (see FIG. 19C).

Figure 20B:
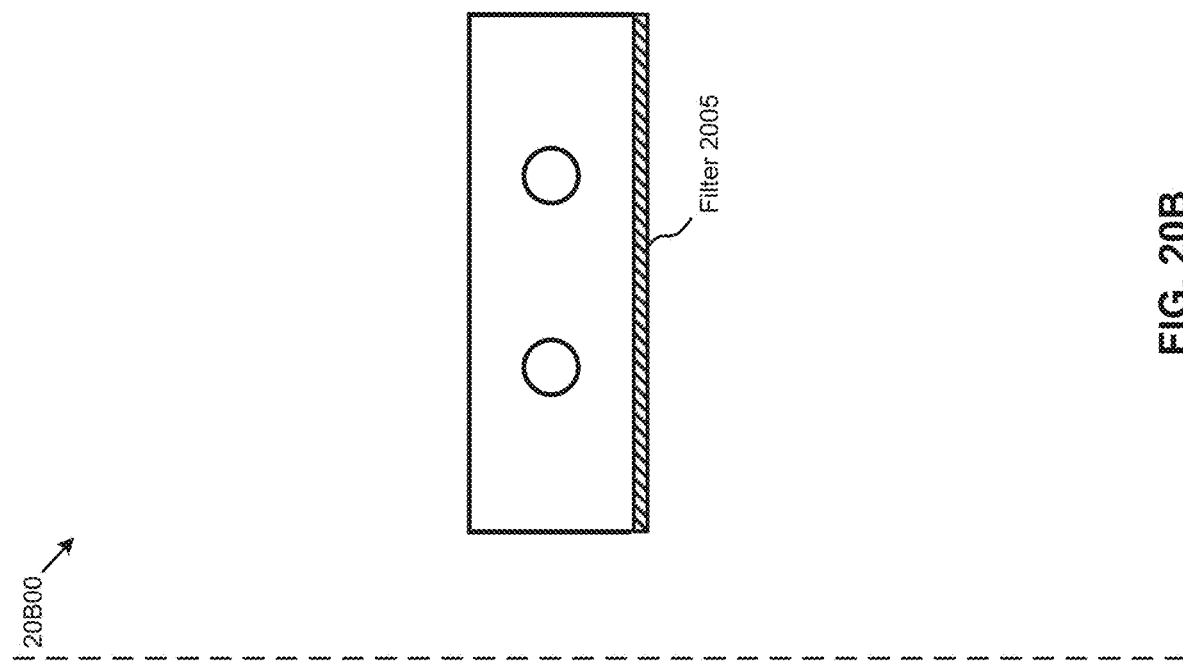
FIG. 20B shows an example using dielectric stacks and compares filtered SPDs under varying conditions, according to some embodiments.
Figure 20A:
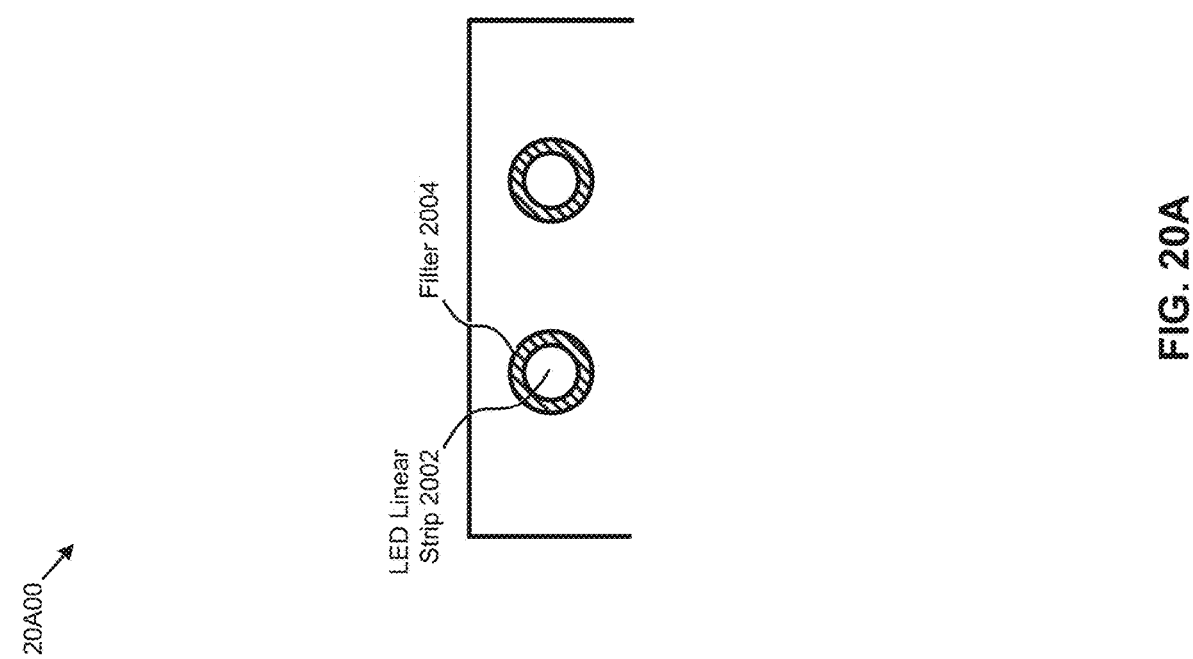
FIG. 20A shows an example using dielectric stacks and compares filtered SPDs under varying conditions, according to some embodiments.

In a linear troffer 20A00, the filter may be placed in front of the LEDs or at the exit port of the luminaire. FIG. 20A shows the cross-section of a troffer with linear LED strips 2002 and a filter 2004 around the LED strips. FIG. 20B shows a linear strip troffer 20B00 with the filter 2005 at the luminaire's exit port.

Figure 20C:
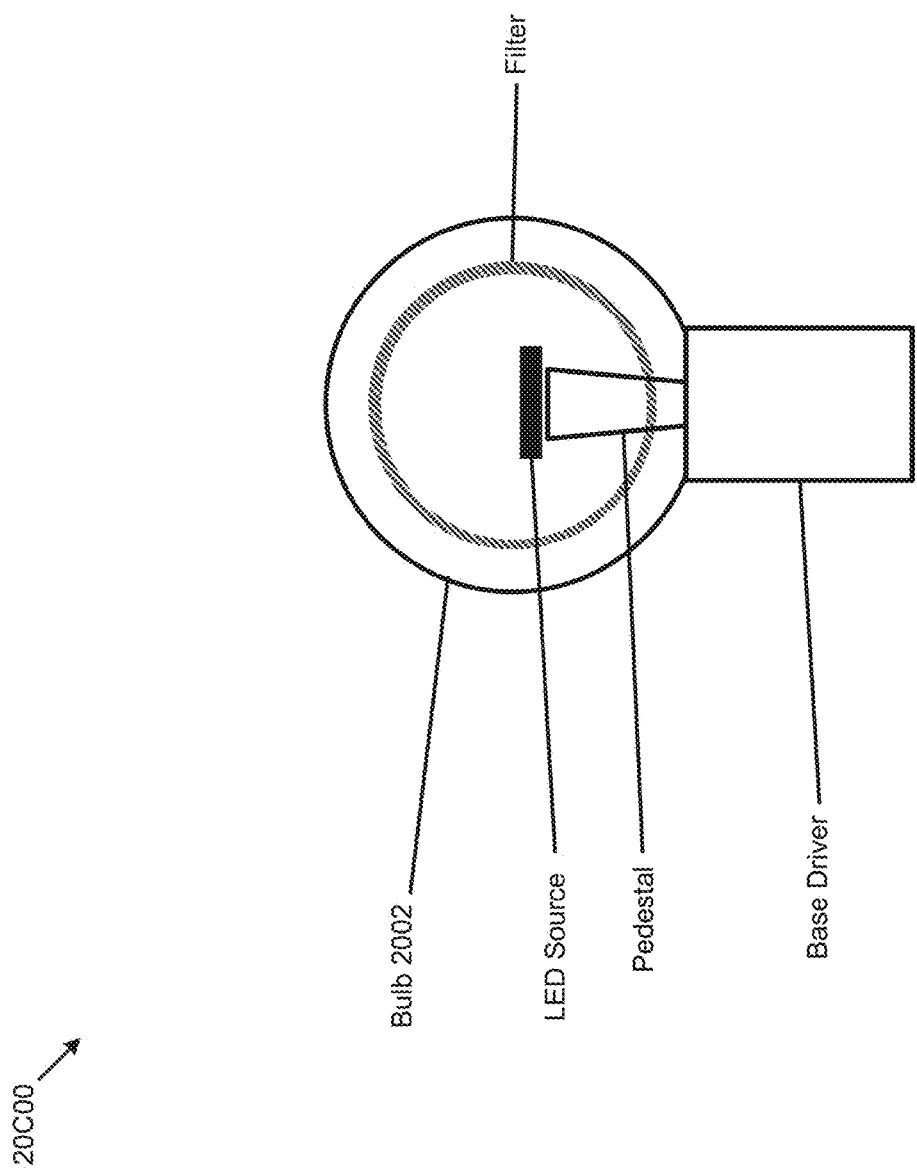
FIG. 20C shows an example using dielectric stacks and compares filtered SPDs under varying conditions, according to some embodiments.

FIG. 20C depicts an A-lamp bulb with a filter 2002. The embodiment is useful for general illumination purposes. In the case of an A-lamp (or other consumer lamps such as BR lamps, for instance) the filter may be placed at various positions in the system. It may be placed in a remote configuration (in-between the LED emitter and a protective envelope) as shown in FIG. 20C. It may also be placed in the vicinity of the LED emitter, or integrated with the protective envelope.

In various embodiments, the system may mix standard sources with high circadian stimulation and circadian-friendly sources with a filter achieving very low circadian stimulation.

As already mentioned, the discussion above uses a simplistic metric (fraction of SPD in the CSR). Other metrics can be used to design the filter, such as the fraction of power Fv in the violet range (for instance 400-440 nm), the fraction of power Fc in the cyan range (for instance, 440-500 nm) and their ratio. For instance, for the filtered spectrum of FIG. 2a, Fv=0.256, Fc=8E−4 and Fc/Fv=0.003. Other cyan ranges (such as 430 nm-500 nm) could also be used. Based on the teachings of this invention, one skilled in the art will know how to select light sources and wavelength converters to obtain spectra with a given SPD fraction in a given range (for instance, a low or high fraction of total SPD power in a given range) and given quality-of-light metrics.

Figure 21B:
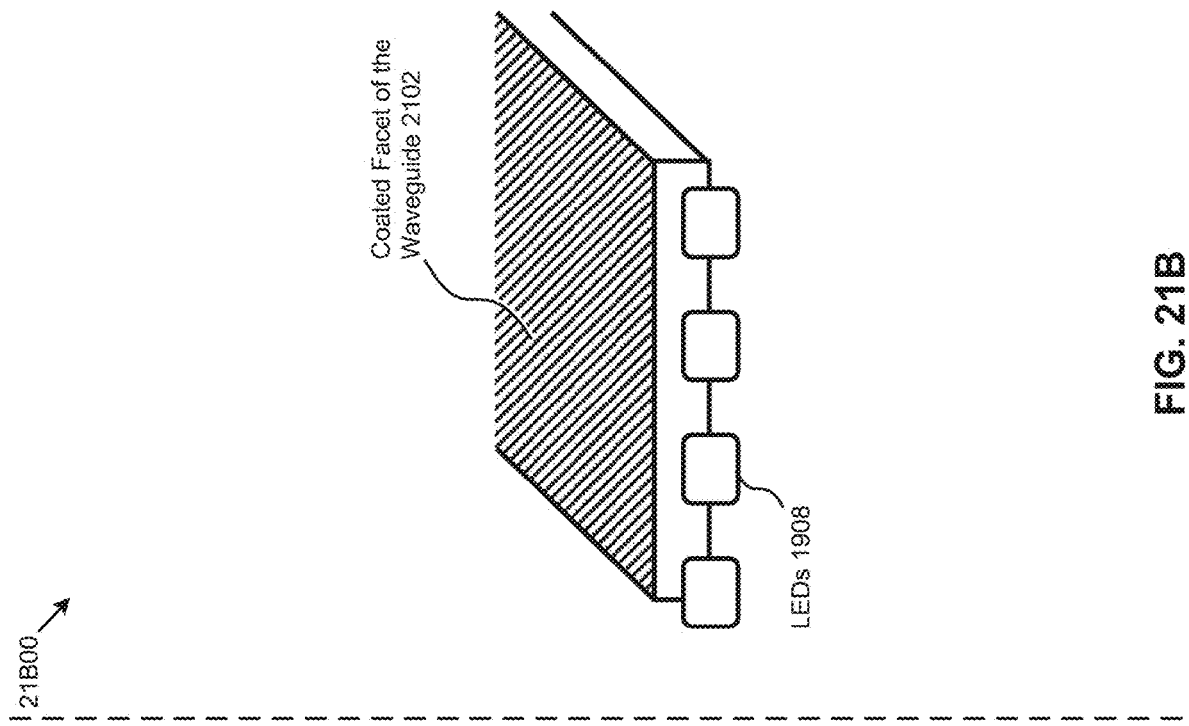
FIG. 21B shows an example using dielectric stacks and compares filtered SPDs under varying conditions, according to some embodiments.
Figure 21A:
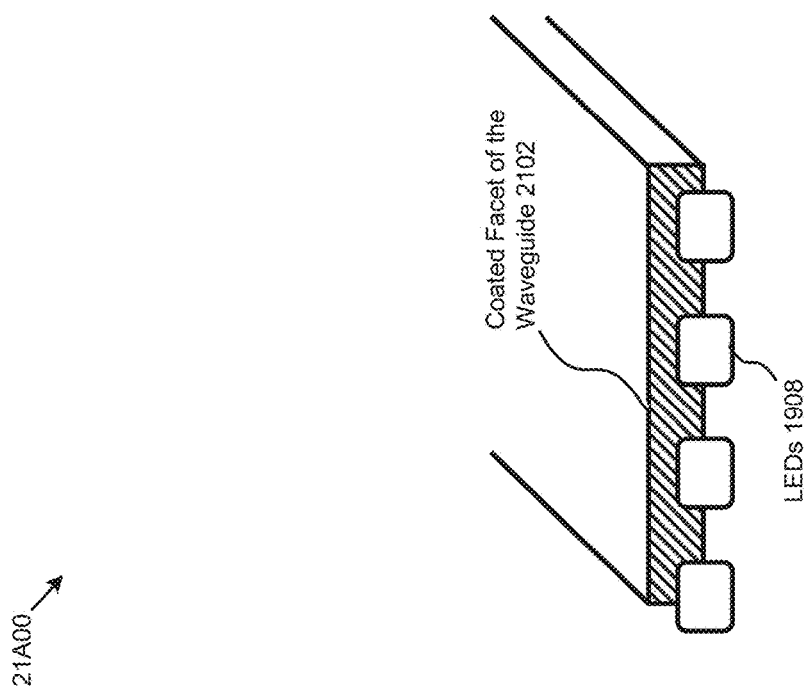
FIG. 21A shows an example using dielectric stacks and compares filtered SPDs under varying conditions, according to some embodiments.

FIG. 21A and FIG. 21B depict two displays architectures using LEDs coupled to waveguides. In each case, a filter is present to remove radiation in the CSR. In the case of FIG. 21A, the filter is placed at the coupling facet. In the case of FIG. 21B, the filter is placed in a layer parallel to the waveguide (for instance, it may be coated on the output facet of the waveguide, or it may be combined with another element of the display such as the RGB filters).

Embodiments using waveguide coupling may be useful for display applications (such as screens, phones, tablets, and other lighted devices), but also for general lighting applications in waveguide-based luminaires.

Figure 22:
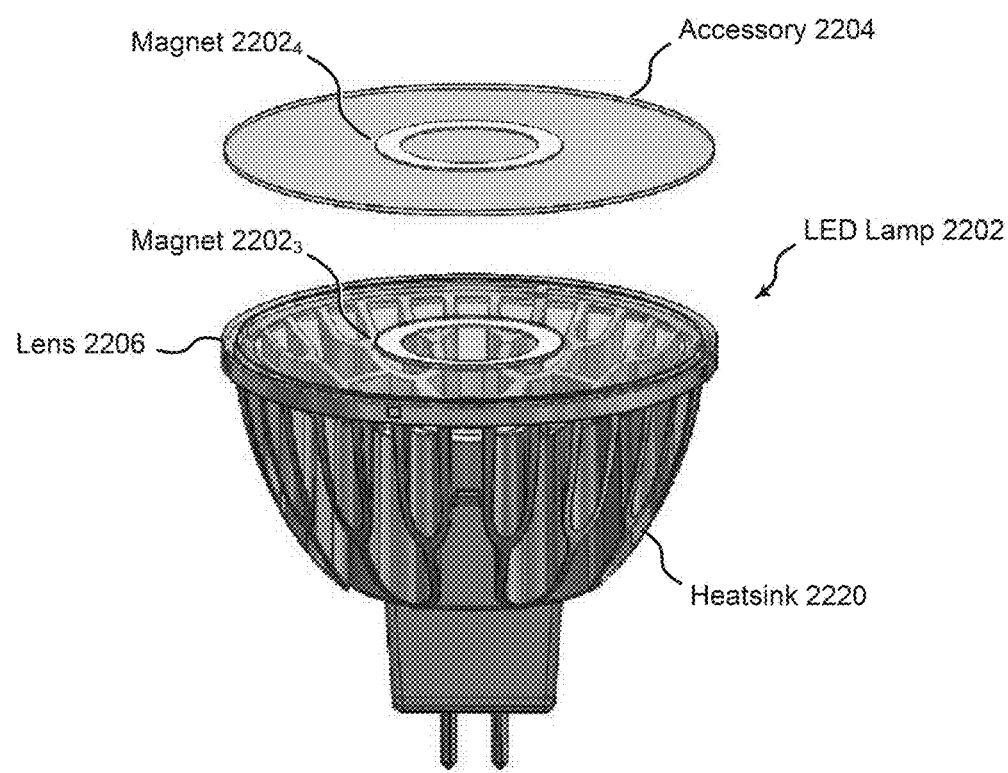
FIG. 22 shows examples using dielectric stacks and compares filtered SPDs under varying conditions, according to some embodiments.

FIG. 22 through FIG. 24 present variations using accessories (e.g., filters) in combination and/or in combination with LED lamps. Filters can be implemented with magnetic or other mating devices, and filters can be designed or combined to project emanated light in selected patterns of intensity. Strictly as an example, exploded perspective view 2200 depicts an MR-16 LED lamp 2202 comprising a heatsink 2220, a lens 2206, and first and second instances of magnets 2202 where the first magnet $2202_3$ is affixed to the lens, and the second magnet $2202_4$ is affixed to an accessory 2204. The accessory can implement filters designed to project emanated light in selected patterns of intensity. For example, FIG. 23 depicts a side view 2302 of a focus spot, and FIG. 24A depicts a side view 2402 of a diffused flood lamp pattern. FIG. 24B depicts a side view 2404 of a medium spot pattern.

Figure 25B:
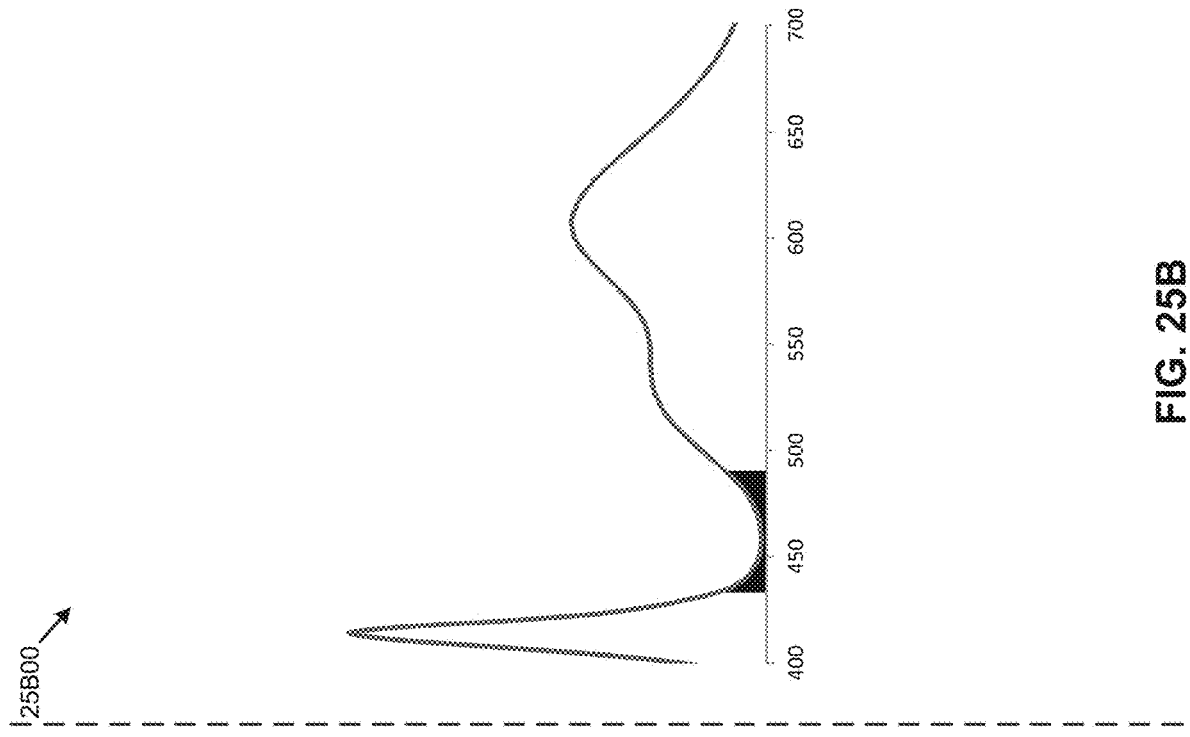
FIG. 25B shows an example using dielectric stacks and compares filtered SPDs under varying conditions, according to some embodiments.
Figure 25A:
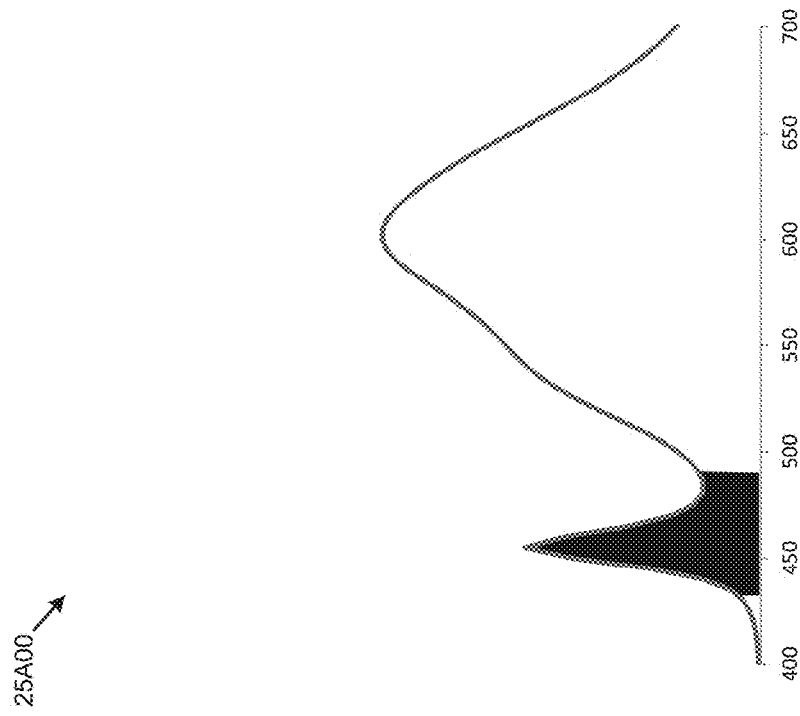
FIG. 25A shows an example using dielectric stacks and compares filtered SPDs under varying conditions, according to some embodiments.

FIG. 25A to FIG. 25E illustrate additional advantages of combining a filter with a spectrum which already has only a small portion of radiation in the CSR. FIGS. 25A and B compare two filtered spectra. In these figures a CSR of 430-490 nm is assumed and the filter cuts off all radiation in this CSR. FIG. 25A is a standard source (specifically, a standard blue-pumped LED source) with a filter; although the presence of the filter ensures little radiation in the CSR, it also induces a significant loss of optical power (black region of FIG. 25A): 11% of the optical power is lost due to filtering. Other standard light sources, such as filament lamps, would incur similar losses with the same filter. In contrast, FIG. 25B shows an embodiment of the invention, combining a spectrum with little radiation in the CSR and a filter cutting off all residual radiation in the CSR. In this case, only 3% of the optical power in the spectrum is lost due to filtering. Therefore, embodiments of the invention may be more radiation-efficient than standard light sources using a filter to reduce circadian stimulation. For example, for the same starting radiated power levels for each of the light sources corresponding to FIGS. 25A and 25B, after filtering, more of the original radiation is retained for FIG. 25B as compared to FIG. 25A. In addition, since so much radiation is removed for the case of FIG. 25A, a large color shift is incurred (e.g., the light source is no longer white), which color shift is not easily corrected. In contrast, for the case of FIG. 25B, only a small chromaticity shift is caused by filtering, which can be easily corrected by slight compensating modifications to the primary violet light emission and/or the phosphor emission.

FIG. 25C and FIG. 25D are similar to the previous figures, but consider a slightly narrower CSR of 440-480 nm. Here again the filter cuts off all radiation in the CSR. When applied to a conventional source, the filter cuts off 8% of the total spectral power whereas when applied to a spectrum with little radiation in the CSR, only 1% of the total spectral power is lost. Therefore, energy savings can be achieved by embodiments combining a spectrum with little radiation in the CSR and a filter blocking light in the CSR, regardless of the specific value of assumed for the CSR.

In addition, the spectra of FIGS. 25A to 25E differ in their chromaticity. This is summarized in the table of FIG. 25E which shows the color coordinates (u'v') and the distance to the Planckian locus (Duv), for unfiltered spectra and for spectra filtered by the two filters considered above. Before filtering, both the conventional spectrum and the embodiment of the invention (with little radiation in the CSR) have a chromaticity which is close to the Planckian locus (the value of Duv is small). Application of the filter induces a chromatic shift, but this shift is more moderate for embodiments of the invention than for standard sources, which may be desirable. The chromatic shifts displayed by filtered standard sources correspond to a pronounced yellowish tint which may be undesirable.

As already mentioned, specific embodiments of the invention further reduce the value of Duv by combining a spectrum which is initially off-Planckian with a filter so that the resulting embodiment is nearly on-Planckian. By the same approach, other embodiments may also aim for a final chromaticity which is not on the Planckian locus, but is for instance below the Planckian locus instead.

In some embodiments of the invention, the optical power lost due to the addition of a filter is less than 8%, less than 5%, less than 3% or less than 1%. In some embodiments of the invention, the chromatic shift (in units of (u'v')) between the unfiltered and the filtered spectra is less than 10E−3, less than 2E−3, less than 1E−3. In some embodiments of the invention, the distance Duv to the Planckian locus of the filtered spectrum is less than 10E−3, less than 2E−3, less than 1E−3.

Figure 26A:
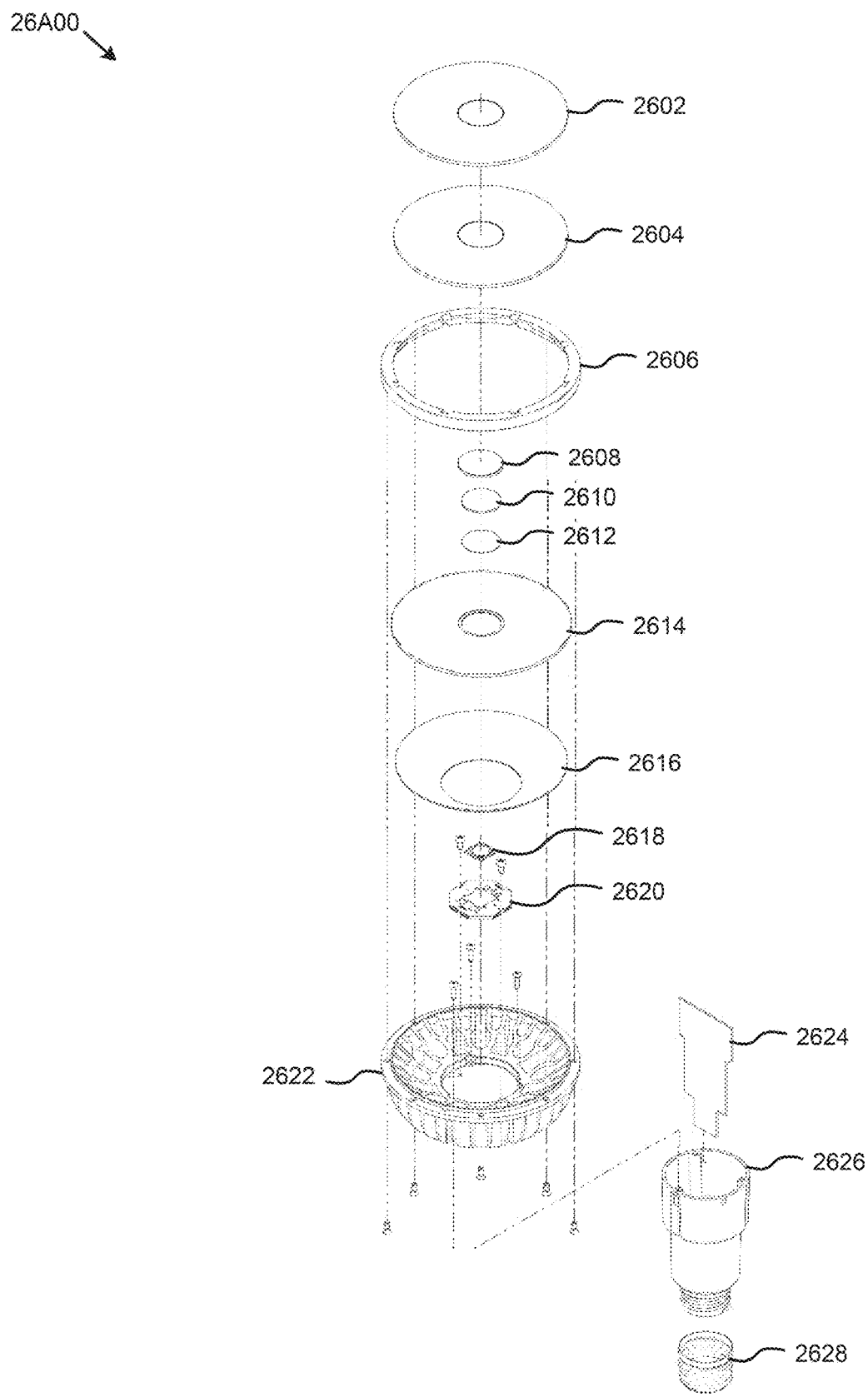
FIG. 26A shows an example using dielectric stacks and compares filtered SPDs under varying conditions, according to some embodiments.

FIG. 26A presents an exploded view 26A00 of an LED lamp used with an interchangeable retaining ring kit for mating to an LED lamp heatsink. As an option, the present exploded view 26A00 may be implemented in the context of the architecture and functionality of the embodiments described herein. The depicted exploded view 26A00 or any aspect thereof may be implemented in any desired environment.

In some embodiments, aspects of the present disclosure can be used in an assembly. As shown in FIG. 26A, the assembly comprises:
  a screw cap 2628
  a driver housing 2626
  a driver board 2624
  a heatsink 2622
  a metal-core printed circuit board 2620
  an LED lightsource 2618
  a dust shield 2616
  a lens 2614
  a reflector disc 2612
  a magnet 2610
  a magnet cap 2608
  a trim ring 2606
  a first accessory 2604
  a second accessory 2602

As shown, the heatsink 2622 and trim ring 2606 can be mated together. In some cases, the trim ring is mated to the heatsink using threads that are present on the trim ring, or using threads present in screw fasteners. Any fastener can be used to affix the trim ring to the heatsink, and different fastening techniques may offer varying degrees of thermal conductivity with the heat sink. A gasket may be used to form a seal between the heat sink and a trim ring.

The components of assembly 26A00 may be described in substantial detail. Some components are 'active components' and some are 'passive' components, and can be variously-described based on the particular component's impact to the overall design, and/or impact(s) to the objective optimization function. A component can be described using a CAD/CAM drawing or model, and the CAD/CAM model can be analyzed so as to extract figures of merit as may pertain to e particular component's impact to the overall design, and/or impact(s) to the objective optimization function. Strictly as one example, a CAD/CAM model of a trim ring is provided in a model corresponding to the drawing of FIG. 26C.

FIG. 26B shows a selection of rings of a kit 26B00 showing an example of interchangeable retaining ring kit for mating to an LED lamp heatsink. As an option, the present selection of rings of a kit 26B00 may be implemented in the context of the architecture and functionality of the embodiments described herein. The depicted selection of rings of a kit 26B00 or any aspect thereof may be implemented in any desired environment.

As shown, a set of trim rings may be combined into a kit such that one or another trim ring can be selected for use with a particular lamp and a particular luminaire. For example the kit of FIG. 26B (top), contains three trim rings as follows:
  A thin trim ring (top left) for use with a PAR30L form factor LED lamp and a luminaire of type PAR30L.
  A thin trim ring (top center) for use with a PAR30L form factor LED lamp and a luminaire of type AR111.
  A thin trim ring (top right) for use with a PAR38 form factor LED lamp and a luminaire of type PAR38.

Figure 26C:
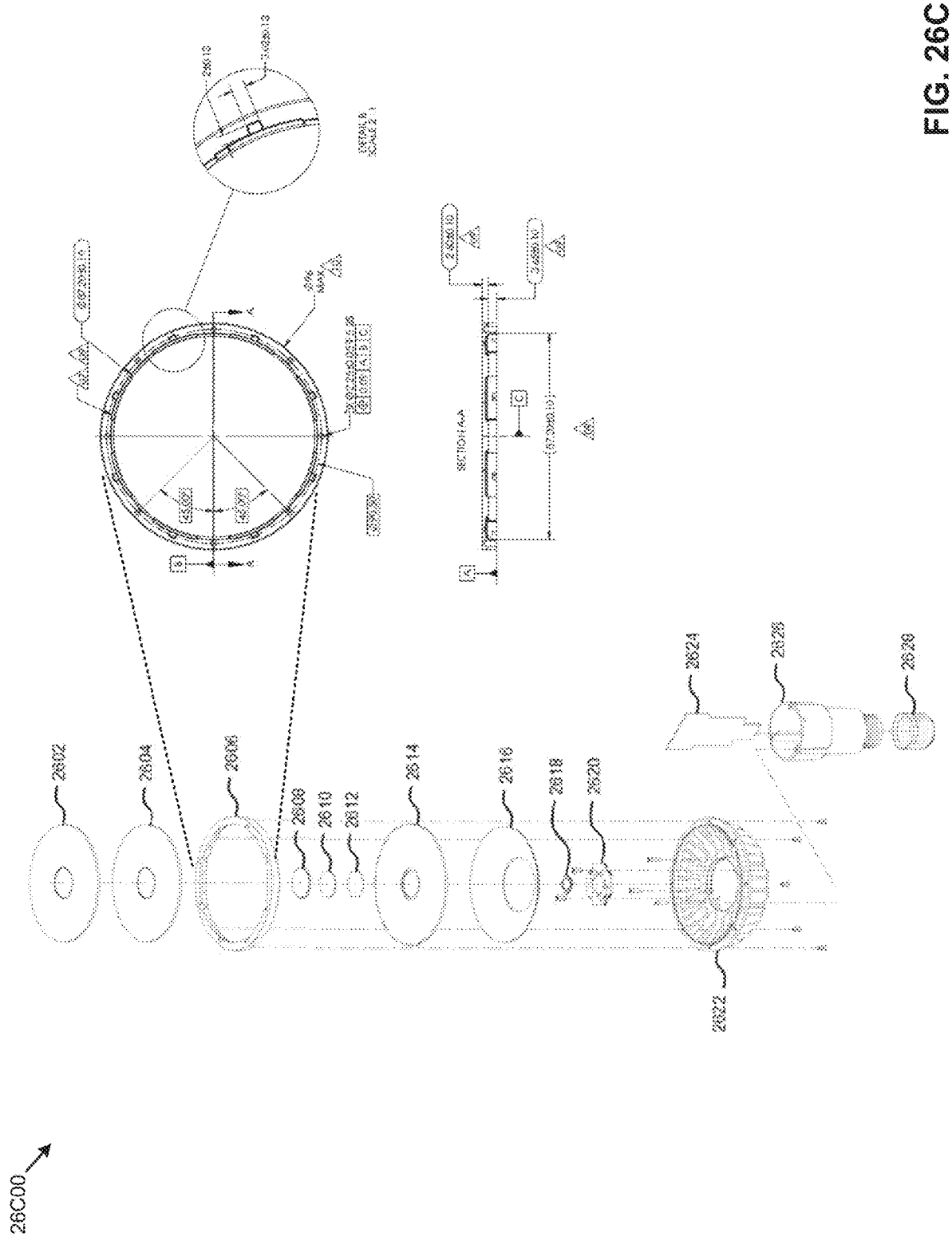
FIG. 26C shows an example using dielectric stacks and compares filtered SPDs under varying conditions, according to some embodiments.

FIG. 26C includes a mechanical drawing inset showing detail of an example component within an interchangeable retaining ring kit for mating to an LED lamp heatsink, according to some embodiments.

A particular trim ring may have a mechanical design so as to provide a positive contact with adjacent components. In particular, a trim ring may contain undulations or detents to facilitate thermal conductivity between the heatsink and any surrounding structures, possibly including the housing of the luminaire.

The particular size and shape of the trim ring may vary to facilitate any particular function, and/or the particular size and shape of the trim ring may vary to accommodate snap-on or other field-replaceable accessories. Examples of the foregoing functions include:

Holding the lens in place within the assembly.
Supporting a snap-on or other field-replaceable diffuser.
Enhance the function of the heatsink (e.g., conduct heat from the heatsink to other structural members and to the air interface).
Provide a mechanical mating between an American National Standards Institute (ANSI) ANSI-standard lamp and a compliant luminaire.
Provide a mechanical mating between an ANSI-standard compliant luminaire and a lamp.
Provide a mechanical mating between an International Electrotechnical Commission (IEC) IEC-standard lamp and a compliant luminaire.
Provide a mechanical mating between an IEC-standard luminaire and a compliant lamp.
Provide a mechanical mating between a National Electrical Manufacturers Association (NEMA) NEMA-standard luminaire and a compliant lamp.
Provide a mechanical mating between a NEMA-standard compliant luminaire and a NEMA-standard lamp.

FIG. 26C includes a mechanical drawing inset 26C00 showing detail of an example component within a interchangeable retaining ring kit for mating to an LED lamp heatsink. As an option, the present mechanical drawing inset 26C00 may be implemented in the context of the architecture and functionality of the embodiments described herein. The depicted mechanical drawing inset 26C00 or any aspect thereof may be implemented in any desired environment.

Following the foregoing, a trim ring may have certain specifications for mating, and such specifications may be defined in conjunction with the mechanical specifications of a heatsink. For example, protrusions and/or depressions, or flanges and/or openings, or zig-zag undulations and/or zag-zig undulations can be specific to a trim ring, and/or a heatsink. Several embodiments can be described as follows:

Embodiment 1. An interchangeable retaining ring kit for mating to an LED lamp heatsink, comprising:
a first trim ring having a first form factor; and
a second trim ring having a second form factor.

Embodiment 2. The interchangeable retaining ring kit of embodiment 1, wherein the first trim ring has protrusions configured to mate mechanically to depressions in the LED lamp heatsink.

Embodiment 3. The interchangeable retaining ring kit of embodiment 1, wherein the first trim ring has depressions configured to mate mechanically to protrusions in the LED lamp heatsink.

Embodiment 4. The interchangeable retaining ring kit of embodiment 1, wherein the first form factor has a first diameter and the second form factor has a second diameter, wherein the first diameter and the second diameter are different.

Embodiment 5. The interchangeable retaining ring kit of embodiment 1 wherein the first form factor has a first thickness and the second form factor has a second thickness, wherein the first thickness and the second thickness are different.

Embodiment 6. The interchangeable retaining ring kit of embodiment 1, further comprising at least one fastener to affix the first trim ring to the LED lamp heatsink.

Circadian filters can be used in combination with any lamp types, and/or with any mating or retaining structures.

Figure 27B:
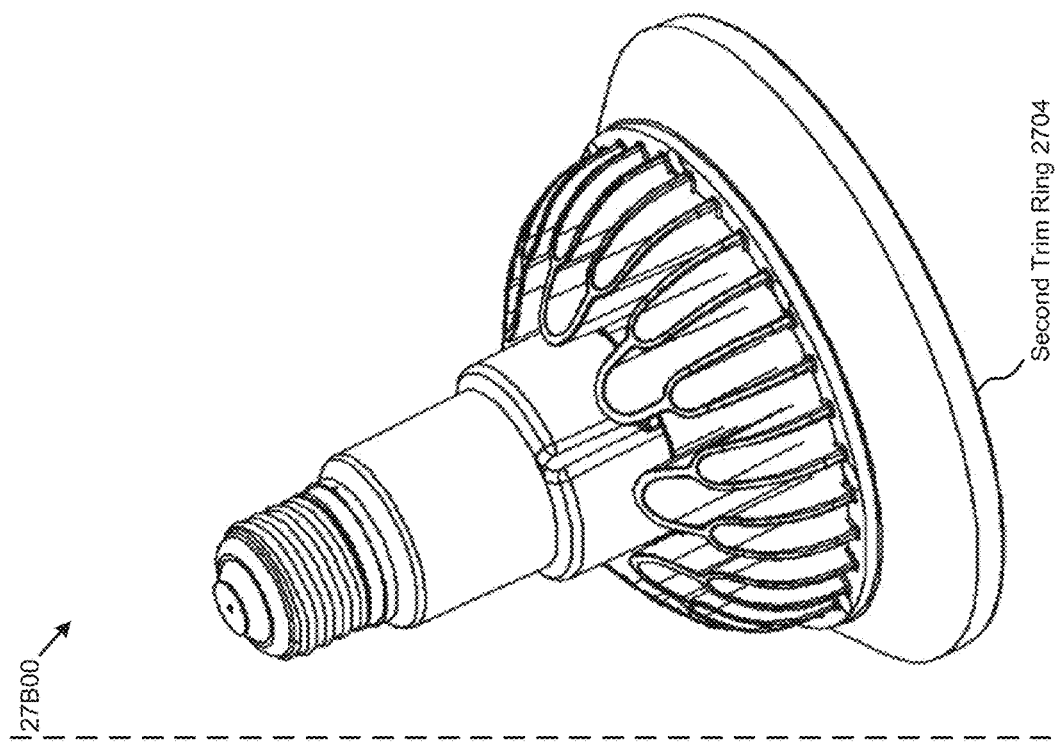
FIG. 27B shows an example using dielectric stacks and compares filtered SPDs under varying conditions, according to some embodiments.
Figure 27A:
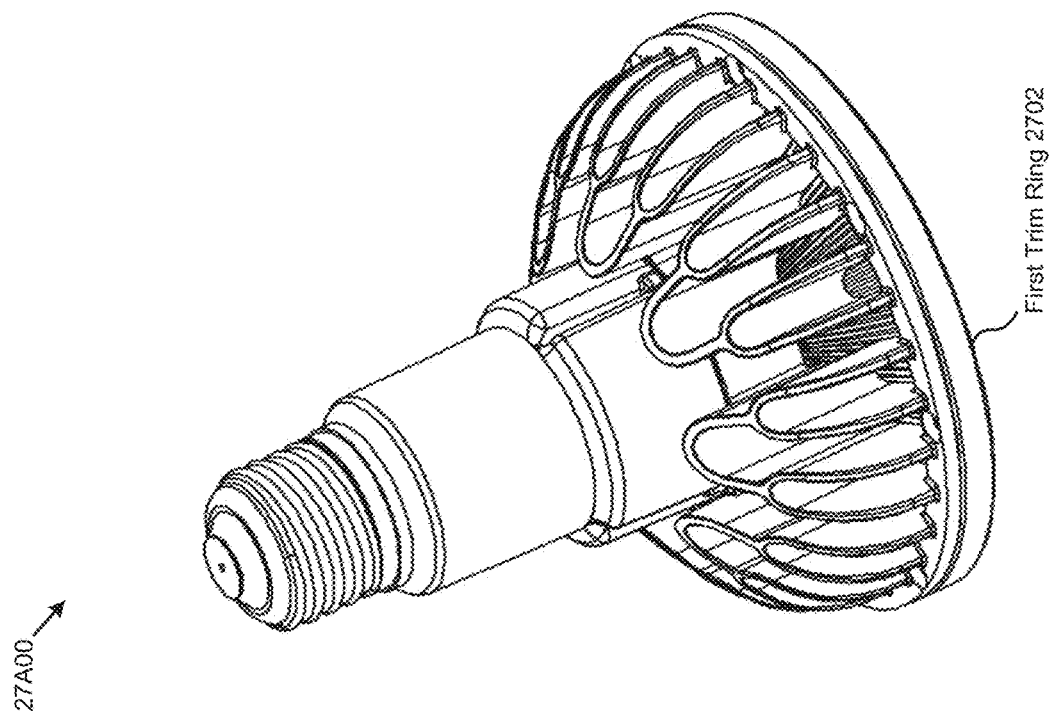
FIG. 27A shows an example using dielectric stacks and compares filtered SPDs under varying conditions, according to some embodiments.

FIGS. 27A and 27B provide images of a lamp system having a trim ring installed. As shown in FIG. 27A, a PAR30 lamp is fitted with a first trim ring 2702 from a kit 11B00. The assembly 27A00 can be installed into a luminaire. As shown in FIG. 27B, a PAR38 lamp is fitted with a second trim ring 2704. The assembly 27B00 can be installed into a luminaire. Both the first trim ring 2702 and the second trim ring 2704 are delivered in a kit.

The foregoing embodiments describe a lamp system and techniques for making and using an interchangeable retaining ring kit. At least some of the components of the kit serve to mate to an LED lamp heatsink. In some assemblies, the lamp system comprises an LED lightsource configured to be disposed at least partially within the LED lamp heatsink, which is then fitted with a first trim ring having a first form factor (e.g., to conform to a first ANSI form factor). The interchangeable retaining ring kit comprises a second trim ring having a second form factor (e.g., to conform to a second ANSI form factor).

To implement some embodiments of the invention, care is taken such that no element in the system provides unwanted emission in the CS stimulation range. In particular, the absence of fluorescent whitening agents (FWAs) may be important. FWAs are particles that can absorb short-wavelength radiation (such as ultraviolet radiation and violet light) and emit fluorescence in the range 440-480 nms; they typically absorb light at wavelengths shorter than 430 nm. They are commonly used in a variety of white materials to enhance the perception of whiteness. Embodiments of the invention comprise an LED emitter which emits violet light. It may be unwanted that such light substantially interact with FWAs as this may result in substantial emission in the CS range. Therefore, it may be desirable to design a system that does not contain a significant presence of FWAs which can interact with light and create fluorescence in the CS spectral range. Similar considerations apply to other fluorescent materials similar to FWAs.

A possible way to test for the effect of FWAs is as follows. One may measure the direct emission of the LED module outside the system, characterized by a normalized spectral power distribution SPD_1. One may then measure the emission of the full system, characterized by a normalized spectral power distribution SPD_2. The ratio R=SPD_2/SPD_1 can then be computed to check for the presence of fluorescence. In the absence of any fluorescence and if the system's optical response is spectrally flat, R should be equal to one. In a more realistic case, the system shows absorption with slight wavelength dependence, and R is a smoothly varying function of wavelength. However, in the presence of fluorescence from FWAs, R shows a pronounced peak with a value above unity in the blue range—this is due to the lack of blue light in SPD_1 and the higher presence of fluorescent blue light in SPD_2.

Figure 28A:
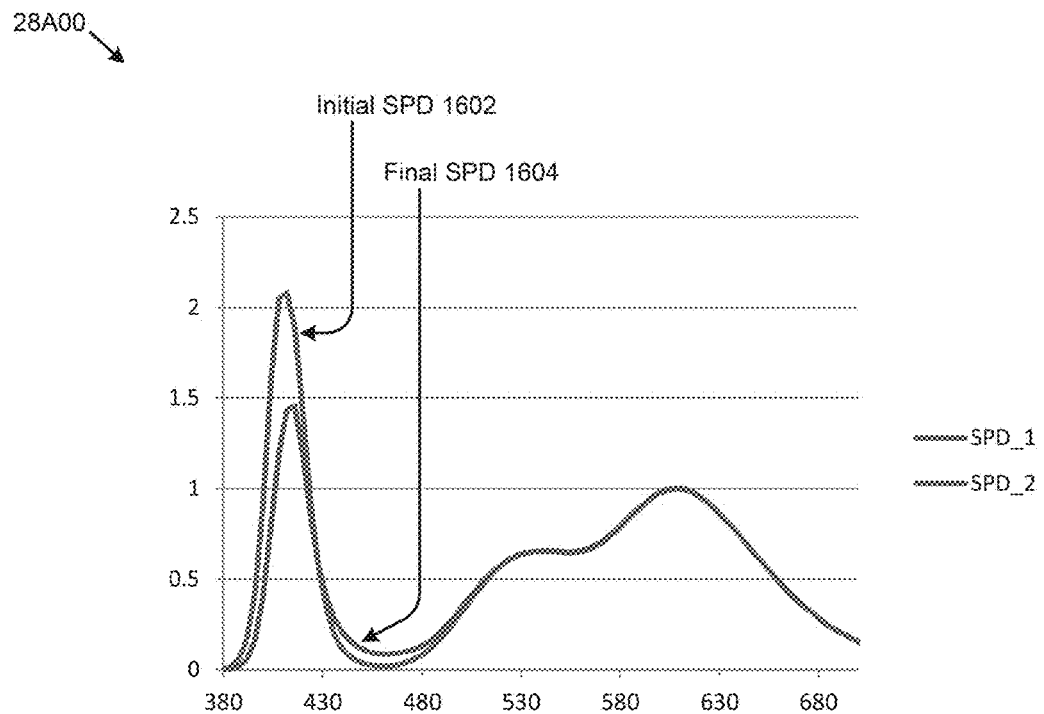
FIG. 28A compares experimental results to conventional LED spectra, according to some embodiments.
Figure 28B:
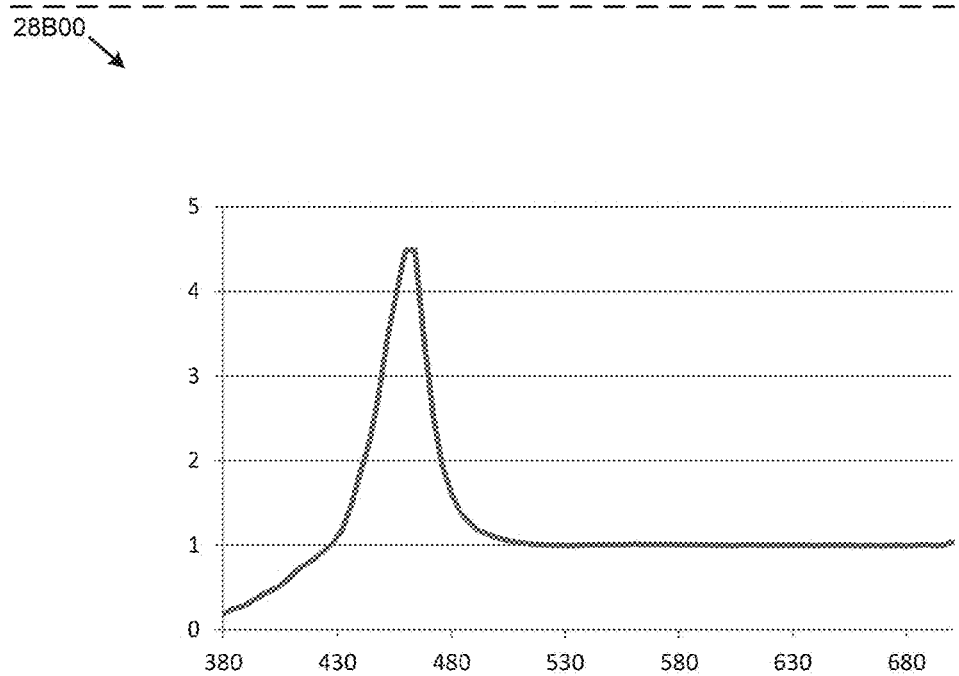
FIG. 28B compares experimental results to conventional LED spectra, according to some embodiments.
Figures 29A, 29B:
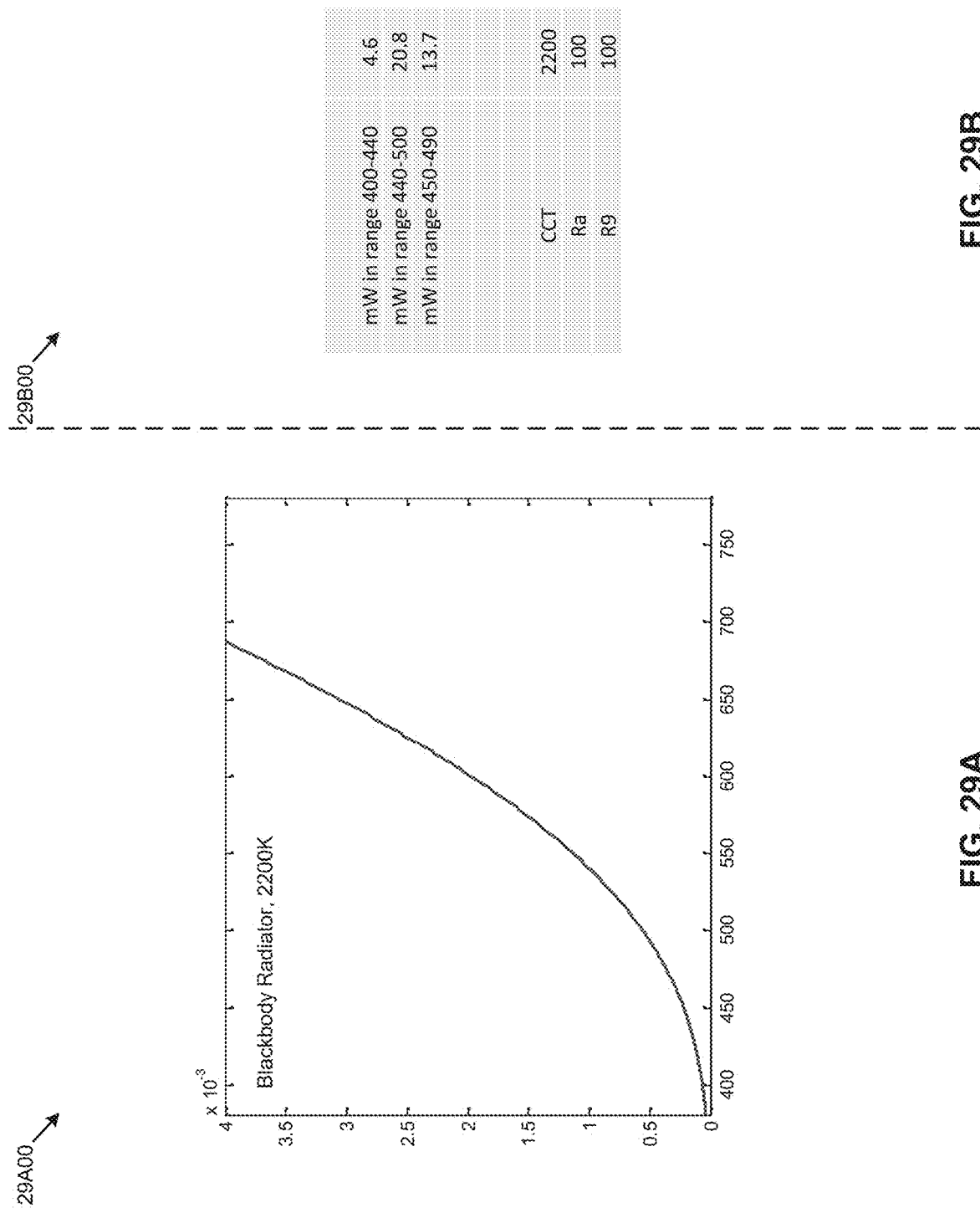
FIG. 29A compares experimental results to conventional LED spectra, according to some embodiments.
FIG. 29B compares experimental results to conventional LED spectra, according to some embodiments.
Figures 30A, 30B:
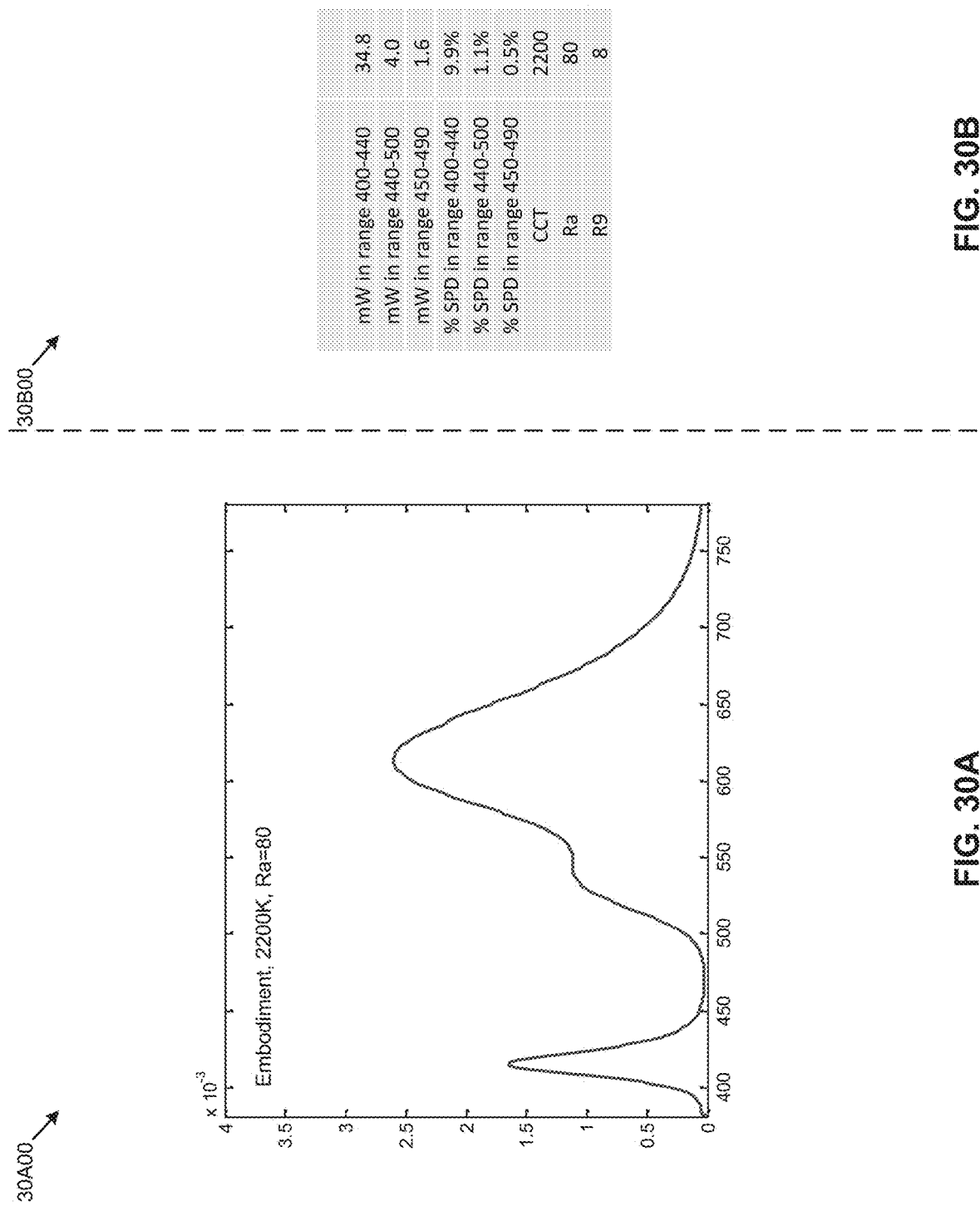
FIG. 30A compares experimental results to conventional LED spectra, according to some embodiments.
FIG. 30B compares experimental results to conventional LED spectra, according to some embodiments.
Figures 31A, 31B:
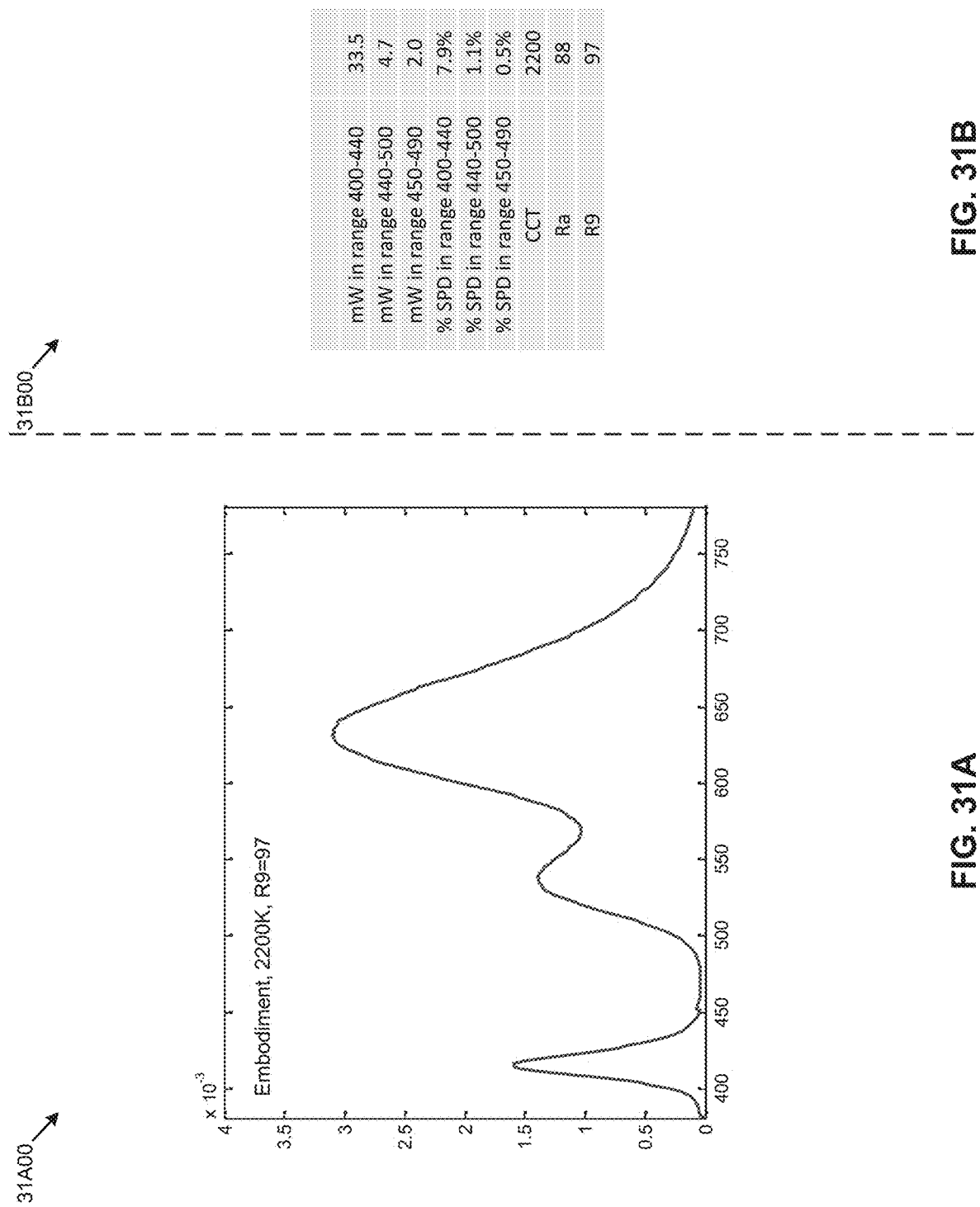
FIG. 31A compares experimental results to conventional LED spectra, according to some embodiments.
FIG. 31B compares experimental results to conventional LED spectra, according to some embodiments.
Figure 32B:
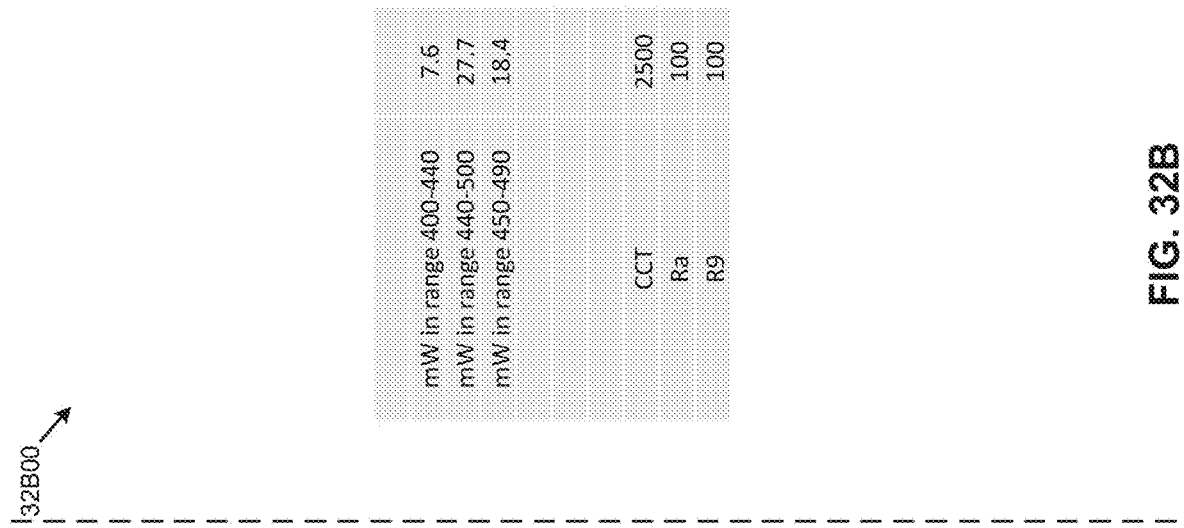
FIG. 32B compares experimental results to conventional LED spectra, according to some embodiments.
Figure 32A:
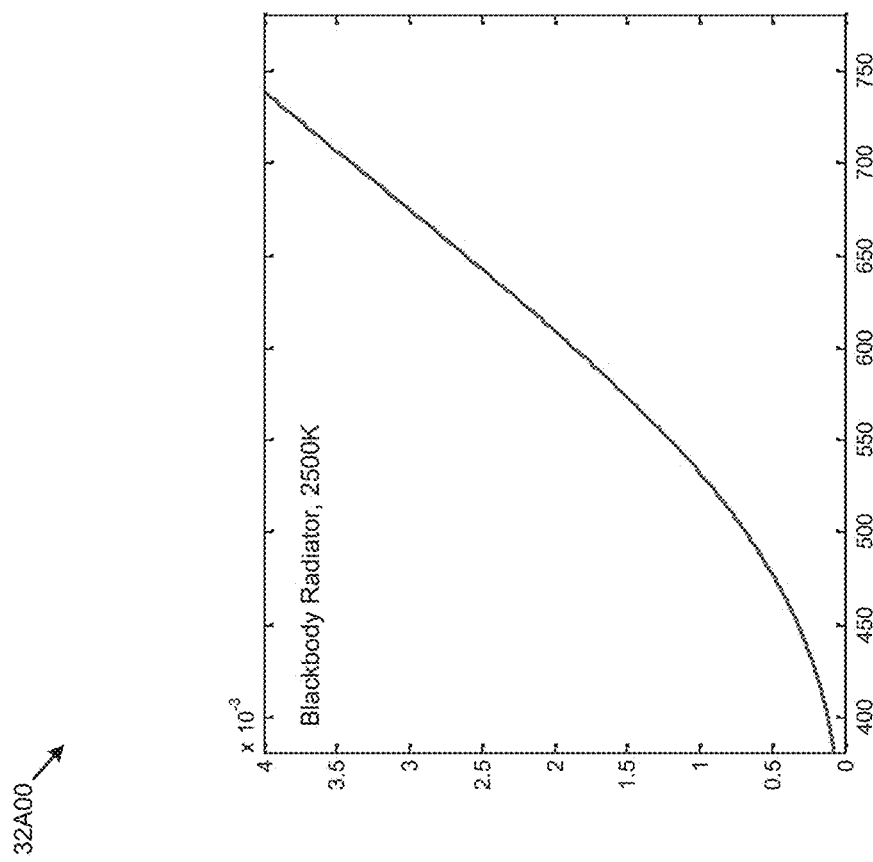
FIG. 32A compares experimental results to conventional LED spectra, according to some embodiments.
Figures 33A, 33B:
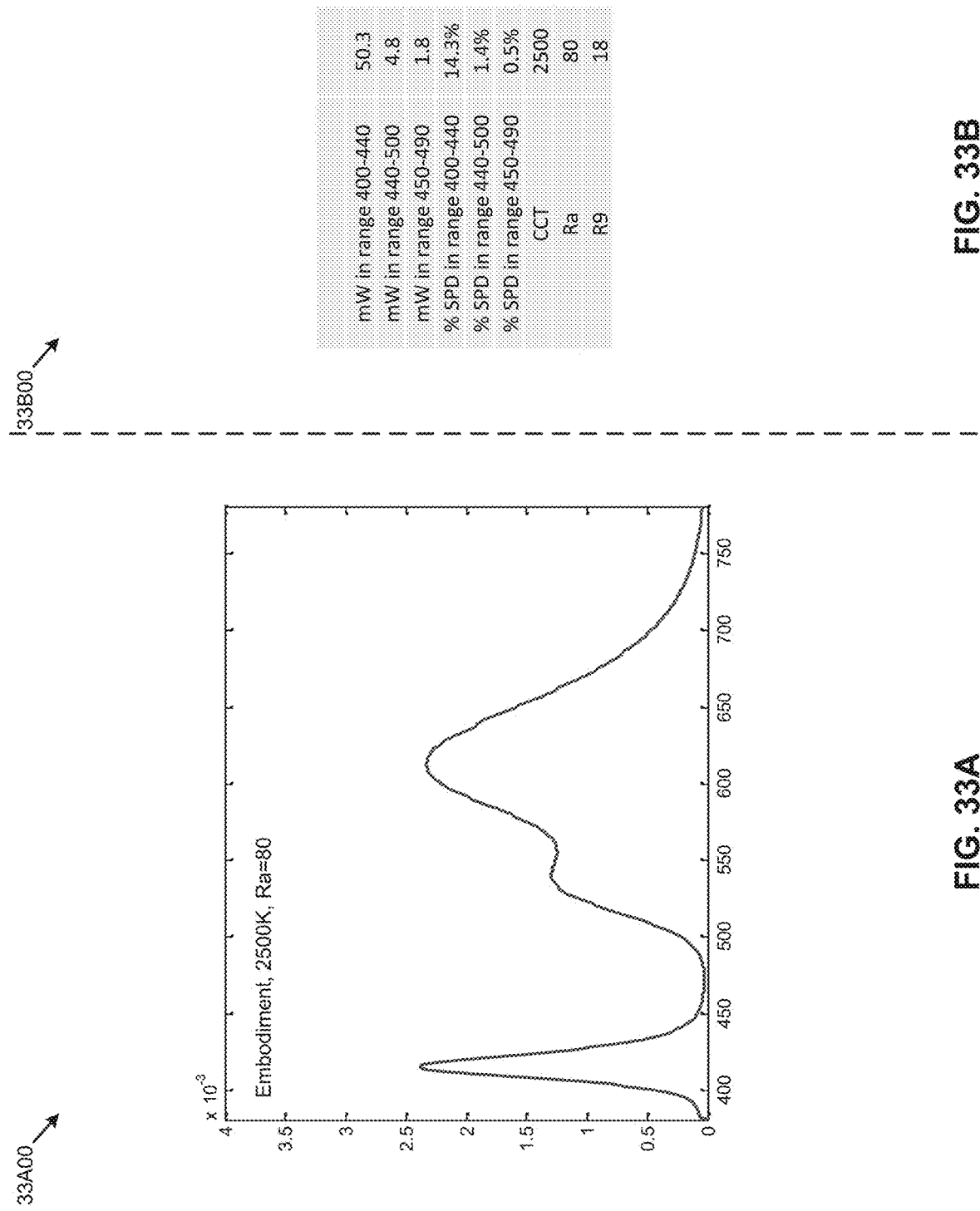
FIG. 33A compares experimental results to conventional LED spectra, according to some embodiments.
FIG. 33B compares experimental results to conventional LED spectra, according to some embodiments.
Figure 35B:
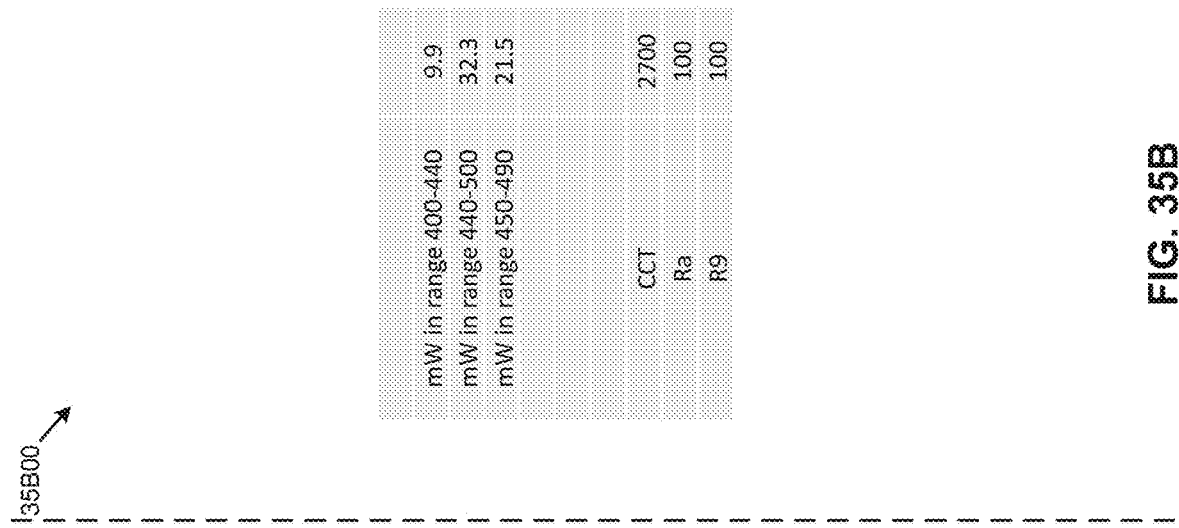
FIG. 35B compares experimental results to conventional LED spectra, according to some embodiments.
Figure 35A:
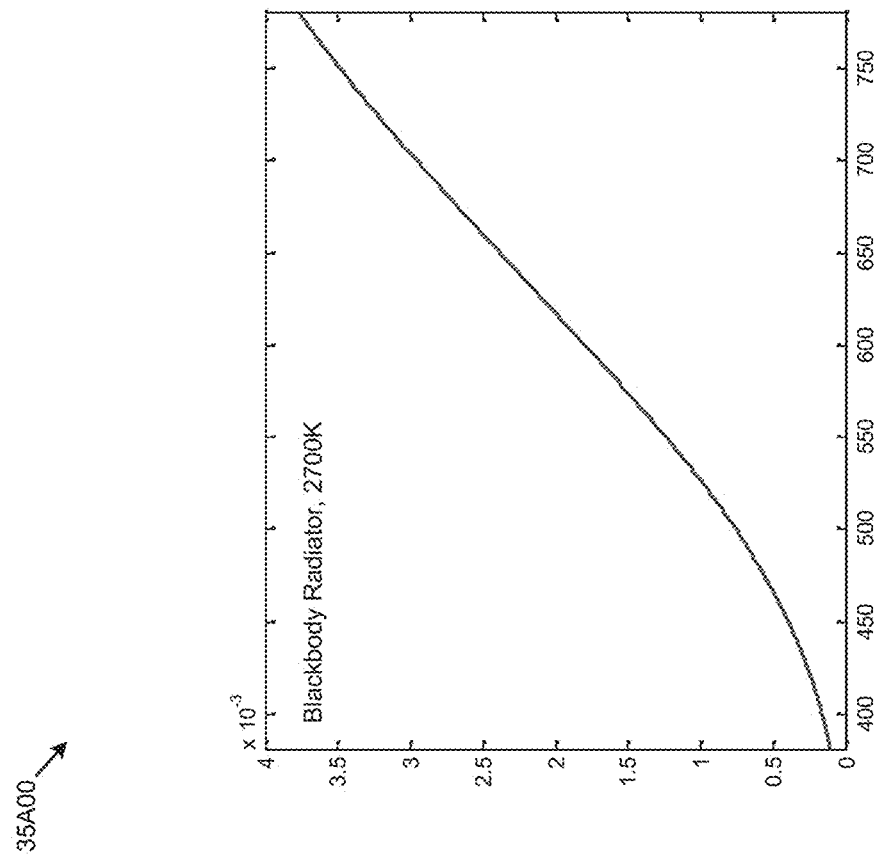
FIG. 35A compares experimental results to conventional LED spectra, according to some embodiments.
Figures 37A, 37B:
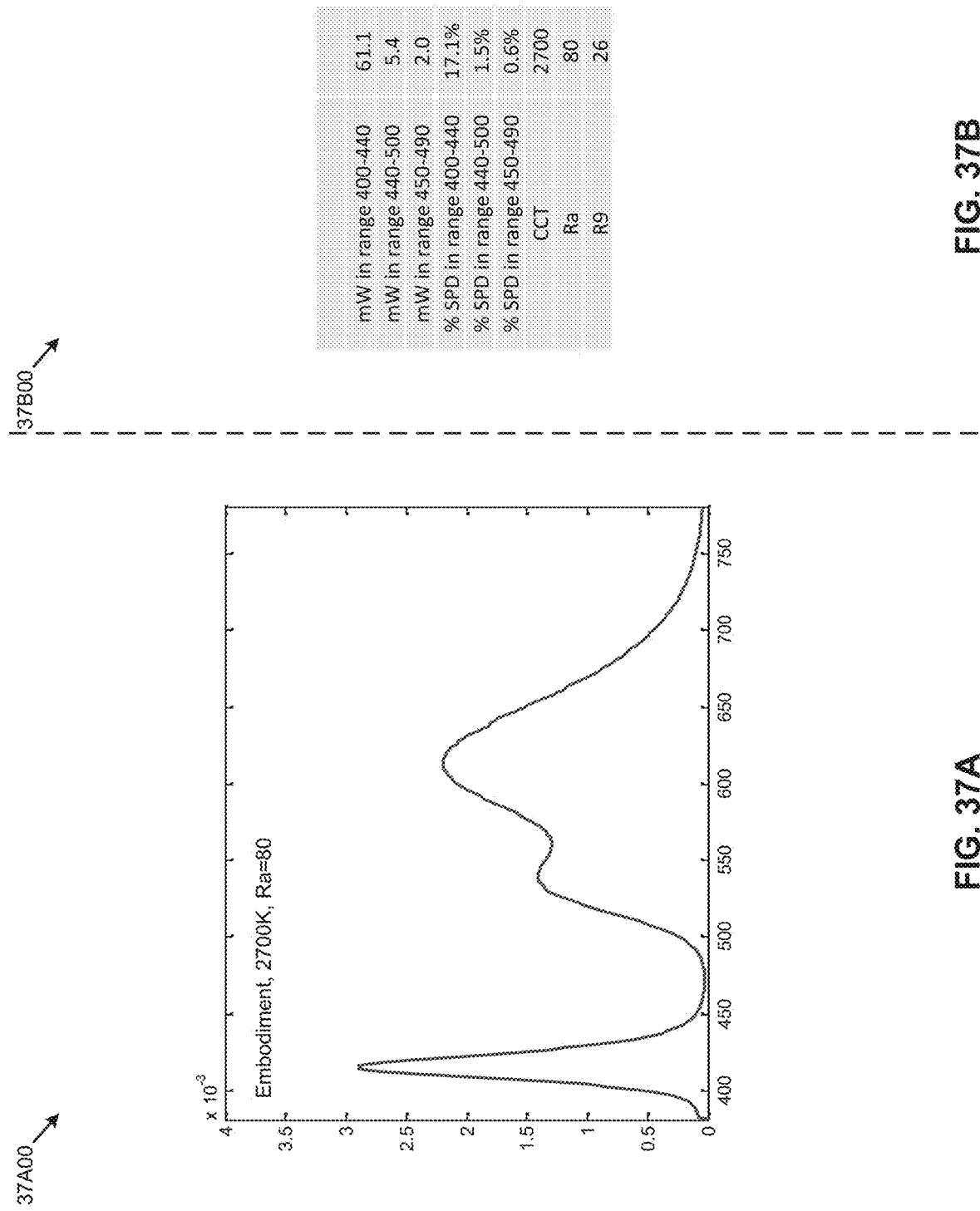
FIG. 37A compares experimental results to conventional LED spectra, according to some embodiments.
FIG. 37B compares experimental results to conventional LED spectra, according to some embodiments.

FIG. 28A and FIG. 28B present experimental results which illustrate this effect. FIG. 28A shows a superposition chart 28A00 that plots a final SPD 1604 over an initial SPD 1602. SPD_1 (see initial SPD 1602) is based on an LED emitter. As shown, SPD_1 has relatively little light in the range 430 nm-480 nm. FIG. 28A also shows SPD_2 (see final SPD 1604) that is measured when the LED emitter is placed in a lighting fixture that contains FWAs. SPD_2 has more light in the same range due to fluorescence. SPD_1 and SPD_2 have been normalized to their peak value in the green-red range for easier comparison. FIG. 28B shows the corresponding ratio R. R shows a pronounced peak centered near 460 nm, which evidences the presence and effect of FWAs on the system.

Another way to ascertain the absence of a significant effect from FWAs is simply to measure the net spectrum emitted by the complete lighting system and to ascertain that it does not contain unwanted radiation in the CS spectral range.

Some embodiments are related to lighting products such as A lamps or BR lamps. Such lamps are common in consumer homes. Their typical CCT is 2700K (for instance standard incandescent), with other common values ranging from 3000K (for instance halogen lamps) to 2500K (for lamps incandescent dimmed to 10-20% of its full optical power).

FIGS. 29-45 compare properties of various spectra, including blackbody radiators and embodiments. The shown SPDs have been normalized to a luminous flux of 1001 lm. Tables indicate corresponding radiometric and colorimetric properties. It has already been demonstrated above that light sources such as filament lamps and conventional LED lamps can cause unwanted circadian stimulation. The discussion below provides additional quantitative examples, and contrasts these with embodiments.

FIGS. 29, 32, 35 and 39 are for blackbody radiators and are representative of conventional filament lamps. The corresponding tables show that, when going from 2700K to 2200K, the total power in the range 450-490 nm is roughly halved. In a scenario where a user dims a light to 20% of its full optical power, which shifts the CCT from 2700K to 2200K, the circadian stimulation in the range 450-490 nm is therefore divided by 10 (a factor of 5 for total flux, and a factor of 2 for relative fraction of power in the relevant spectral range).

FIGS. 36 and 40 show conventional LED spectra. The total power in the range 450-490 nm is roughly similar to that of filament lamps, indicating a similar CS—which can be called a "regular CS". Similar conclusions are reached when assuming other CS ranges of action, such as 440-500 nm.

Embodiments of the invention shown on FIGS. 30, 31, 33, 34, 37, 38, and 41 have a power in the range 450-490 nm which is about 10% of the power of a blackbody radiator of the same CCT and same luminous flux. Therefore, for a given CCT, circadian stimulation is reduced by a factor of 10. Other CS ranges of action give slightly different results—for instance the range 440-500 nm leads to a reduction by a factor of five. In general, such reductions in CS are termed as sources with "low CS". In addition, as mentioned elsewhere herein, a more complex metric may be used than the fraction of the SPD in a given range. Rather, a circadian action spectrum may be chosen and integrate the SPD using this action spectrum as a weighing function, thus obtaining the "circadian stimulation" described elsewhere. This more sophisticated figure of merit leads to the same quantitative conclusions as that described herein: it is possible to design a light source which reduces the "circadian stimulation" by one order of magnitude, two orders of magnitude or more versus a conventional light source, and maintains aspect of quality-of-light (CCT, chromaticity, Ra, R9 . . . )

A low CS can also be quantified by the amount of optical power (for a SPD normalized to an illuminance of 100 lm) in a CS wavelength range of interest, such as 430-510 nm, 440-500 nm or 450-490 nm. A low spectral content in a given CS range may correspond for instance to less than 10 mW, less than 5 mW, less than 2 mW. This can be compared to values of about 20-40 mW for blackbody radiator at 2700K.

FIG. 46 shows how a 3000K halogen undergoes a CCT shift as it is dimmed. The CCT is indicated as a function of the input electrical power. Other filament lamps, such as incandescent lamps, also undergo a similar shift.

FIG. 47 shows how a 3000K halogen undergoes a CCT shift as it is dimmed. The CCT is indicated as a function of the emitted optical power. Other filament lamps, such as incandescent lamps, also undergo a similar shift.

Some embodiments of the invention approximate the CCT shift as the lighting level is dimmed. This can follow various curves such as are presented below in FIG. 46 and FIG. 47. In this case, for any dimming level, the embodiments have a CS which is about ten times lower than conventional lamps.

Some spectra shown on FIGS. 29-45 demonstrate that embodiments can achieve a CRI Ra above 80, for CCTs in the range 2200-3000K. Other spectra shown on FIGS. 29-45 demonstrate that embodiments can achieve a high deep-red rendering index R9 in the range 96-97, for CCTs in the range 2200-3000K. These embodiments were obtained by tuning the center wavelength of the red phosphor. Further tuning can be achieved by selecting the shape and center wavelength of various phosphors. Therefore, embodiments of the invention can achieve good or excellent color rendering while maintaining a low CS.

When comparing embodiments to standard LED sources radiators with the same luminous flux, it is possible to consider the power in a given spectral range or the percentage of the SPD in a given spectral range. When comparing embodiments to blackbody radiators with the same luminous flux, it is most appropriate to consider the power in a given spectral range (percentage of the SPD is less practical due to the large infrared tail of blackbody radiators).

In some embodiments, the invention is a lamp with two independent strings of LEDs. One string has a CCT of 2700K and a low CS, similar to the spectrum of FIG. 37. The other has a CCT of 2200K and a low CS, similar to the spectrum of FIG. 30. Upon dimming the lamp, the CCT shifts according to curves similar to those of FIG. 46 and FIG. 47; this is achieved by driving the power in each string accordingly. At all dimming powers, CS is low.

In other embodiments, the invention is a lamp with two independent strings of LEDs. One string has a CCT of 2700K and a regular CS—this can be achieved by using any standard white LED with a usual amount of blue-cyan radiation. The other string has a CCT of 2200K and a low CS, similar to the spectrum of FIG. 30. Upon dimming the lamp, the CCT shifts according to curves similar to those of FIG. 46 and FIG. 47; this is achieved by driving the power in each string accordingly. At full power, light is emitted from the first string and CS is high; at low power (for instance, 10% or 20% optical power), light is emitted from the second string and CS is low.

In other embodiments, different combinations of CCTs and CS can be used.

In other embodiments, only one string is present. It has a CCT of 2700K and a low CS, similar to the spectra of FIG. 37-38. The lamp always provides a low CS.

In some applications, lamps with a varying spectrum are desirable. This includes variations in CCT, intensity, etc. This can be done, for instance, with a three-color RGB LED lamp where the three channels are driven separately and mixed to generate a desired spectrum. However, although they are able to produce many different spectra, such highly-configurable tunable spectrum sources are expensive and sometimes complex to control. In some cases, only a few specific spectra are desirable—for instance white spectra at a few or several CCTs. One example is the 3-way incandescent bulb. Control of a 3-way bulb is simple and inexpensive, and often is based on an inexpensive mechanical selector. 3-way LED lamps can be useful in various situations where a simple way to switch between emitted spectra is desired. In the context of the invention, 3-way lamps can be used to switch between circadian-friendly spectra and other spectra.

In some embodiments, the lamp is a 3-way lamp. It includes two strings. One has a regular CS, and the other has a low CS. As the 3-way switch is cycled, one or the other filament is turned on. In some embodiments the two strings have the same CCT. In some embodiments the two strings have a different CCT—for instance, the first string has a CCT of 3000K and a regular CS; the other has a CCT of 2500K and a low CS. In some embodiments there is an indicator on the bulb which indicates which string is active. In some embodiments, more than two strings are present. In some embodiments the power emitted by the two strings is different—for instance the first string has a regular CS and a first light output, the second string has a low CS and a second output which is half the first output.

In further embodiments, control is provided through a computer interface rather than by a manual control (such as a dimmer or switch). Said control may correspond to switching between two strings of LEDs, such as strings of different CCTs or strings of different CS. For instance, control can be provided through a smartphone or another smart device (watch, tablet . . . etc.). Several embodiments of 3-way lamps are shown and discussed as pertaining to FIG. 48A through 48E.

In some cases the control is automated. For instance, transition from a string of high CS to a string of low CS happens at a given time of the day.

In some embodiments of the invention, some of all of the light is provided by a narrow emitter such as a laser, a laser diode (LD), or a superluminescent LED.

In an embodiment, violet light is provided by a laser diode; the laser further pumps a green and a red phosphor. This results in a spectrum with no blue light and a sharp cutoff of violet light, thanks to the narrow emission spectrum of the LD. FIG. 45A shows such an embodiment, on-Planckian with a CCT of 2700K, where the laser wavelength is 420 nm and the laser line's width is 3 nm. Other wavelengths can be used; other widths (such as 1 nm or less) can be used with very similar results. Likewise, slightly broader widths (as might be obtained by a superluminescent LED) can also be used with very similar results. FIG. 42A also shows that such laser-based embodiments can reach CRI Ra values above 80. FIG. 43A shows a similar embodiment with a shifted red phosphor, having a high R9 value of 97.

In the hypothesis that the CS action spectrum is still significant in the violet range (for instance down to 430 nm or 425 nm), such embodiments are desirable: they enable on-Planckian white light with good color rendering and with very little CS.

Further, embodiments may utilize a violet laser and a green/yellow laser. FIG. 44 shows such an embodiment, on-Planckian with a CCT of 2700K, where one laser has a wavelength of 420 nm and the other a wavelength of 518 nm. In this case, for a 100 lm spectrum, the total power in the range 422-516 nm is less than 2 mW, as compared to 51 mW for a 2700K Blackbody radiator. Therefore, even in the hypothesis of a very broad CS action spectrum, this SPD would cause minimal CS.

Yet other embodiments use three laser lines (violet, green/yellow and red) or more. FIG. 45 shows such an embodiment.

Some embodiments employ both a violet LD and a blue LD, or a violet LD and a blue LED. In such embodiments, the ratio of power driving the violet and the blue emitter may be modulated in order to tune the CS of the emitted SPD.

In embodiments combining lasers and phosphors, the phosphor may be configured in a remote configuration; or it may be configured in proximity to the LD that pumps it. For instance, in a given embodiment, a violet LD pumps a red phosphor and a green phosphor; the mixture of the violet, green and red light emits the embodiment's SPD. In another embodiment, a violet LD pumps a red phosphor and a green LD doesn't significantly pump the red phosphor. In yet another embodiment, a green LD pumps a red phosphor and a violet LD doesn't significantly pump the red phosphor.

Although light sources using one or more laser lines are known in the art, embodiments are distinguished by their low CS. Indeed, if CS were not considered, the natural choice for one skilled in the art would be to employ a LD with a wavelength of about 440-470 nm to optimize the luminous efficacy (LE). This is demonstrated in Reference [Phillips07], where a series of optimized laser-illuminants are designed: they employ a blue LD with emission in the range 458-463 nm. Therefore, embodiments of the invention are non-obvious in that they employ violet LDs, for instance with a wavelength below 430 nm: this reduces CS, at the expense of a lower LE. Some embodiments are characterized by a low CS or by a low spectral content (for an SPD normalized to an illuminance of 100 lm) in a CS wavelength range such as 430-520 nm, 440-510 nm or 450-500 nm. A low spectral content may correspond to less than 10 mW, less than 5 mW, less than 2 mW in said wavelength range.

In various embodiments employing LDs or other narrow-band sources, the wavelength of said sources can be optimized, together with the spectral characteristics of the phosphors (peak and width) in order to maximize properties of the emitted light while maintaining a desired CS. These properties include the luminous efficacy, and various color rendition metrics such as CRA Ra, R9, CQS, color gamut metrics, IES color metrics Rf and Rg.

FIG. 48A shows a 3-way bulb in an A-lamp form factor. The shown 3-way bulb has two different incandescent filaments (e.g., filament1 4802, filament2 4804), which can be independently controlled for ON/OFF modes of operation.

FIG. 48B shows a 3-way bulb with a screw-in socket. The 3-way bulb takes advantage of the fact that, for conventional A-lamps with a screw-in socket, there are two points of contact (e.g., line1 4806 and line2 4808) for the positive signal (e.g., positive 4810). By wiring each point to a different incandescent filament (e.g., filament1 4802, filament2 4804), several operation modes can be enabled. In the off position, both lines are off. In position A, line 1 carries current and the corresponding filament lights up. In position B line, 2 carries current and the corresponding filament lights up. In position C, both lines carry current and both filaments light up. In a typical 3-way bulb, positions A, B and C are respectively identified as low, medium and high light output.

The 3-way bulb concept has also been adapted to other technologies, such as fluorescent and LED bulbs. However, the 3-way control is used to provide different levels of illumination, as in an incandescent 3-way LED.

The following figures disclose an LED lamp that can output a few specific spectra and be controlled by a simple mechanical switch as heretofore described. In one implementation, the lamp is embodied as a 3-way A-blub containing two LED sources (e.g., LED1 4842, LED2 4844 as shown in FIG. 48C and FIG. 48D), each with different CCTs. For example:
   cool white (~5000K)
   warm white (~3000K)

The bulb is compatible with a regular 3-way fixture. Depending on the switch position, the lamp emits light at 3000K, 5000K or about 4000K (e.g., when both LED sources are mixed).

FIG. 48C shows a 3-way bulb with two filament-like LED sources. In the case of FIG. 48C, the two LED strings are wired directly to lines 1 and 2. LEDs 1 and 2 have different emission spectra such that the visible spectra can emanate from LED1 or from LED2 or from both.

FIG. 48D shows a driver 4819 disposed inside the bulb. Lines 1 and 2 both connect to an electrical driver 4819. In this embodiment, the driver serves several functions:
   It converts the current from AC to a different electrical signal (for instance DC, or a rectified waveform more amenable to driving LEDs), and
   It also performs logic functions such as determining connectivity and/or routing current and/or varying the magnitude of the current.

For instance, in a given embodiment, about 10 watts of power are consumed by the lamp. LED1 has a CCT of 3000K. LED2 has a CCT of 5000K. In position A, only LED1 receives power. In position B, LEDs 1 and 2 receive power yielding a CCT between 3000K and 5000K. In position C, only LED2 receives power. In all positions, a similar amount of light is emitted because the same amount of power is driven through the LEDs. In position B, the balance of power feeding LEDs 1 and 2 can be tuned to achieve a desired spectrum.

In another embodiment, the total power consumed by the lamp varies with power. LED1 has a CCT of 2500K, and LED2 has a CCT of 3000K. In position A, only LED1 receives 4 W of power. In position B, LEDs 1 and 2 receive a total power of 7 W. In position C, only LED2 receives 10 W of power. Thus the CCT of the lamp and its light output vary when the lamp is switched between positions. The LEDs and combinations may be configured to reproduce the warm-dimming effect of halogen lamps.

Various other CCT mixes are possible in other embodiments. In some cases the LEDs may be configured to manage light that has a chromaticities off of the Planckian locus. Some users prefer chromaticities below the Planckian locus.

FIG. 48E shows such an embodiment. FIG. 48E shows the 1931 (x-y) chromaticity diagram. The Planckian locus is shown, together with the chromaticity of LEDs 1 and 2. LED2, which are both substantially on-Planckian with a CCT of 5000K. LED1 is below the Planckian with a CCT of 3000K. Some embodiments are configured such that the mixture of LEDs 1 and 2 is off-Planckian with a CCT of about 4000K.

In another embodiment, three LEDs are present rather than two. Each LED has a different spectrum. Each position of the 3-way bulb corresponds to driving one or several of the three LEDs.

In some embodiments, the LED sources include violet dies. In some embodiments they include blue dies. In some embodiments the spectra emitted by the distinct LEDs have a different ratio of blue to violet; for instance, one LED has only violet dies and phosphors, and the second LED has only blue dies and phosphors.

Typically a 3-way bulb has to be used in a compatible fixture with a 3-way switch, which will contact either or both of the lines. In some embodiments however, a 3-way switch is integrated to the bulb, rather than being in the socket. Therefore the bulb can be placed in a conventional non-3-way fixture. The selection of the emitted spectrum can be obtained by using the 3-way switch on the bulb.

Aspects of embodiments can be combined, resulting in a light bulb having two or more LED sources, the two or more LED sources having different spectra, the bulb having at least three electrodes, such that upon driving current in the electrodes the several LED sources can be driven in at least two configurations to emit two different spectra.

Some phosphors suitable for embodiments have already been discussed in this application. The following FIG. 49A through FIG. 49C, discuss and exemplify phosphors enabling embodiments. More particularly, some LEDs illumination products have a spectrum (esp. emissions in the blue range) that impacts human circadian cycles and produces unwanted effects in the human response system.

Embodiments described herein address the problem of how to suppress unwanted impacts of certain wavelengths of light on humans. Additionally, disclosed herein are several embodiment of lighting apparatus that exhibits a "circadian-friendly" spectrum. The exhibited minimum in the blue part of the spectrum (e.g., between about 440 and about 480 nm) reduces impact on human circadian cycles and reduces the related negative effects. The suppression in the blue part of the spectrum is achieved by using combinations LED chips and LED phosphors emitting in specific spectral regions. An unexpected result is that this approach produces white light balanced on or near the Planckian locus and with general CRI equal to or greater than 80, as well as an R9 value greater than 0.

FIG. 49A, FIG. 49B, and FIG. 49C shows the experimental spectra of three working examples. The examples describe in detail examples of constituent elements of the herein-disclosed embodiments. It will be apparent to those skilled in the art that many modifications, both to materials and methods, may be practiced without departing from the scope of the disclosure.

Strictly as examples, some embodiment have been verified experimentally. Working Example 49A00 is using a blend of BOSE phosphor having an emission peak near 525 nm and SCASN phosphor having an emission peak near 620 nm, excited by an LED pump with a peak at 414 nm (=see the spectrum in FIG. 49A). The BOSE phosphor is an alkaline earth orthosilicate doped with $Eu^{2+}$ and is typically represented as $(Ba,Sr)_2SiO_4:Eu^{2+}$. The SCASN phosphor is an alkaline earth nitridoaluminosilicate doped with $Eu^{2+}$ and is typically represented as $(Sr,Ca)SiAlN_3:Eu^{2+}$. With CCT=2984K, Duv=+0.0015, 83 CRI and R9=16, 1.24% of this spectrum falls between 440 nm and 480 nm. Working Example 49B00 is using a blend of a $3-sialon doped with $Eu^{2+}$'phosphor having an emission peak near 530 nm and the same SCASN phosphor and LED pump as in Working Example 49 (see the spectrum of Working Example 49B00 in FIG. 49B). With CCT=3048K, Duv=+0.0003, 80 CRI and R9=27, 0.73% of this spectrum falls between 440 nm and 480 nm. Working Example 49C00 has the same phosphors as Working Example 49B00 but is using an LED pump having a peak at 409 nm (see the spectrum in FIG. 49C). With CCT=3029K, Duv=+0.0001, 84 CRI and R9=13, 1.21% of this spectrum falls between 440 nm and 480 nm. In the examples provided here, emission peaks are quoted for the pure phosphors used.

For the implementation of this invention, it may be important to avoid the use of SSL pumps emitting with a peak between 435 nm and 480 nm and phosphors emitting with a peak between 400 nm and 500 nm. One possible emission peak wavelength for the LED pump is in the region between 400 nm and 435 nm, more preferably between 405 nm and 425 nm. The SSL pump may be an LED chip or SSL laser. The emission peak of phosphors used in this invention may be above 500 nm, with no primary or secondary emission peak present between 400 nm and 500 nm. Examples of phosphors not meeting the latter criterion are:

(Ba,Sr,Ca,Mg)$_5$(PO$_4$)$_3$(Cl,F,Br,OH):Eu$^{2+}$;
(Ca,Sr,Ba)$_3$MgSi$_2$O$_8$:Eu$^{2+}$;
(Ba,Sr,Ca)MgAl$_{10}$O$_{17}$:Eu$^{2+}$;
Ce$_x$(Mg,Ca,Sr,Ba)$_y$(Sc,Y,La,Gd,Lu)$_{1-x-y}$Al(Si$_{6-z+y}$Al$_{z-y}$)(N$_{10-z}$O$_z$) (where x,y<1, y≥0 and z~1);
(Mg,Ca,Sr,Ba)(Y,Sc,Gd,Tb,La,Lu)$_2$S$_4$:Ce$^{3+}$, (which have an emission peak between 400 nm and 500 nm), and (Ba,Sr,Ca,Mg)$_5$(PO$_4$)$_3$(Cl,F,Br,OH):Eu$^{2+}$, Mn$^{2+}$;
(Ca,Sr,Ba)$_3$MgSi$_2$O$_8$:Eu$^{2+}$, Mn$^{2+}$;
(Ba,Sr,Ca)MgAl$_{10}$O$_{17}$:Eu$^{2+}$, Mn$^{2+}$ which have a "secondary" (i.e., of lower intensity) emission peak between 400 nm and 500 nm from Eu$^{2+}$ emission, even though their "primary" (i.e., of highest intensity) emission peak is above 500 nm from Mn$^{2+}$ emission through energy transfer from Eu$^{2+}$ to Mn$^{2+}$, producing a total of 2 peaks in the emission spectrum of each of the latter 3 phosphors.

As a general rule, near UV or violet excitable phosphors co-doped by 2 activators exhibit a residual blue emission peak from a co-activator emitting at higher energy (typically Eu$^{2+}$ or Ce$^{3+}$) required to provide energy to the co-activator emitting at lower energy (typically Mn$^{2+}$), which may render such phosphors unsuitable for some embodiments of this invention.

Suitable classes of first phosphors with an emission peak between 500 nm and 550 nm include silicates or fluorosilicates doped with Eu$^{2+}$; chalcogenides doped with Eu$^{2+}$; nitridosilicates, oxynitridosilicates, oxynitridoaluminosilicates or beta-sialons doped with Eu$^{2+}$ and carbidooxynitridosilicates doped with Eu$^{2+}$. Specific non-limiting examples of suitable first phosphors include:

(Ba,Sr)$_2$SiO$_4$:Eu$^{2+}$ (a typical formulation of "BOSE")
(Mg,Ca,Sr,Ba,Zn)$_2$SiO$_4$:Eu$^{2+}$ (a broader formulation of "BOSE")
(Sr,Ca,Ba)(Al,Ga)$_2$S$_4$:Eu$^{2+}$
Eu$_x$(A1)$_{6-z}$(A2)$_z$O$_y$N$_{8-z}$(A3)$_{2(x+z-y)}$, where 0≤z≤4.2; 0≤y≤z; 0<x≤0.1; A1 is Si, C, Ge, and/or Sn; A2 is Al, B, Ga, and/or In; A3 is F, Cl, Br, and/or I
M(II)$_{1-x-z}$M(I)$_z$M(III)$_{x-xy-z}$Si$_{1-x+xy+z}$N$_{2-x-xy-2w/3}$C$_{xy}$O$_{w-v/2}$H$_v$:A and
M(II)$_{1-x-z}$M(I)$_z$M(III)$_{x-xy-z}$Si$_{1-x+xy+z}$N$_{2-x-xy-2w/3-v/3}$C$_{xy}$O$_w$H$_v$:A, wherein 0<x<1, 0<y<1, 0≤z<1, 0≤v<1, 0<w<1, x+z<1, x>xy+z, and 0<x−xy−z<1, M(II) is at least one divalent cation, M(I) is at least one monovalent cation, M(III) is at least one trivalent cation, H is at least one monovalent anion, and A is a luminescence activator doped in the crystal structure.

Suitable classes of second phosphors with an emission peak between 600 nm and 670 nm include nitridosilicates doped with Eu$^{2+}$; carbidonitridosilicates doped at least with Eu$^{2+}$; chalcogenides doped with Eu$^{2+}$ and oxides, oxyfluorides or complex fluorides doped with Mn$^{4+}$. Specific non-limiting examples of suitable second phosphors include:

(Sr,Ca)AlSiN$_3$:Eu$^{2+}$ (a typical formulation of "SCASN")
(Ba,Sr,Ca,Mg)AlSiN$_3$:Eu$^{2+}$ (a broader formulation of "SCASN")
(Ba,Sr,Ca,Mg)$_x$Si$_y$N$_z$:Eu$^{2+}$ (where 2x+4y=3z)

The group:

$$Ca_{1-x}Al_{x-xy}Si_{1-x+xy}N_{2-x-xy}C_{xy}:A \quad (1);$$

$$Ca_{1-x-z}Na_zM(III)_{x-xy-z}Si_{1-x+xy+z}N_{2-x-xy}C_{xy}:A \quad (2);$$

$$M(II)_{1-x-z}M(I)_zM(III)_{x-xy-z}Si_{1-x+xy+z}N_{2-x-xy}C_{xy}:A \quad (3);$$

wherein 0<x<1, 0<y<1, 0≤z<1, 0≤v<1, 0<w<1, x+z<1, x>xy+z, and 0<x−xy−z<1, M(II) is at least one divalent cation, M(I) is at least one monovalent cation, M(III) is at least one trivalent cation, H is at least one monovalent anion, and A is a luminescence activator doped in the crystal structure.

(Na,K,Rb,Cs)$_2$[(Si,Ge,Ti,Zr,Hf,Sn)F$_6$]:Mn$^{4+}$
(Mg,Ca,Zr,Ba,Zn) [(Si,Ge,Ti,Zr,Hf,Sn)F$_6$]:Mn$^{4+}$
(Mg,Ca,Sr,Ba)(S,Se):Eu$^{2+}$
(Na,K,Rb,Cs)$_2$[(Si,Ge,Ti,Zr,Hf,Sn)F$_6$]:Mn$^{4+}$
(Mg,Ca,Zr,Ba,Zn) [(Si,Ge,Ti,Zr,Hf,Sn)F$_6$]:Mn$^{4+}$
Sr[LiAl$_3$N$_4$]:Eu$^{2+}$.

In some embodiments, this invention makes use of a first phosphor with an emission peak between 500 nm and 550 nm and a second phosphor with an emission peak between 600 nm and 670 nm. Optionally, one or more additional phosphor(s) may be used as needed to optimize the luminous flux or the color rendering properties of the LED. The additional phosphor(s) may have an emission peak between 500 nm and 670 nm, preferably between 550 nm and 600 nm. Examples of suitable classes of additional phosphors include those of the aforementioned first and second phosphors classes emitting at different peak wavelengths than the specific first and second phosphors selected, plus garnets doped with Ce$^{3+}$, nitrides doped with Ce$^{3+}$ and alpha-sialons doped with Eu$^{2+}$. Some specific non-limiting examples of such additional phosphors include:

(Y,Gd,Tb,La,Sm,Pr,Lu)$_3$(Sc,Al,Ga)$_5$O$_{12}$:Ce$^{3+}$
(La,Y,Lu)$_3$Si$_6$N$_{11}$:Ce$^{3+}$
(Lu,Ca,Li,Mg,Y) alpha-SiAlON doped with Eu$^{2+}$ and/or Ce$^{3+}$.

LED phosphors are typically used as a blend coupled radiationally to the SSL pump, to provide a light spectrum balanced to a certain chromaticity ("color point") in a given CIE chromaticity diagram, preferably on or near the Planckian locus, e.g., to within +/−0.010 Duv in the CIE u, v diagram. The correlated color temperature (CCT) of interest typically lies between 2200K and 7000K, with CCT values above 2500K preferred for general lighting applications.

Alternatively, the phosphors can be layered sequentially in layers or laid out in a parallel fashion (e.g., in a pattern of small patches) around the LED pump.

One skilled in the art will know how to adjust the amount of each phosphor in the phosphor blends, layers or patterns in order to target any given color point of interest, obtainable per the color mixing rule as long as it lies within the region subtended by the color points of each phosphor and the LED pump in the CIE chromaticity diagram. Achieving LED spectra with good color rendering properties (e.g., as described by the CIE general color rendering index Ra further referred to as "CRI" and the CIE special color rendering index for deep red further referred to as "R9") is however not straightforward since the influences of different spectral components are highly non-linear, and there are no simple rules but rather an element of art involved in obtaining desirable CRI and R9 values, for example. It is traditionally assumed in the lighting industry that a white spectrum with good color rendering for general lighting purposes (e.g., with a CRI value of 80 or higher and an R9 value higher than 0) should have a substantial emission in the blue wavelength region, especially for CCT values above 2500K. For instance, it has been first predicted by numerical modeling and later demonstrated experimentally that SPDs with peaks around 450 nm, 540 nm and 610 nm provide a CRI of 80 or greater when color-balanced on the Planckian locus across the range of CCT values used in general lighting. As a consequence, the tri-phosphor fluorescent lamp technology was developed based on those specific emission peak wavelengths. LED spectra in the known art have either a pump LED emission peak or a phosphor emission peak in the blue spectral region between 435 nm and 500 nm, wherein that phosphor emission peak may be primary or secondary, as explained earlier. Since some white "circadian-friendly" spectrum embodiments need to have emission between 440 nm and 480 nm suppressed, a related impact on the CRI value from this spectral deficiency around the 450 nm wavelength (widely considered critical to CRI based on the aforementioned precedents) can be reasonably expected in comparison to typical white blue-pumped LEDs containing the same green and red phosphors or white violet-pumped LEDs containing a blue-emitting phosphor and the same green and red phosphors. Unexpectedly, some embodiments disclosed here are able to obtain white "circadian-friendly" LEDs exhibiting a local minimum in their spectral power distribution (SPD) between 440 nm and 480 nm and color-balanced near the Planckian locus with both general CRI≥80 and R9≥0, as shown in the examples given here. This is achieved by using an excess of violet light from the LED chip (relative to the blackbody spectrum reference) to balance the color near the Planckian locus, which, contrary to conventional wisdom, affords good CRI (≥80) and R9 (≥0) values without the usage of any peak between 435 nm and 500 nm in the spectrum, whether it be from an LED chip or a phosphor.

The SPD of "circadian-friendly" LEDs prepared according to this invention may contain less than 2% of its radiant emission (preferably, less than 1% of its radiant emission) in the spectral region from 440 nm to 480 nm, as demonstrated in the working examples given. When used for general lighting applications, such LEDs can have a general CRI (Ra) value greater than 80 and a special R9 CRI value greater than 0, as also demonstrated in the working examples given.

The lighting apparatus disclosed here can be an LED package or module, a solid state lamp (including direct replacement lamps for incandescent, halogen or fluorescent lamps), solid state lighting ("SSL") fixture, light engine (the light generating component of a fixture), backlighting unit, etc. Whenever the word "LED" is used in the foregoing specification, it is includes various lighting apparatus, and is not limiting the scope of applicability of this invention.

In various embodiments related to lighting, the spectrum emitted by the embodiment may be optimized for one or several metrics related to quality of the light. Such metrics may include lumens, luminous efficacy of radiation, chromaticity, CIE Ra, CIE R9 or other special indices, IES Rf, IES Rg, other gamut metrics (such as GAI). This optimization can be achieved by selecting the spectral properties of LED emitters and phosphors, as is known in the art. Several examples of such optimization have been provided in this disclosure—for instance how the choice of the phosphors enables desirable values of Ra (say >80) or R9 (say >0). In some embodiments, this optimization is carried out while also optimizing the spectrum for its circadian properties—for instance by ensuring little radiation is present in a given range of circadian stimulation (such as 430-480 nm or others). There is in general a tradeoff between this latter circadian-friendly criterion and other aspects of quality of light; for instance, a paucity of light in the blue-cyan range may be detrimental to luminous efficacy of radiation, color rendering (Ra and others), chromaticity, etc. Therefore, simultaneous optimization for low circadian stimulation and other aspects is non-trivial and distinguishes embodiments of the invention from conventional light sources, where one would naturally include radiation in the blue-cyan range.

In the following, we discuss additional considerations for embodiments of the invention used in display systems.

In some cases the display is based on an LCD technology and uses color filters. Embodiments of the invention use LCDs and filters with high transmission at short wavelength. For instance, the relative transmission of the stack composed of the LCD and the blue filter may be higher than 1%, higher than 10%, higher than 20%, or higher than 50% at a wavelength of 415 nm or 420 nm.

FIG. 50A shows an embodiment that uses a white LED based on violet emission with low CS. The LED is combined with three color filters and with LCDs to produce an RGB screen. Unlike some conventional displays, the short-wavelength transmission of the system (including the transmission of the blue filter and of the LCD) is maintained at wavelengths in the range of about 410 to about 430 nm.

In some embodiments the system uses more than one primary LED source. This may include a violet and a cyan LED. This is advantageous because it increases the gamut of the display. The display may use four filters (violet, cyan, green, red); or it may use only three filters (violet-cyan, green, red) and modulate the violet and cyan LEDs on and off at the same time as the violet-cyan filter, in order to emulate a violet pixel and a cyan pixel.

FIG. 50B shows a system with a standard blue-pumped white LED and a violet LED. Such a system can operate in a circadian stimulating regime and in a circadian non-stimulating regime. In the stimulating regime, the white LED is on at all times. In the non-stimulating regime, the white LED is on and the violet LED is off when the green and red filters are transmitting; the white LED is off and the violet LED is on when the blue filter is transmitting.

FIG. 50C shows another embodiment where four primaries are used. Here, the switch between non-stimulating and stimulating regime can be obtained by modulating the blue and violet LEDs. Alternately, in stimulating mode, both the violet and the blue LED may be used alternatively in order to enhance the color gamut of the screen.

In some embodiments for display systems, care is taken to use materials and filters with moderate absorption in the violet range (for instance, in the range of about 410 to about 430 nm). Indeed, violet light may be a necessary aspect to embodiments of the invention as it may replace unwanted blue and cyan light. In some embodiments of the invention, the total transmission of the display system (which may be due to filters, waveguides, diffusers, polarizers and other elements) varies by less than 50% (or less than 20%, less than 10%) between 420 nm and 450 nm. In some embodiments, the total transmission of the display system in the range of about 410 to about 430 nm is more than 20%, more than 50%, more than 80%.

In some embodiments, the display uses direct emission from LEDs without filters. For instance, each pixel may contain three LEDs (violet, green and red) or four LEDs (violet, blue/cyan, green and red). An advantage of this configuration is the higher efficiency since no filters are necessary.

FIG. 50D shows an embodiment with four LEDs in each pixel. Such embodiments contain no color filters or LCD filters, such that transmission of short-wavelength light is not reduced.

In some embodiments, the CCT of the display is tuned during the day/night (for instance the CCT becomes warmer at night). This can be scheduled, or linked to an ambient light sensor (photodiode or CCD). In some cases the ambient CCT is measured and the screen CCT is adapted to match the ambient CCT.

In some embodiments with four or more primaries, the emitted spectrum can be tuned to change the CS. For instance in a system with a violet light source and a blue/cyan light source, the relative amount of violet and cyan/blue can be tuned from low to high CS.

In some embodiments, the display's brightness can be tuned in relationship to other quantities like the CCT and the CS. For instance, lower brightness can be associated with a spectrum with lower CS. Again this can be automated following a schedule (which may take into account seasons and time of day), and/or a schedule can be learned from the user's behavior, and/or controlled by the environment (e.g., level of light, CCT of the ambient light, etc.).

In an embodiment, the system incorporates a digital camera with a CCD sensor; a light level sensor; and a display with a violet and a cyan/blue LED whose intensities can be tuned to modify the CS of the screen's white point. The CCD is used to infer the CCT of ambient light, and the CCT of the screen is adapted accordingly. When the ambient light level is low, the screen brightness is lowered and its CS is low. When the ambient light level is high, the screen brightness is high and its CS is high.

Additional Embodiments

Any one or more of the herein-discussed techniques can be used to make light sources (e.g., lamps, display systems, etc.) using the structures and characteristics of the embodiments below.

Embodiment 1. A light source comprising:
at least one first LED emission source characterized by a first emission; and
at least one second LED emission source characterized by a second emission; wherein
the first emission and the second emission are configured to provide a first combined emission and a second combined emission;
the first combined emission is characterized by a first SPD and fractions Fv1 and Fc1;
the second combined emission is characterized by a second SPD and fractions Fv2 and Fc2;
Fv1 represents the fraction of power of the first SPD in the wavelength range from 400 nm to 440 nm;
Fc1 represents the fraction of power of the first SPD in the wavelength range from 440 nm to 500 nm;
Fv2 represents the fraction of power of the second SPD in the wavelength range from 400 nm to 440 nm;
Fc2 represents the fraction of power of the second SPD in the wavelength range from 440 nm to 500 nm;
the first SPD and the second SPD have a color rendering index above 80;
Fv1 is at least 0.05;
Fc2 is at least 0.1; and
Fc1 is less than Fc2 by at least 0.02.

Embodiment 2. The light source of embodiment 1, wherein,
the first combined emission is characterized by a first circadian stimulation;
the second combined emission is characterized by a second circadian stimulation; and
the second circadian stimulation is at least twice the first circadian stimulation.

Embodiment 3. The light source of embodiment 1, wherein the first LED emission source comprises at least one LED characterized by a peak emission in the range 405 nm to 430 nm.

Embodiment 4. The light source of embodiment 1, wherein,
the first emission and the second emission are configured to provide a third combined emission;
the third combined emission is characterized by a third SPD, a fraction Fv3, a fraction Fc3, and a third circadian stimulation;
Fv3 represents the fraction of power of the third SPD in the wavelength range from 400 nm to 440 nm;
Fc3 represents the fraction of power of the third SPD in the wavelength range from 440 nm to 500 nm;
the third SPD has a coloring rendering index above 80; and
the first circadian stimulation and the third circadian stimulation are different.

Embodiment 5. The light source of embodiment 1, wherein the second emission comprises blue emission from a wavelength down-conversion material.

Embodiment 6. The light source of embodiment 1, wherein the second emission comprises direct blue emission from an LED.

Embodiment 7. The light source of embodiment 1, wherein one of the combined emissions induces a circadian stimulation similar to a circadian stimulation of a D65 reference illuminant.

Embodiment 8. The light source of embodiment 1, wherein one of the combined emissions induces a circadian stimulation that is less than a circadian stimulation of a CIE A reference illuminant.

Embodiment 9. The light source of embodiment 1, wherein the at least one first LED emission source and the at least one second LED emission source are configured in an intermixed physical arrangement.

Embodiment 10. The light source of embodiment 1, wherein each of the first SPD and the second SPD is characterized by a chromaticity within the white light bounding region 514 of FIG. 5B.

Embodiment 11. The light source of embodiment 10, wherein each of the first SPD and the second SPD is characterized by a chromaticity bounded by ±0.005 of a Planckian loci and by ±0.005 of a minimum-hue-shift curve in a CIE chromaticity diagram.

Embodiment 12. The light source of embodiment 1, wherein each of the first SPD and the second SPD is characterized by a chromaticity within +/−five Du'v' points of a Planckian loci.

Embodiment 13. The light source of embodiment 1, wherein exposure of a subject to the second SPD with an illuminance of 100 lx for ninety minutes results in a suppression of blood melatonin concentration in the subject of at least 20%.

Embodiment 14. The light source of embodiment 1, wherein exposure of a subject to the first SPD with an illuminance of 100 lx for ninety minutes results in a suppression blood melatonin concentration in the subject of at most 20%.

Embodiment 15. The light source of embodiment 1, wherein Fc1 is at most 0.06.

Embodiment 16. A display system comprising:
 a first LED emission source characterized by a first emission; and
 a display configured to emit a first SPD characterized by a first fraction Fv1 of power in the range 400 nm to 435 nm; wherein,
 the display system is characterized by a color gamut of at least 70% of NTSC;
 the first SPD is substantially white with a CCT in a range from 3000K to 9000K; and
 Fv1 is at least 0.05.

Embodiment 17. The display system of embodiment 16, wherein the display comprises an emission spectrum characterized by a circadian stimulation that is less than a circadian stimulation of a reference illuminant having the same CCT.

Embodiment 18. The display system of embodiment 16, further comprising a color filter set and a liquid crystal display.

Embodiment 19. The display system of embodiment 18, wherein,
 the first SPD is characterized by a peak in the wavelength range from 400 nm to 435 nm at a wavelength w;
 the color filter set comprises a blue filter characterized by a maximum transmission Tm, and by a transmission Tw at wavelength w; and
 Tw/Tm>0.8.

Embodiment 20. The display system of embodiment 16, further comprising a second LED emission source characterized by a second emission, wherein a ratio of the first emission and the second emission are configured to be adjusted to change a circadian stimulation.

Embodiment 21. The display system of embodiment 16, wherein the display system is configured for use with a TV, desktop PC, notebook PC, laptop PC, tablet, smartphone, MP3 player.

Embodiment 22. The display system of embodiment 16, wherein less than 5% of the total power of the first SPD is in a wavelength range from 440 nm to 500 nm.

FIG. 51A and FIG. 51B illustrate reducing loss by generating a spectrum that already has only a small portion of radiation in the CSR, in cases wherein radiation within the CSR is desired to be completely or near-completely removed by absorption and/or filtering. The two original spectral power distributions are both observed by human viewers as having substantially the same chromaticity. In the case of FIG. 51A and FIG. 51B specifically, they are both white emitters (near the blackbody loci) and further demonstrate reasonably high color rendering (CRI of 80). This is possible since human visual sensation of blue light can be stimulated by blue light or a violet light. In many cases a relatively larger amount of power in violet ranges (FIG. 51B) produces the same human sensation as a relatively smaller amount of power in blue wavelength ranges (FIG. 51A).

However, filtering of emitted blue light (e.g., so as to completely or near-completely remove radiation in the CSR) as shown in FIG. 51A has the side effect of significantly reducing power efficiency of the corresponding lamp, as well as significantly changing its chromaticity (i.e., making the emission appear strongly yellow). In contrast, the spectral power distribution as shown in FIG. 51B does not produce a substantial amount of radiation in the CSR in the first place, and so does not suffer significantly reduced useful radiation when residual emission in the CSR is removed. Furthermore, its chromaticity is only slightly affected by removing light in the CSR and can be easily compensated for (to retain a white color point) through slight modifications to the phosphor and/or primary violet LED emissions.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A backlight for emitting emitted light comprising:
 at least a first light emitting circuit and a second light emitting circuit; and
 a controller for discretely powering said at least first light emitting circuit and second light emitting circuit in two modes, a low CS mode and a normal mode;
 wherein in said normal mode, a first emitted light is emitted, said first emitted light has a first correlated color temperature (CCT), a first illuminance of about 50 lux to about 5000 lux, and a first CS;
 wherein in said low CS mode, a second emitted light is emitted, said second emitted light has a second correlated color temperature (CCI), a second illuminance of about 50 lux to about 5000 lux, and a second CS;
 wherein said second CS is no greater than about 50% of said first CS; and
 wherein said first and second CCTs are at least 2500K.

2. The backlight of claim 1, wherein said first and second CCTs are about the same.

3. The backlight of claim 1, wherein said first and second illuminances are about the same.

4. The backlight of claim 1 wherein said second CS is no greater than about 20% of said first CS.

5. The backlight of claim 1, wherein said first light emitting circuit comprises at least one light-emitting diode or one laser diode emitting having a peak wavelength in a range 380 440 nm, said second light emitting circuit has an emission spectrum having a peak between 500 nm and 550 nm.

6. The backlight of claim 1, wherein said first light emitting circuit does not emit light with a peak wavelength greater than 440 nm and less than 500 nm.

7. The backlight of claim 1, wherein said first light emitting circuit has an SPD in a spectral region between 440 nm and 480 nm and a power in the SPD between 440 nm and 480 nm is less than 2% of a power of the SPD between 380 nm and 780 nm.

8. The backlight of claim 1, wherein said first and second emitted lights each has a CRI Ra higher than 80 and a CRI Ra higher than 0.

9. The backlight of claim 1, wherein said first and second emitted lights each has a CRI Ra higher than 80.

10. The backlight of claim 1, wherein said certain first and second CCTs are at least 2700 K, and said first and second emitted lights having a Duv +/−0.01 from the Planckian locus.

11. The backlight of claim 1, wherein the illuminance is a retinal illuminance.

\* \* \* \* \*